US011358989B2

(12) United States Patent
Luesch et al.

(10) Patent No.: US 11,358,989 B2
(45) Date of Patent: Jun. 14, 2022

(54) APRATYRAMIDE THERAPEUTIC AGENTS AND METHODS OF TREATMENT

(71) Applicants: University of Florida Research Foundation, Incorporated, Gainesville, FL (US); Smithsonian Institution, Washington, DC (US)

(72) Inventors: Hendrik Luesch, Gainesville, FL (US); Weijing Cai, Gainesville, FL (US); Valerie J. Paul, Fort Pierce, FL (US); Lilibeth A. Salvador, Metro Manila (PH)

(73) Assignees: University of Florida Research Foundation, Incorporated, Gainesville, FL (US); Smithsonian Institution, Washington, DC (US)

( * ) Notice: Subject to any disclaimer, the term of this patent is extended or adjusted under 35 U.S.C. 154(b) by 0 days.

(21) Appl. No.: 16/765,969

(22) PCT Filed: Nov. 21, 2018

(86) PCT No.: PCT/US2018/062289
§ 371 (c)(1),
(2) Date: May 21, 2020

(87) PCT Pub. No.: WO2019/104200
PCT Pub. Date: May 31, 2019

(65) Prior Publication Data
US 2020/0361995 A1 Nov. 19, 2020

Related U.S. Application Data

(60) Provisional application No. 62/589,955, filed on Nov. 22, 2017.

(51) Int. Cl.
*A61K 38/00* (2006.01)
*C07K 11/00* (2006.01)
*A61P 17/02* (2006.01)

(52) U.S. Cl.
CPC .............. *C07K 11/00* (2013.01); *A61P 17/02* (2018.01); *A61K 38/00* (2013.01)

(58) Field of Classification Search
CPC .......... A61P 17/02; C07K 11/00; A61K 38/00
See application file for complete search history.

(56) References Cited

U.S. PATENT DOCUMENTS

2007/0021342 A1  1/2007  Breen et al.
2011/0110875 A1  5/2011  Lee et al.
2017/0121372 A1  5/2017  Peoples et al.

OTHER PUBLICATIONS

Stacker et al. Emerging Roles for VEGF-D in Human Disease. Biomolecules 2018, 8, 1 (Year: 2018).*
Takahashi et al. The vascular endothelial growth factor (VEGF)/VEGF receptor system and its role under physiological and pathological conditions. Clin Sci (Lond) (2005) 109 (3): 227-241 (Year: 2005).*
Shibuya et al. VEGF-VEGFR Signals in Health and Disease. Biomol Ther 22(1), 1-9 (2014) (Year: 2014).*
Cai et al. Apratyramide, a Marine-Derived Peptidic Stimulator of VEGF-A and Other Growth Factors with Potential Application in Wound Healing. ACS Chem Biol. Jan. 19, 2018; 13(1): 91-99. (Year: 2018).*
Robert Gale; Merck Manual accessed May 8, 2020. Cancer treatment principles (Year: 2018) (Year: 2018).*
International Search Report and Written Opinion dated Jan. 16, 2019 in connection with PCT/US2018/062289.
Cai et al., Apratyramide, a Marine-Derived Peptidic Stimulator of VEGF-A and Other Growth Factors with Potential Application in Wound Healing. ACS Chem Biol. 2018;13(1):91-99. doi:10.1021/acschembio.7b00827.
Cai et al., Discovery, synthesis, and biological evaluation of apratyramide, a marine-derived transcriptional stimulator of VEGF-A. Planta Medica. 2015;81(11);PK9. Abstract Only.
Shah et al., Structural Diversity, Biological Properties and Applications of Natural Products from Cyanobacteria. A Review. Mar Drugs. 2017;15(11):354. Published Nov. 10, 2017. doi:10.3390/md15110354.
Xiong et al., Total synthesis and structure-activity relationship studies of a series of selective G protein inhibitors. Nat Chem. 2016;8(11):1035-1041. doi:10.1038/nchem.2577.
PCT/US2018/062289, dated Jan. 16, 2019, International Search Report and Written Opinion.

* cited by examiner

*Primary Examiner* — Aradhana Sasan
*Assistant Examiner* — Mercy H Sabila
(74) *Attorney, Agent, or Firm* — Wolf, Greenfield & Sacks, P.C.

(57) ABSTRACT

The invention is directed towards Apratyramide linear depsipeptide compounds, pharmaceutical compositions thereof, and methods of affecting wound healing, and methods of affecting the biological processes involved in wound healing (e.g., inflammation, cell proliferation, tissue granulation, remodeling of scar tissue, etc.).

12 Claims, 18 Drawing Sheets

FIG. 3

| Unit | C/H no | δ_H (J in Hz) | δc | COSY | HMBC | Key NOESY |
|---|---|---|---|---|---|---|
| N,N-di MeTyr(OMe) | 1 | | 170.62 | | | |
| | 2 | 3.46, dd (9.4, 6.2) | 68.28 | H-3a, H-3b | C-3, C-1, NMe | |
| | 3a | 2.82, dd (13.4, 9.4) | 34.41 | H-3b, H-2 | C-9/C-5, C-4, C-2, C-1 | |
| | 3b | 2.77, dd (13.4, 6.2) | 34.41 | H-3a, H-2 | C-9/C-5, C-4, C-2, C-1 | |
| | 4 | | 130.2 | | | |
| | 5, 9 | 7.10, d (8.7) | 130 | H-6, H-8 | C-9/C-5, C-7, C-3 | |
| | 6, 8 | 6.79, d (8.7) | 113.55 | H-5, H-9 | C-7, C-4 | |
| | 7 | | 157.74 | | | |
| | NMe | 2.28, s | 41.11 | | C-2, NMe | |
| | OMe | 3.69 | 54.98 | | C-7 | |
| Hmpa | 1 | | 168.71 | | | |
| | 2 | 4.81, d (3.8) | 75.09 | H-3 | C-1, C-6, C-3, C-4, C-1 (N,N-diMeTyr(OMe)) | NH (Val) |
| | 3 | 1.72, m | 36.28 | H-2, H-6 | C-6, C-4 | NH (Val) |
| | 4a | 1.03, m | 25.33 | H-5, H-4b | C-5, C-6, C-3 | |
| | 4b | 0.91, m | 25.33 | H-5, H-4a | C-5, C-6, C-3 | |
| | 5 | 0.69, t (7.5) | 11.28 | H-4a, H-4b | C-4, C-3 | C-8 (N,N-diMeTyr(OMe)), C-9 (N,N-diMeTyr(OMe)) |
| | 6 | 0.68, d (7.0) | 13.83 | H-3 | C-2 | |
| Val | 1 | | 170.58 | | | |
| | 2 | 4.45, t (8.6) | 53.65 | H-3, NH | C-1, C-3, C-4, C-5, C-1 (Ile acid) | |
| | 3 | 1.9, m | 29.63 | H-2, H-4, H-5 | C-5, C-4, C-2 | |
| | 4 | 0.77, d (6.7) | 17.83 | H-3 | C-5, C-3, C-2 | |
| | 5 | 0.78, d (6.7) | 19.27 | H-3 | C-4, C-3, C-2 | |
| | NH | 8.08 | | H-2 | C-2, C-1 (Ile acid) | H-2 (Ile acid), H-5 (Ile acid) |

FIG. 3 (continued)

| Unit | C/H no | $\delta_H$ (J in Hz) | $\delta_C$ | COSY | HMBC | Key NOESY |
|---|---|---|---|---|---|---|
| N-MeTyr | 1 | | 168.52 | | | |
| | 2 | 5.27, dd (10.0, 3.8) | 54.93 | H-3a, H-3b | C-4, C-3, C-1, C-1 (Val), N-Me | |
| | 3a | 3.09, dd (13.0, 10.0) | 33.77 | H-3b, H-2 | C-9/C-5, C-4, C-2, C-1 | |
| | 3b | 2.33, dd (13.0, 3.8) | 33.77 | H-3b, H-2 | C-9/C-5, C-4, C-2, C-1 | |
| | 4 | | 128 | | | |
| | 5, 9 | 6.98, d (7.9) | 130.18 | H-6/H-8 | C-9/C-5, C-7, C-3 | |
| | 6, 8 | 6.68, d (7.9) | 115 | H-5/H-9 | C-7, C-4 | |
| | 7 | | 155.8 | | | |
| | 7-OH | 9.27, brs | | | | |
| | NMe | 2.70, s | 30.07 | | C-1 (Val) | |
| | | | | | | |
| N-MeTyr (1-OMe) | 1 | | 170.42 | | | |
| | 2 | 4.53, dd (11.8, 4.5) | 61.28 | H-3a, H-3b | C-3, C-1, C-1 (N-MeTyr), N-Me | |
| | 3a | 2.98, dd (14.0, 4.5) | 32.45 | H-3b, H-2 | C-9/C-5, C-4, C-2 | |
| | 3b | 2.83, dd (14.0, 11.8) | 32.45 | H-3b, H-2 | C-9/C-5, C-4, C-2, C-1 | |
| | 4 | | 127.2 | | | |
| | 5, 9 | 6.57, d (8.5) | 129.8 | H-6/H-8 | C-9/C-5, C-7, C-3 | |
| | 6, 8 | 6.51, d (8.5) | 115.14 | H-5/H-9 | C-7, C-4 | |
| | 7 | | 155.8 | | | |
| | 7-OH | 9.28, brs | | | | |
| | NMe | 2.44, s | 34.47 | | C-2, C-1 (N-MeTyr) | |
| | 1-OMe | 3.59, s | 51.47 | | C-1 | |

FIG. 15

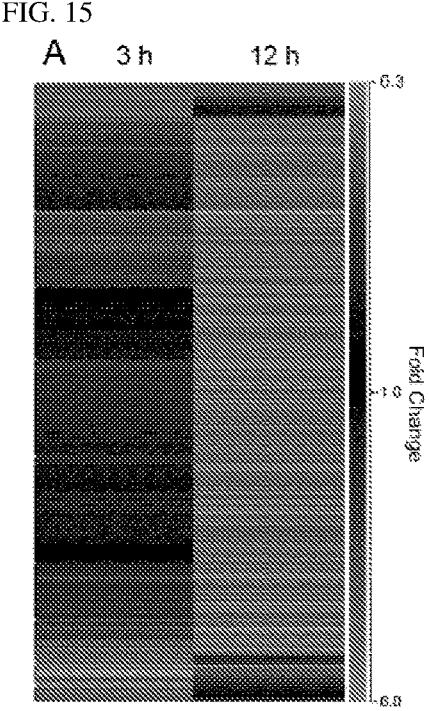

FIG. 16

|  | Up-regulated genes, FDR correction, 12 h | Down-regulated genes, FDR correction, 12 h |
|---|---|---|
| Growth factor | *AREG, VEGFA, HBEGF, EREG* |  |
| Cytokine | *IL1A, IL1B, MYDGF* | *SCGB1A1, CXCL1, CCL2, TNFSF10* |
| Transcription regulator | *DDIT3, CREB3L2, XBP1, ETV5, ATF4, JUND, ZNF165, ETV4, ATF3, MYC, NFE2L1, KLF6, SQSTM1, DAP, PREB, NFKB2, FOXE1, MEF2D, MAGED1, IRF2BP2, BHLHE40* | *GMNN, UHRF1, GTF2I, VGLL1, DLX5, E2F8, SMAD6, ID3, GRHL3* |
| G-protein coupled receptor | *GPR1* | *P2RY2* |
| MicroRNA |  | *MIR-3143, MIR-554, MIR-548* |

[a] The P values obtained were controlled for multiple testing (false discovery rate) using the Benjamini-Hochberg method. Differentially expressed genes were then ranked by the P values, genes with P < 0.05 (with FDR correction) and fold change >1.5 or <0.67 were considered as differentially expressed genes at a statistically significant level, which were grouped based on functions. Selected groups are presented above. See Supporting Information Table S2 for a full list of top up- and down-regulated genes.

FIG. 20

| | Up-regulationed genes, FDR correction, 12 h | Down-regulationed genes, FDR correction, 12 h |
| --- | --- | --- |
| Growth factor | AREG, VEGFA, HBEGF, EREG | |
| Cytokine | IL1A, IL1B, MYDGF | SCGB1A1, CXCL1, CCL2, TNFSF10 |
| Transcription regulator | DDIT3, CREB3L2, XBP1, ETV5, ATF4, JUND, ZNF165, ETV4, ATF3, MYC, NFE2L1, KLF6, SQSTM1, DAP, PREB, NFKB2, FOXE1, MEF2D, MAGED1, IRF2BP2, BHLHE40 | GMNN, UHRF1, GTF2I, VGLL1, DLX5, E2F8, SMAD6, ID3, GRHL3 |
| Transporter | SLC7A11, SEC24D, LCN2, SLC33A1, LDLR, SYVN1, COPG1, SLC1A5, SEC61A1, SLC6A9, SEC23B, SLC39A7, STX5, NPC1, SLC1A4, SLC43A1, TMCO3, SEC63, SLC50A1, SEC61B, TMED10, OSBP | ATP1B1, ATP1B3, TFRC, SCFD2, SLC12A2, AQP3, SLC39A10, SLC6A6, SLC1A3 |
| Kinase | TRIB3, PCK2, ERN1, NDRG1 | EPHA4 |
| G-protein coupled receptor | GPR1 | P2RY2 |
| Ion channel | CLIC4, CLCN6, CACNB1 | KCNJ15 |
| Transmembrane receptor | F3 | BCAM |
| Phosphatase | PLPP5, LPIN1, DUSP6, MTMR4 | ALPPL2, DUSP10 |
| Peptidase | ABHD4, PRSS8, LONP1 | MMP13 |
| Enzyme | CYP1A1, ASNS, GFPT1, CTH, WARS, SARS, MTHFD2, PSAT1, CYP1B1, AARS, UPP1, CYP51A1, FUT3, SCD, HSPA5, CBS/CBSL, MICAL2, DHCR7, CYP4F11, ALG2, PYCR1, FKBP11, EDEM2, MARS, PDIA4, GPT2, NCF2, EDEM1, CARS, PHGDH, OSTC, GARS, GMPPA, ANXA3, IARS, PYGB, SMOX, MSMO1, CHPF, SHMT2, UAP1, FDFT1, SND1, GTPBP2, YARS, MVD, LSS, SDR42E1, DNASE2, NEU1, PDIA6, RAB6A, P4HB, SQLE, MTHFD1L, TXNDC11, ODC1, DTD1, ACSL3 | HSPA8, MSH2, DHFR, ESCO2, TYMS, GLUL, PCNA, RHOBTB3, MCM6, POP1, AKR1B10, HSPA1A/HSPA1B, CROT, HAS2, RNF152 |
| MicroRNA | | MIR3143, MIR-554, MIR-548 |

A
Ex Vivo Rabbit Corneal Epithelial Model 6 mm diameter wounded area of cornea

B

VEGF-A Transcript
Ex Vivo Rabbit Corneal Epithelial Model

APRATYRAMIDE THERAPEUTIC AGENTS AND METHODS OF TREATMENT

CROSS-REFERENCE TO RELATED APPLICATIONS

This application is a National Phase Application under 35 U.S.C. 371 of PCT International Application No. PCT/US2018/062289, filed Nov. 21, 2018, which claims priority to U.S. Provisional Application No. 62/589,955, filed Nov. 22, 2017, which applications are incorporated herein by reference in their entirety.

STATEMENT OF RIGHTS TO INVENTIONS MADE UNDER FEDERALLY SPONSORED RESEARCH

This invention was made with government support under CA172310 awarded by the National Institutes of Health. The government has certain rights in the invention.

BACKGROUND

Wound healing is a complex biological process and consists of a series of events including inflammation, cell proliferation, tissue granulation and remodeling of scar tissue, which involves the coordinated efforts of several cell types, such as keratinocytes, fibroblasts, endothelial cells, macrophages, and platelets (Clark, R. A. (1985) Cutaneous tissue repair: basic biologic considerations. I. J. Am. Acad. Dermatol. 13, 701-725; Greaves, N. S., Ashcroft, K. J., Baguneid, M., and Bayat, A. (2013) Current understanding of molecular and cellular mechanisms in fibroplasia and angiogenesis during acute wound healing. J. Dermatol. Sci. 72, 206-217; Goren, I., Müller, E., Schiefelbein, D., Gutwein, P., Seitz, O., Pfeilschifter, J., and Frank, S. (2009) Akt1 controls insulin-driven VEGF biosynthesis from keratinocytes: implications for normal and diabetes-impaired skin repair in mice. J. Invest. Dermatol. 129, 752-764). A wide variety of growth factors and cytokines are involved in each stage of the wound healing process: platelet-derived growth factors (PDGFs), vascular endothelial growth factors (VEGFs), basic fibroblast growth factors (bFGFs), and granulocyte-macrophage colony stimulating factor (GM-CSF), and many studies have shed light on the crucial roles of these growth factors on initiating and facilitating wound healing (Greaves, N. S., Ashcroft, K. J., Baguneid, M., and Bayat, A. (2013) Current understanding of molecular and cellular mechanisms in fibroplasia and angiogenesis during acute wound healing. J. Dermatol. Sci. 72, 206-217; Barrientos, S., Stojadinovic, O., Golinko, M. S., Brem, H., and Tomic-Canic, M. (2008) Growth factors and cytokines in wound healing. Wound Repair Regen. 16, 585-601). Dysregulation of these growth factors could delay wound closure and result in chronic wounds (e.g., diabetic foot ulcers [DFUs], pressure ulcers [PUs], and chronic venous leg ulcers [VUs]), which represent a major healthcare burden in the US (Falanga, V. (2005) Wound healing and its impairment in the diabetic foot. Lancet 366, 1736-1743; Brem, H., and Tomic-Canic, M. (2007) Cellular and molecular basis of wound healing in diabetes. J. Clin. Invest. 117, 1219).

Despite many efforts that have been spent on the development of growth factors as therapeutic agents, to date, this field has been disappointing. There is only one Federal Drug Administration (FDA) approved growth factor on the market for the treatment of DFUs: recombinant platelet-derived growth factor, rhPDGF-BB, Becaplermin (Barrientos, S., Brem, H., Stojadinovic, O., and Tomic-Canic, M. (2014) Clinical application of growth factors and cytokines in wound healing. Wound Repair Regen. 22, 569-578). There are also other growth factors under clinical trials, including VEGF, bFGF and GM-CSF (Barrientos, S., Brem, H., Stojadinovic, O., and Tomic-Canic, M. (2014) Clinical application of growth factors and cytokines in wound healing. Wound Repair Regen. 22, 569-578). One of the limitations for topical administration of exogenous growth factors is low absorption due to the protein nature of these growth factors (Dou, C., Lay, F., Ansari, A. M., Rees, D. J., Ahmed, A. K., Kovbasnjuk, O., Matsangos, A. E., Du, J., Hosseini, S. M., Steenbergen, C., Fox-Talbot, K., Tabor, A. T., Williams, J. A., Liu, L., Marti, G. P., and Harmon, J. W. (2014) Strengthening the skin with topical delivery of keratinocyte growth factor-1 using a novel DNA plasmid. Mol. Ther. 22, 752-761; Kryger, Z., Zhang, F., Dogan, T., Cheng, C., Lineaweaver, W. C., and Buncke, H. J. (2000) The effects of VEGF on survival of a random flap in the rat: examination of various routes of administration. Br. J. Plast. Surg. 53, 234-239; Andrews, S. N., Jeong, E., and Prausnitz, M. R. (2013) Transdermal delivery of molecules is limited by full epidermis, not just stratum corneum. Pharm. Res. 30, 1099-1109). Therefore, an alternative therapeutic method aimed at stimulating the production and secretion of endogenous growth factors from wound tissue by small molecules might be more promising.

VEGF is one of the most potent angiogenic growth factors and promotes all steps in the angiogenic cascade (Ferrara, N. (1999) Role of vascular endothelial growth factor in the regulation of angiogenesis. Kidney Int. 56, 794-814). In the VEGF family, VEGF-A is the best studied angiogenic growth factor regulating both physiological and disease processes such as tumor growth, psoriasis and wound healing (Ferrara, N., Hillan, K. J., Gerber, H.-P., and Novotny, W. (2004) Discovery and development of bevacizumab, an anti-VEGF antibody for treating cancer. Nat. Rev. Drug Discov. 3, 391-400; McColl, B. K., Stacker, S. A., and Achen, M. G. (2004) Molecular regulation of the VEGF family—Inducers of angiogenesis and lymphangiogenesis. Apmis 112, 463-480; Carmeliet, P., and Jain, R. K. (2011) Molecular mechanisms and clinical applications of angiogenesis. Nature 473, 298-307). VEGF-A is produced by keratinocytes, fibroblast smooth muscle cells, platelets, neutrophils, and macrophages during wound healing, and keratinocytes are thought to be a major source of VEGF-A after injury (Rossiter, H., Barresi, C., Pammer, J., Rendl, M., Haigh, J., Wagner, E. F., and Tschachler, E. (2004) Loss of vascular endothelial growth factor A activity in murine epidermal keratinocytes delays wound healing and inhibits tumor formation. Cancer Res. 64, 3508-3516; Frank, S., Hübner, G., Breier, G., Longaker, M. T., Greenhalgh, D. G., and Werner, S. (1995) Regulation of vascular endothelial growth factor expression in cultured keratinocytes. Implications for normal and impaired wound healing. J. Biol. Chem. 270, 12607-12613; Brown, L. F., Yeo, K., Berse, B., Yeo, T. K., Senger, D. R., Dvorak, H. F., and Van De Water, L. (1992) Expression of vascular permeability factor (vascular endothelial growth factor) by epidermal keratinocytes during wound healing. J. Exp. Med. 176, 1375-1379). VEGF-A stimulates angiogenesis by acting on endothelial cells in the wound sites (Bao, P., Kodra, A., Tomic-Canic, M., Golinko, M. S., Ehrlich, H. P., and Brem, H. (2009) The Role of Vascular Endothelial Growth Factor in Wound Healing. J. Surg. Res. 153, 347-358). It has been found that VEGF-A gene expression is up-regulated in the skin after wounding (Frank, S., Hübner, G., Breier, G., Longaker, M.

T., Greenhalgh, D. G., and Werner, S. (1995) Regulation of vascular endothelial growth factor expression in cultured keratinocytes. Implications for normal and impaired wound healing. *J. Biol. Chem.* 270, 12607-12613). Furthermore, the altered expression pattern of VEGF mRNA during skin repair in genetically diabetic (db/db) mice suggested that the impairment in VEGF synthesis and release at the wound site might contribute to chronic wounds (Frank, S., Hübner, G., Breier, G., Longaker, M. T., Greenhalgh, D. G., and Werner, S. (1995) Regulation of vascular endothelial growth factor expression in cultured keratinocytes. Implications for normal and impaired wound healing. *J. Biol. Chem.* 270, 12607-12613). In agreement with these observations, many in vitro and in vivo studies have shown that administration of VEGF-A topically or by gene transfer accelerates experimental wound healing through stimulation of angiogenesis, re-epithelialization, collagen deposition, and synthesis and maturation of extracellular matrix (Di Peppe, S. R., Mangoni, A., Zambruno, G., Spinetti, G., Melillo, G., Napolitano, M., and Capogrossi, M. C. (2002) Adenovirus-mediated VEGF(165) gene transfer enhances wound healing by promoting angiogenesis in CD1 diabetic mice. *Gene Ther.* 9, 1271; Galeano, M., Deodato, B., Altavilla, D., Cucinotta, D., Arsic, N., Marini, H., Torre, V., Giacca, M., and Squadrito, F. (2003) Adeno-associated viral vector-mediated human vascular endothelial growth factor gene transfer stimulates angiogenesis and wound healing in the genetically diabetic mouse. *Diabetologia* 46, 546-555; Michaels, J., Dobryansky, M., Galiano, R. D., Bhatt, K. A., Ashinoff, R., Ceradini, D. J., and Gurtner, G. C. (2005) Topical vascular endothelial growth factor reverses delayed wound healing secondary to angiogenesis inhibitor administration. *Wound Repair Regen.* 13, 506-512; Brem, H., Kodra, A., Golinko, M. S., Entero, H., Stojadinovic, O., Wang, V. M., Sheahan, C. M., Weinberg, A. D., Woo, S. L. C., Ehrlich, H. P., and Tomic-Canic, M. (2009) Mechanism of sustained release of vascular endothelial growth factor in accelerating experimental diabetic healing. *J. Invest. Dermatol.* 129, 2275-2287). Therefore, the above information strongly suggests the therapeutic application of VEGF-A inducers in the treatment of chronic wounds.

The use of natural products for the treatment of wounds and injuries is as old as civilization. Since ancient times, people have recognized the healing properties of herbs, honey, leaves, oil, etc (Forrest, R. D. (1982) Early history of wound treatment. *J. R. Soc. Med.* 75, 198-205). So far, some but not all of the active components of these natural wound healers that are identified fall into several structural classes: vitamins, terpenes or terpenoids, polyphenols, and alkaloids (Reichrath, J., Lehmann, B., Carlberg, C., Varani, J., and Zouboulis, C. C. (2007) Vitamins as hormones. *Horm. Metab. Res.* 39, 71-84; Lin, T. S., Abd Latiff, A., Abd Hamid, N. A., Ngah, W., and Mazlan, M. (2012) Evaluation of Topical Tocopherol Cream on Cutaneous Wound Healing in Streptozotocin-Induced Diabetic Rats. *Evidence-Based Complement. Altern. Med*; MacKay, D., and Miller, A. L. (2003) Nutritional support for wound healing. *Altern. Med. Rev.* 8, 359-378; Shim, K. M., Choi, S. H., Jeong, M. J., and Kang, S. S. (2007) Effects of aucubin on the healing of oral wounds. In Vivo (Brooklyn). 21, 1037-1041; Sevimli-Gür, C., Onbaylar, I., Atilla, P., Genç, R., Çakarc, N., Deliloğlu-Gürhan, I., and Bedir, E. (2011) In vitro growth stimulatory and in vivo wound healing studies on cycloartane-type saponins of *Astragalus* genus. *J. Ethnopharmacol.* 134, 844-850; Shukla, A., Rasik, A. M., Jain, G. K., Shankar, R., Kulshrestha, D. K., and Dhawan, B. N. (1999) In vitro and in vivo wound healing activity of asiaticoside isolated from *Centella asiatica*. *J. Ethnopharmacol.* 65, 1-11; Moon, E. J., Lee, Y. M., Lee, O. H., Lee, M. J., Lee, S. K., Chung, M. H., Park, Y. I., Sung, C. K., Choi, J. S., and Kim, K. W. (1999) A novel angiogenic factor derived from Aloe vera gel: beta-sitosterol, a plant sterol. *Angiogenesis* 3, 117-123; Schmidt, C. A., Murillo, R., Bruhn, T., Bringmann, G., Goettert, M., Heinzmann, B., Brecht, V., Laufer, S. A., and Merfort, I. (2010) Catechin derivatives from *Parapiptadenia rigida* with in vitro wound-healing properties. *J. Nat. Prod.* 73, 2035-2041; Clericuzio, M., Tinello, S., Burlando, B., Ranzato, E., Martinotti, S., Cornara, L., and La Rocca, A. (2012) Flavonoid oligoglycosides from *Ophioglossum vulgatum* L. Having wound healing properties. *Planta Med.* 78, 1639-1644; Wang, R., Lechtenberg, M., Sendker, J., Petereit, F., Deters, A., and Hensel, A. (2013) Wound-healing plants from TCM: In vitro investigations on selected TCM plants and their influence on human dermal fibroblasts and keratinocytes. *Fitoterapia* 84, 308-317; Sharifi, R., Pasalar, P., Kamalinejad, M., Dehpour, A. R., Tavangar, S. M., Paknejad, M., Mehrabani Natanzi, M., Nourbakhsh, M., Ahmadi Ashtiani, H. R., Akbari, M., and Rastegar, H. (2013) The effect of silymarin (*Silybum marianum*) on human skin fibroblasts in an in vitro wound healing model. Pharm. Biol. 51, 298-303; Porras-Reyes, B. H., Lewis, W. H., Roman, J., Simchowitz, L., and Mustoe, T. A. (1993) Enhancement of wound healing by the alkaloid taspine defining mechanism of action. *Proc Soc Exp Biol Med* 203, 18-25; Nesterova, Y. V., Povetieva, T. N., Suslov, N. I., Zhdanov, V. V., Hrichkova, T. Y., Udut, E. V., Chaykovskiy, A. S., Gaydamovich, N. N., Andreeva, T. I., and Dygai, A. M. (2012) Regeneratory characteristics of complex extract and isolated diterpene alkaloids of aconitum baikalense. *Bull. Exp. Biol. Med.* 152, 439-443). These compounds enhance wound healing through various mechanisms, including promoting skin cells proliferation and migration, angiogenesis, collagen synthesis, as well as, exerting anti-inflammatory and antiseptic activities (Tsala, D. E., Amadou, D., and Habtemariam, S. (2013) Natural wound healing and bioactive natural products. *Phytopharmacology* 4, 532-560). In addition to these traditional natural sources, marine organisms are becoming a rich source for new drugs. For example, pseudopterosins are a series of a diterpene-pentoseglycoside compounds from gorgonian corals that enhance wound healing through anti-inflammation (Mayer, A. M. S., Glaser, K. B., Cuevas, C., Jacobs, R. S., Kem, W., Little, R. D., McIntosh, J. M., Newman, D. J., Potts, B. C., and Shuster, D. E. (2010) The odyssey of marine pharmaceuticals: a current pipeline perspective. *Trends Pharmacol. Sci.* 31, 255-265; Day, D. R., Jabaiah, S., Jacobs, R. S., and Little, R. D. (2013) Cyclodextrin formulation of the marine natural product pseudopterosin a uncovers optimal pharmacodynamics in proliferation studies of human umbilical vein endothelial cells. *Mar. Drugs* 11, 3258-3271).

Marine cyanobacteria produce various secondary metabolites which belong to peptides, polyketides or hybrid of peptide-polyketides (Tan, L. T. (2007) Bioactive natural products from marine cyanobacteria for drug discovery. *Phytochemistry* 68, 954-979). Despite the fact that marine cyanobacteria produce compounds with a broad spectrum of biological activities, including anticancer, antimicrobial, protease inhibitory, immunomodulatory, neuromodulatory properties, and considered a valuable source for medicinal therapeutic use, they have not yet been linked to activities associated with wound healing, to the best of our knowledge. Described herein are novel linear depsipeptides isolated from marine cyanobacteria as a growth factor inducer with potential wound healing properties and, thus, provide new insights into the role of small peptides in wound healing and broadens the spectrum of activities of compounds from marine cyanobacteria.

BRIEF SUMMARY OF THE INVENTION

The invention is directed towards Apratyramide linear depsipeptide compounds, pharmaceutical compositions thereof, methods of affecting wound healing, and methods of affecting the biological processes involved in wound healing (e.g., inflammation, cell proliferation, tissue granulation, remodeling of scar tissue, and the like).

In one embodiment, the invention provides a compound according to the formula:

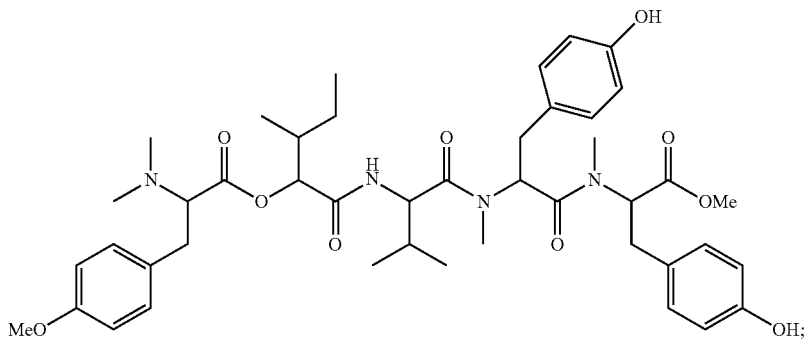 [SMILES: CCC(C)C(OC(=O)C(Cc1ccc(OC)cc1)N(C)C)C(=O)NC(C(=O)N(C)C(Cc1ccc(O)cc1)C(=O)N(C)C(Cc1ccc(O)cc1)C(=O)OC)C(C)C]

or pharmaceutically acceptable salts, solvates, hydrate, prodrugs, or stereoisomers thereof.

In another embodiment, the compound of the invention is one of:

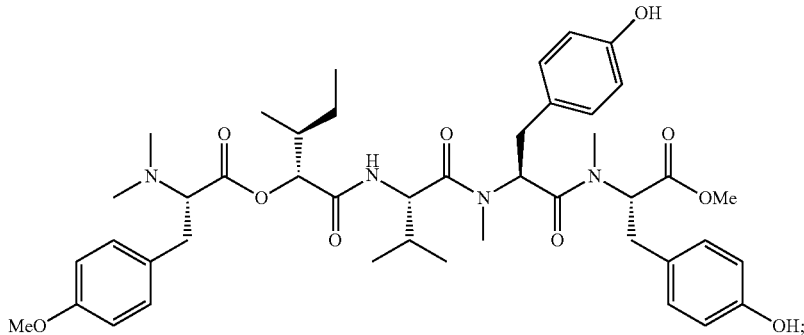

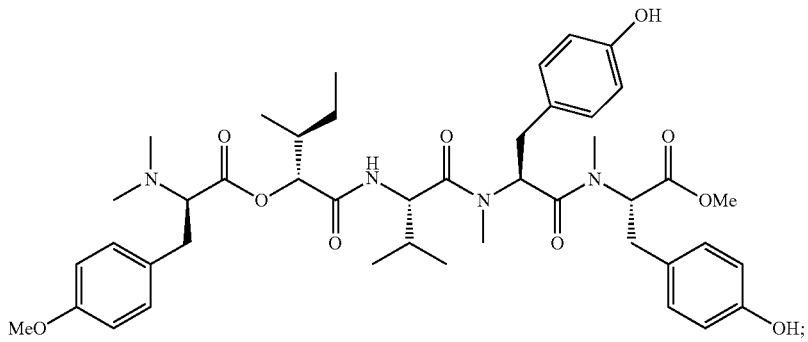

-continued
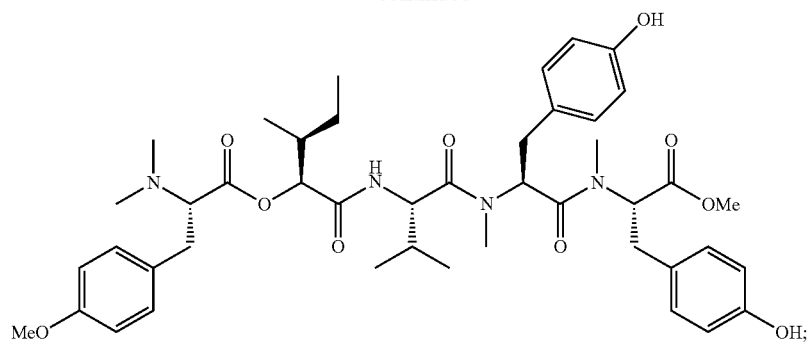
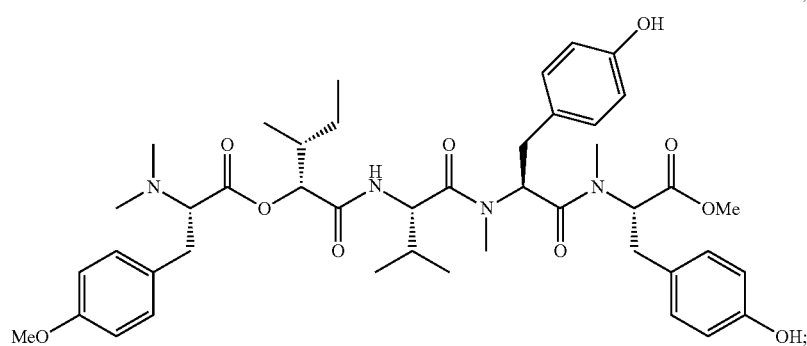
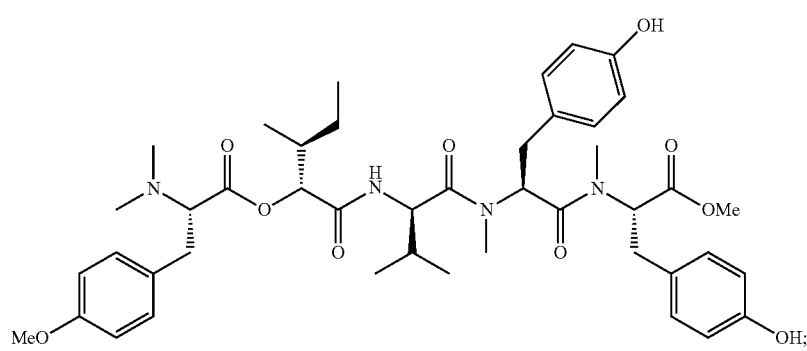
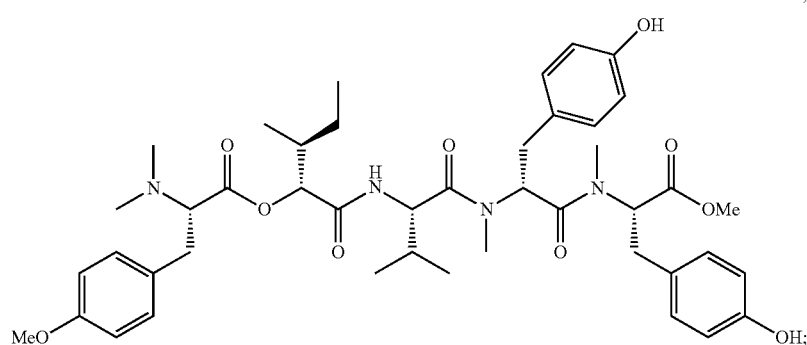
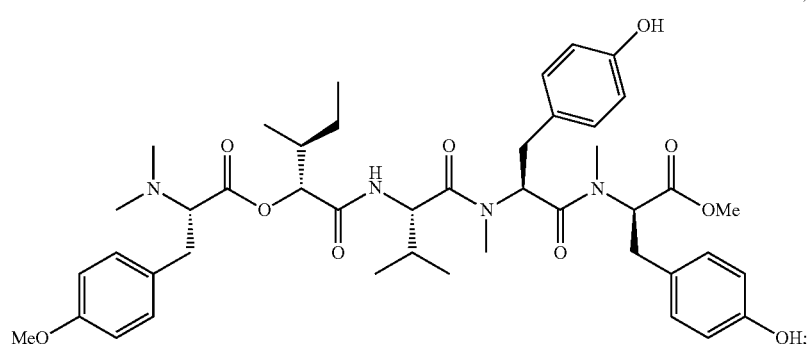

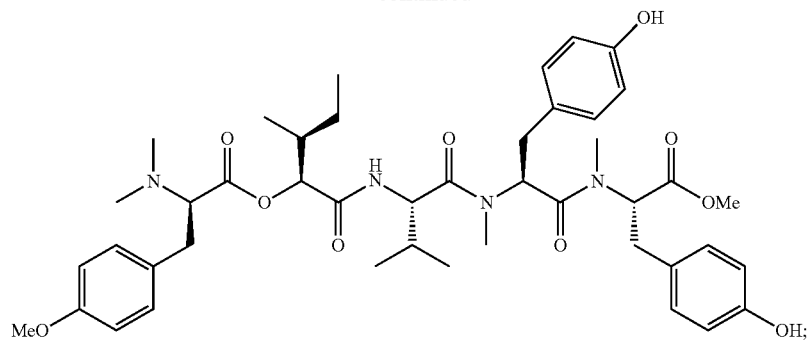
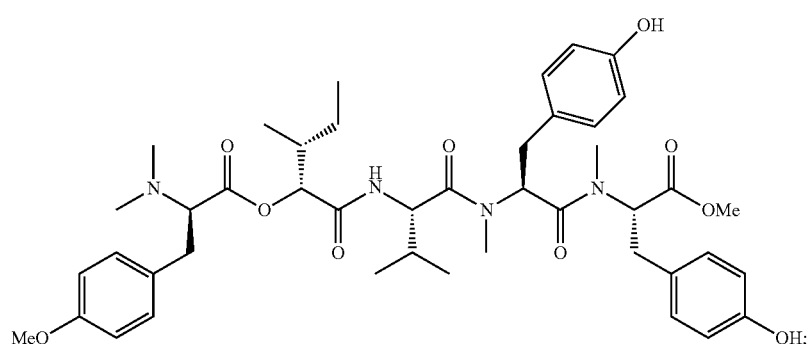
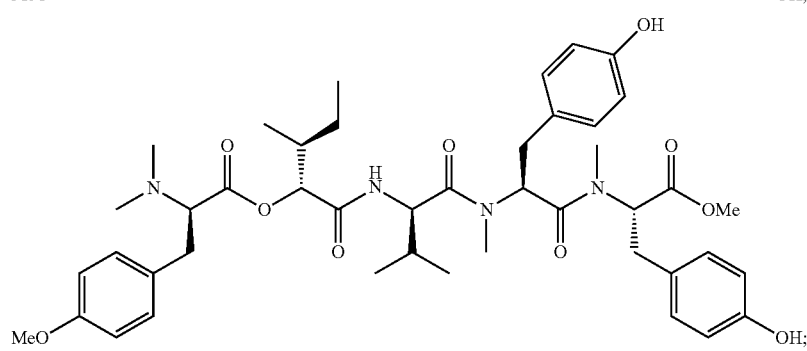
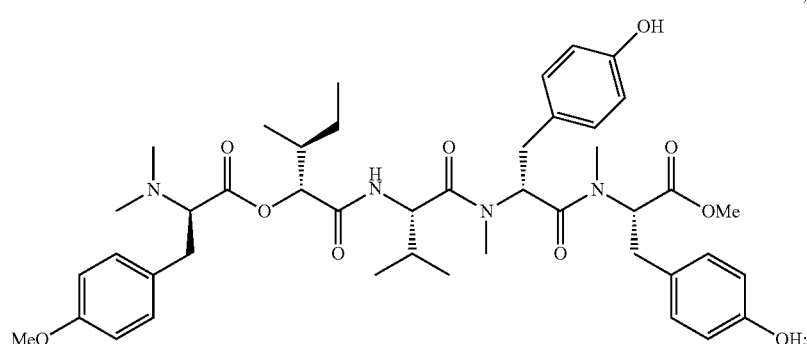
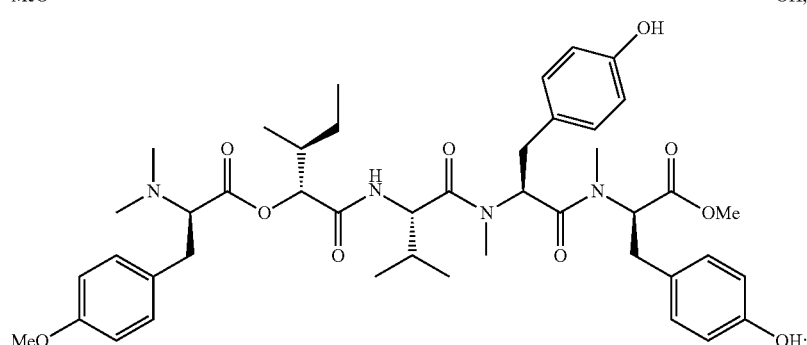

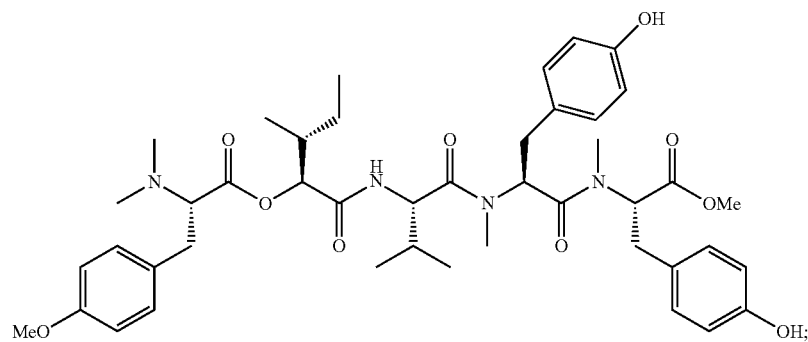
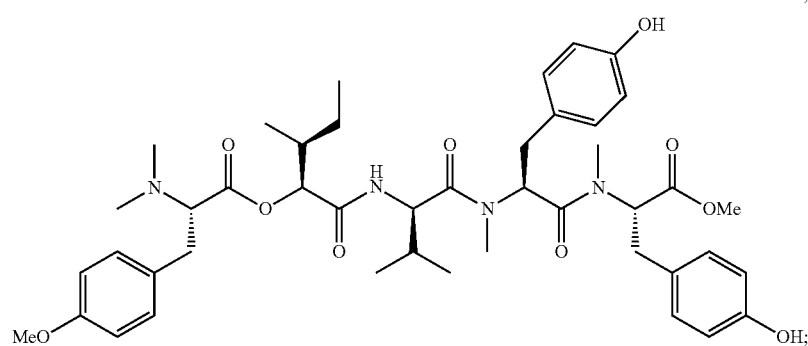
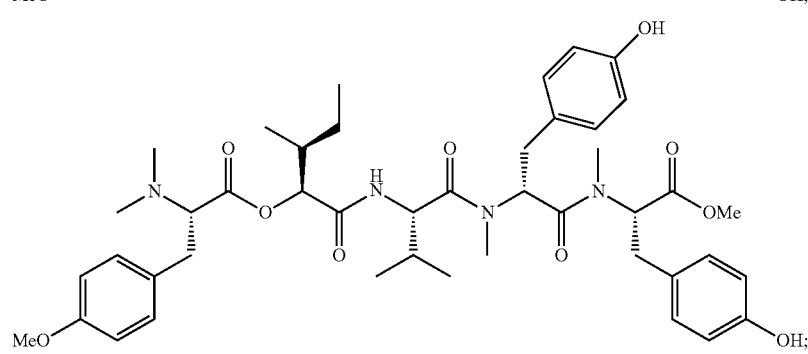
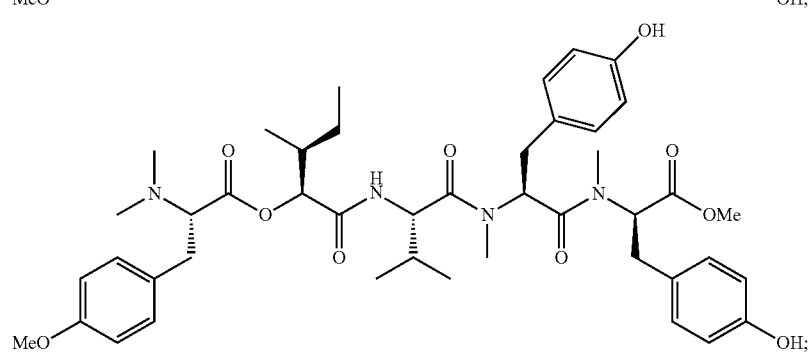
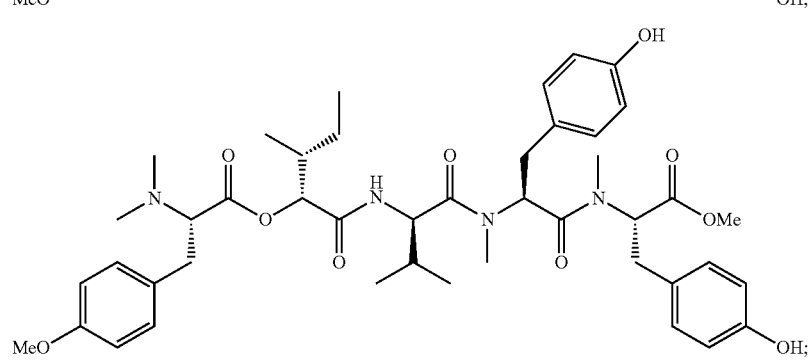

-continued
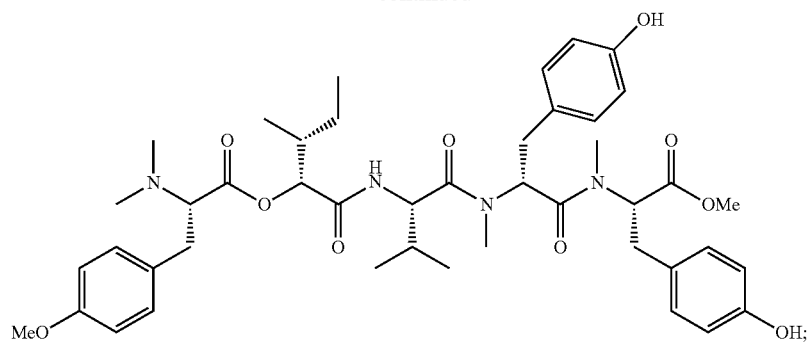 [SMILES: CCC(C)C(OC(=O)C(Cc1ccc(OC)cc1)N(C)C)C(=O)NC(C(=O)N(C)C(Cc1ccc(O)cc1)C(=O)N(C)C(Cc1ccc(O)cc1)C(=O)OC)C(C)C]
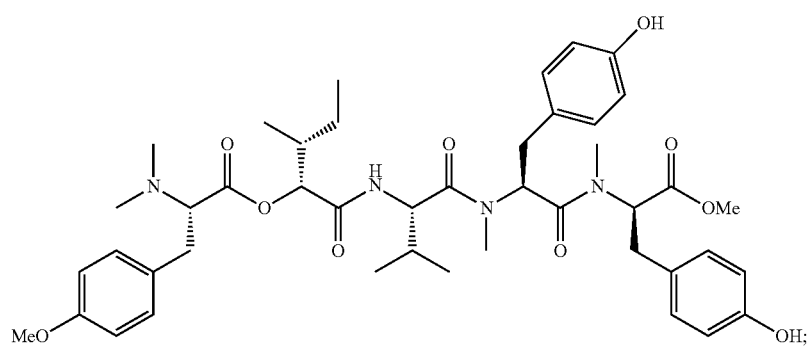
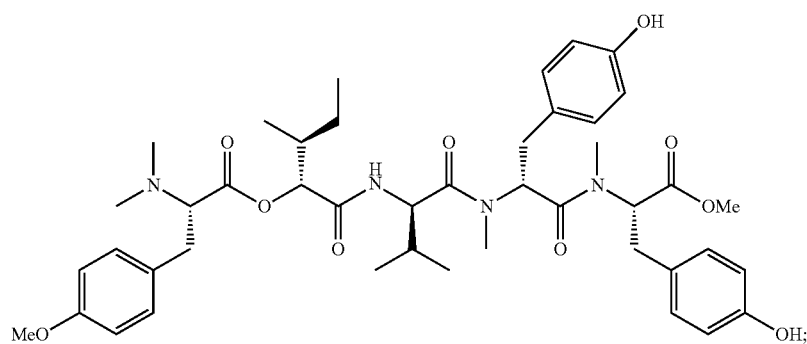
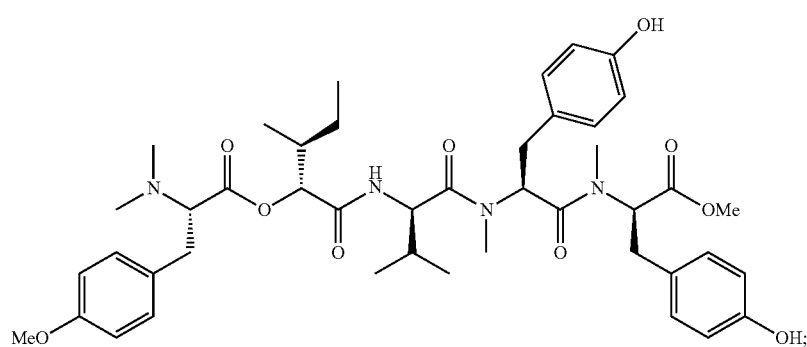
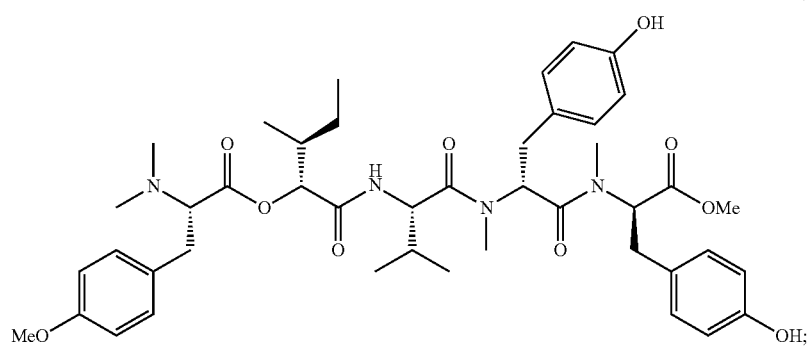

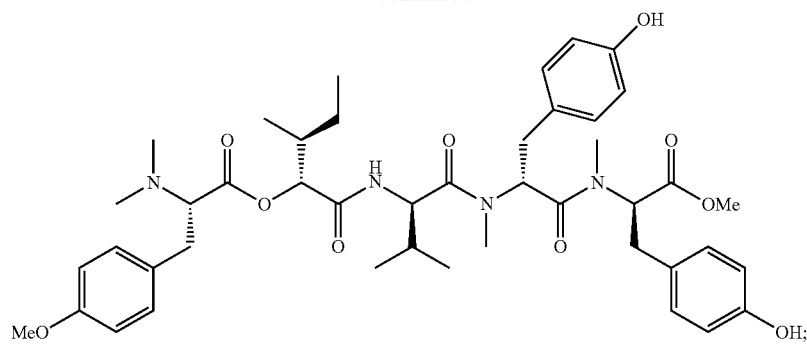
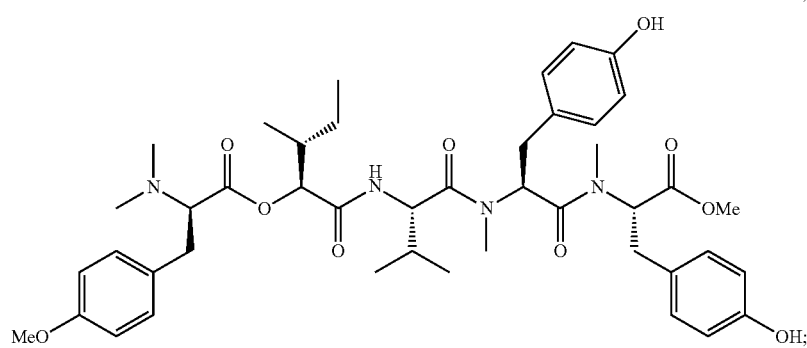
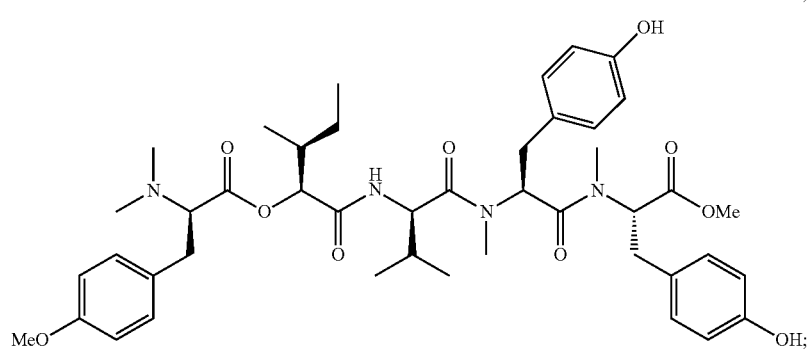
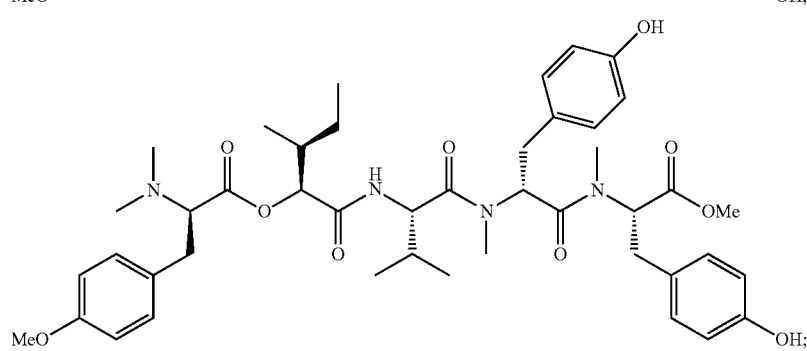
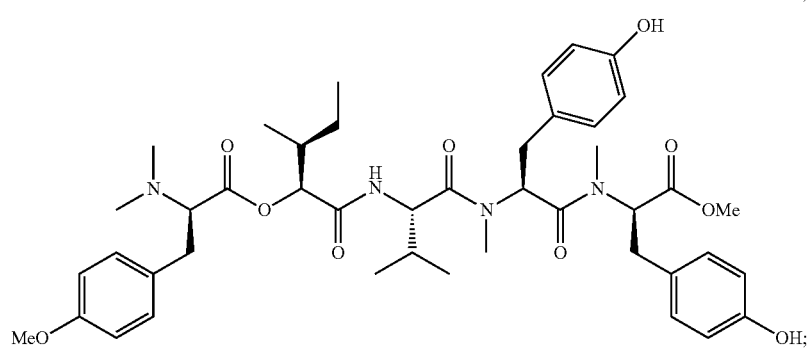

-continued
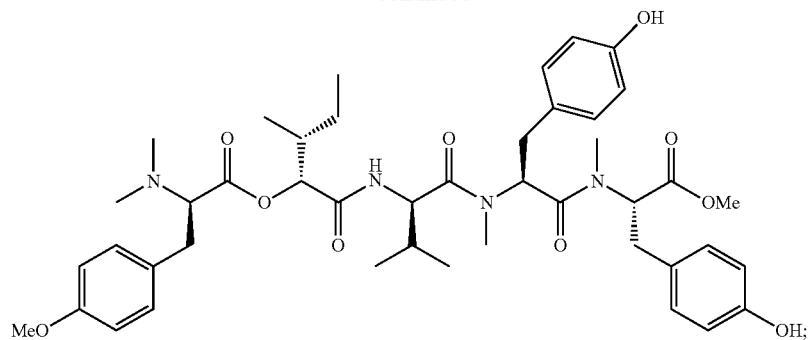
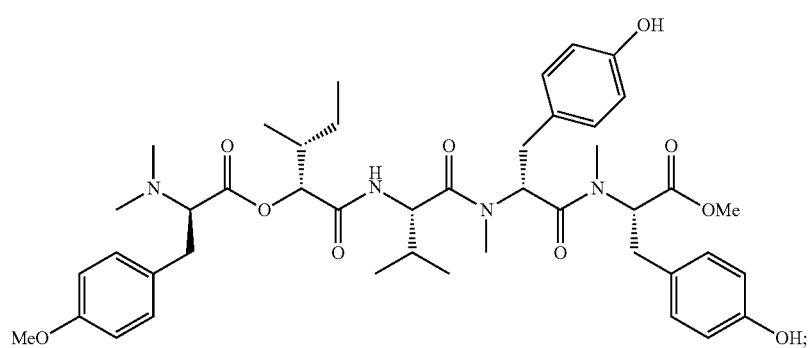
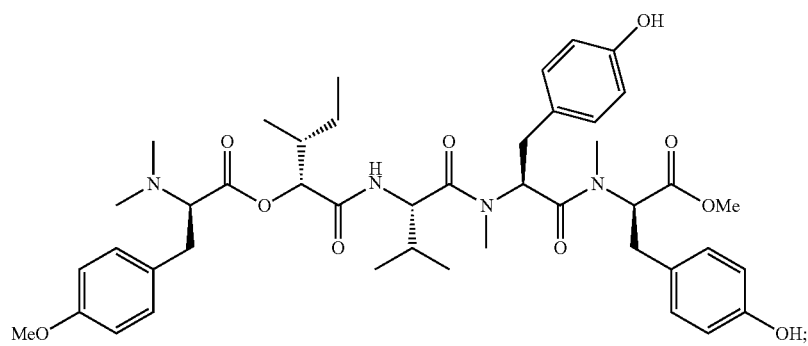
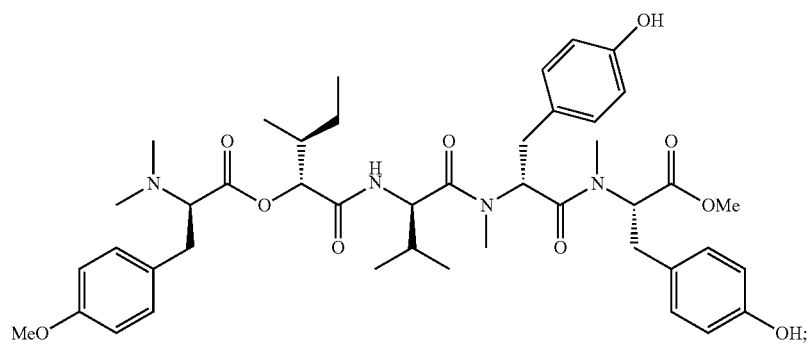
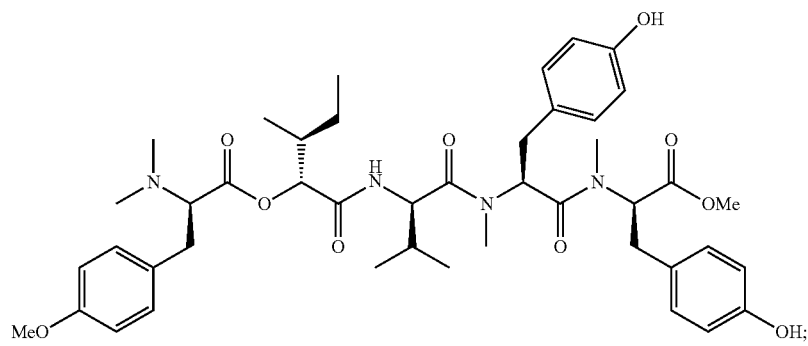

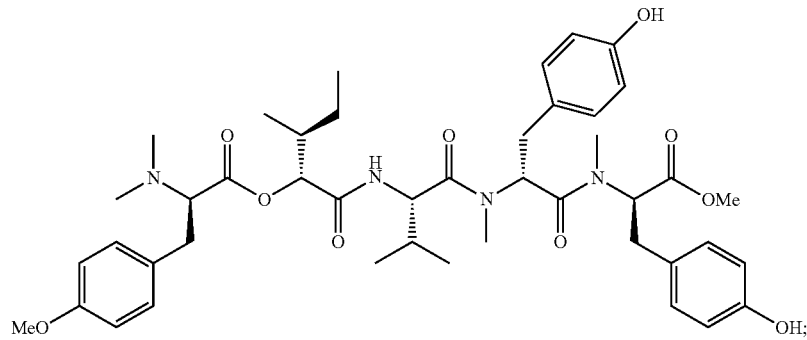
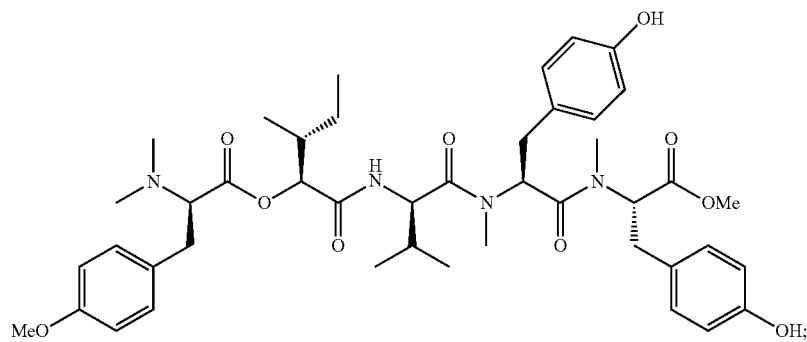
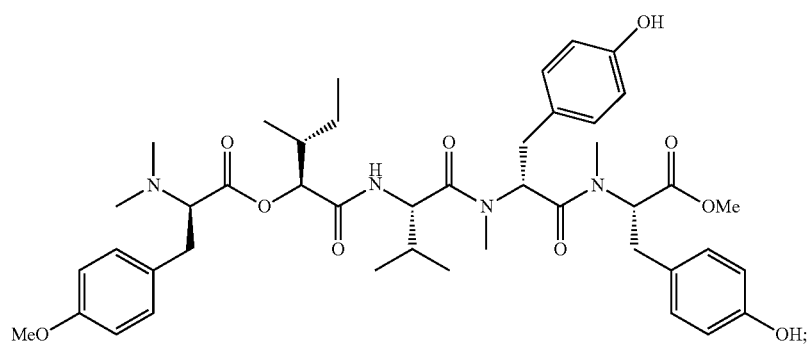
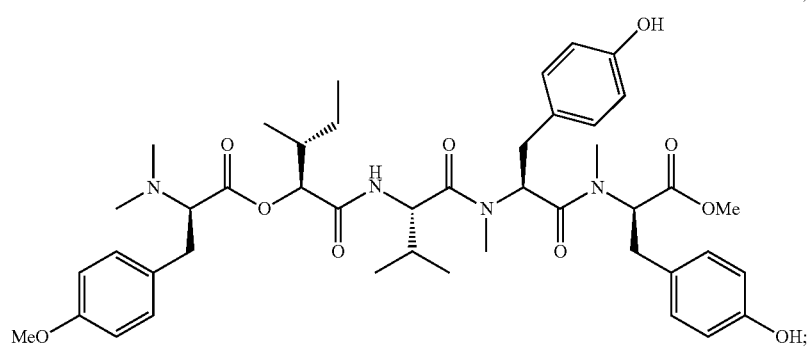
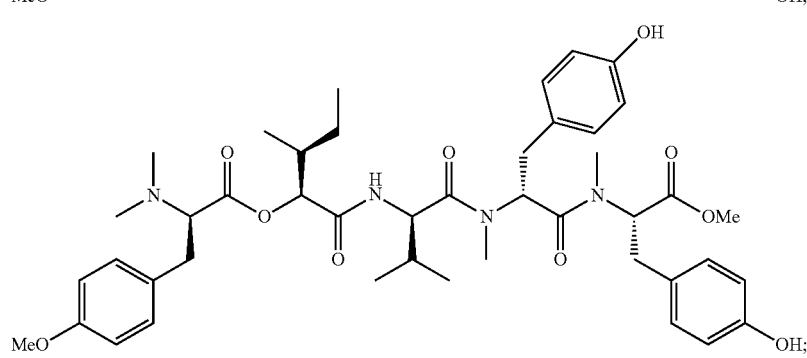

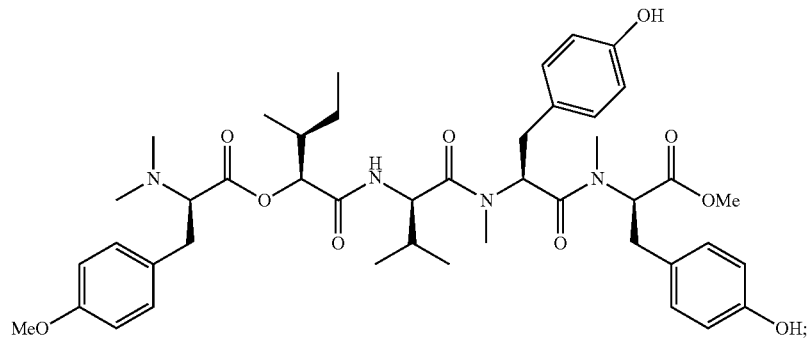
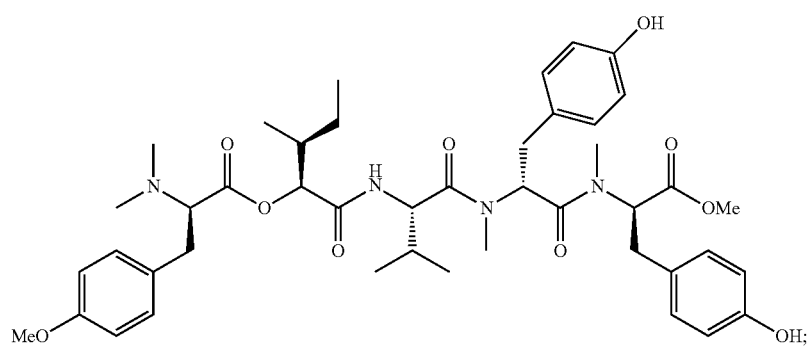
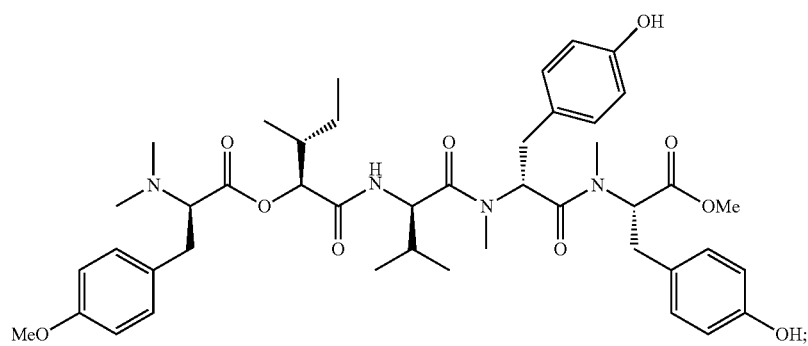
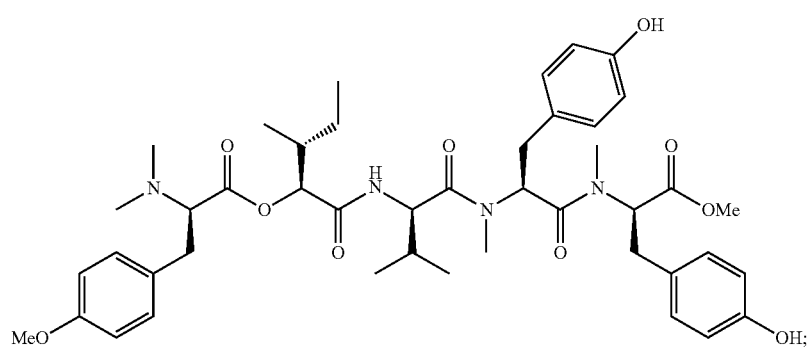
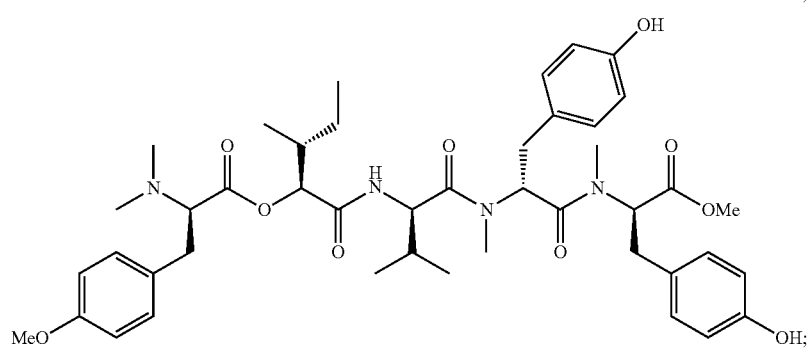

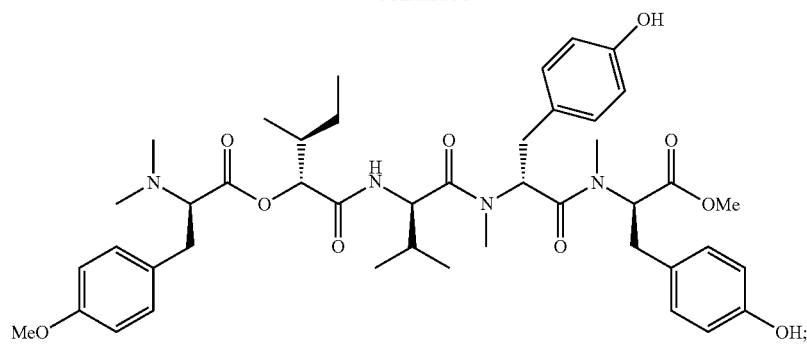
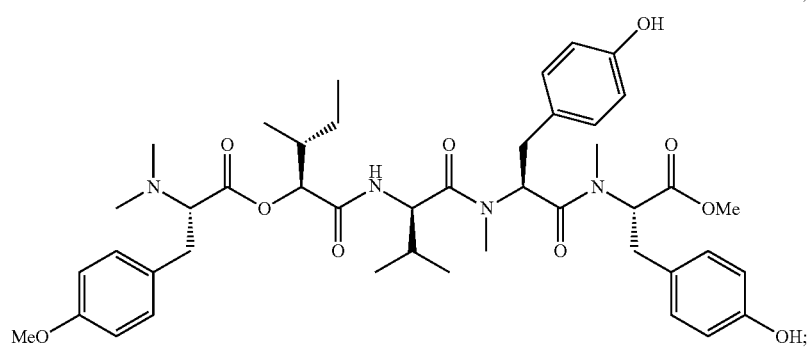
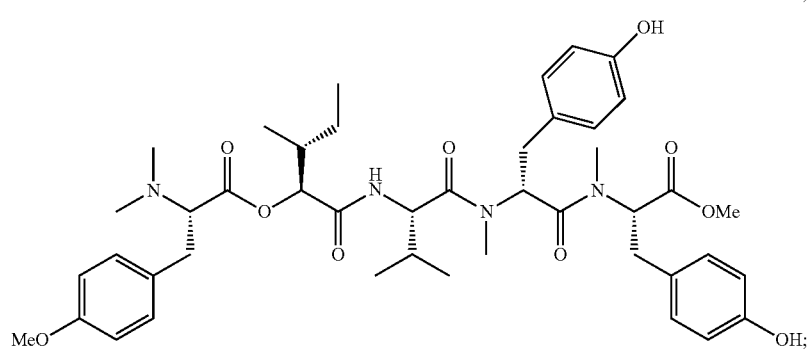
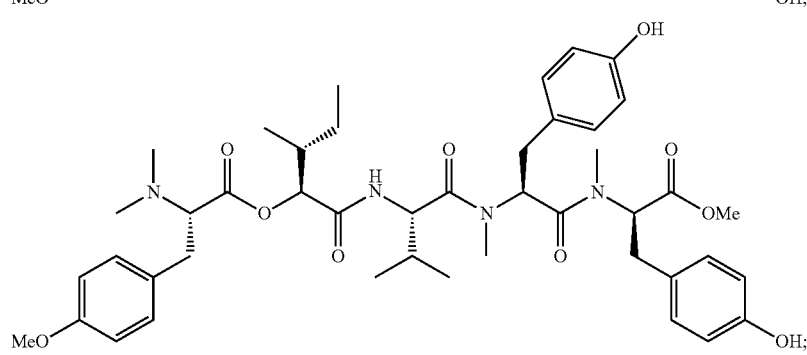
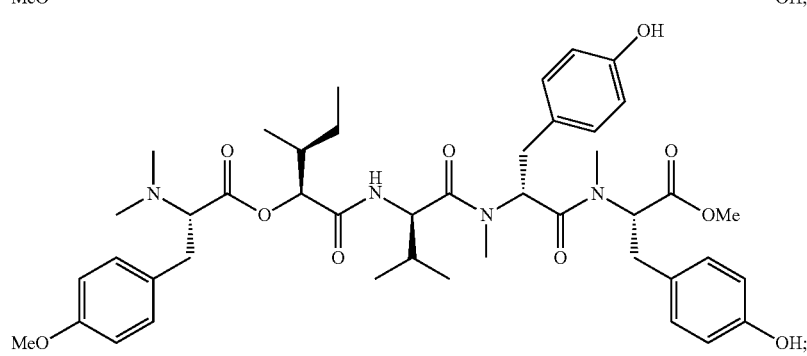

-continued
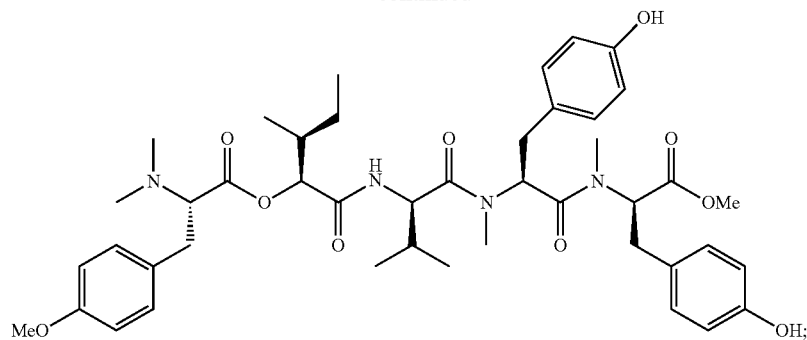
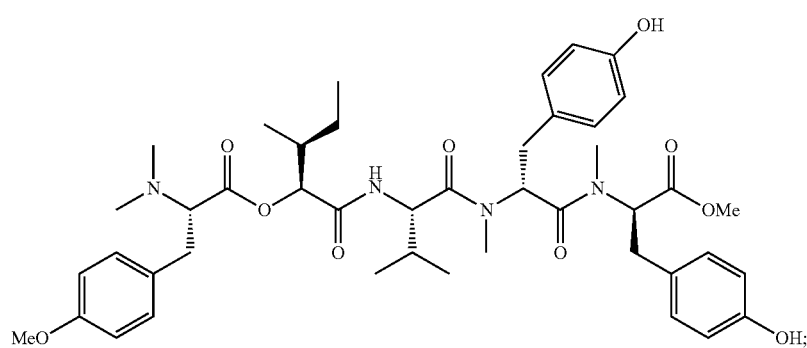
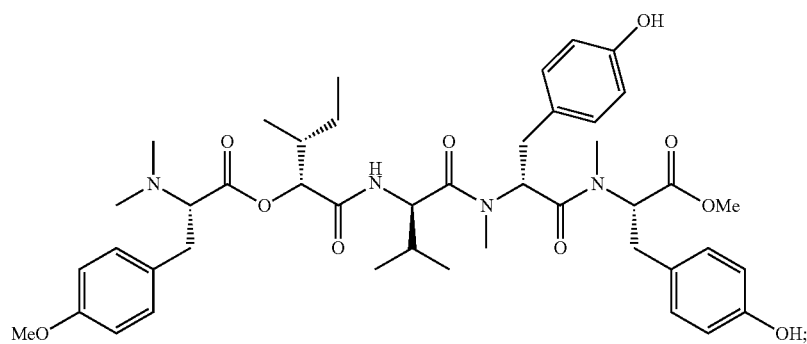
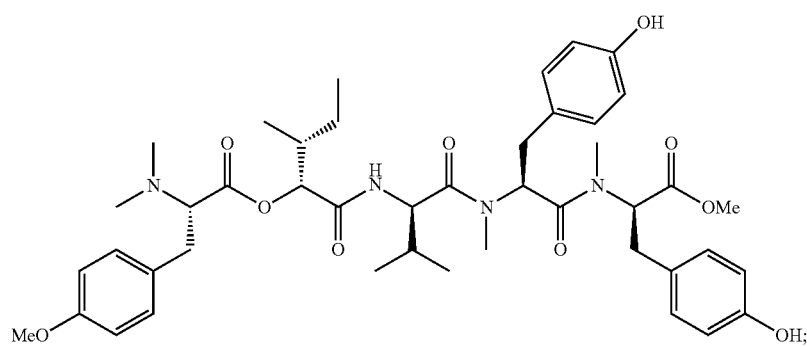
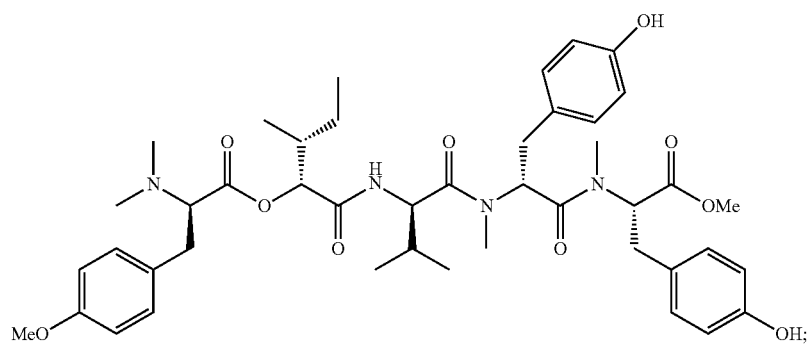

-continued
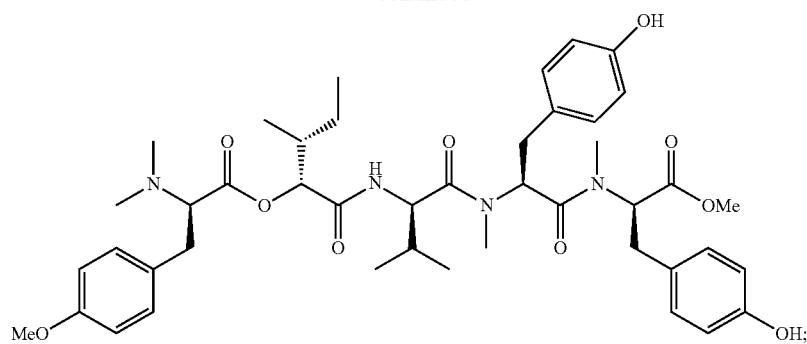
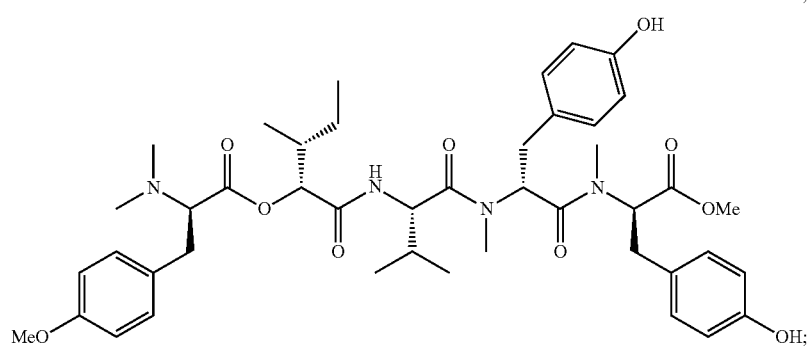
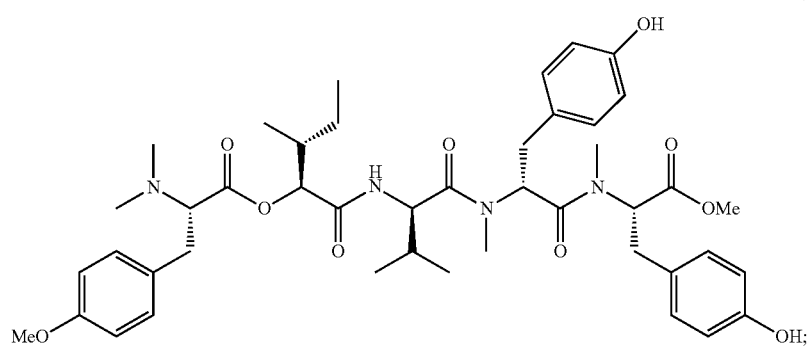
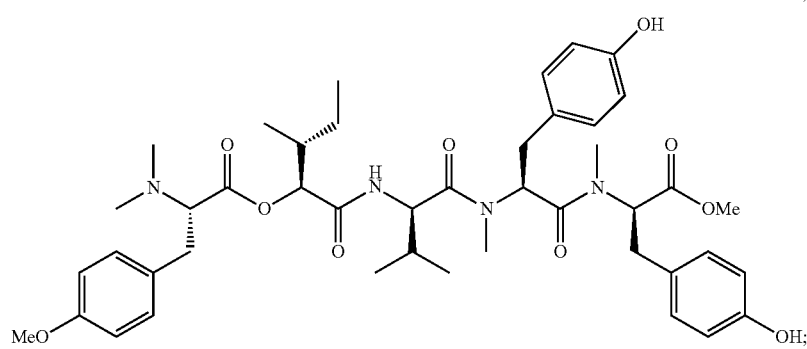
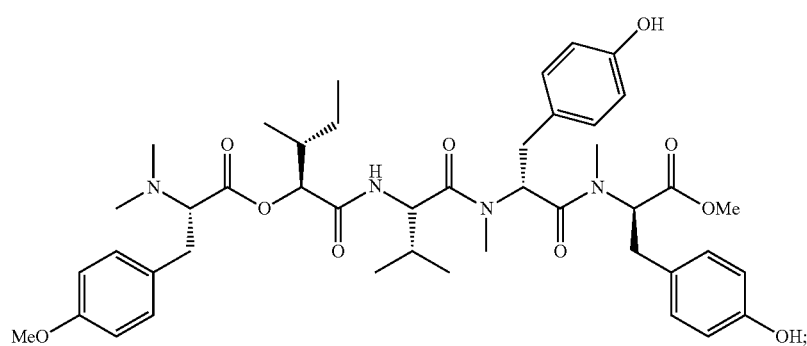

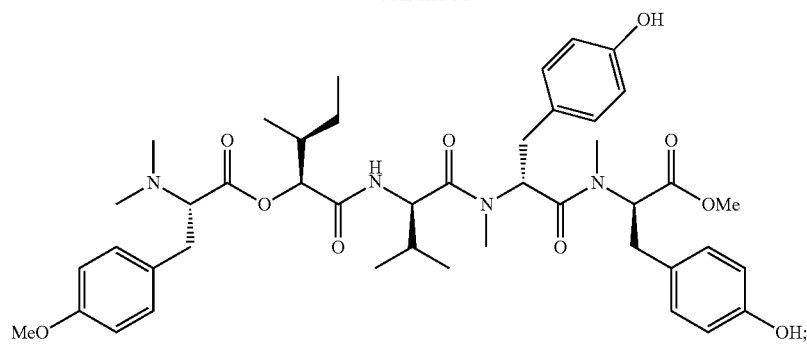
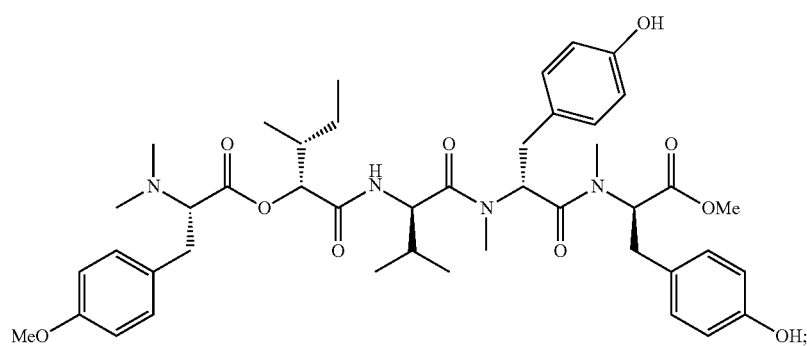
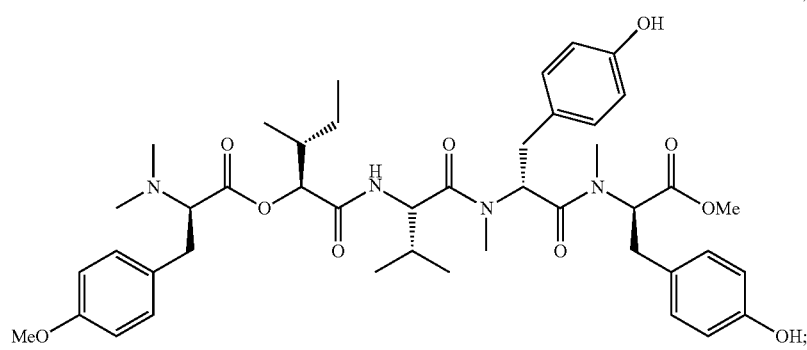
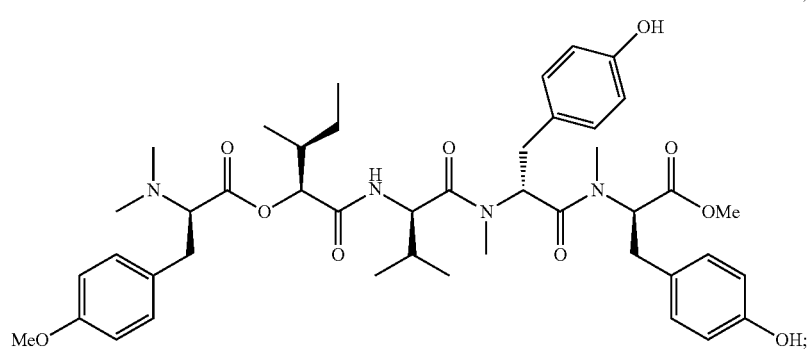
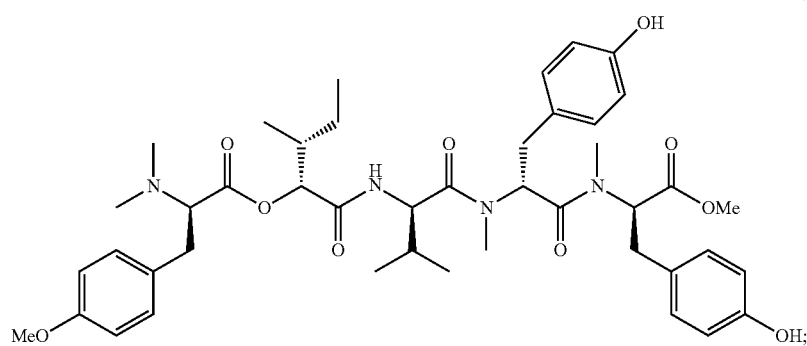

-continued

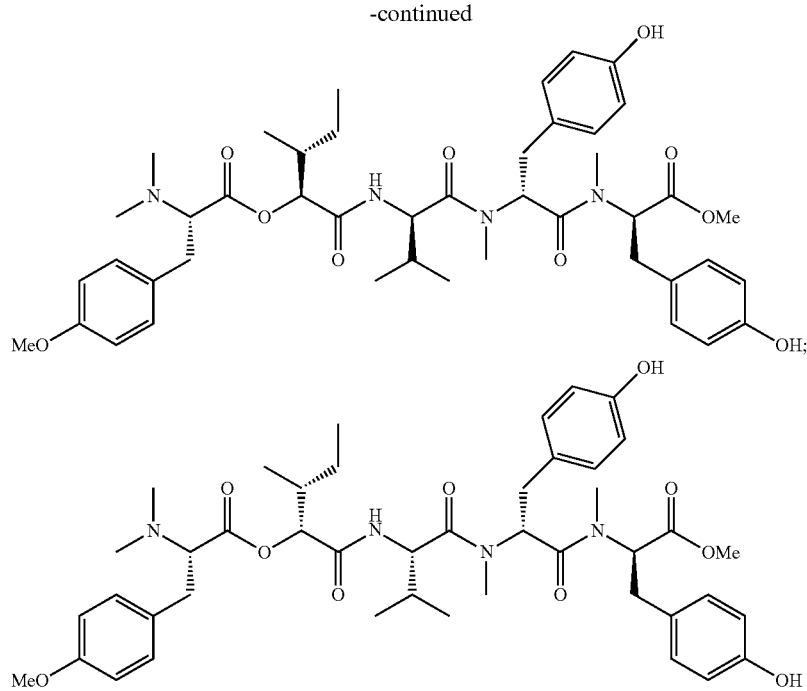

or pharmaceutically acceptable salts, solvates, hydrate, prodrugs, or stereoisomers thereof.

In another aspect, the invention provides a pharmaceutical composition comprising the compound of any of the formulae herein, or pharmaceutically acceptable salts, solvates, hydrate, prodrugs, or stereoisomers thereof, and a pharmaceutically acceptable carrier.

In another aspect, the invention provides a topical pharmaceutical composition comprising the compound of any of the formulae herein, or pharmaceutically acceptable salts, solvates, hydrate, prodrugs, or stereoisomers thereof, and a pharmaceutically acceptable topical carrier.

In one aspect, the invention provides a method of treating a disease, disorder, or symptom thereof in a subject, comprising administering to said subject a compound of any of the formulae herein, or pharmaceutically acceptable salts, solvates, hydrate, prodrugs, or stereoisomers thereof.

In another aspect, the invention provides a method of treating a subject suffering from or susceptible to a wound, comprising administering to said subject in need thereof, an effective amount of a compound, or pharmaceutically acceptable salts, solvates, hydrate, prodrugs, or stereoisomers thereof, or pharmaceutical composition of any of the formulae herein, such that said subject is treated for said wound. In another aspect, the wound is a chronic wound. In another aspect, the chronic wound is a diabetic foot ulcer [DFU], pressure ulcer [PU], or chronic venous leg ulcer [VU].

In another aspect, the invention provides a method of accelerating wound healing in a subject, comprising administering to said subject in need thereof, an effective amount of a compound, or pharmaceutically acceptable salts, solvates, hydrate, prodrugs, or stereoisomers thereof, or pharmaceutical composition of any of the formulae herein, such that the healing of said wound in said subject is accelerated.

In another aspect, the wound is a chronic wound. In another aspect, the chronic wound is a diabetic foot ulcer [DFU], pressure ulcer [PU], or chronic venous leg ulcer [VU]. In an embodiment the acceleration is relative to the level of wound healing in the absence of administration of the recited compound.

In another aspect, the invention provides a method of treating a subject suffering from or susceptible to a disorder or disease mediated by VEGF (e.g., VEGF-A), comprising administering to said subject in need thereof, an effective amount of a compound, or pharmaceutically acceptable salts, solvates, hydrate, prodrugs, or stereoisomers thereof, or pharmaceutical composition of any of the formulae herein. In another aspect, the disorder or disease mediated by VEGF (e.g., VEGF-A) is a wound. In another aspect, the wound is a chronic wound. In another aspect, the chronic wound is a diabetic foot ulcer [DFU], pressure ulcer [PU], or chronic venous leg ulcer [VU].

In another aspect, the invention provides a method of inducing VEGF (e.g., VEGF-A) in a subject, comprising administering to said subject an effective amount of a compound, or pharmaceutically acceptable salts, solvates, hydrate, prodrugs, or stereoisomers thereof, or pharmaceutical composition of any of the formulae herein.

In another aspect, the invention provides a method for increasing angiogenesis in a subject, comprising administering to said subject an effective amount of a compound, or pharmaceutically acceptable salts, solvates, hydrate, prodrugs, or stereoisomers thereof, or pharmaceutical composition of any of the formulae herein. In an embodiment the increasing is relative to the level of angiogenesis in the absence of administration of the recited compound.

In another aspect, the invention provides a method of inducing VEGF (e.g., VEGF-A), comprising administering an effective amount of a compound, or pharmaceutically acceptable salts, solvates, hydrate, prodrugs, or stereoisomers thereof, or pharmaceutical composition of any of the formulae herein.

In another aspect, the invention provides a method for increasing angiogenesis, comprising administering an effective amount of a compound, or pharmaceutically acceptable salts, solvates, hydrate, prodrugs, or stereoisomers thereof, or pharmaceutical composition of any of the formulae herein. In an embodiment the increasing is relative to the level of angiogenesis in the absence of administration of the recited compound.

Another aspect is a kit comprising an effective amount of any of the compounds described herein, or pharmaceutically acceptable salts, solvates, hydrate, prodrugs, or stereoisomers thereof, in unit dosage form, together with instructions for administering the compound to a subject suffering from or susceptible to a wound. In another aspect, the wound is a chronic wound. In another aspect, the chronic wound is a diabetic foot ulcer [DFU], pressure ulcer [PU], or chronic venous leg ulcer [VU].

BRIEF DESCRIPTION OF THE DRAWINGS

The present invention is further described below with reference to the following non-limiting examples and with reference to the following figures, in which:

FIG. 3. depicts NMR spectroscopic data of apratyramide (1) in DMSO-$d_6$.

FIG. 15. depicts a heat map for transcript changes after 3 h and 12 h treatment with 30 μM 1.

FIG. 16. depicts selected groups of top up- and down-regulated genes after 12 h treatment with 30 μM apratyramide (1).

FIG. 20. depicts a full list of up and down regulated genes after 12 h treatment with 30 μM apratyramide.

DETAILED DESCRIPTION

Definitions

Figure 1:
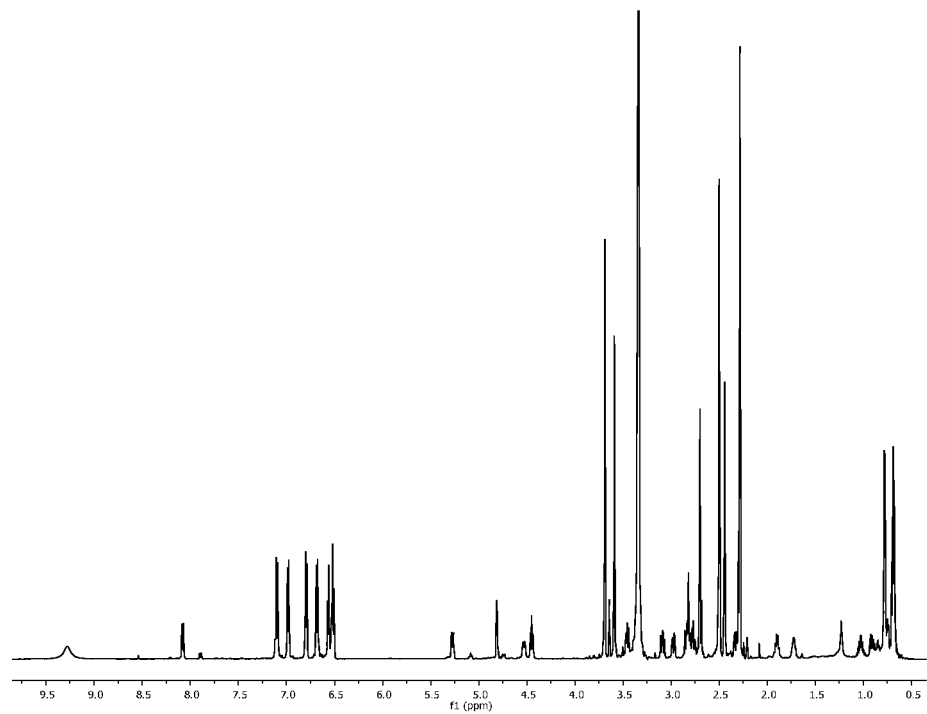
FIG. 1. depicts the $^1$H NMR spectrum of natural product apratyramide (1) in DMSO-$d_6$ (600 MHz).

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression.

The term "modulate" refers to increases or decreases in the activity of a cell in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "protein" refers to series of amino acid residues connected one to the other by peptide bonds between the alpha-amino and carboxy groups of adjacent residues.

Amino acids may be referred to herein by either their commonly known three letter symbols or by the one-letter symbols recommended by the IUPAC-IUB Biochemical Nomenclature Commission.

As to amino acid sequences, one of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I. The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the elastase inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 µg/kg to about 200 mg/kg, preferably about 0.1 mg/kg to about 200 mg/kg, more preferably about 10 mg/kg to about 100 mg/kg of body weight. In other embodiments, the therapeutically effect amount may range from about 1.0 µM to about 500 nM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 µg/kg to about 200 mg/kg of body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The term "subject" refers to animals such as mammals, including, but not limited to, primates (e.g., humans), cows, sheep, goats, horses, dogs, cats, rabbits, rats, mice and the like. In certain embodiments, the subject is a human.

Furthermore the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)

C(O)Ot-Bu), phosphonates (e.g., —OP(O)(OEt)₂), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Compounds of the Invention

In one embodiment, the invention provides a compound according to the formula:

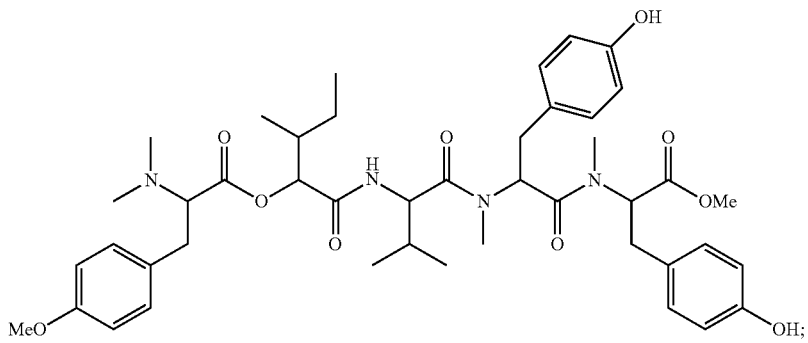 [SMILES: CCC(C)C(OC(=O)C(Cc1ccc(OC)cc1)N(C)C)C(=O)NC(C(=O)N(C)C(Cc1ccc(O)cc1)C(=O)N(C)C(Cc1ccc(O)cc1)C(=O)OC)C(C)C]

or pharmaceutically acceptable salts, solvates, hydrate, prodrugs, or stereoisomers thereof.

In another embodiment, the compound of the invention is one of:

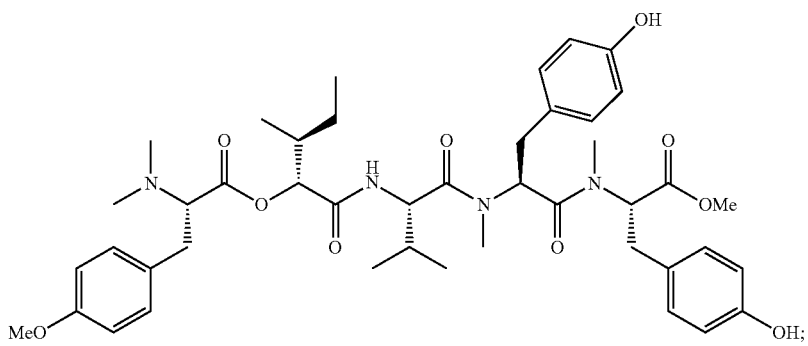

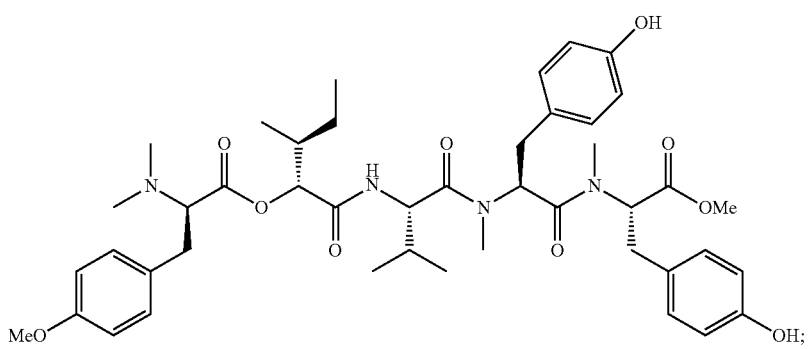

-continued
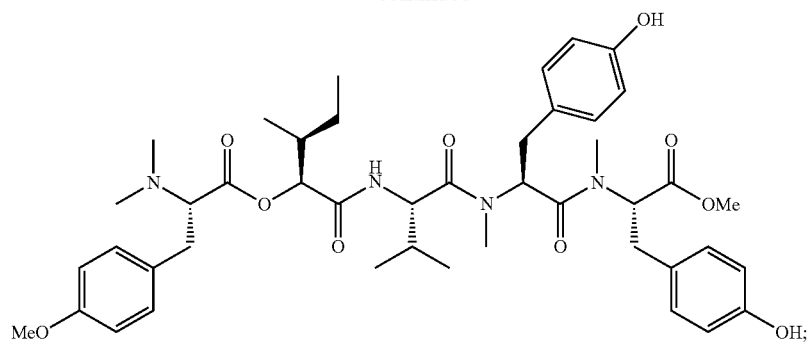
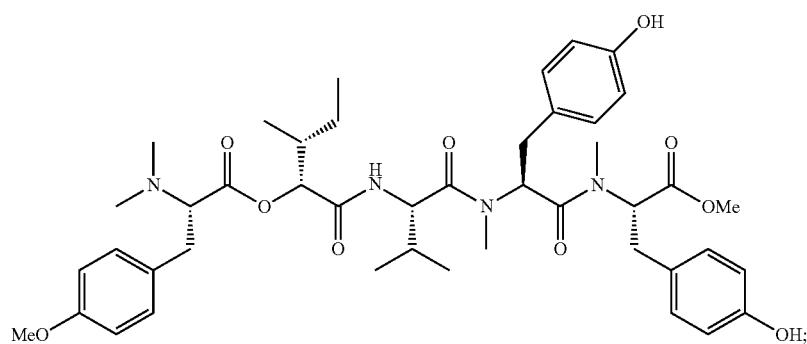
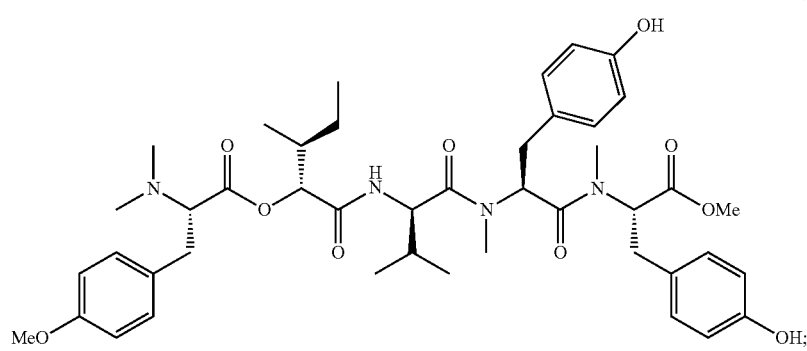
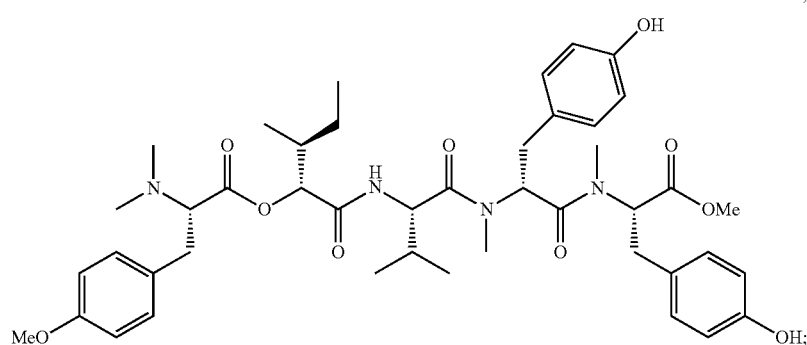
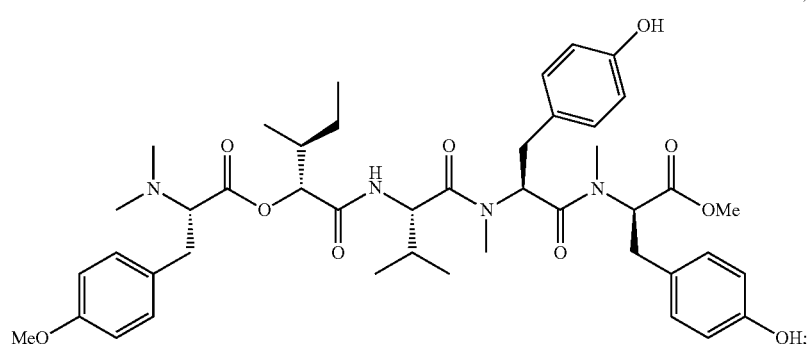

-continued
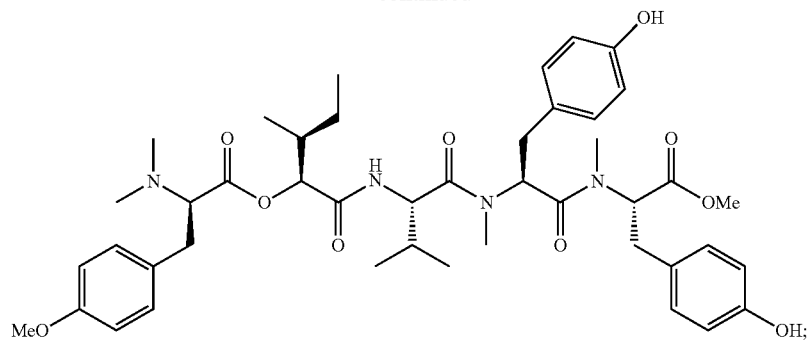
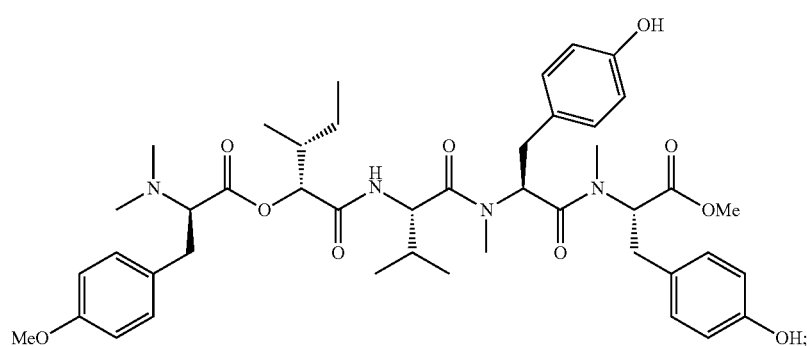
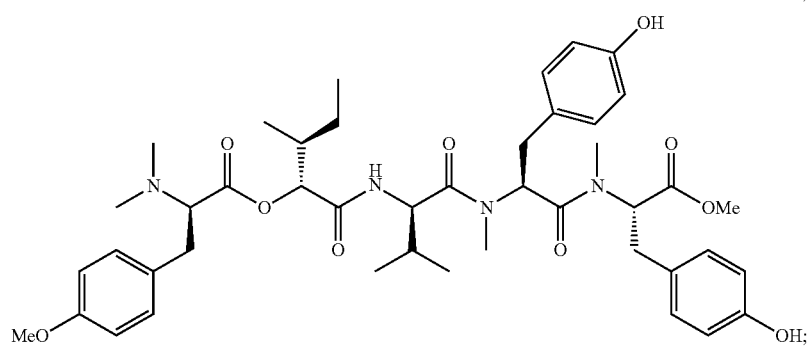
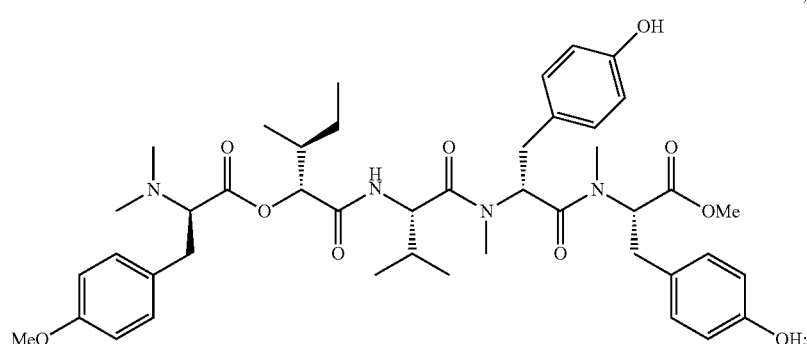
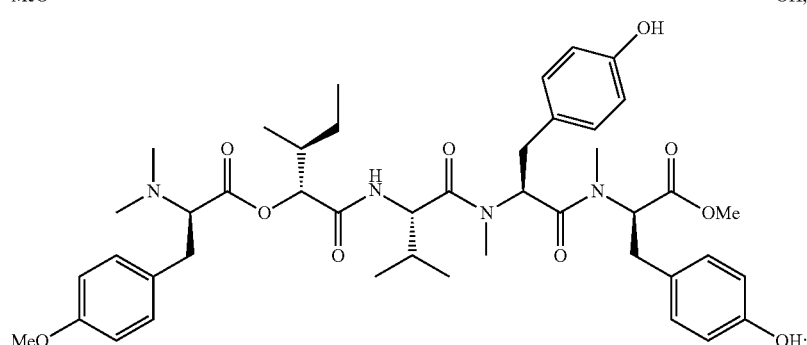

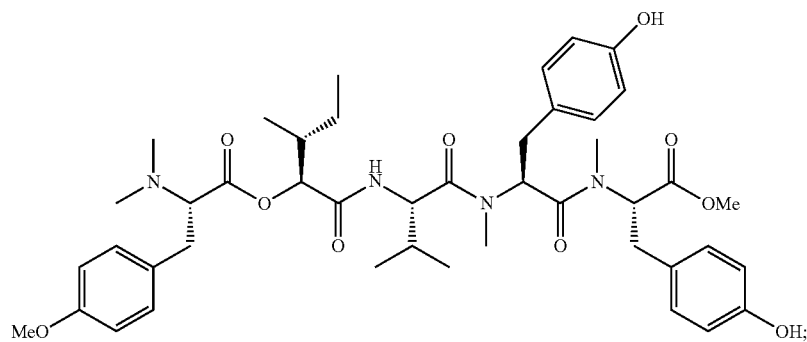
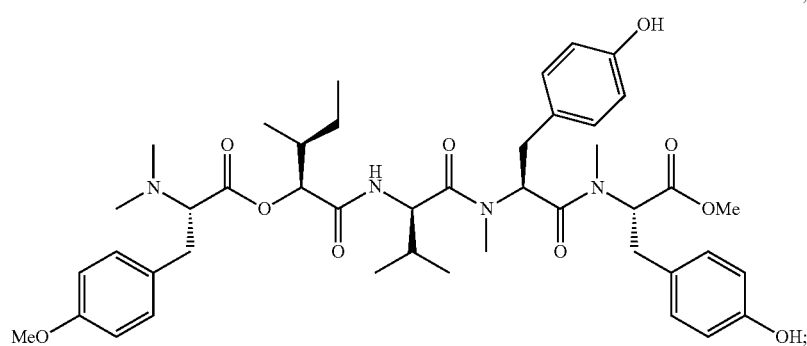
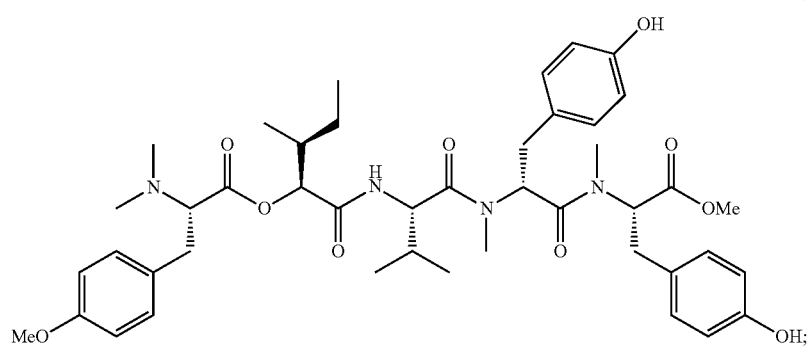
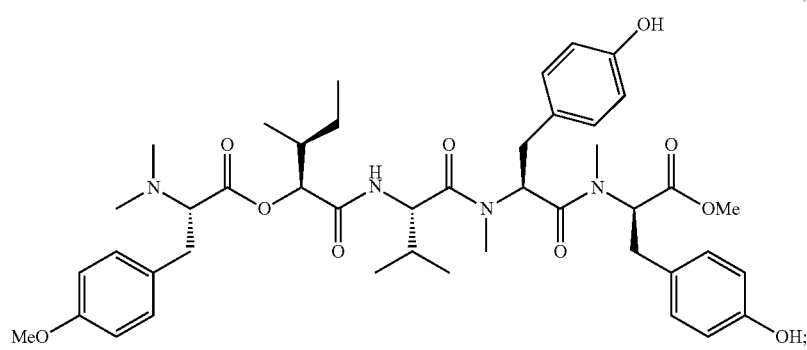
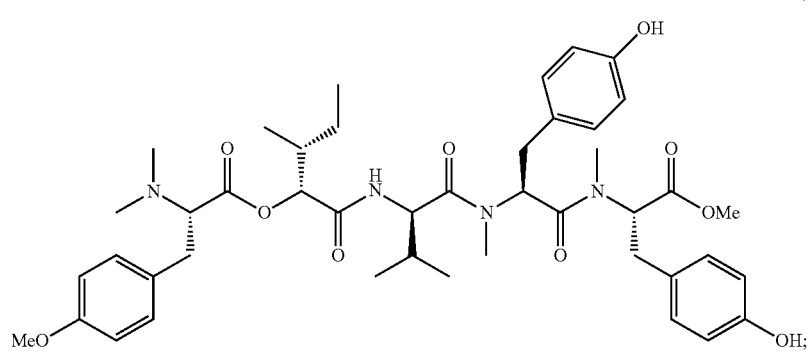

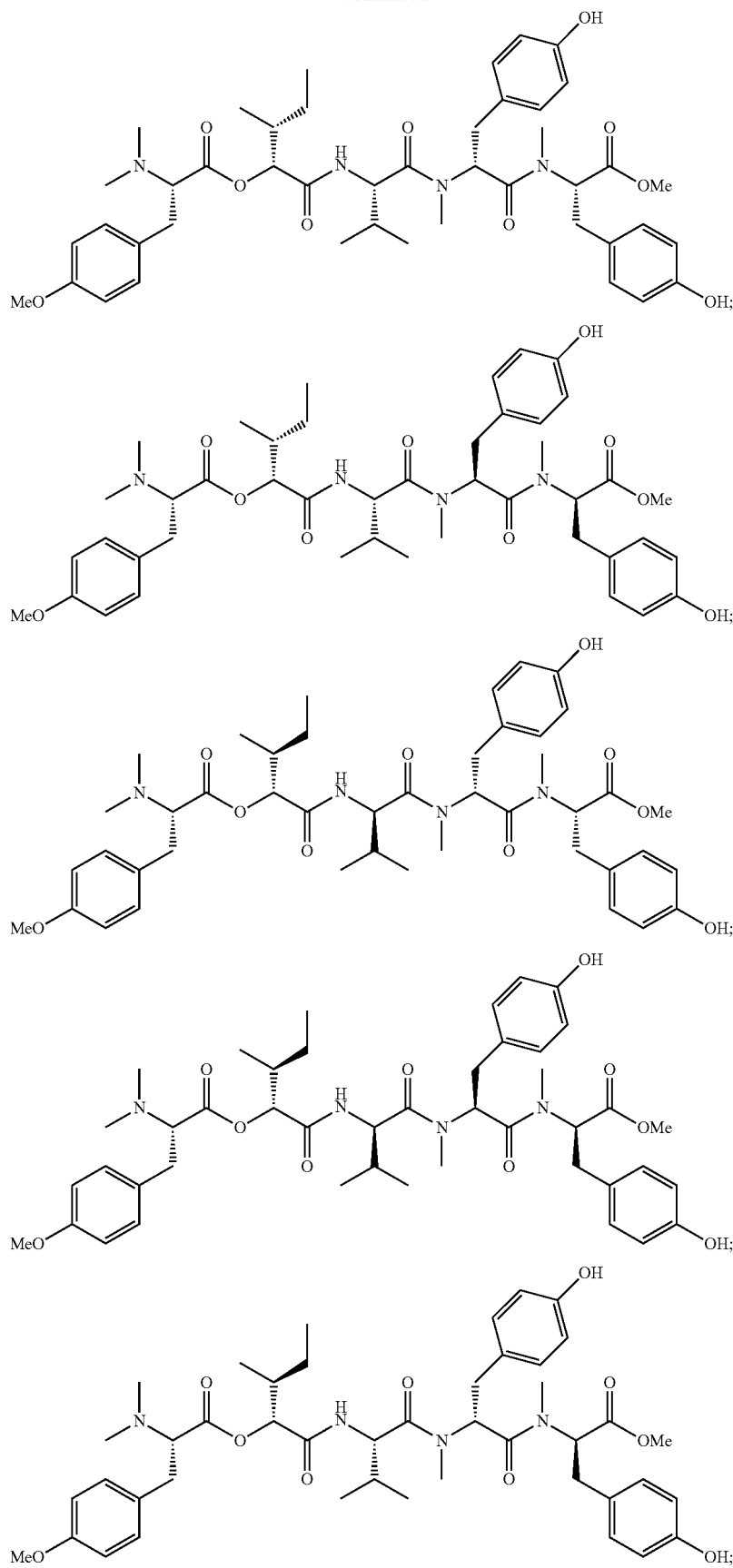

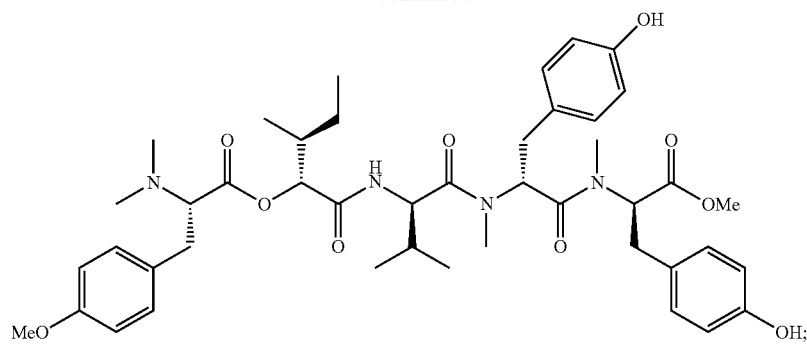
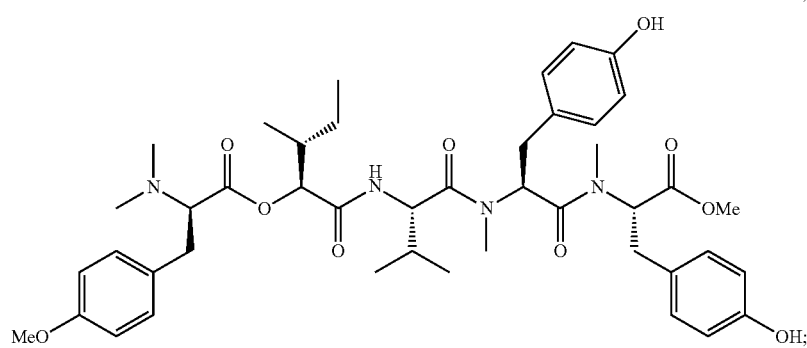
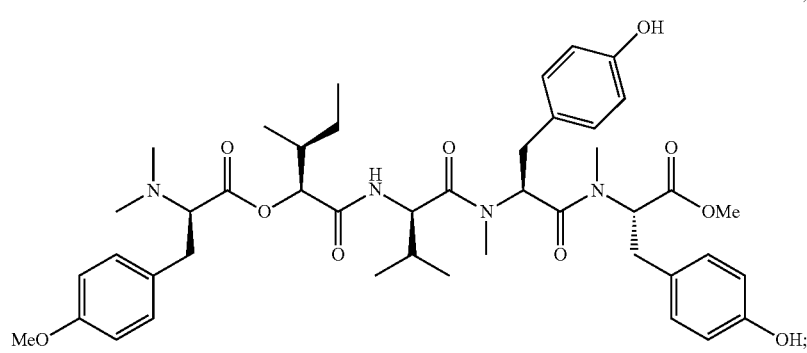
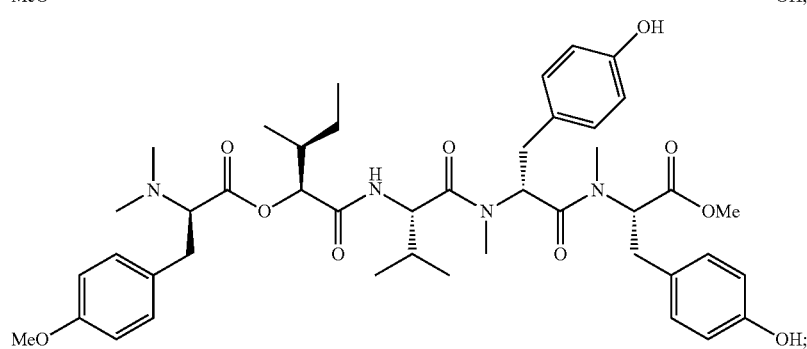
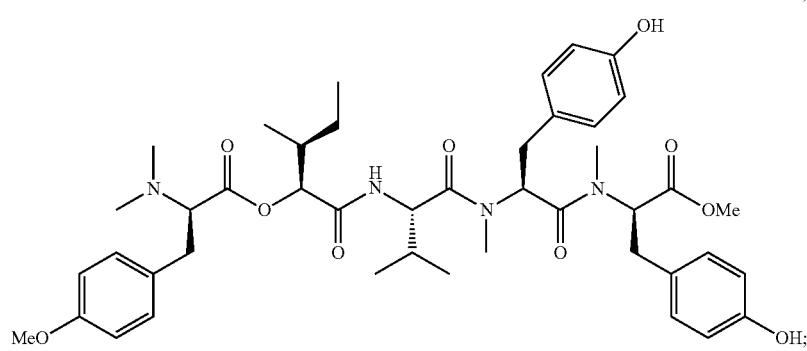

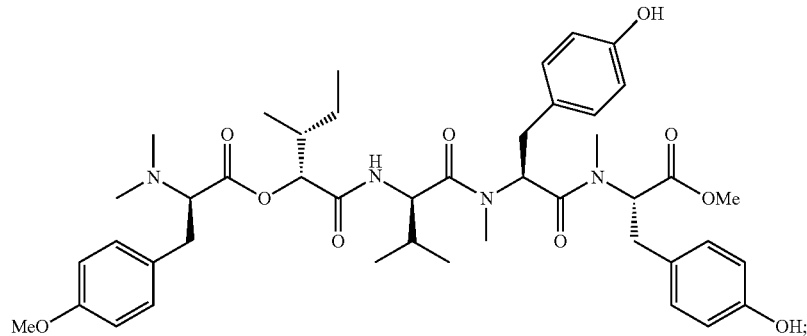
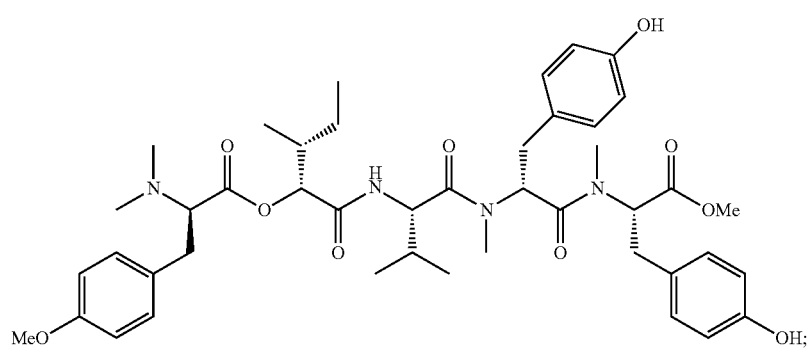
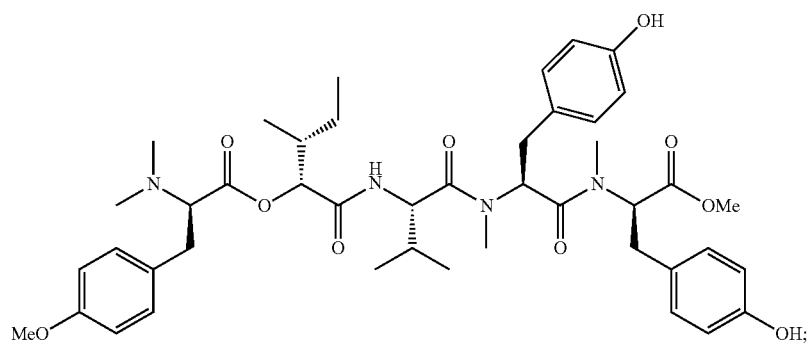
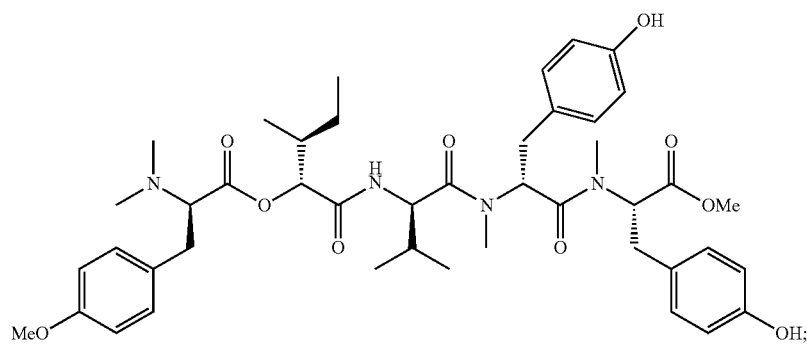
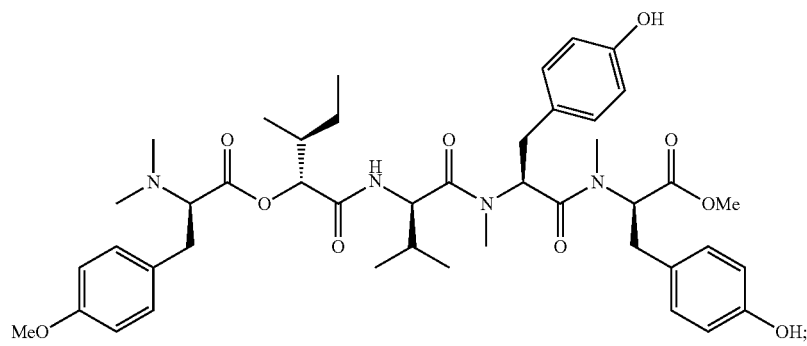

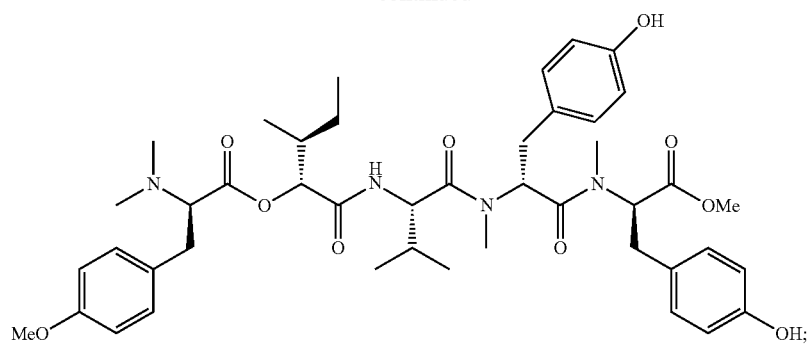
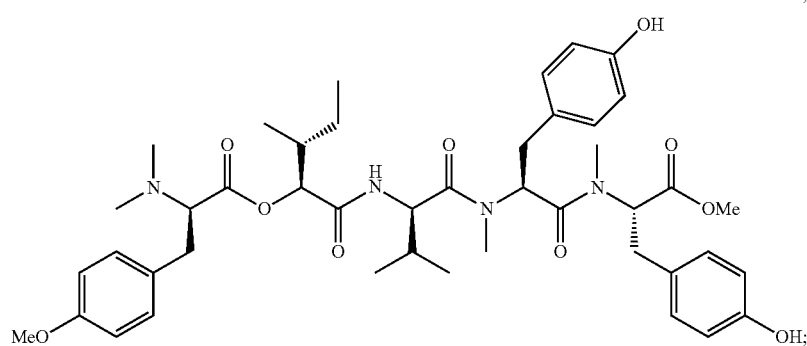
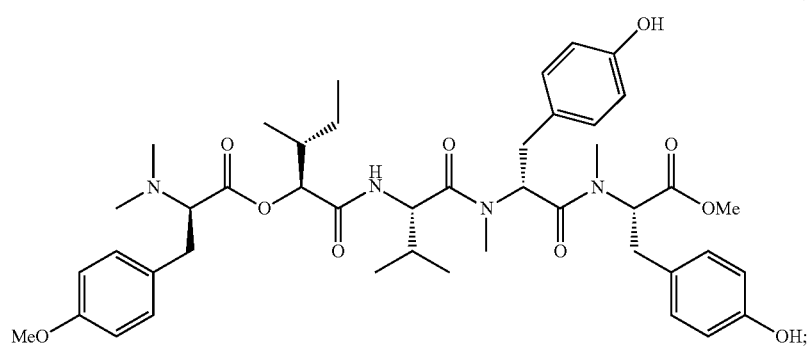
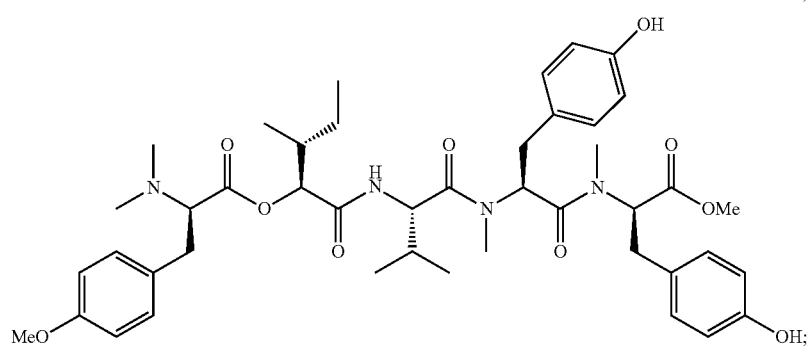
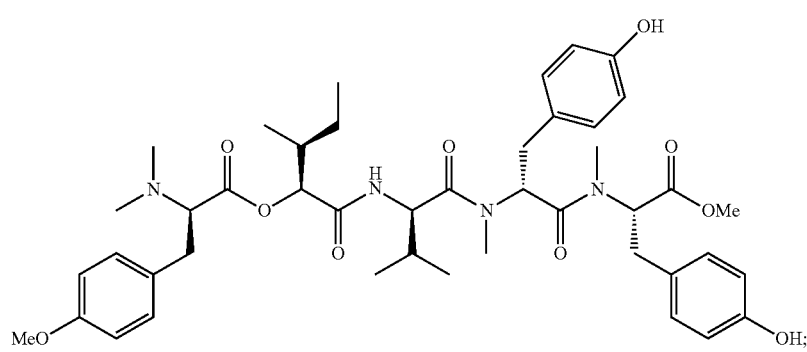

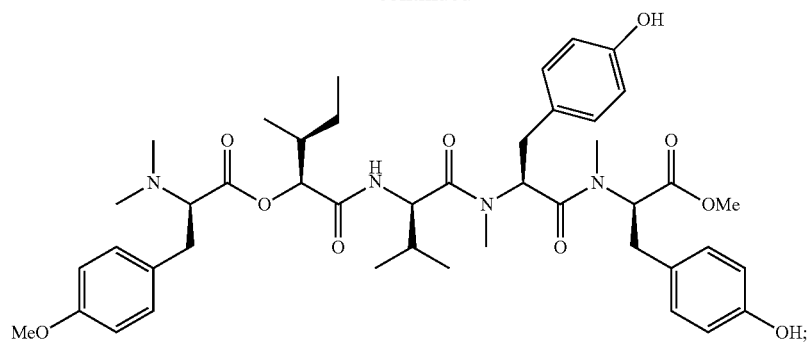
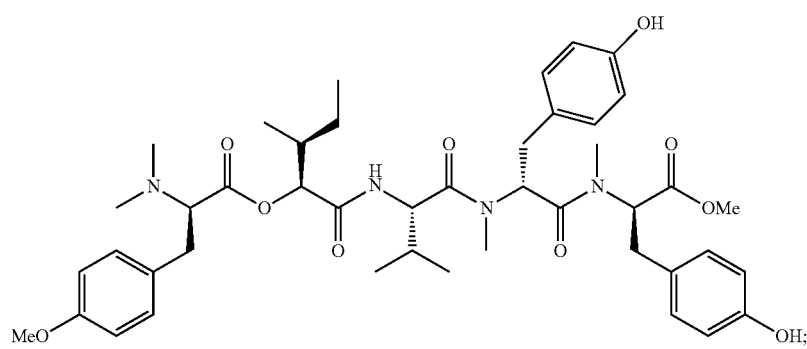
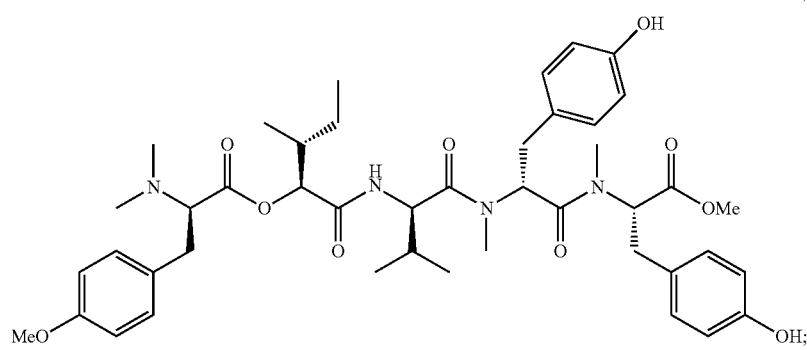
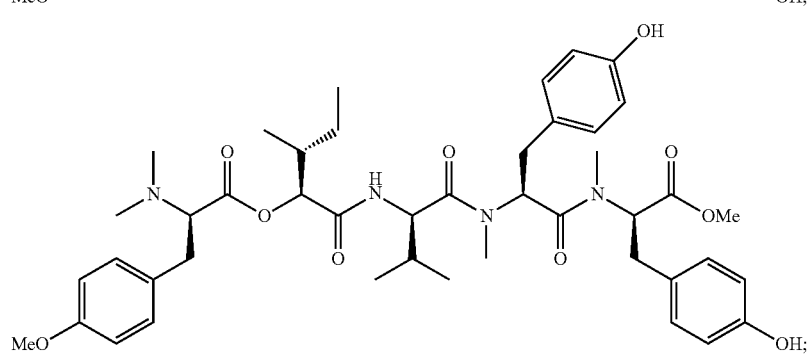
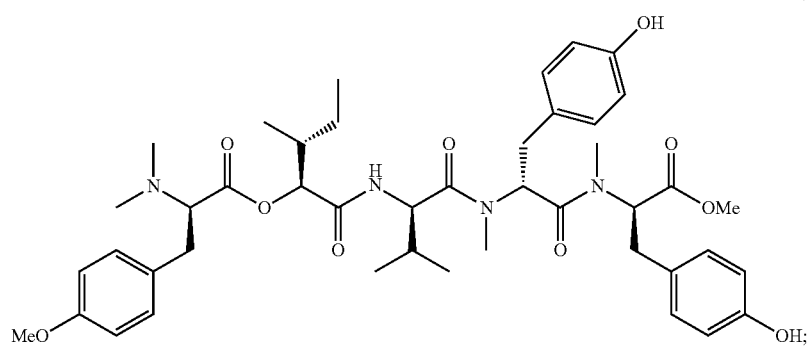

-continued
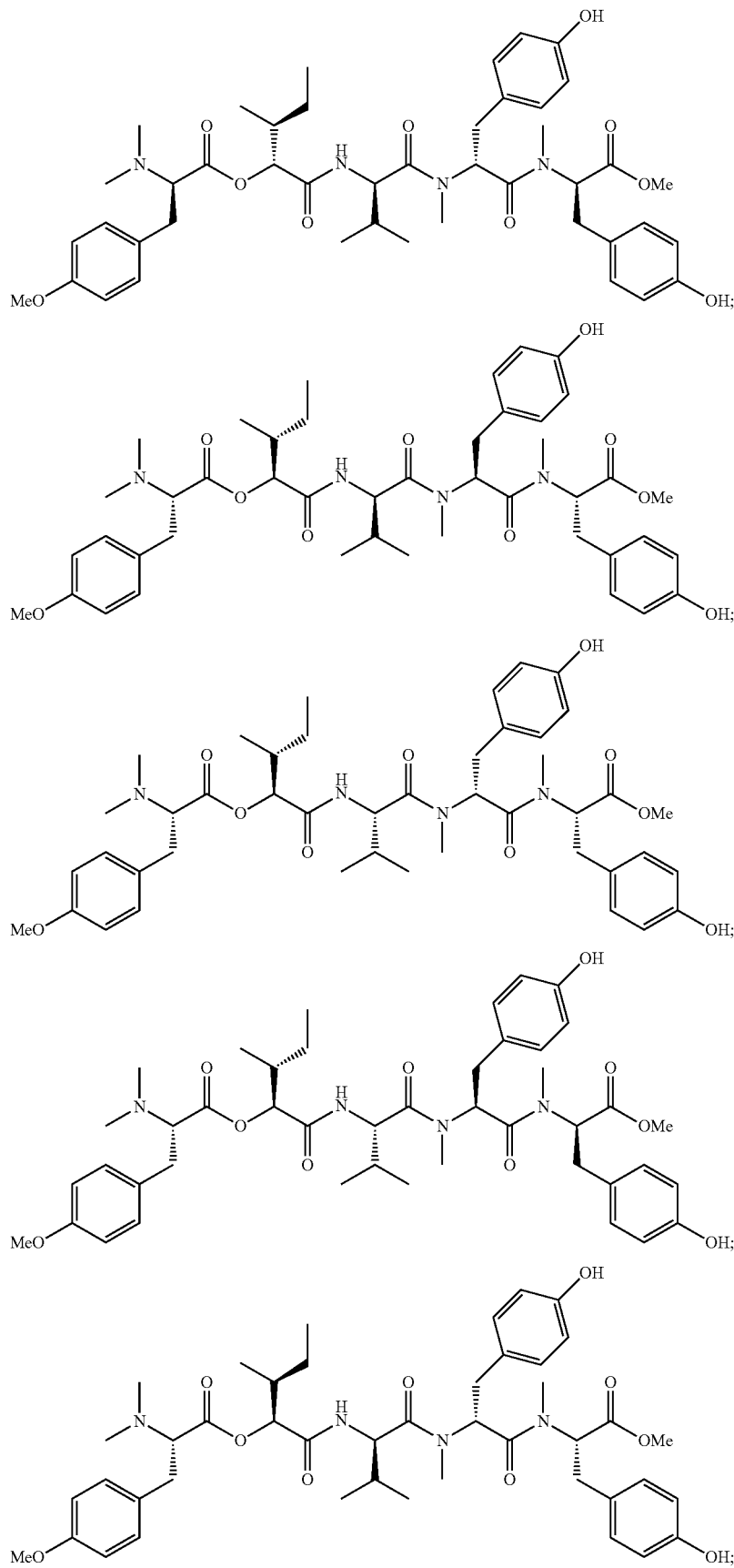

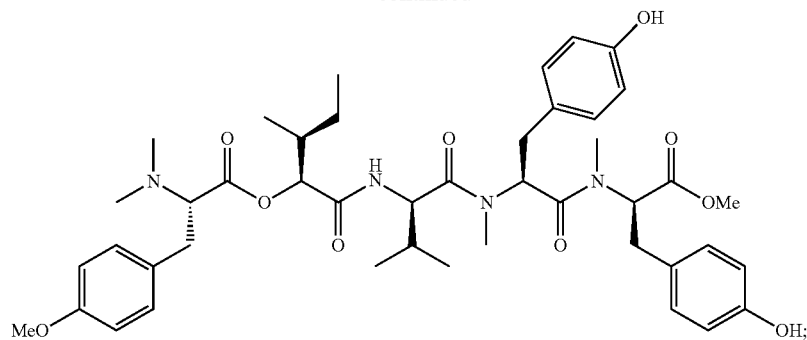
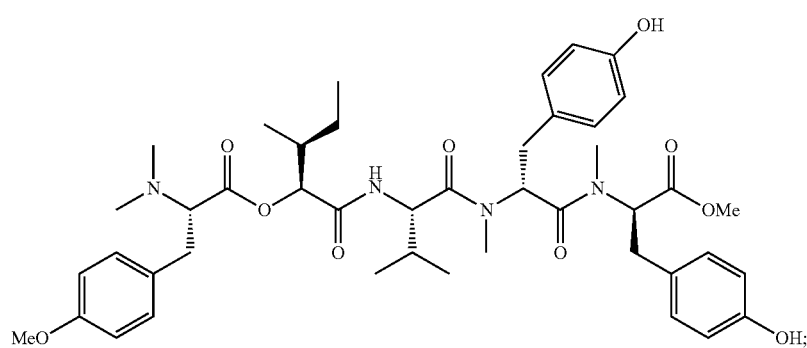
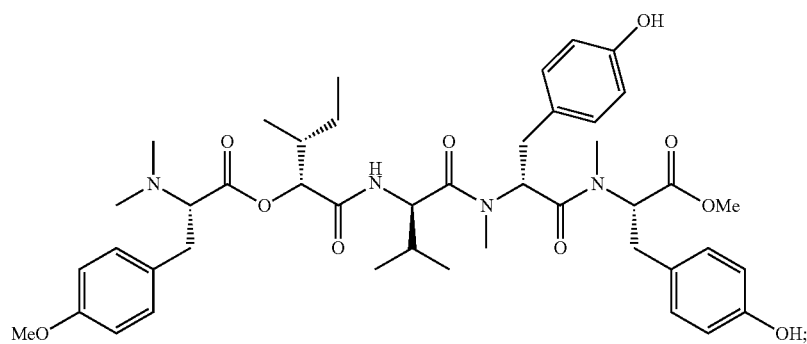
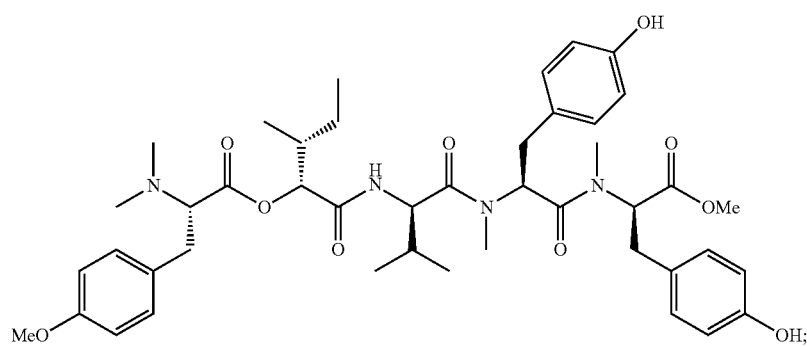
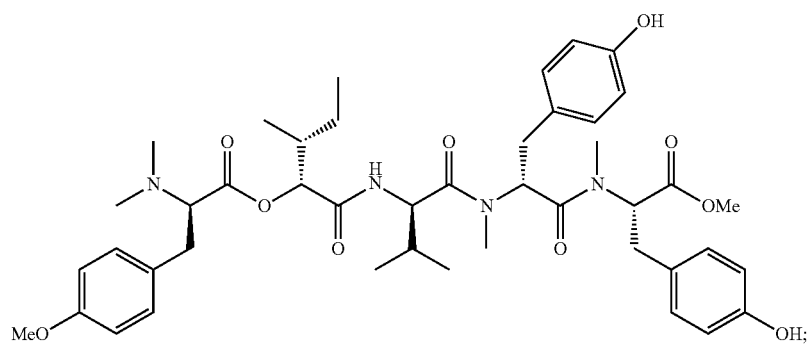

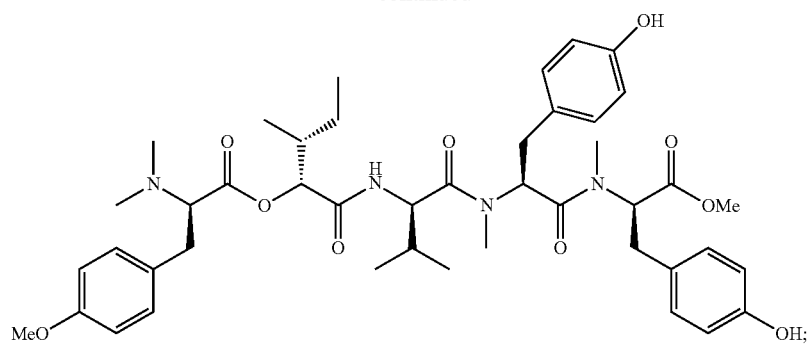
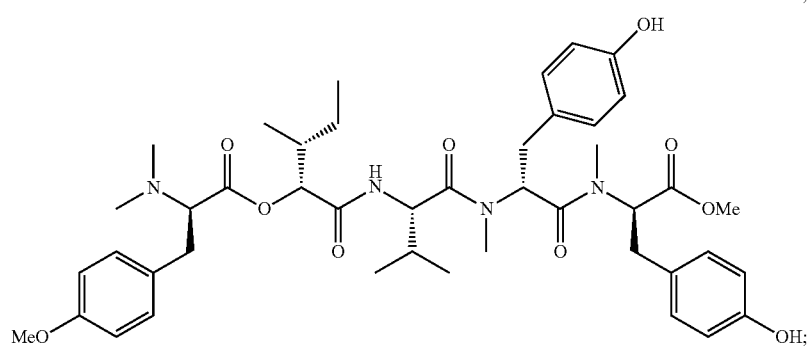
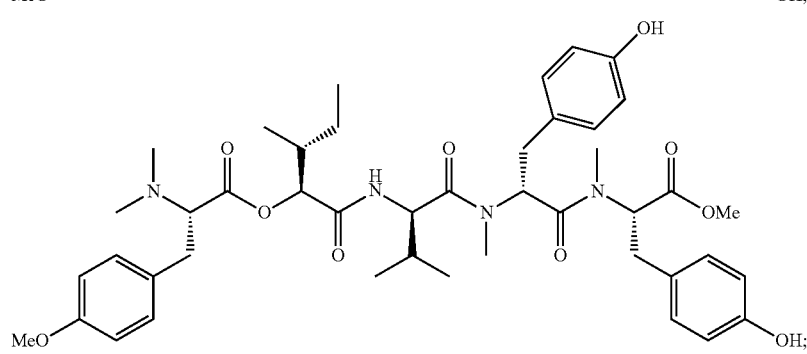
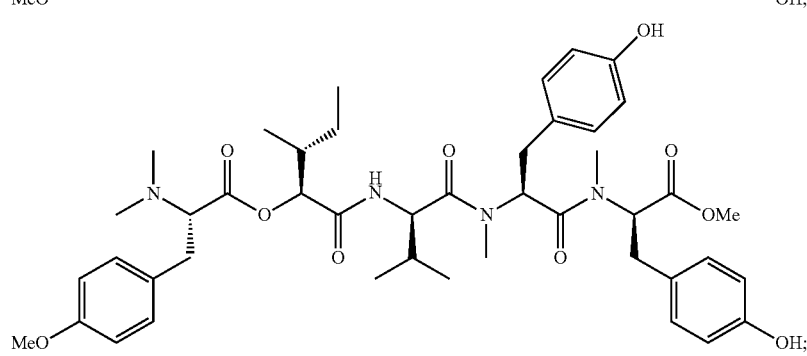
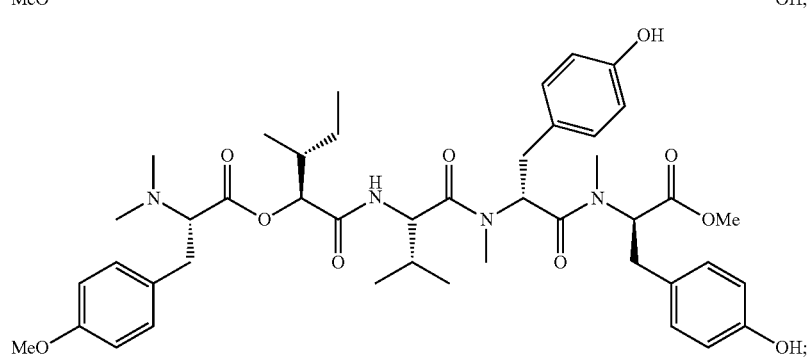

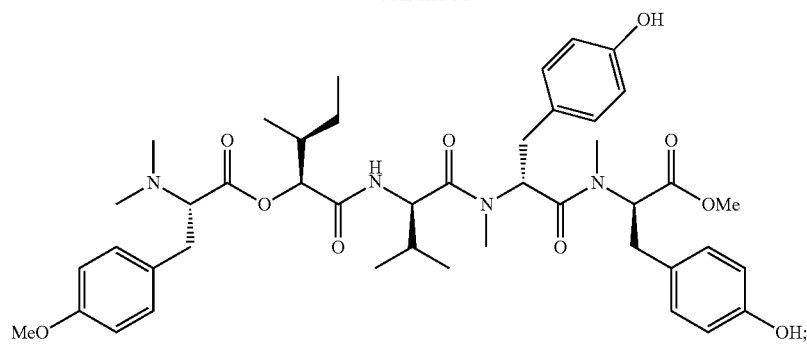
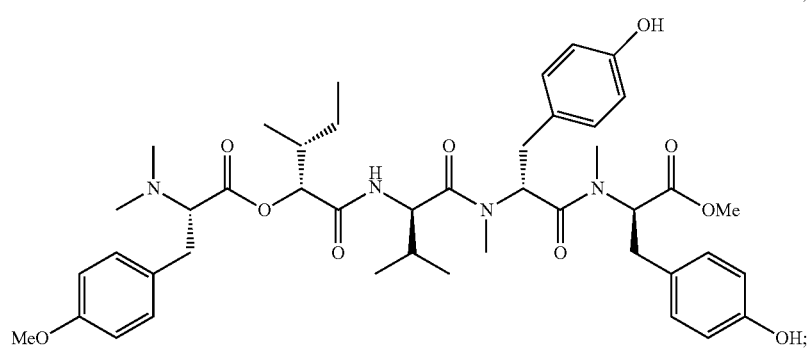
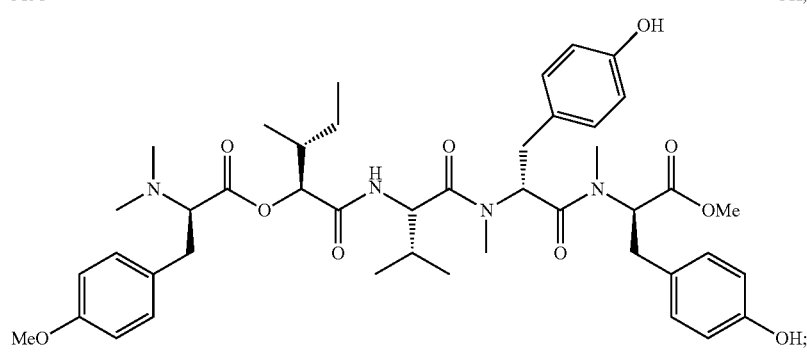
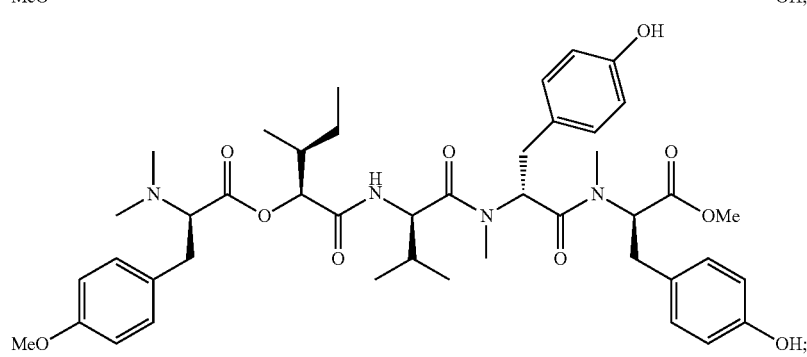
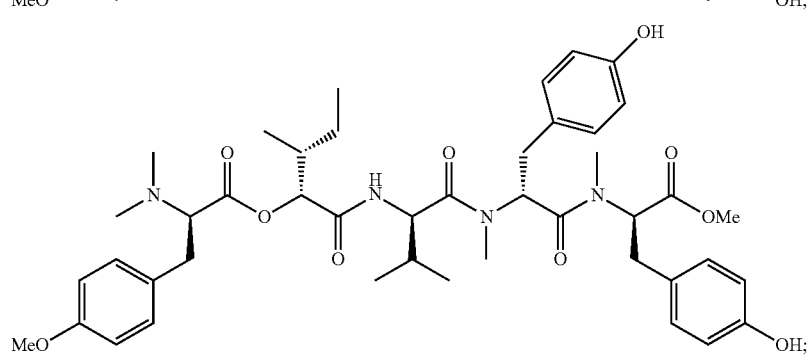

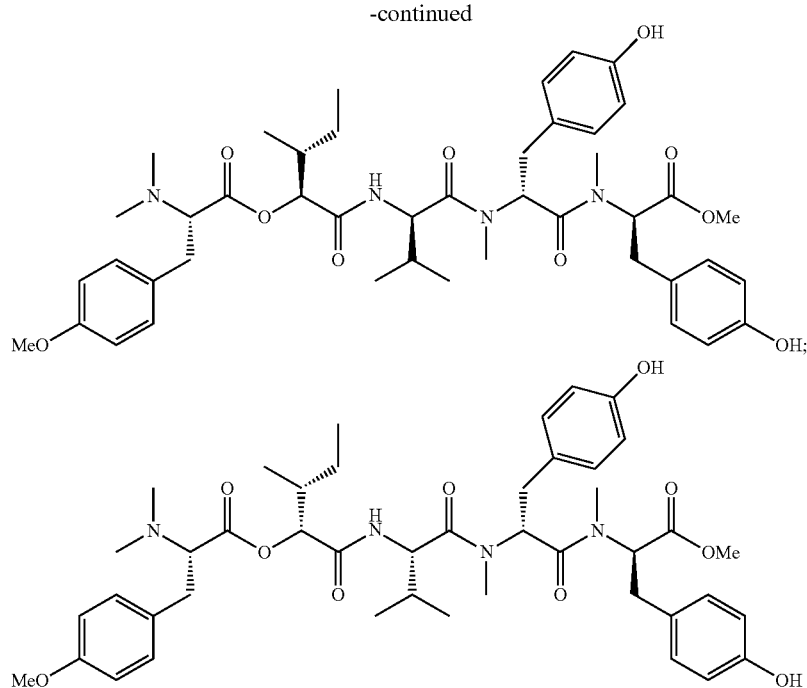

or pharmaceutically acceptable salts, solvates, hydrate, prodrugs, or stereoisomers thereof.

Compounds of the invention can be obtained from natural sources or made or modified made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, $2^{nd}$ Edition*, Carlson R, Ed, 2005; Elsevier Science Ltd.; Jahnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database. For example, compounds of formulae I-VIII can be made using methodology known in the art, including Doi et al., Org Lett. 2006 Feb. 2; 8(3):531-4; Ma, et al., Chemistry. 2006 Oct. 10; 12(29):7615-26; and Chen et al., Proc Natl Acad Sci USA. 2004 Aug. 17; 101(33):12067-72.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Methods of Treatment

In one aspect, the invention provides a method of treating a disease, disorder, or symptom thereof in a subject, comprising administering to said subject a compound of any of the formulae herein, or pharmaceutically acceptable salts, solvates, hydrate, prodrugs, or stereoisomers thereof.

In another aspect, the invention provides a method of treating a subject suffering from or susceptible to a wound, comprising administering to said subject in need thereof, an effective amount of a compound, or pharmaceutically acceptable salts, solvates, hydrate, prodrugs, or stereoisomers thereof, or pharmaceutical composition of any of the formulae herein, such that said subject is treated for said wound. In another aspect, the wound is a chronic wound. In another aspect, the chronic wound is a diabetic foot ulcer [DFU], pressure ulcer [PU], or chronic venous leg ulcer [VU].

In another aspect, the invention provides a method of accelerating wound healing in a subject, comprising administering to said subject in need thereof, an effective amount of a compound, or pharmaceutically acceptable salts, solvates, hydrate, prodrugs, or stereoisomers thereof, or pharmaceutical composition of any of the formulae herein, such that the healing of said wound in said subject is accelerated. In another aspect, the wound is a chronic wound. In another aspect, the chronic wound is a diabetic foot ulcer [DFU], pressure ulcer [PU], or chronic venous leg ulcer [VU].

In another aspect, the invention provides a method of treating a subject suffering from or susceptible to a disorder or disease mediated by VEGF (e.g., VEGF-A), comprising administering to said subject in need thereof, an effective amount of a compound, or pharmaceutically acceptable salts, solvates, hydrate, prodrugs, or stereoisomers thereof, or pharmaceutical composition of any of the formulae herein. In another aspect, the disorder or disease mediated by VEGF (e.g., VEGF-A) is a wound. In another aspect, the wound is a chronic wound. In another aspect, the chronic wound is a diabetic foot ulcer [DFU], pressure ulcer [PU], or chronic venous leg ulcer [VU].

In another aspect, the invention provides a method of inducing VEGF (e.g., VEGF-A) in a subject, comprising administering to said subject an effective amount of a compound, or pharmaceutically acceptable salts, solvates, hydrate, prodrugs, or stereoisomers thereof, or pharmaceutical composition of any of the formulae herein.

In another aspect, the invention provides a method for increasing angiogenesis in a subject, comprising administering to said subject an effective amount of a compound, or pharmaceutically acceptable salts, solvates, hydrate, prodrugs, or stereoisomers thereof, or pharmaceutical composition of any of the formulae herein.

In another aspect, the invention provides a method of inducing VEGF (e.g., VEGF-A), comprising administering an effective amount of a compound, or pharmaceutically acceptable salts, solvates, hydrate, prodrugs, or stereoisomers thereof, or pharmaceutical composition of any of the formulae herein.

In another aspect, the invention provides a method for increasing angiogenesis, comprising administering an effective amount of a compound, or pharmaceutically acceptable salts, solvates, hydrate, prodrugs, or stereoisomers thereof, or pharmaceutical composition of any of the formulae herein.

Another object of the present invention is the use of a compound as described herein (e.g., of any formulae herein), or pharmaceutically acceptable salts, solvates, hydrate, prodrugs, or stereoisomers thereof, in the manufacture of a medicament for use in the treatment of a wound. Another object of the present invention is the use of a compound as described herein (e.g., of any formulae herein), or pharmaceutically acceptable salts, solvates, hydrate, prodrugs, or stereoisomers thereof, for use in the treatment of a wound. In another aspect, the wound is a chronic wound. In another aspect, the chronic wound is a diabetic foot ulcer [DFU], pressure ulcer [PU], or chronic venous leg ulcer [VU].

Pharmaceutical Compositions

In one aspect, the invention provides a pharmaceutical composition comprising the compound of any of the formulae herein, or pharmaceutically acceptable salts, solvates, hydrate, prodrugs, or stereoisomers thereof, and a pharmaceutically acceptable carrier.

In another aspect, the invention provides a topical pharmaceutical composition comprising the compound of any of the formulae herein, or pharmaceutically acceptable salts, solvates, hydrate, prodrugs, or stereoisomers thereof, and a pharmaceutically acceptable carrier. In one embodiment the compounds of any of the formuale herein, or pharmaceutically acceptable salts, solvates, hydrate, prodrugs, or stereoisomers thereof, are particularly suited for administration directly to the wound via topical administration, and thus are advantageously administered via cream, lotion, gel directly to the wound or transdermally to the wound area. In another embodiment, the topical composition can be applied via patch, bandage, or other dressing having the compounds of any of the formulae, or pharmaceutically acceptable salts, solvates, hydrate, prodrugs, or stereoisomers thereof, therein.

In one embodiment, the invention provides a pharmaceutical composition wherein the compound is of the formula:

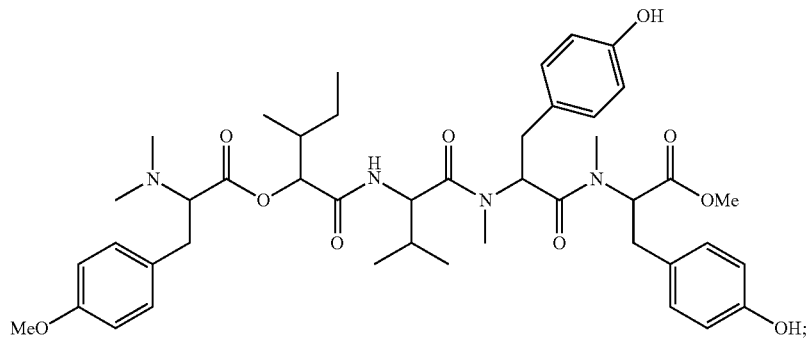

or pharmaceutically acceptable salts, solvates, hydrate, prodrugs, or stereoisomers thereof.

In one embodiment, the invention provides a pharmaceutical composition wherein the compound is one of:
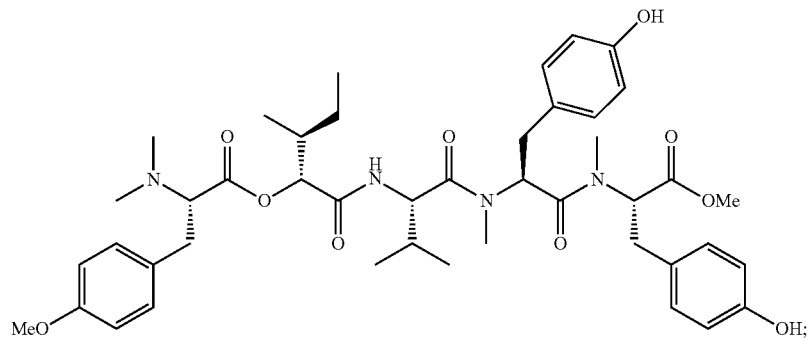
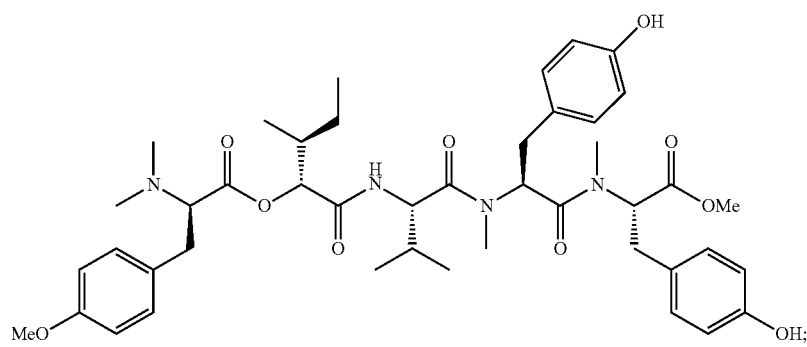
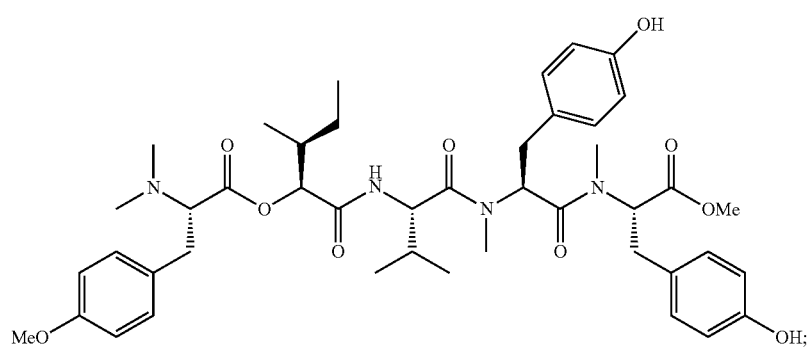
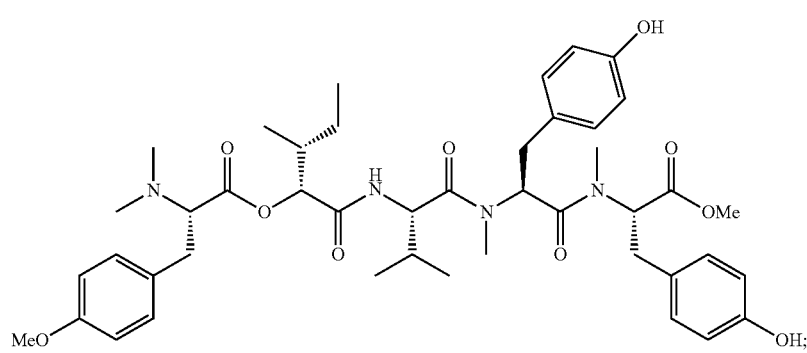

-continued
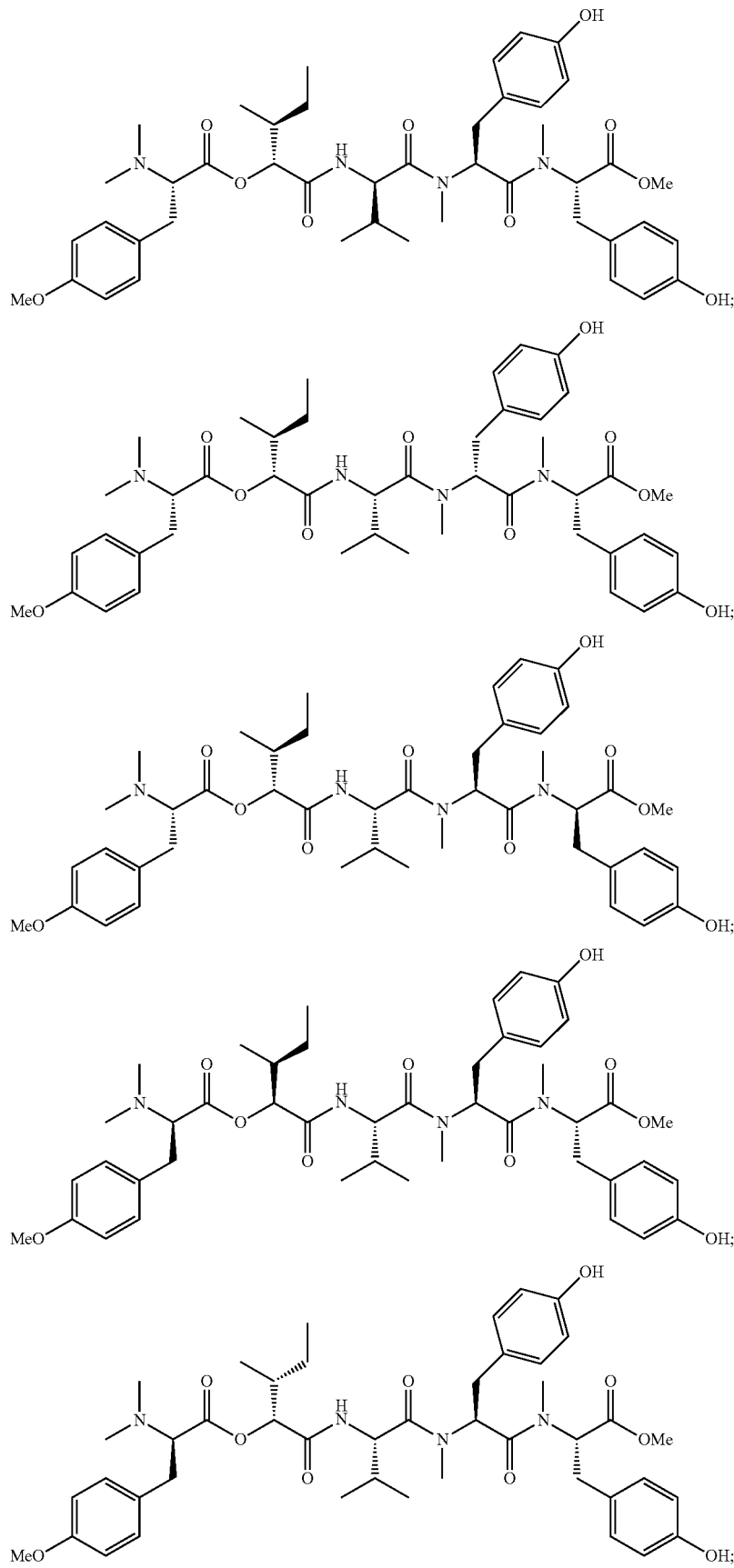

-continued
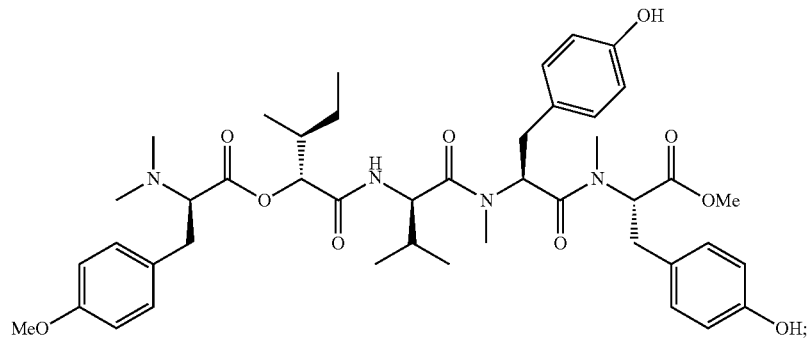
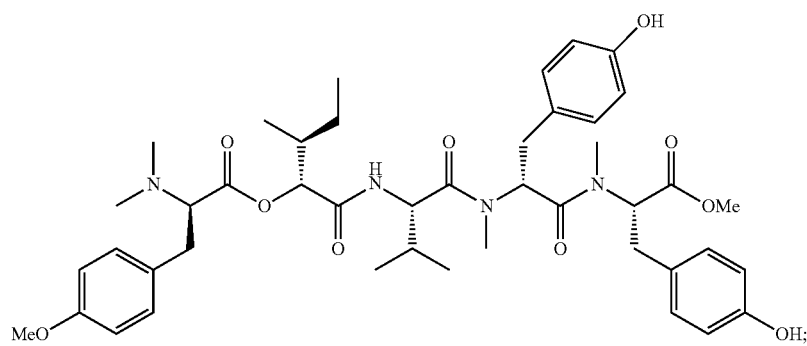
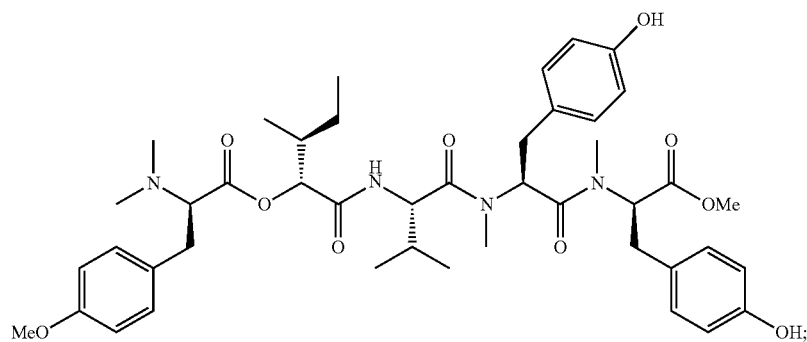
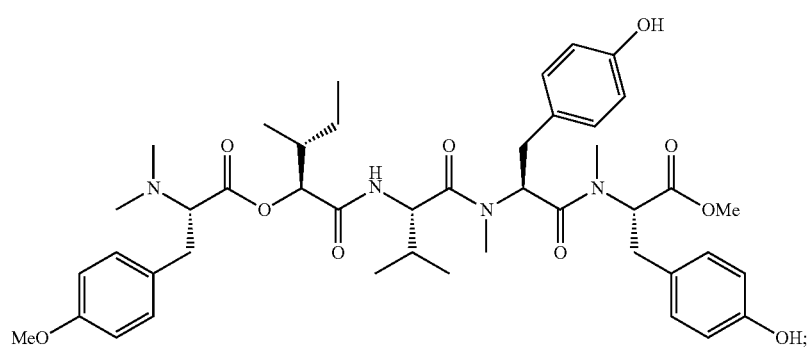
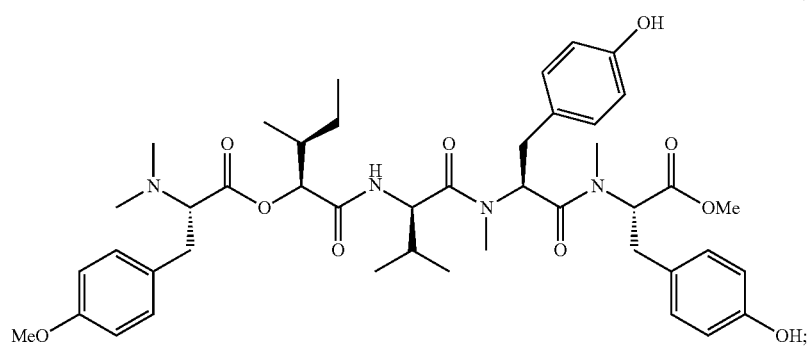

-continued
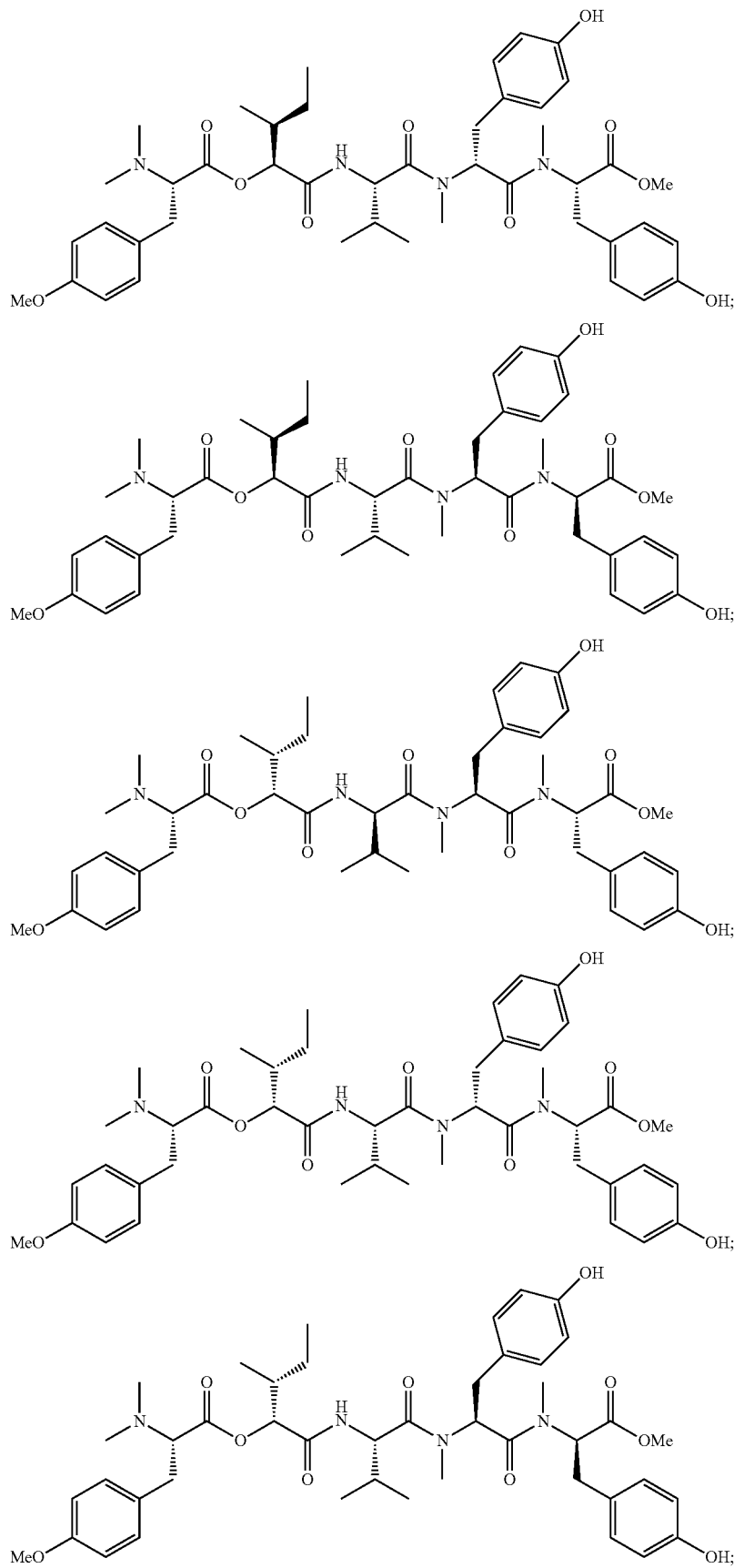

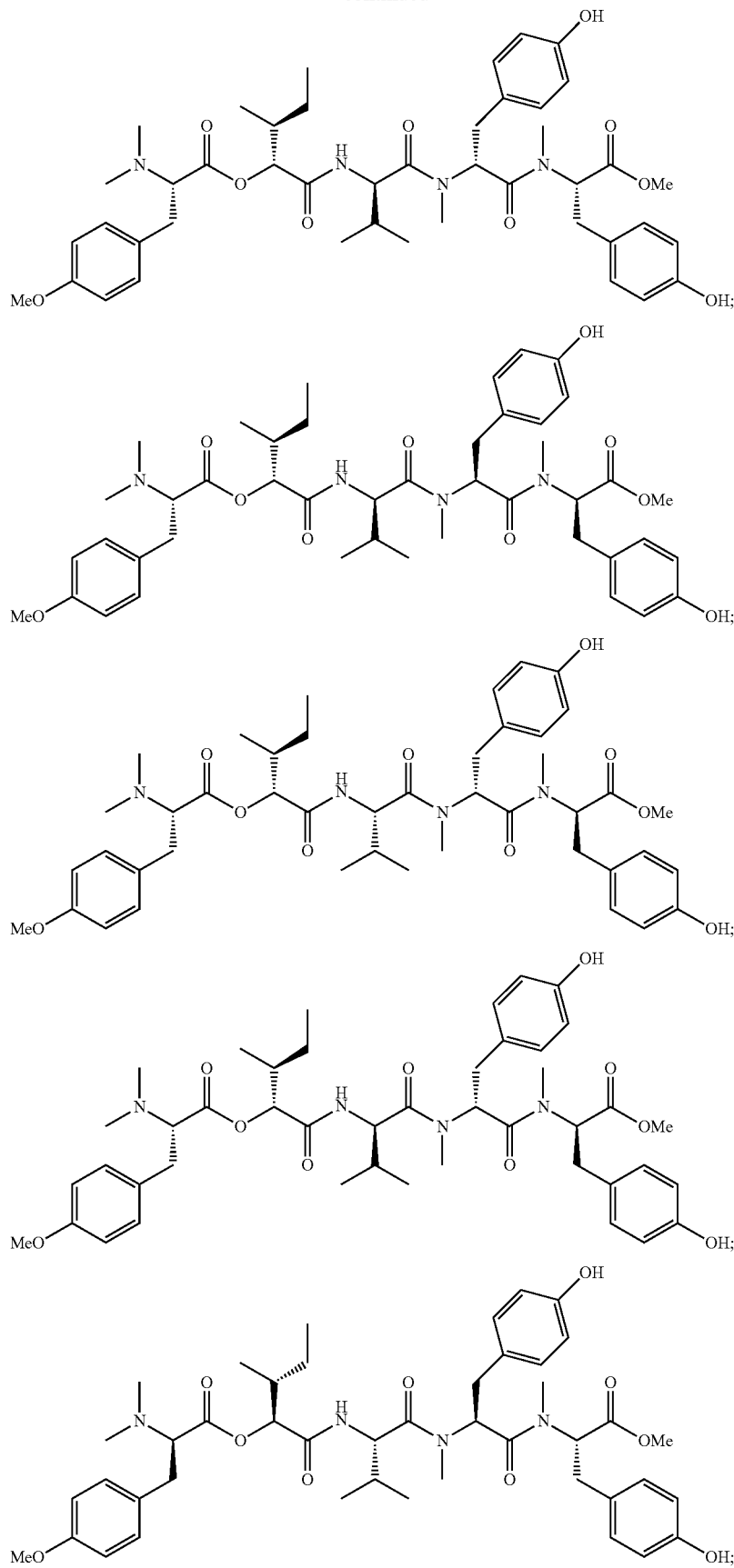

-continued
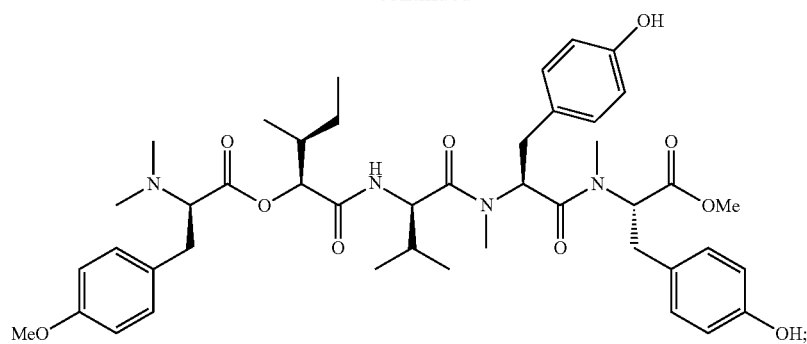
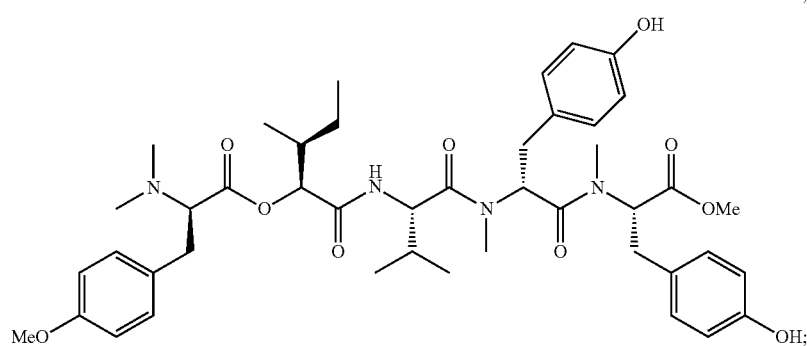
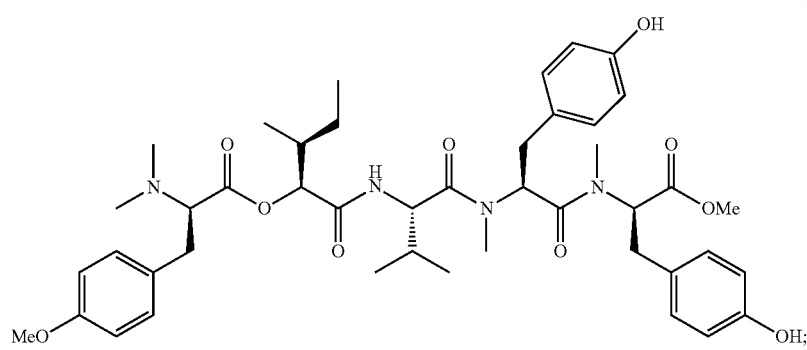
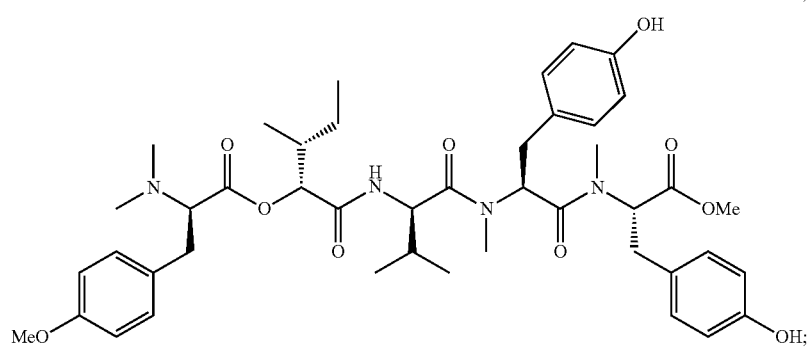
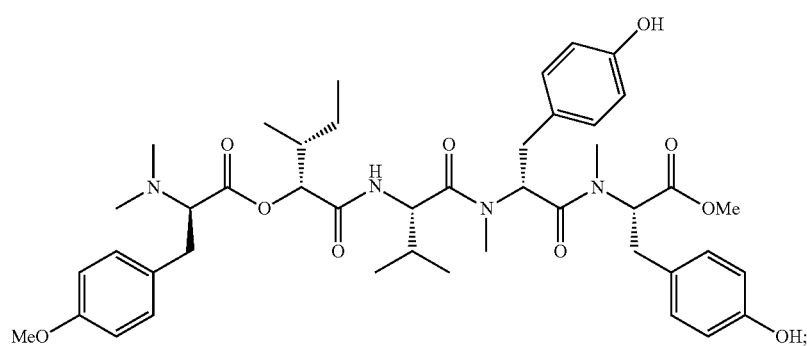

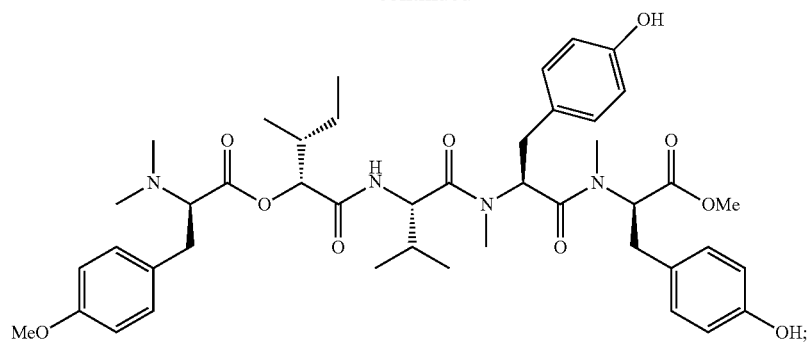
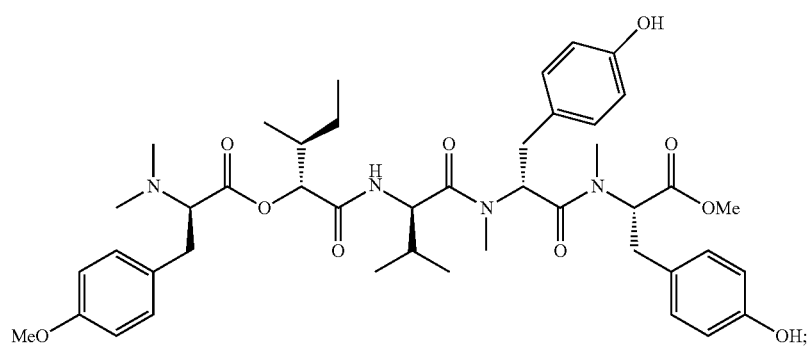
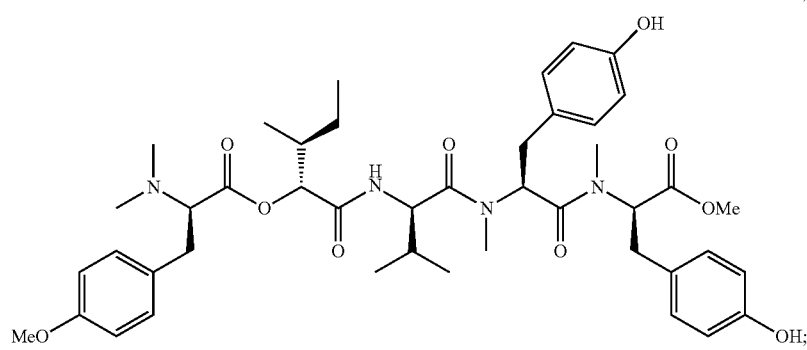
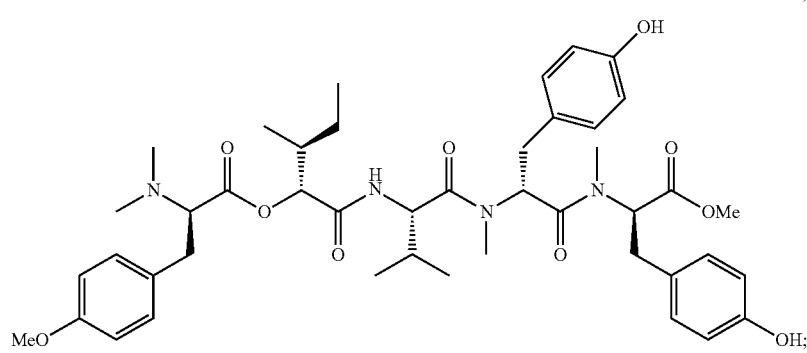
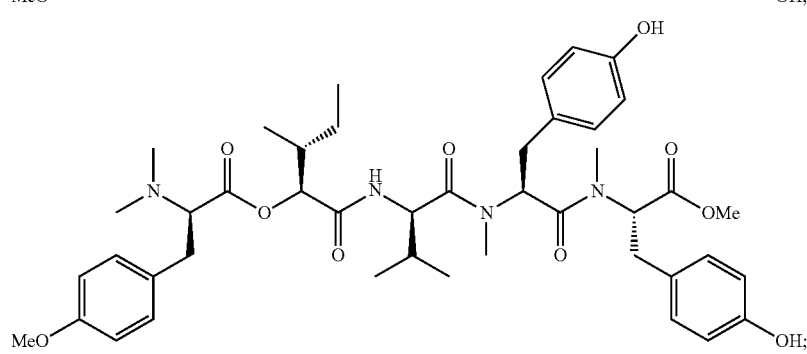

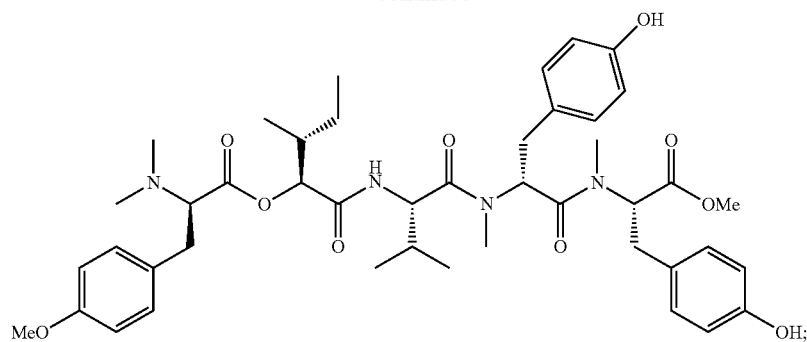
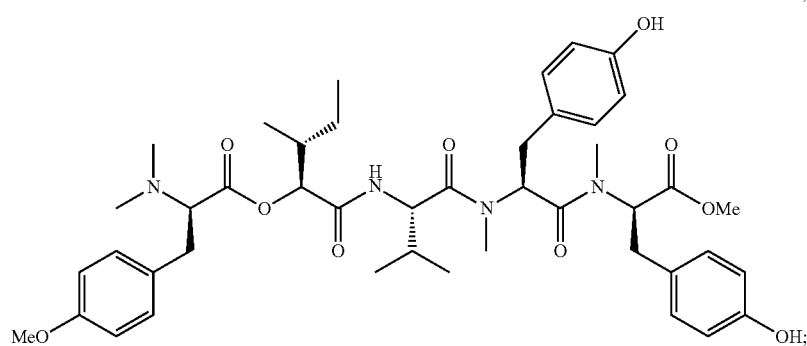
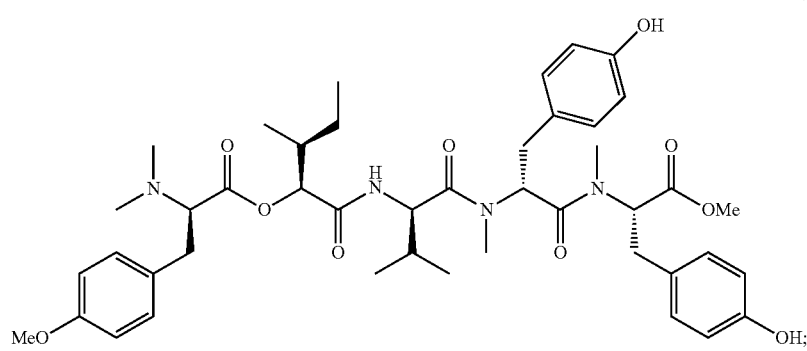
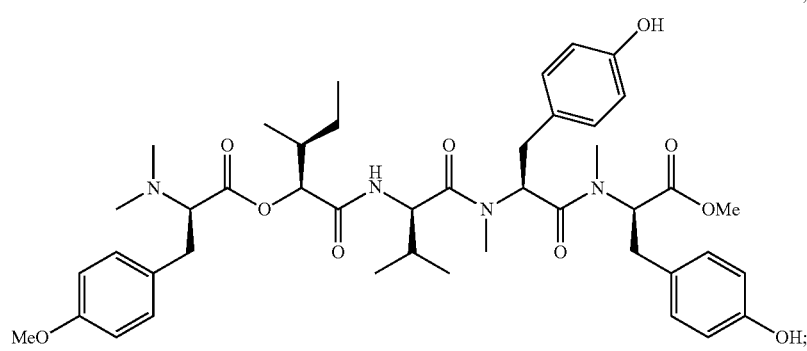
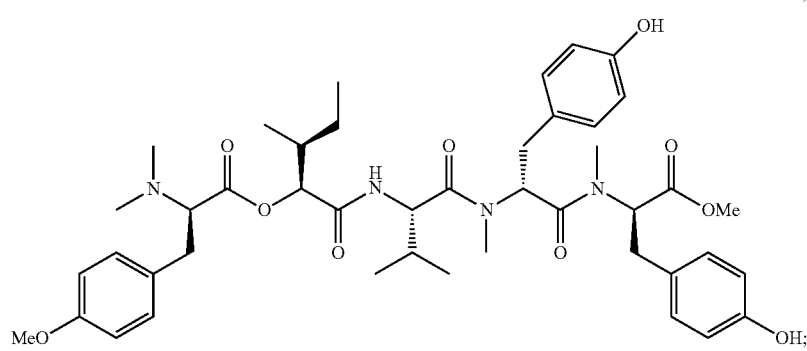

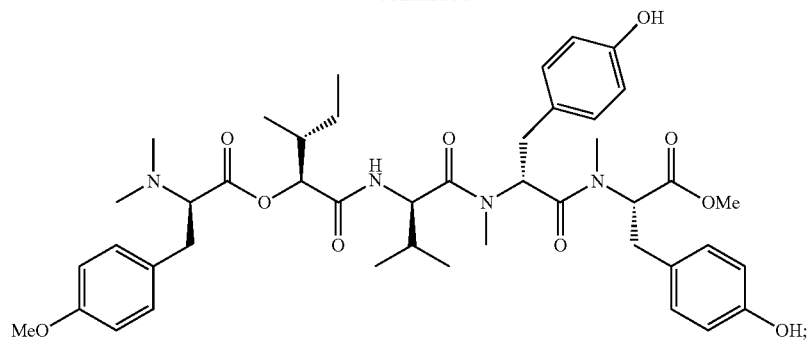
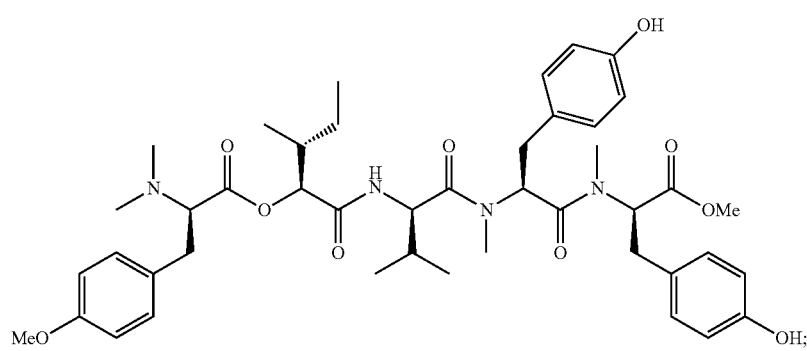
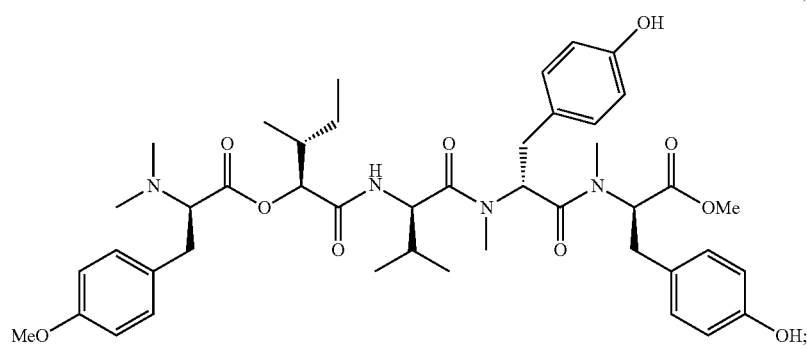
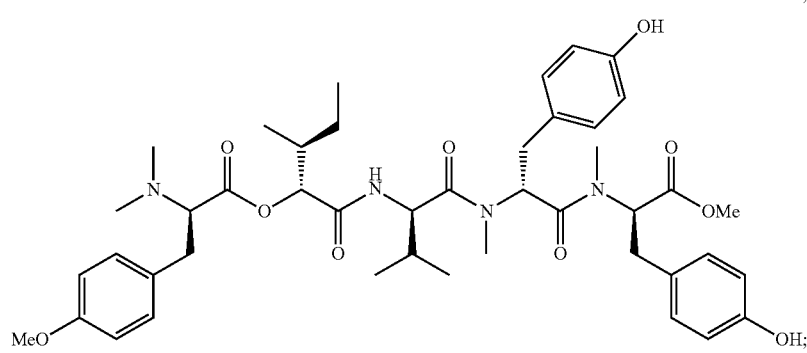
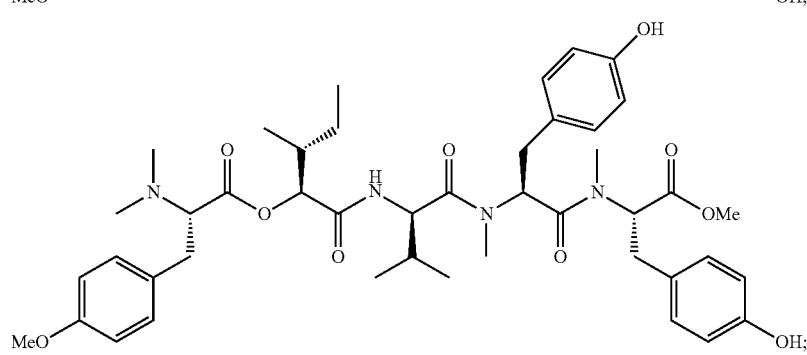

-continued
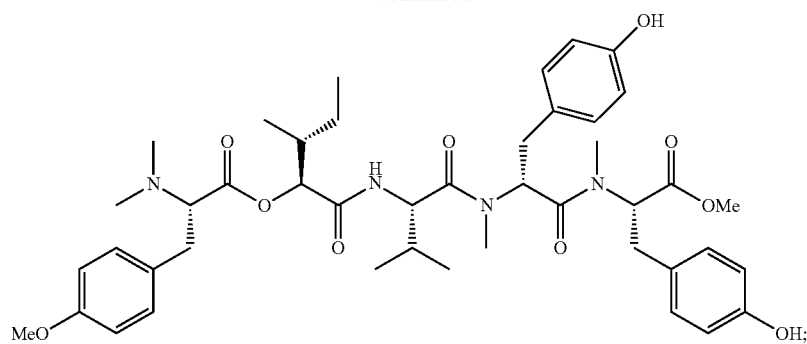
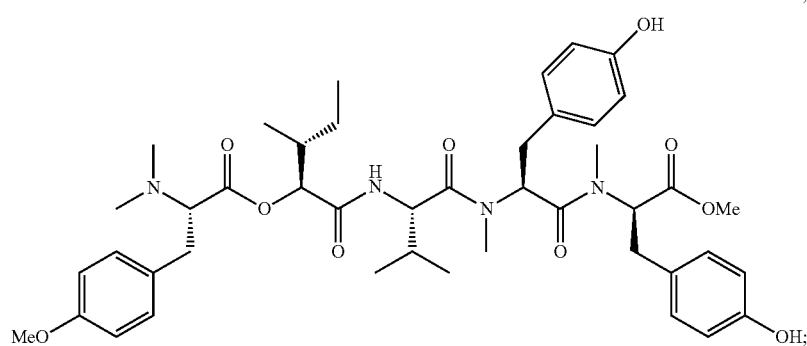
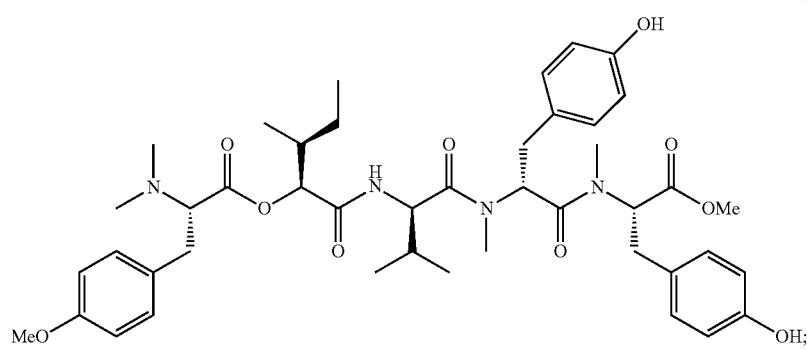
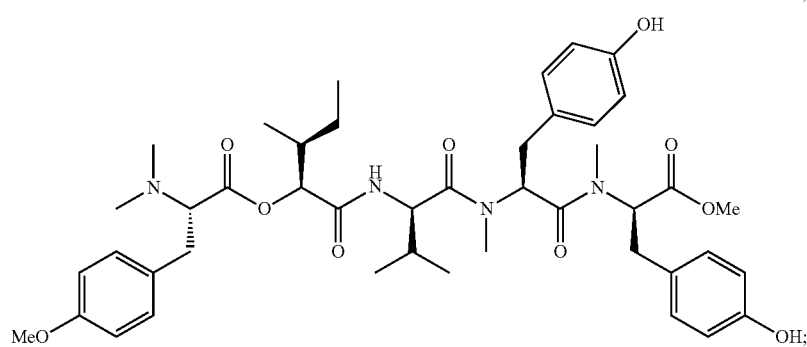
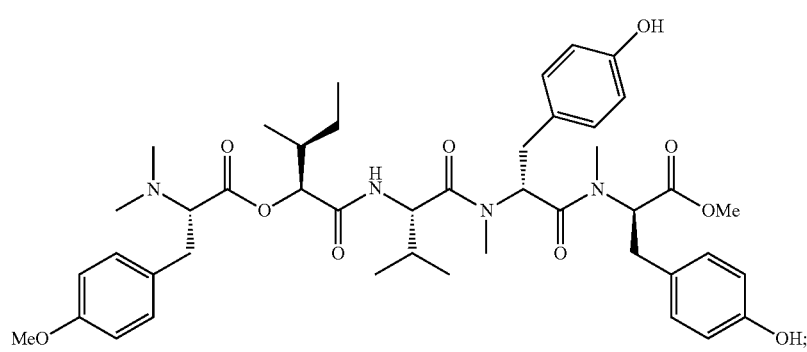

-continued
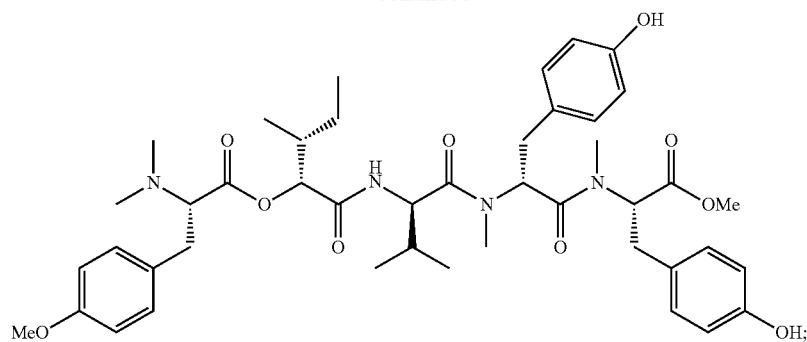
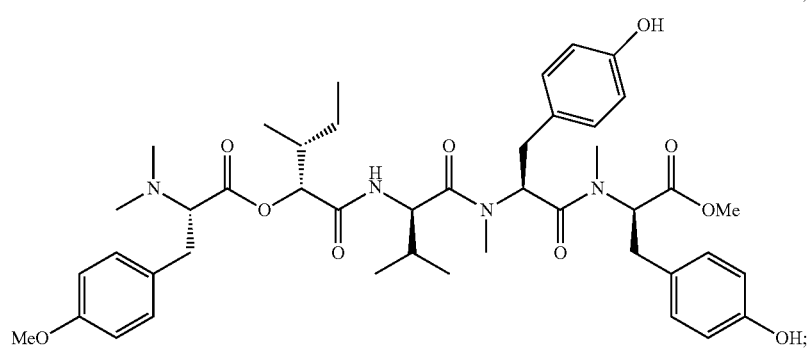
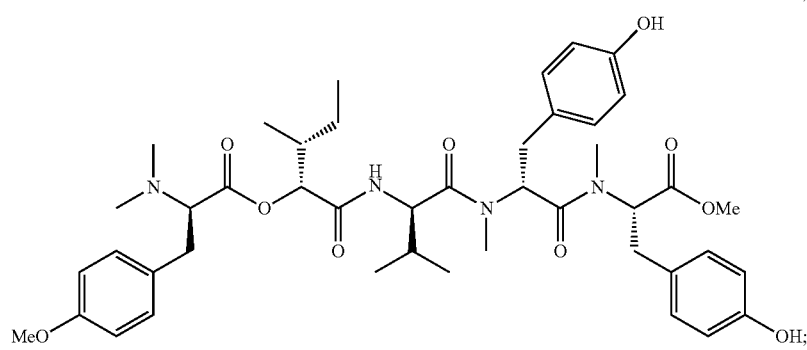
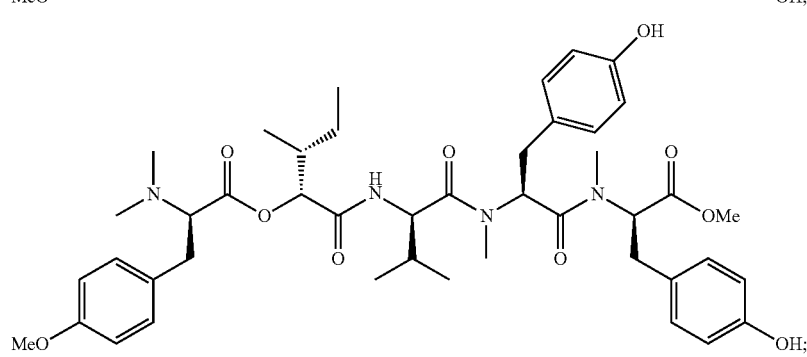
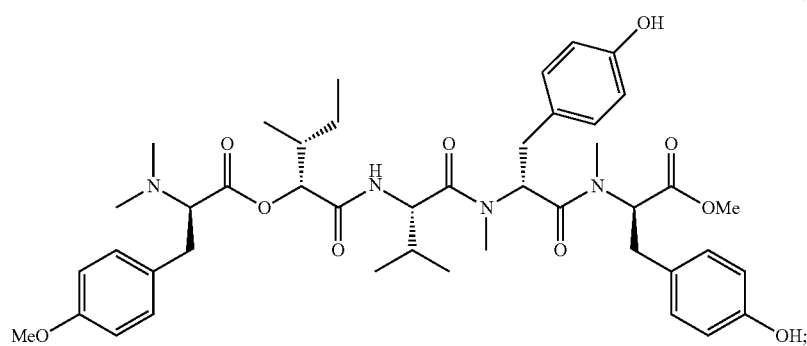

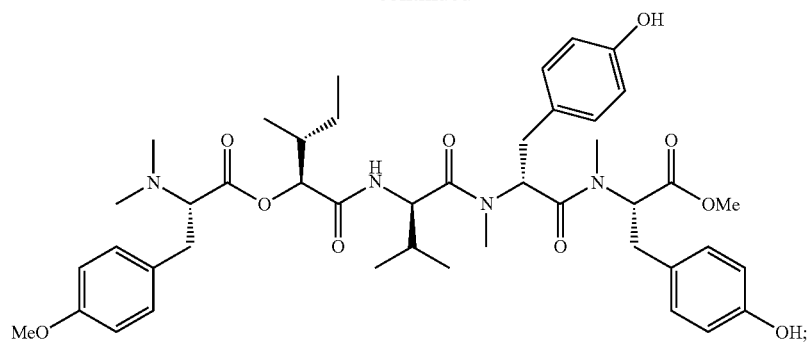
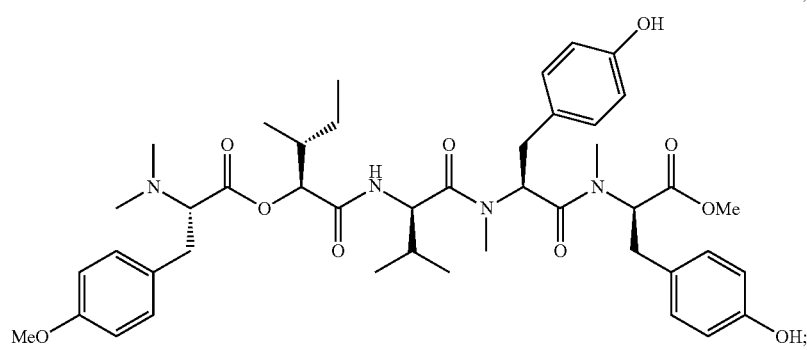
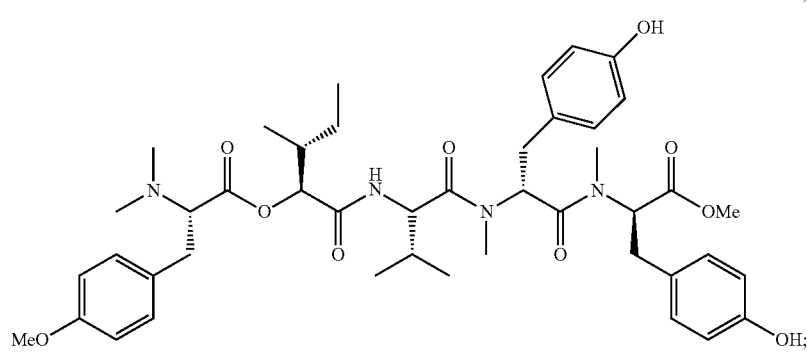
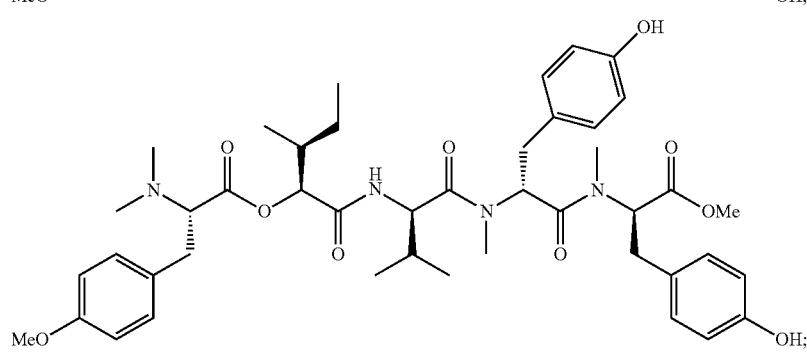
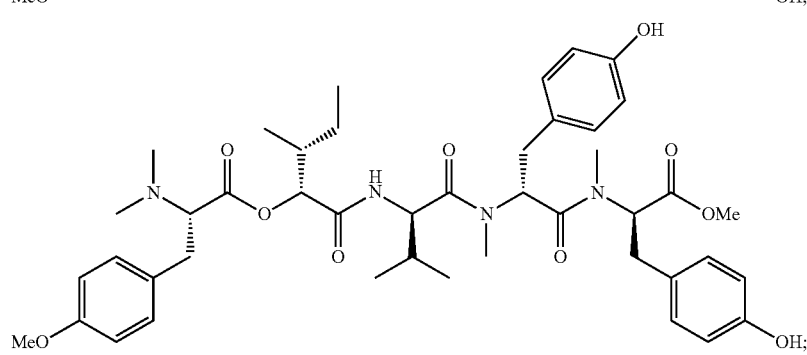

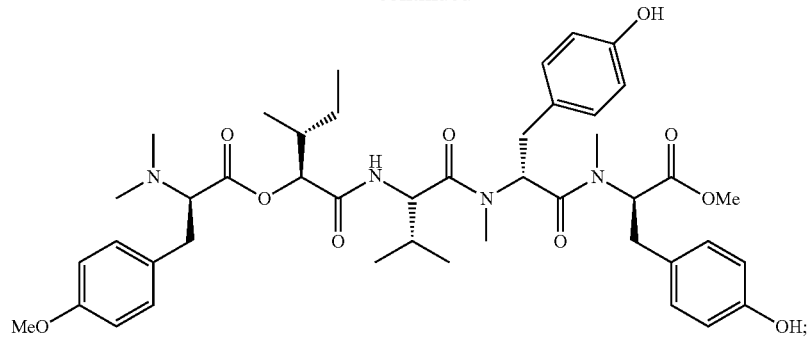
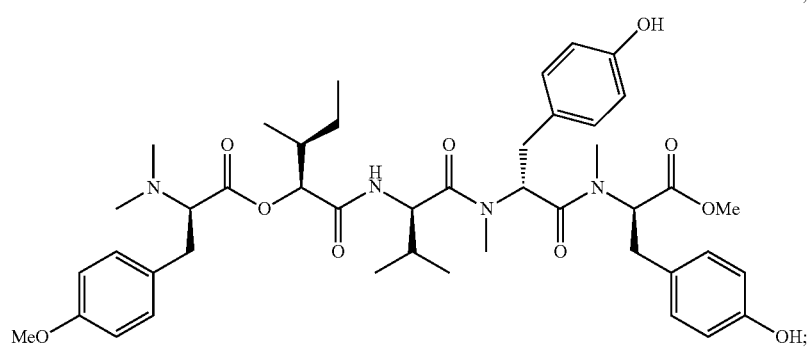
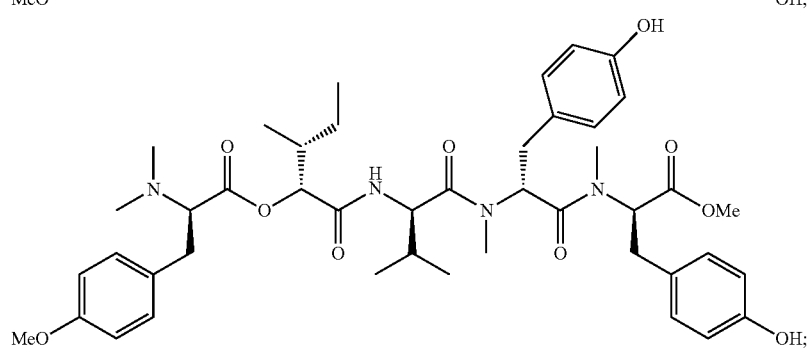
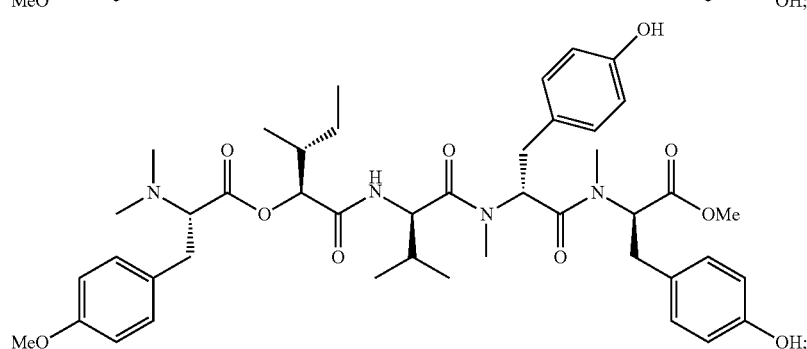
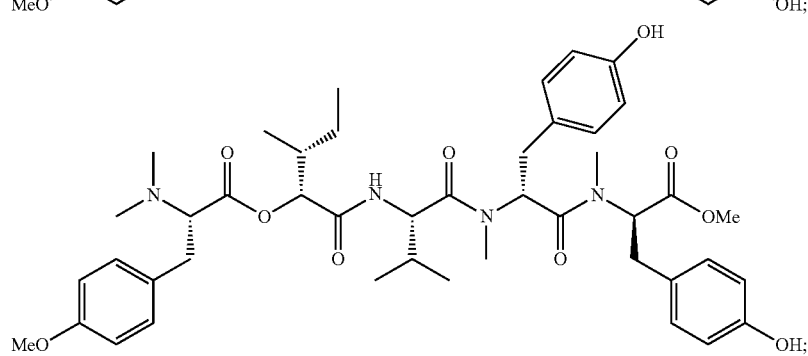

or pharmaceutically acceptable salts, solvates, hydrate, prodrugs, or stereoisomers thereof.

In another embodiment, the invention provides a pharmaceutical composition further comprising an additional therapeutic agent.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebro ventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific apratyramide compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

The compound may be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage. The carrier can be a solvent or dispersion medium containing, for example, water, DMSO, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compound of the invention in the required amount in the appropriate solvent with various of the other ingredients enumerated above, as required, followed by filtered sterilization. Generally, dispersions are prepared by incorporating the various sterilized compounds into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yields a powder of the active ingredient plus any additional desired ingredient from previously sterile-filtered solution thereof.

For oral therapeutic administration, the compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains compound concentration sufficient to treat a disorder in a subject.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present.

Pharmaceutical compositions comprising the active compounds of the presently disclosed subject matter (or prodrugs thereof) can be manufactured by means of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

Pharmaceutical compositions of the presently disclosed subject matter can take a form suitable for virtually any mode of administration, including, for example, topical, ocular, oral, buccal, systemic, nasal, injection, transdermal, rectal, vaginal, and the like, or a form suitable for administration by inhalation or insufflation.

For topical administration, the active compound(s) or prodrug(s) can be formulated as solutions, gels, ointments, creams, suspensions, and the like.

Systemic formulations include those designed for administration by injection, e.g., subcutaneous, intravenous, intramuscular, intrathecal or intraperitoneal injection, as well as those designed for transdermal, transmucosal, oral, or pulmonary administration.

Useful injectable preparations include sterile suspensions, solutions or emulsions of the active compound(s) in aqueous or oily vehicles. The compositions also can contain formulating agents, such as suspending, stabilizing and/or dispersing agent. The formulations for injection can be presented in unit dosage form (e.g., in ampules or in multidose containers) and can contain added preservatives.

Alternatively, the injectable formulation can be provided in powder form for reconstitution with a suitable vehicle, including but not limited to sterile pyrogen free water, buffer, dextrose solution, and the like, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, lozenges, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p-hydroxybenzoates or sorbic acid). The preparations also can contain buffer salts, preservatives, flavoring, coloring and sweetening agents as appropriate.

Preparations for oral administration can be suitably formulated to give controlled release of the active compound or prodrug, as is well known.

For buccal administration, the compositions can take the form of tablets or lozenges formulated in a conventional manner.

For rectal and vaginal routes of administration, the active compound(s) can be formulated as solutions (for retention enemas), suppositories, or ointments containing conventional suppository bases, such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH5 to pH7, with a pH of about pH 5.5 being typical.

For ocular administration, the active compound(s) or prodrug(s) can be formulated as a solution, emulsion, suspension, and the like, suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851, each of which is incorporated herein by reference in its entirety.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed.

The pharmaceutical compositions can, if desired, be presented in a pack or dispenser device which can contain one or more unit dosage forms containing the active compound (s). The pack can, for example, comprise metal or plastic foil, such as a blister pack. The pack or dispenser device can be accompanied by instructions for administration.

The active compound(s) or prodrug(s) of the presently disclosed subject matter, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound can be administered to a patient at risk of developing one of the previously described diseases. A patient at risk of developing a disease can be a patient having characteristics placing the patient in a designated group of at risk patients, as defined by an appropriate medical professional or group. A patient at risk may also be a patient that is commonly or routinely in a setting where development of the underlying disease that may be treated by administration of a metalloenzyme inhibitor according to the invention could occur. In other words, the at risk patient is one who is commonly or routinely exposed to the disease or illness causing conditions or may be acutely exposed for a limited time. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. Calculating dosages to achieve such circulating blood or serum concentrations taking into account the bioavailability of the particular compound is well within the capabilities of skilled artisans. For guidance, see Fingl & Woodbury, "General Principles," In: *Goodman and Gilman's The Pharmaceutical Basis of Therapeutics*, Chapter 1, pp. 1-46, latest edition, Pagamonon Press, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician. Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups.

The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

The present invention will now be demonstrated using specific examples that are not to be construed as limiting.

General Experimental Procedures

Solvents were purified by standard methods. TLCs were carried out on Merck 60 $F_{254}$ silica gel plates and visualized by UV irradiation or by staining with aqueous acidic ammonium molybdate solution as appropriate. Flash column chromatography was performed on silica gel (170-400 mesh, Fisher, USA). Optical rotations were measured on a Perkin-Elmer 341 polarimeter. Nuclear magnetic resonance (NMR) spectra were recorded on a Varian 400 MHz or Bruker Avance II 600 MHz spectrometer as indicated in the data list. Chemical shifts for proton nuclear magnetic resonance ($^1$H NMR) spectra are reported in parts per million relative to the signal residual $CDCl_3$ at 7.26 ppm and DMSO-$d_6$ at 2.50 ppm. Chemicals shifts for carbon nuclear magnetic resonance ($^{13}$C NMR) spectra are reported in parts per million relative to the center line of the $CDCl_3$ triplet at 77.0 ppm and DMSO-$d_6$ at 40.0 ppm. Data are described as following: chemical shift, multiplicity (s=singlet, d=doublet, t=triplet, q=quartet, br=broad, m=multiplet), coupling constants (Hz), integration, and assignment. HRESIMS data were obtained using an Agilent LC-TOF mass spectrometer equipped with an APCI/ESI multimode ion source detector.

Example 1: Isolation and Structure Determination of Apratyramide (1)

Five different Guamanian collections of freeze dried apratoxins-producing *Moorea bouillonii* were collected from Fingers Reef, Guam (Luesch, H., Yoshida, W. Y., Moore, R. E., Paul, V. J., and Corbett, T. H. (2001) Total structure determination of apratoxin A, a potent novel cytotoxin from the marine cyanobacterium *Lyngbya majuscula*. J. Am. Chem. Soc. 123, 5418-5423). Each were individually extracted with $CH_2Cl_2$ and MeOH (2:1) followed by solvent partitioning, silica chromatography, and reversed-phase HPLC purification to yield optically active compound 1 as a minor metabolite (2.0 mg, $[\alpha]_D^{20}$ −101.9 (c 0.59, MeOH)).

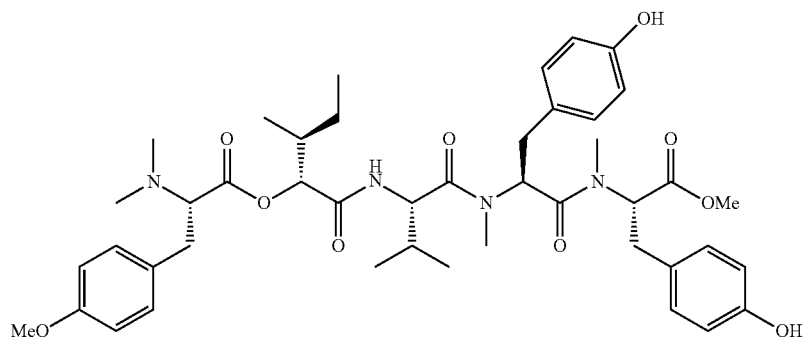 [SMILES: CC[C@H](C)[C@@H](OC(=O)[C@H](Cc1ccc(OC)cc1)N(C)C)C(=O)N[C@H](C(=O)N(C)[C@@H](Cc1ccc(O)cc1)C(=O)N(C)[C@@H](Cc1ccc(O)cc1)C(=O)OC)C(C)C]

Apratyramide (1)

Figure 2:
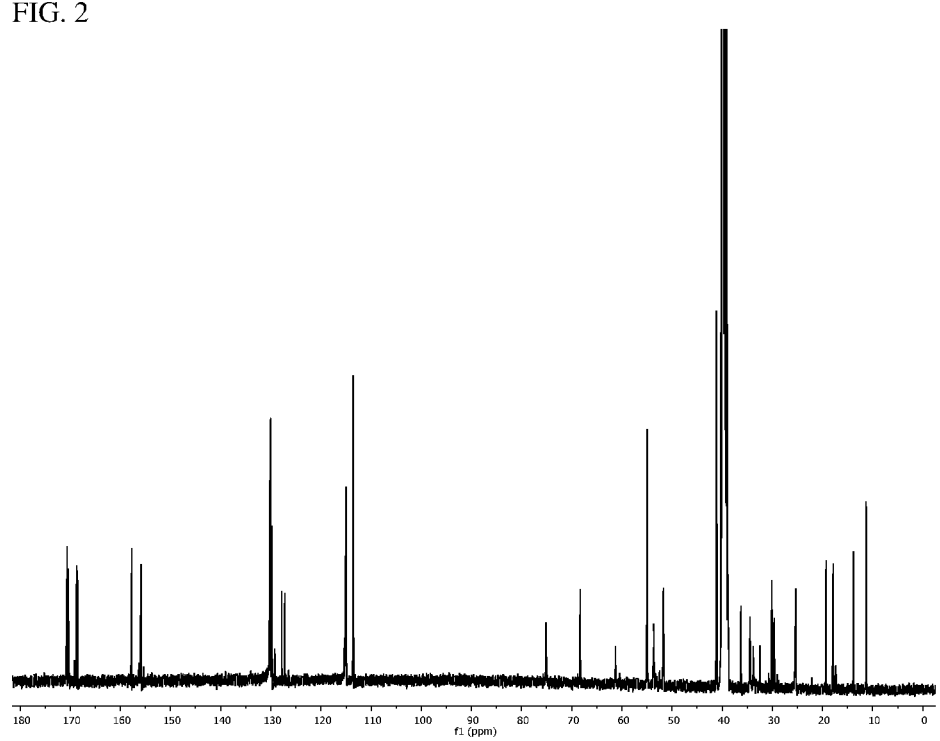
FIG. 2. depicts the $^{13}$C NMR spectrum of natural product apratyramide (1) in DMSO-$d_6$ (600 MHz).
Figure 4:
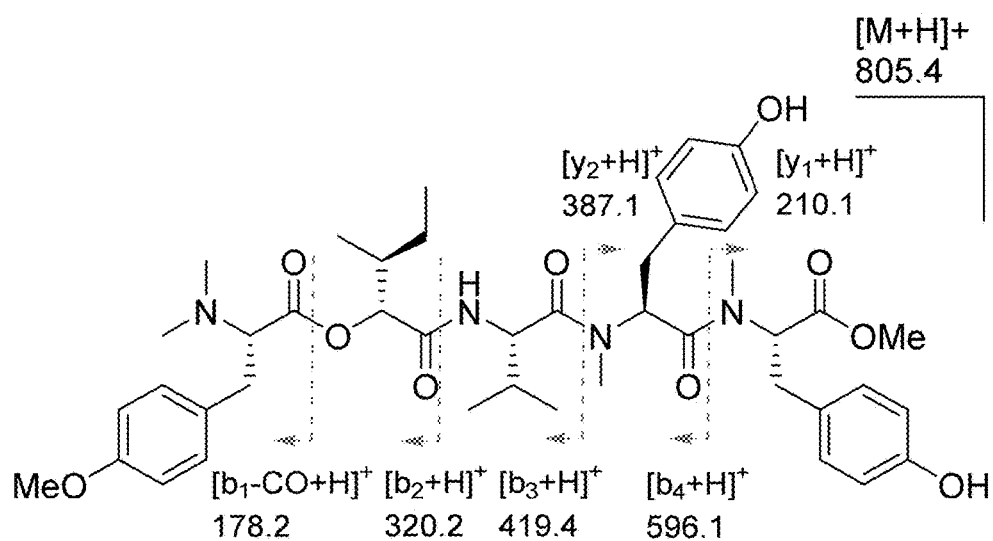
FIG. 4. depicts the ESIMS fragmentation pattern of 1.

The HRESIMS of 1 in the positive mode showed a molecular ion peak at m/z 805.4388 $[M+H]^+$, suggesting a molecular formula of $C_{44}H_{60}N_4O_{10}$ with seventeen degrees of unsaturation. The $^1$H NMR spectrum of 1 (FIG. 1) displayed characteristic peptide signals for several α-protons (δH 3.4-5.3), an exchangeable proton of amide (δH 8.08), four N-methyls (δH 2.2-2.8) and two O-methyls (δH 3.5-3.7). A signal at $\delta_C$ 75.09 in $^{13}$C NMR spectrum (FIG. 2), corresponding to a typical oxygenated sp$^3$ carbon, suggested the presence of a hydroxy acid in addition to amino acids. Following the interpretation of 1D and 2D NMR experiments, $^1$H and $^{13}$C NMR signals (FIG. 3) were assignable into five partial structures: three modified tyrosines [N-Me-Tyr, N-Me-Tyr(1-OMe) and N,N-diMe-Tyr(OMe)], one proteinogenic amino acid (Val) and one α-hydroxy acid moiety [2-hydroxy-3-methylpentanoic acid (Hmpa)]. The sequence of these units was established on the basis of HMBC and NOESY correlations (FIG. 3) and was further verified by ESIMS fragmentation (FIG. 4). The absolute configuration of 1 was determined by enantioselective HPLC analysis and comparison with authentic standards.

Example 2: General Synthesis of Apratyramides

The following scheme illustrates the synthetic process for the preparation of Apratyramides.

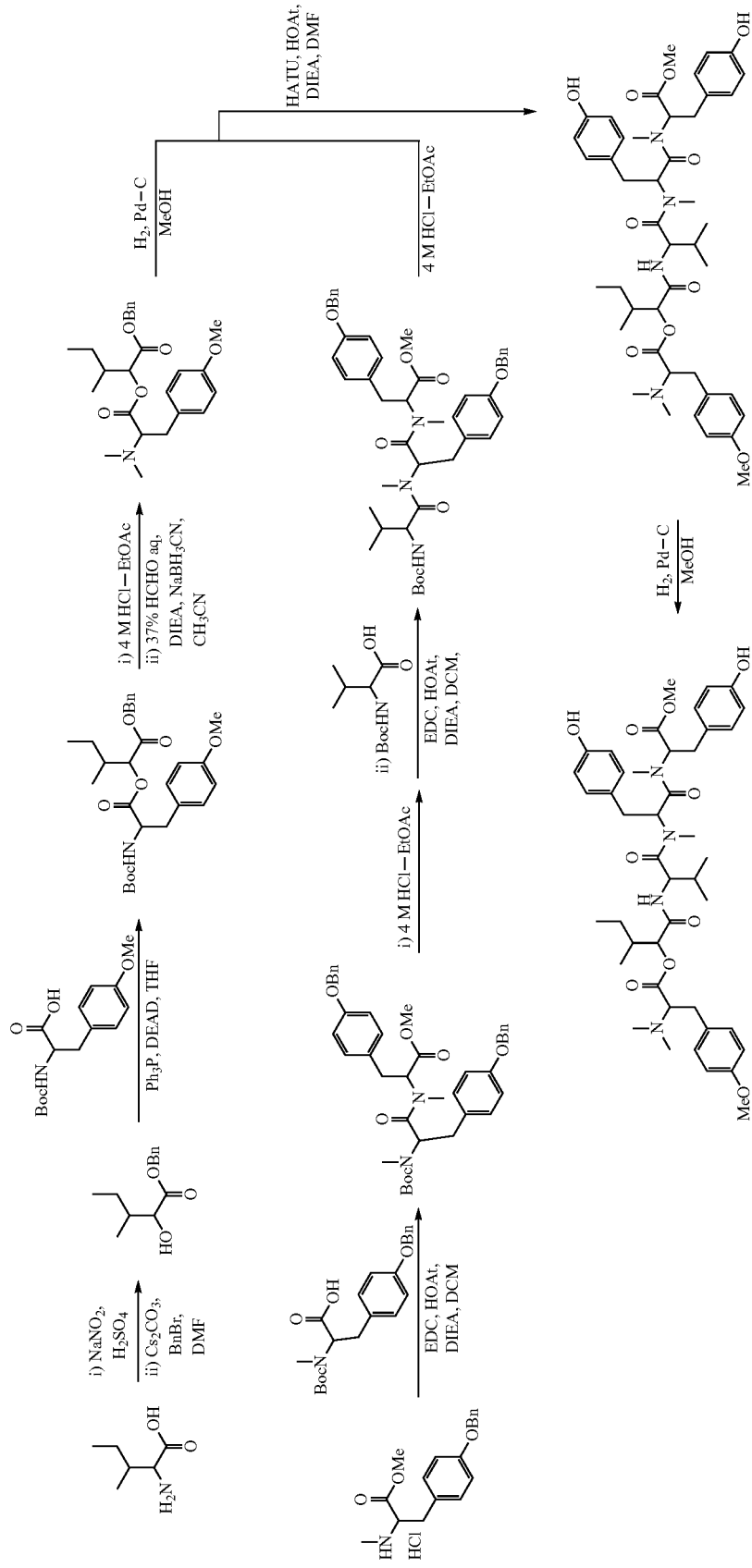

Although the above scheme represents the compounds illustrated therein without specifying the corresponding specific absolute configurations, all diastereoisomers, enantiomers, regioisomers, structural isomers, rotational isomers, and tautomers are expressly included in the above scheme. One skilled in the art would understand and appreciate that any specific stereoisomer of the above compounds can be afforded using the process delineated in the above scheme by selecting the appropriate absolute configuration for each of the starting amino acid starting materials.

Example 3: Total Synthesis of Apratyramide (1)

Figure 5:
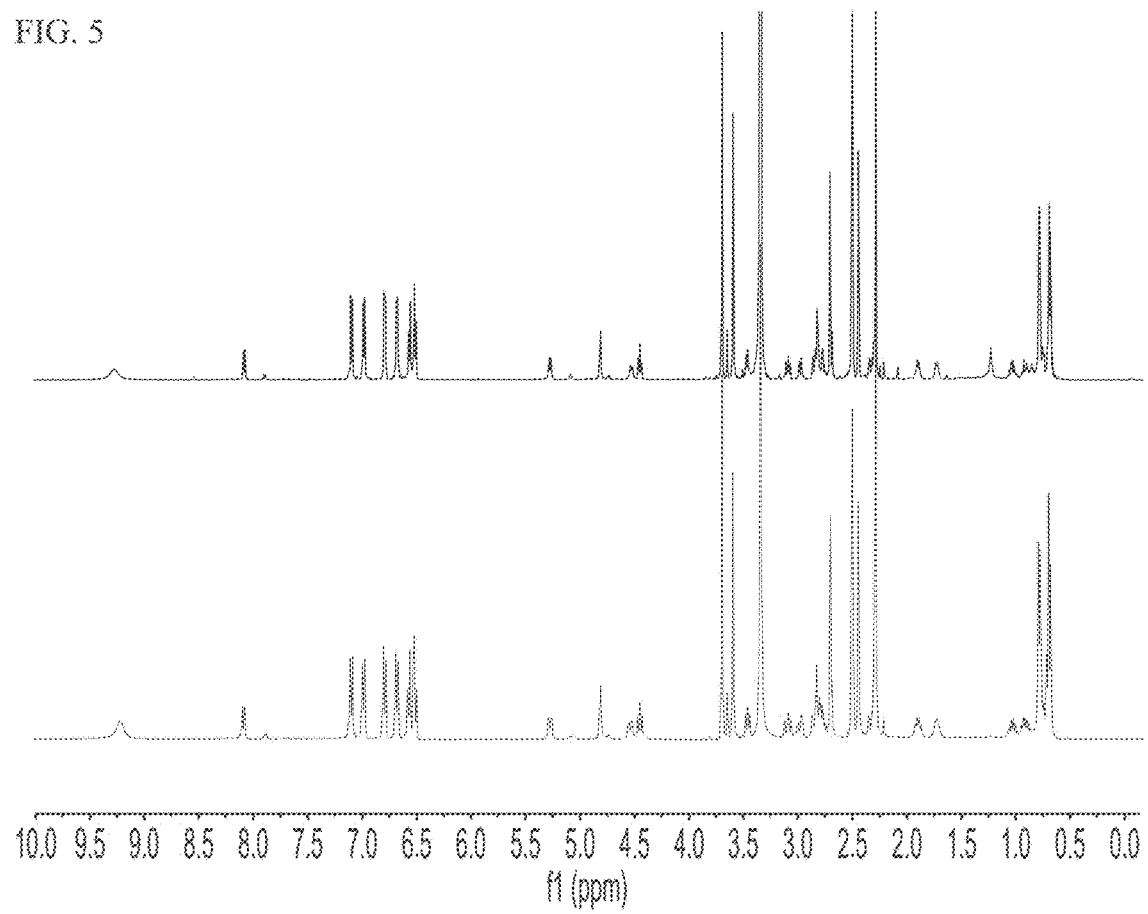
FIG. 5. depicts the $^1$H NMR spectrum of natural product (black, DMSO-$d_6$ (600 MHz)) and synthetic (blue, DMSO-$d_6$ (400 MHz)) apratyramide (1).
Figure 6:
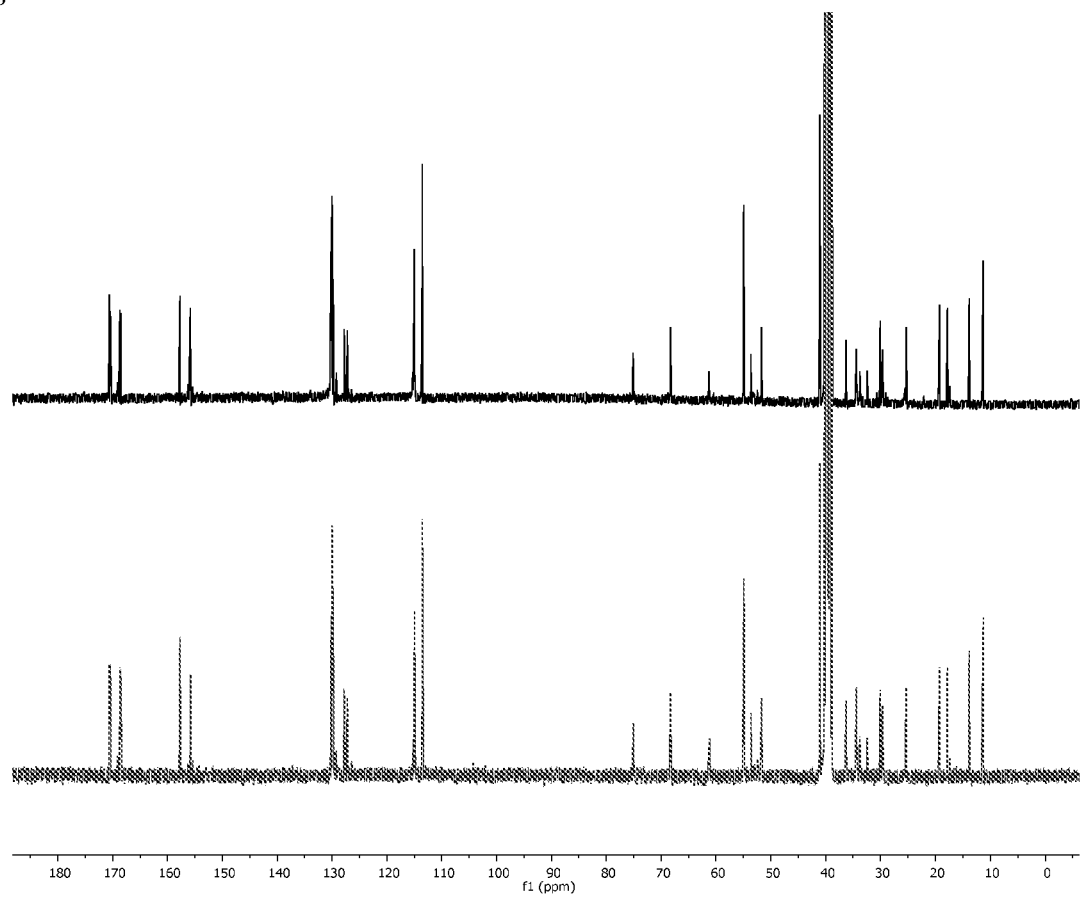
FIG. 6. depicts the $^{13}$C NMR spectrum of natural product (black, DMSO-$d_6$ (150 MHz)) and synthetic (blue, DMSO-$d_6$ (100 MHz)) apratyramide (1).

Owing to the limited supply of apratyramide from nature, the total synthesis was performed in order to obtain more material for biological evaluation. The convergent synthesis below was conducted by obtaining two building blocks: an ester and a tripeptide. To construct the ester, two commercially available amino acids were obtained as starting materials. The α-hydroxy carboxylic acid 4 was prepared from L-isoleucine by a published protocol (Poterala, M., and Plenkiewicz, J. (2011) Synthesis of new chiral ionic liquids from α-hydroxycarboxylic acids. *Tetrahedron Asymmetry* 22, 294-299). The esterification of N-Boc-O-Me-tyrosine with acid 4 provided ester 5 in 96% yield by Mitsunobu reaction ($Ph_3P$/DEAD) (Grab, T., and Bräse, S. (2005) Efficient synthesis of lactate-containing depsipeptides by the mitsunobu reaction of lactates. *Adv. Synth. Catal.* 347, 1765-1768). The Boc group of ester 5 was removed using 4 M HCl in ethyl acetate. Then, the desired N,N-dimethylated amino ester 2 was formed by a reductive alkylation reaction of the free amine of 5 using a mixture of aq. HCHO and $NaBH_3CN$ (Conroy, T., Guo, J. T., Linington, R. G., Hunt, N. H., and Payne, R. J. (2011) Total synthesis, stereochemical assignment, and antimalarial activity of gallinamide A. *Chem.—A Eur. J.* 17, 13544-13552). The end acid group of ester 2 was liberated by hydrogenation with $Pd/C/H_2$ in MeOH. The tripeptide 3 was constructed smoothly by sequential coupling of N-Boc-N-Me-tyrosine(OBn) with methyl ester of N-Me-tyrosine(OBn), then with N-Boc-valine using the coupling system EDCI/HOAt (Chen, Y., Bilban, M., Foster, C. A., and Boger, D. L. (2002) Solution-phase parallel synthesis of a pharmacophore library of HUN-7293 analogues: A general chemical mutagenesis approach to defining structure-function properties of naturally occurring cyclic (depsi)peptides. *J. Am. Chem. Soc.* 124, 5431-5440). The Boc group in 3 was cleaved by 4 M HCl in ethyl acetate to obtain the acetate free amine, which was then coupled with the free acid of ester 2 to provide precursor 7 using HATU/HOAt in DMF. Finally, the hydrogenation of 7 by $Pd/C/H_2$ in MeOH afforded final product 1 in 63% yield. The NMR spectra for natural and synthetic apratyramide (1) were identical (FIGS. 5 and 6). Comparison of optical activity and HR-MS of natural and synthetic 1 further confirmed the structural assignment for the natural product.

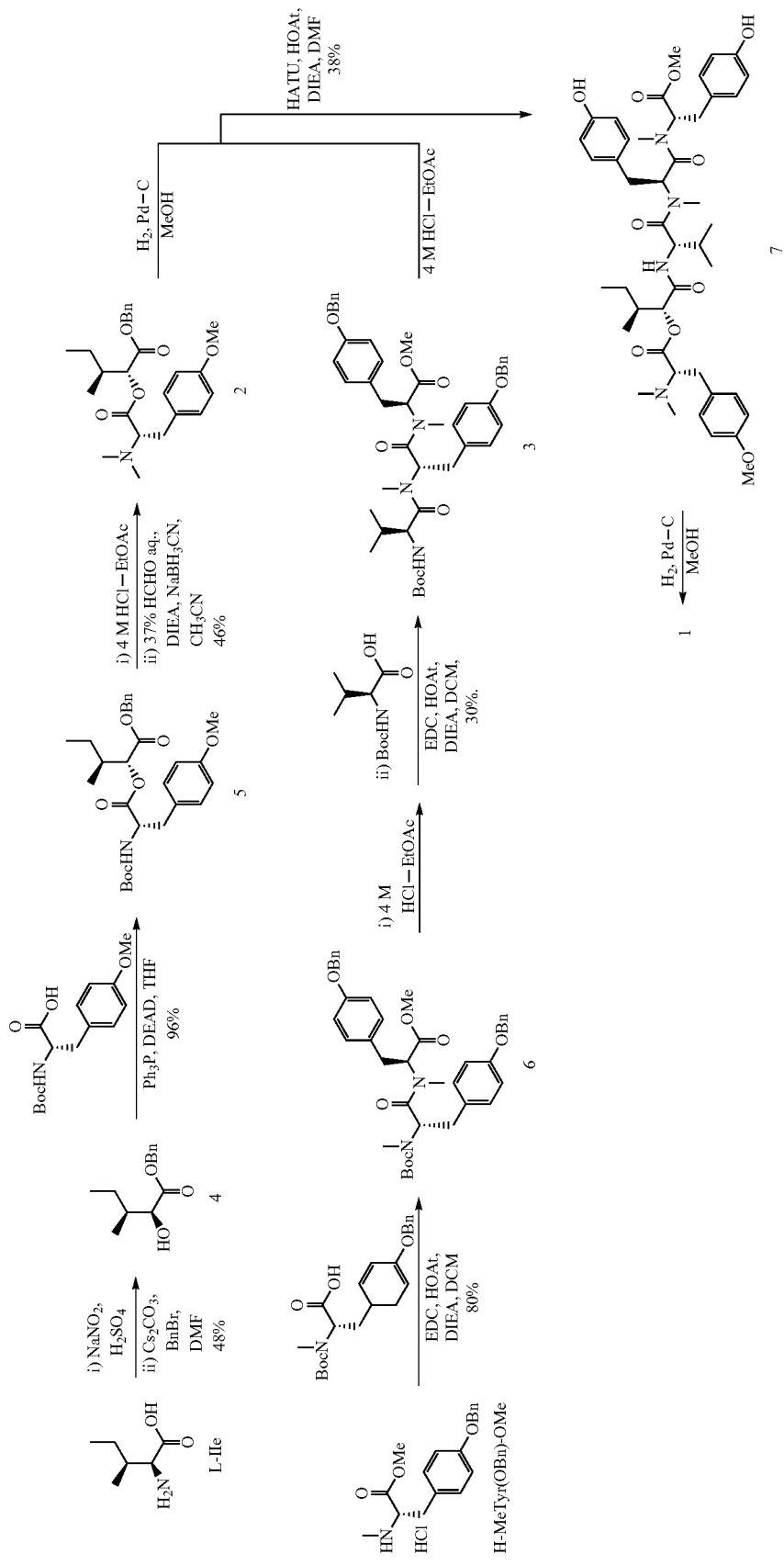

Synthesis of Compound 4

7.87 g (60 mmol) of 1-Ile was dissolved in ice-cold $H_2SO_4$ (40 mL, 2.5 mol/L). 6.21 g (90 mmol) of $NaNO_2$ was dissolved in 30 mL of $H_2O$, and was added to the above solution dropwise. The mixture was kept at 0° C. for 2 h, then warmed to rt and stirred for another 16 h. After extraction with EtOAc (200 mL×1, 100 mL×3), the combined organic phase was washed with brine (50 mL×1), dried over $Na_2SO_4$, and concentrated in vacuo, giving the α-hydroxy acid (4.50 g, 57%) as a colorless oil, which was used for next step without further purification.

To a solution of the α-hydroxy acid (2.64 g, 20 mmol) obtained above in a mixed solvent ($MeOH/H_2O$, 60 mL/15 mL), was added $Cs_2CO_3$ (3.91 g, 12 mmol) in 20 mL of $H_2O$. The mixture was concentrated to dryness after stirring for 5 min. The crude cesium salt was redissolved in 30 mL of DMF, followed by the addition of BnBr (2.85 mL, 24.0 mmol), and then stirred for 24 h.

After filtration and removal of the solvent, the residue was suspended in water (50 mL) and extracted with $Et_2O$ (150 mL×1, 50 mL×3). The extracts were combined, dried over $Na_2SO_4$, and concentrated in vacuo. The residue was purified by chromatography on silica gel to give the desired benzyl ester (4) as a colorless oil (3.45 g, 78%).

Compound 4. $[\alpha]_D^{20}$ −13.4 (c 1.58, MeOH); $^1$H NMR ($CDCl_3$, 400 MHz) δ 7.30-7.28 (m, 5H, ArH), 5.23 (d, J=12.2 Hz, 1H, PhCHaHb), 5.17 (d, J=12.2 Hz, 1H, PhCHaHb), 4.11 (dd, J=3.2, 1.6 Hz, 1H, H-2), 2.79 (brs, 1H, OH), 1.88-1.75 (m, 1H, H-3), 1.35-1.30 (m, 1H, H-4a), 1.27-1.16 (m, 1H, H-4b), 0.96 (d, J=6.9 Hz, 3H, $CH_3$), 0.84 (t, J=8.2 Hz, 3H, $CH_3$); $^{13}$C NMR ($CDCl_3$, 100 MHz) δ 175.0, 135.4, 128.8, 128.7, 128.6, 75.0, 67.3, 39.3, 23.8, 15.6, 11.9; ESI-MS (m/z) 245.3 [M+Na]$^+$; HRESIMS $C_{13}H_{18}O_3Na$ calcd 245.1148 [M+Na]$^+$, found 245.1155.

Synthesis of Compound 5

Boc-Tyr(OMe)-OH (708.7 mg, 2.4 mmol), alcohol 4 (444.6 mg, 2.0 mmol), and $Ph_3P$ (786.9 mg, 3.0 mmol) were dissolved in 50 mL of dry THF. After cooling with an ice-water bath for 20 min, 1.40 mL (3.0 mmol) of DEAD (40% solution in toluene) was added dropwise to this mixture. After stirring at 0° C. for 1 h and then at rt for another 15 h, the solvent was removed in vacuo. The residue was purified by chromatography on silica gel, giving the desired compound (5) as a colorless oil (954.80 mg, 96%).

Compound 5. $[\alpha]_D^{20}$ +2.9 (c 0.51, MeOH); $^1$H NMR ($CDCl_3$, 400 MHz) δ 7.36-7.28 (m, 5H, ArH), 7.05 (d, J=8.6 Hz, 2H, Ar—H), 6.80 (d, J=8.5 Hz, 2H, Ar H), 5.18 (d, J=12.2 Hz, 1H, $C_6H_5C\underline{Ha}HbO$), 5.13 (d, J=12.2 Hz, 1H, $C_6H_5CHa\underline{Hb}O$), 5.01 (d, J=3.4 Hz, 1H), 4.93 (d, J=7.8 Hz, 1H), 4.61 (dd, J=13.8, 6.6 Hz, 1H, Tyr αH), 3.75 (s, 3H, $OCH_3$), 3.08 (dd, J=14.1, 6.1 Hz, 1H, p-MeO$C_6H_4$C$\underline{Ha}$Hb), 2.96 (dd, J=14.1, 6.6 Hz, 1H, p-MeO$C_6H_4$CHa$\underline{Hb}$), 1.97-1.93 (m, 1H, Hmp H-3), 1.39 (s, 9H, Boc), 1.34-1.28 (m, 1H, Hmp H-4a), 1.24-1.14 (m, 1H, Hmp H-4b), 0.866 (d, J=6.4 Hz, 3H, Hmp $CH_3$), 0.865 (t, J=7.0 Hz, 3H, Hmp $CH_3$); $^{13}$C NMR ($CDCl_3$, 100 MHz) δ 171.9, 169.5, 158.8, 155.1, 135.5, 130.5, 128.8, 128.6, 128.5, 128.1, 114.1, 80.0, 75.8, 67.2, 55.4, 54.8, 37.6, 36.8, 28.5, 26.0, 14.4, 11.8; ESI-MS (m/z) 522.4 [M+Na]$^+$; HRESIMS $C_{28}H_{37}NO_7Na$ calcd 522.2469 [M+Na]$^+$, found 522.2483.

Synthesis of Compound 2

499.6 mg (1.0 mmol) of compound 5 was treated with 4M HCl-EtOAc (5 mL) for 1 h. After concentration to dryness, 5 mL of EtOAc was added and the solution was concentrated again. The residue was dissolved in $CH_3CN$ (5 mL), followed by the addition of DIEA (248 µL, 1.5 mmol) at 0° C., and then a 37% aqueous formaldehyde solution followed by AcOH (0.1 mL). After stirring for 1 h, $NaBH_3CN$ (188.5 mg, 3.0 mmol) was added carefully. AcOH was added periodically to maintain a pH of 5-7, and the mixture was stirred for another 24 h at rt. After concentration in vacuo, the residue was re-dissolved in EtOAc, washed with saturated $Na_2CO_3$ solution and brine, dried over $Na_2SO_4$, and then purified by column chromatography to give compound 2 as a colorless oil (46% Yield).

Compound 2. $[\alpha]_D^{20}$ +58.7 (c 1.46, MeOH); $^1$H NMR ($CDCl_3$, 400 MHz) δ 7.35-7.30 (m, 5H, ArH), 7.09 (d, J=8.4 Hz, 2H, ArH), 6.77 (d, J=8.5 Hz, 2H, ArH), 5.17 (d, J=12.2 Hz, 1H, $C_6HC\underline{Ha}HbO$), 5.11 (d, J=12.2 Hz, 1H, $C_6HCHa\underline{Hb}O$), 4.89 (d, J=3.2 Hz, 1H, Hmp αH), 3.74 (s, 3H, $OCH_3$), 3.46 (dd, J=9.7, 5.7 Hz, 1H, Tyr αH), 2.98 (dd, J=13.2, 10.0 Hz, 1H, p-MeO$C_6H_4$C$\underline{Ha}$Hb), 2.86 (dd, J=13.4, 5.6 Hz, 1H, p-MeO$C_6H_4$CHa$\underline{Hb}$), 2.39 (s, 6H, $NMe_2$), 1.86-1.78 (m, 1H, Hmp H-3), 1.01-0.84 (m, 2H, Hmp H-4), 0.75 (d, J=6.8 Hz, 3H, Hmp $CH_3$), 0.68 (t, J=7.3 Hz, 3H, Hmp $CH_3$); $^{13}$C NMR ($CDCl_3$, 100 MHz) δ 171.7, 170.0, 158.4, 135.5, 130.3, 130.0, 128.7, 128.6, 114.0, 74.7, 69.5, 67.1, 55.4, 41.8, 36.6, 36.2, 25.8, 14.4, 11.7; ESI-MS (m/z) 428.5 [M+H]$^+$; HRESIMS $C_{25}H_{34}NO_5$ calcd 428.2431 [M+H]$^+$, found 428.2438.

Synthesis of Compound 6

H-MeTyr(OBn)-OMe hydrochloride (1007.5 mg, 3.0 mmol) and 1079.0 mg (2.8 mmol) of Boc-MeTyr(OBn)-OH were dissolved in 60 mL of iced-cold DCM. EDC (644.0 mg, 3.36 mmol), HOAt (457.0 mg, 3.36 mmol) and DIEA (926 µL, 5.6 mmol) were added, respectively. The mixture was stirred at 0° C. for 2 h, and then at rt for another 16 h before being diluted with 200 mL of EtOAc. The organic phase was washed with 1 mol/L HCl (20 mL×3), saturated $NaHCO_3$ (20 mL×3), brine (20 mL×3), dried over $Na_2SO_4$, and concentrated in vacuo. The residue was purified by column chromatography to give the desired dipeptide 6 (1500.7 mg, 80%) as a colorless oil.

Compound 6. $[\alpha]_D^{20}$ −103.2 (c 0.50, MeOH); $^1$H NMR ($CDCl_3$, 400 MHz, mixture of rotamers) δ 7.38-7.27 (m, 10H, ArH), 7.17-7.02 (m, 2H, ArH), 6.88-6.77 (m, 6H, ArH), 5.17-5.06 (m, 1H, Tyr αH), 5.03-4.96 (brd, overlapped, 4H, $C_6H_5CH_2O$×2), 4.72 (dd like overlapped, 1H, Tyr αH), 3.72, 3.702, 3.695, 3.688 (each s, total 3H, $CO_2CH_3$), 3.33-3.19, 3.02-2.96, 2.92-2.89, 2.73-2.72 (dd like overlapped, total 4H, p-BnO$C_6H_4CH_2$×2), 2.93, 2.85, 2.76, 2.68, 2.65, 2.60, 2.39, 2.28 (each s, total 6H, N—$CH_3$×2), 1.32, 1.27, 1.17, 1.14 (each s, total 9H, Boc); $^{13}$C NMR (100 MHz, $CDCl_3$, mixture of rotamers) δ 171.1, 170.6, 157.7, 157.6, 155.3, 137.4, 137.2, 130.8, 130.7, 129.9, 128.8, 128.7, 128.13, 128.07, 127.6, 127.5, 115.3, 114.8, 80.5, 70.2, 58.6, 56.5, 52.5, 34.5, 33.7, 32.7, 29.3, 28.4; ESI-MS (m/z) 689.5 [M+Na]$^+$; HRESIMS $C_{40}H_{46}N_2O_7Na$ calcd 689.3197 [M+Na]$^+$, found 689.3197.

Synthesis of Compound 3

Dipeptide 6 (641.7 mg, 0.96 mmol) was treated with 4M HCl-EtOAc (5 mL) for 1 h. After concentration to dryness, 5 mL of EtOAc was added and the solution concentrated again. The resulting amine hydrochloride and Boc-Val-OH (209.0 mg, 0.96 mmol) were dissolved in 15 mL of dry DCM and cooled with an ice-water bath. EDC (220.8 mg, 1.15 mmol), HOAt (156.8 mg, 1.15 mmol) and DIEA (317 µL, 1.9 mmol) were added, respectively. The mixture was stirred at this temperature for 2 h and at rt for another 16 h. Then the mixture was diluted with 150 mL of EtOAc, washed with 1 mol/L HCl (20 mL×3), saturated $NaHCO_3$ (20 mL×3), brine (20 mL×3), dried over $Na_2SO_4$, and concentrated in vacuo. The residue was purified by column chromatography to give the desired tripeptide 3 (220.9 mg, 30%) as a white foam.

Compound 3. $[\alpha]_D^{20}$ −165.2 (c 0.25, MeOH); $^1$H NMR (CDCl$_3$, 400 MHz, mixture of rotamers) δ 7.38-7.27 (m, 10H, ArH), 7.15 (d, J=8.4 Hz, 2H, ArH), 6.87 (d, J=8.4 Hz, 2H, ArH), 6.80-6.75 (m, 4H, ArH), 5.49 (t like, J=7.6, 6.6 Hz, 1H), 5.04-4.94 (m, 4H, C$_6$H$_5$CH$_2$O×2), 4.83-4.77 (m, 1H), 4.30 (dd, J=9.1, 4.9 Hz, 1H), 3.67 (s, 3H, CO$_2$CH$_3$), 3.27-3.17 (m, 2H, ArCH$_2$), 2.96-2.81 (m, 2H, ArCH$_2$), 2.61 (s, 3H, N—CH$_3$), 2.59 (s, 3H, N—CH$_3$), 1.78-1.69 (m, 1H, Val βH), 1.41 (s, 9H, Boc), 0.89 (d, J=6.6 Hz, 3H, Val CH$_3$), 0.77 (d, J=6.3 Hz, 3H, Val CH$_3$); $^{13}$C NMR (CDCl$_3$, 100 MHz, mixture of rotamers) δ 171.9, 170.9, 169.9, 158.1, 157.8, 155.9, 137.3, 137.0, 130.8, 130.0, 129.4, 128.8, 128.7, 128.2, 128.0, 127.7, 127.62, 127.59, 115.1, 114.8, 79.7, 70.2, 70.1, 60.6, 55.2, 53.4, 52.5, 34.3, 33.6, 31.1, 30.7, 30.4, 28.5, 20.1, 16.8; ESI-MS (m/z) 788.5 [M+Na]$^+$; HRESIMS C$_{45}$H$_{55}$N$_3$O$_8$Na calcd 788.3881 [M+Na]$^+$, found 788.3881.

Synthesis of Compound 1

Hydrogenation of 2 (50.0 mg, 0.12 mmol) was carried out in MeOH (5 mL) in the presence of a catalytic amount of Pd—C(10%) under hydrogen at rt. Pd—C was removed by filtration through celite and concentrated under reduced pressure to give the corresponding carboxylic acid, which was used directly in the next step.

The tripeptide 3 (89.6 mg, 0.12 mmol) was treated with 4M HCl-EtOAc (3 mL) for 1 h and the solution was concentrated under reduced pressure. The residue was re-dissolved in 5 mL of EtOAc and concentrated again, giving the corresponding amine as its hydrochloride salt.

The carboxylic acid and the amine (as its hydrochloride) obtained above were dissolved in DMF (5 mL) and cooled with an ice-water bath. HATU (54.0 mg, 0.14 mmol), HOAt (19.0 mg, 0.14 mmol), and DIEA (78 μL, 0.47 mmol) were added, respectively. The mixture was stirred at 0° C. for 1 h, and then at rt for another 16 h. The solvent was diluted with EtOAc (100 mL), washed with water (10 mL×3), 1 mol/L HCl (10 mL×3), saturated NaHCO$_3$ (10 mL×3), brine (10 mL×3), dried over Na$_2$SO$_4$, and concentrated in vacuo. The residue was purified by preparative TLC to give the crude fully protected pentapeptide 7 {43.6 mg, 38%; ESI-MS (m/z) 985.6 [M+H]$^+$}, which was used for next step without further characterization.

Compound 7 (48.0 mg, 0.049 mmol) was hydrogenated for 2 h in the presence of catalytic palladium on charcoal (10 wt %), giving the crude pentapeptide 1, which was purified by semi-preparative RP-HPLC (Phenomenex Luna 5 μm, 250×10 mm, 2.0 mL/min, gradient elution with 75% to 100% MeOH—H$_2$O over 30 min) to give the pure compound 1 (24.9 mg, 63%).

Compound 1. $[\alpha]_D^{20}$ −101.8 (c 0.22, MeOH); $^1$H NMR (DMSO-d$_6$, 400 MHz) 9.22 (brs, 2H, Tyr OH×2), 8.09 (d, J=8.9 Hz, 1H, Val NH), 7.10 (d, J=8.5 Hz, 2H, ArH), 6.99 (d, J=8.4 Hz, 2H, ArH), 6.79 (d, J=8.6 Hz, 2H, ArH), 6.68 (d, J=8.4 Hz, 2H, ArH), 6.57 (d, J=8.4 Hz, 2H, ArH), 6.51 (d, J=8.4 Hz, 2H, ArH), 5.27 (dd, J=9.8, 3.8 Hz, 1H, NMeTyr-1 αH), 4.81 (d, J=3.7 Hz, 1H, Hmp αH), 4.54 (dd, J=11.4, 4.2 Hz, 1H, NMeTyr-2 αH), 4.45 (t, J=8.4 Hz, 1H, Val αH), 3.69 (s, 3H, N,N diMeTyr(OMe) O-Me), 3.59 (s, 3H, Hmp CO$_2$CH$_3$), 3.46 (dd, J=8.8, 6.6 Hz, 1H, N,N diMeTyr(OMe) αH), 3.09 (dd, J=12.4, 10.5 Hz, 1H, NMeTyr-1H-3a), 2.98 (dd, J=13.9, 4.1 Hz, 1H, NMeTyr-2H-3a), 2.87-2.80 (dd, overlapped, 2H, ArCH$_2$), 2.76 (dd, J=13.7, 6.5 Hz, 1H, ArCHaHb), 2.70 (s, 3H, NMeTyr-1 N-Me), 2.44 (s, 3H, NMeTyr-2 N-Me), 2.34 (dd, J=13.2, 3.7 Hz, 1H, NMeTyr-1H-3b), 2.29 (s, 6H, NMe$_2$), 1.94-1.85 (m, 1H, Val H-3), 1.76-1.68 (m, 1H, Hmp H-3), 1.08-0.98 (m, 1H, Hmp H-4a), 0.96-0.86 (m, 1H, Hmp H-4b), 0.78 (br d, J=6.6 Hz, 6H, Val CH$_3$×2), 0.69 (t like, J=7.2, 7.0 Hz, 6H, Hmp CH$_3$×2); $^{13}$C NMR (DMSO-d$_6$, 100 MHz) 170.62, 170.58, 170.4, 168.7, 168.5, 157.8, 155.82, 155.78, 130.2, 130.0, 129.80, 129.76, 127.8, 127.2, 115.01, 114.97, 113.6, 75.1, 68.3, 61.2, 54.9, 53.7, 51.7, 41.1, 36.3, 34.4, 33.8, 32.5, 30.1, 29.6, 25.3, 19.3, 17.8, 13.8, 11.3; ESI-MS (m/z) 805.7 [M+H]$^+$; HRESIMS C$_{44}$H$_{61}$N$_4$O$_{10}$ calcd 805.4382 [M+H]$^+$, found 805.4371.

The following compounds can be prepared using a similar procedure as those described in Examples 2 and 3:

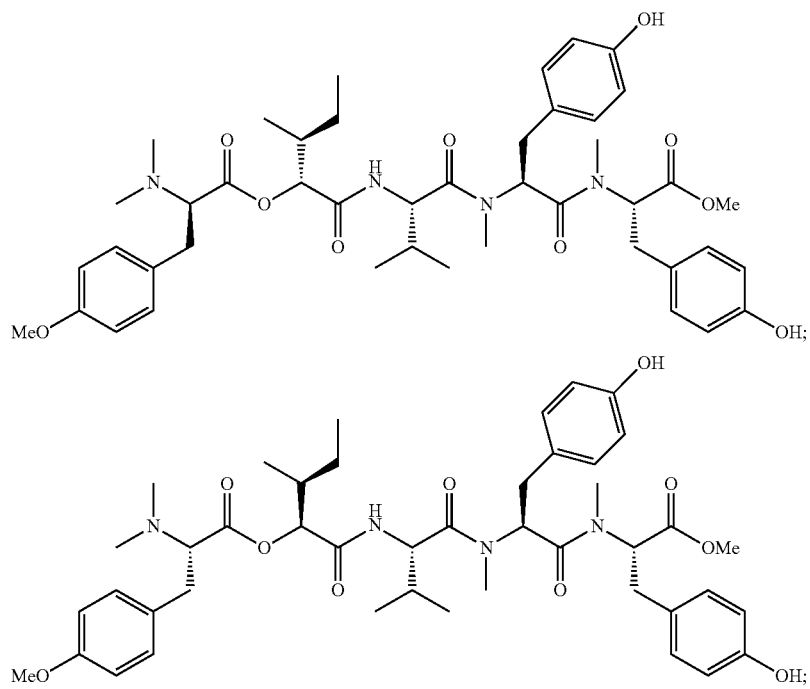

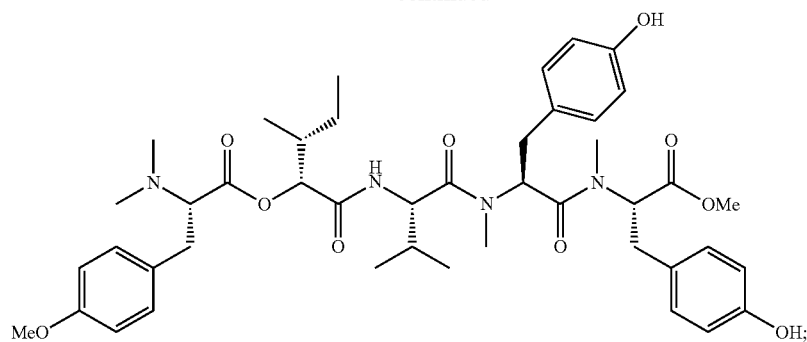
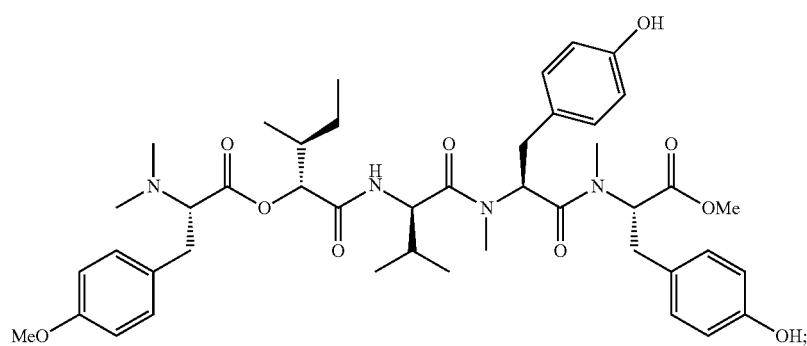
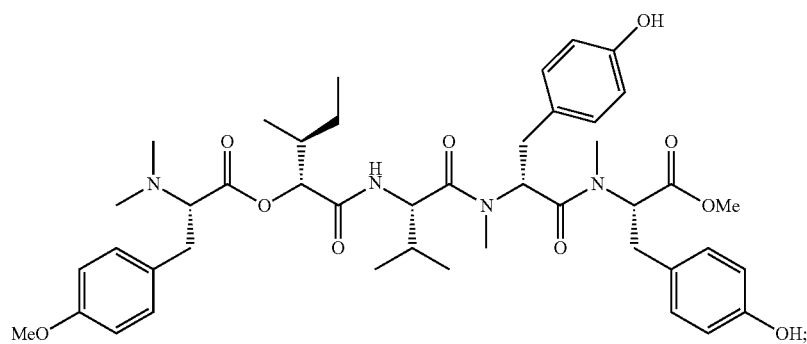
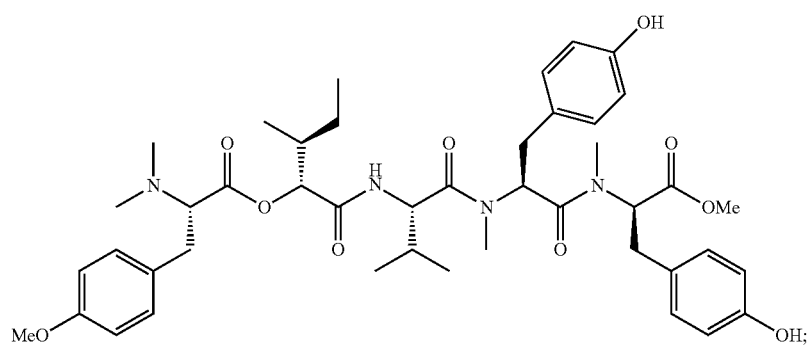
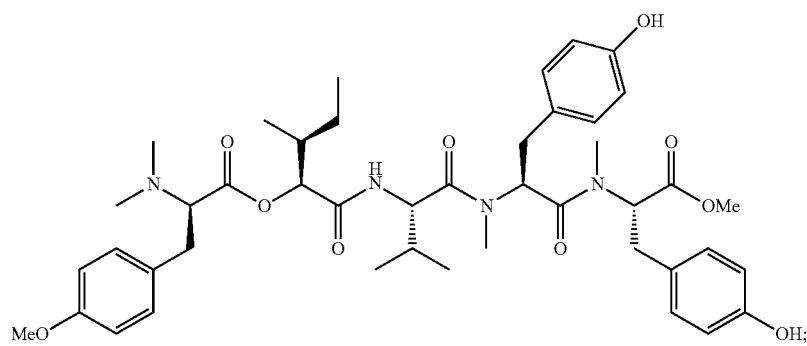

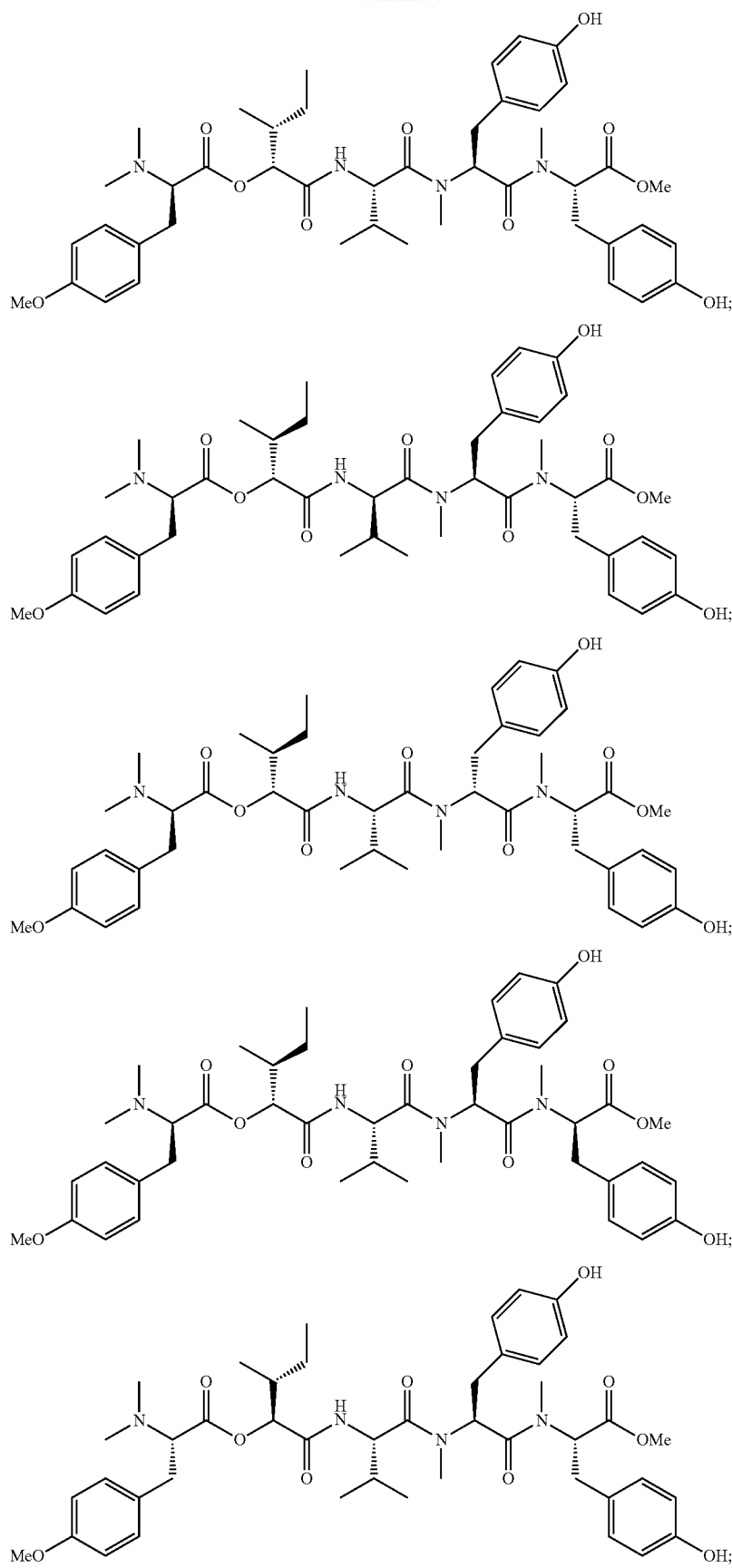

-continued
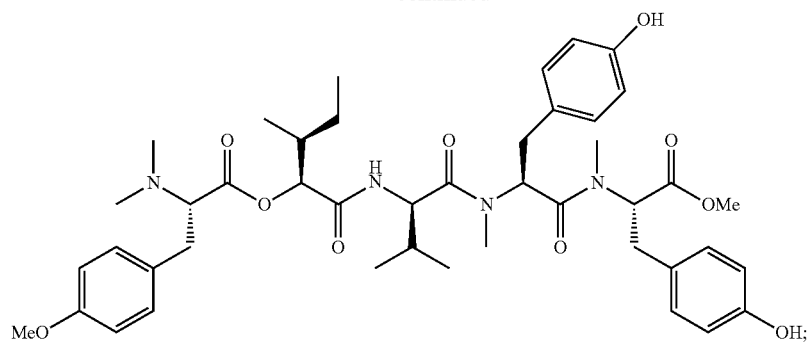
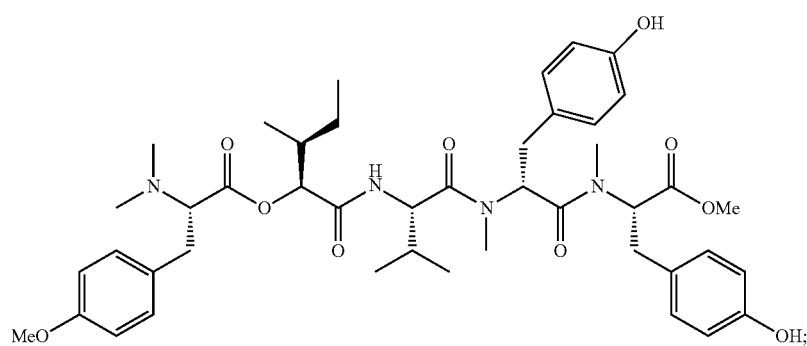
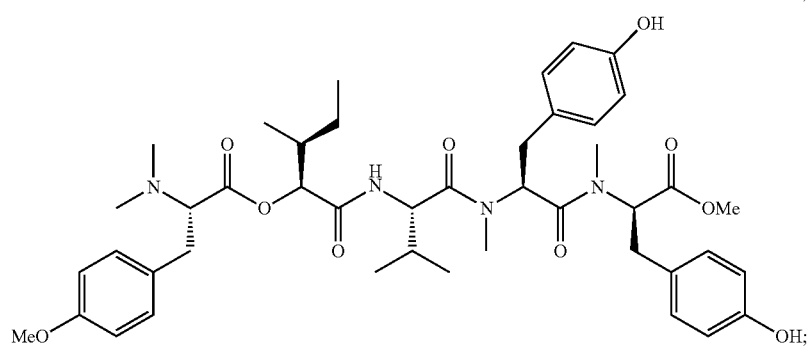
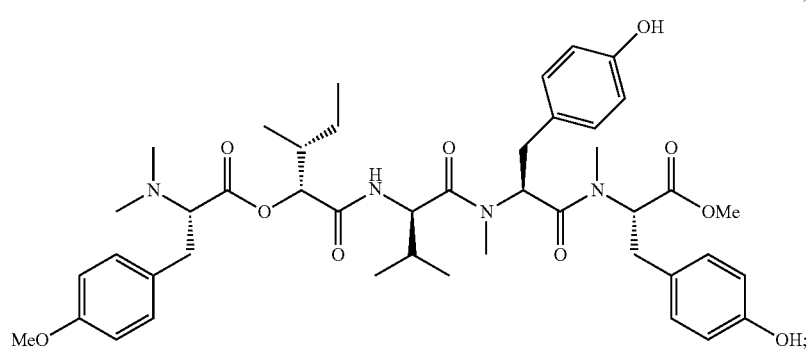
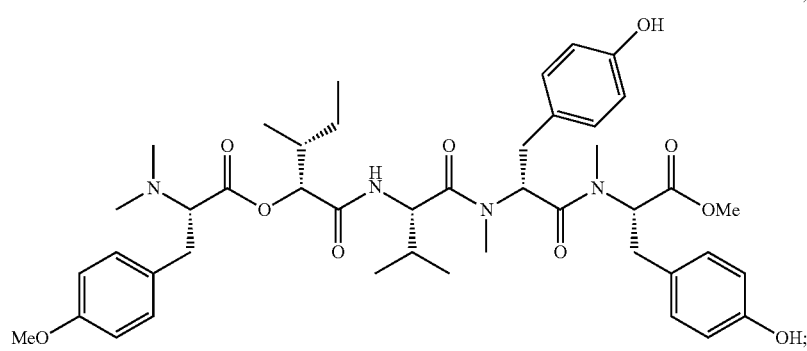

-continued
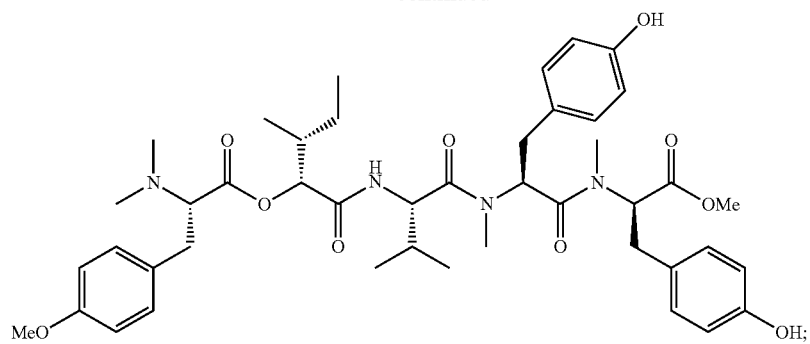
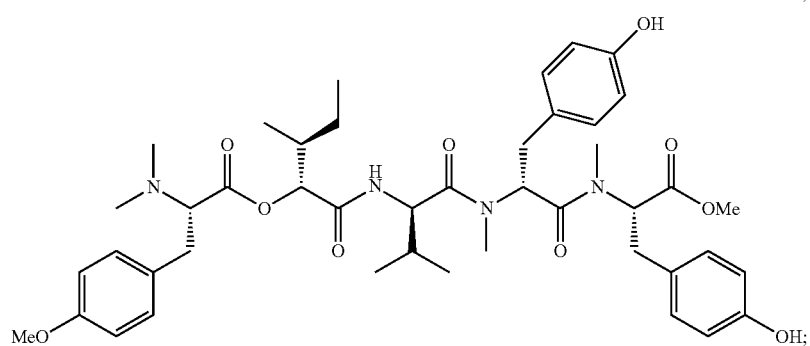
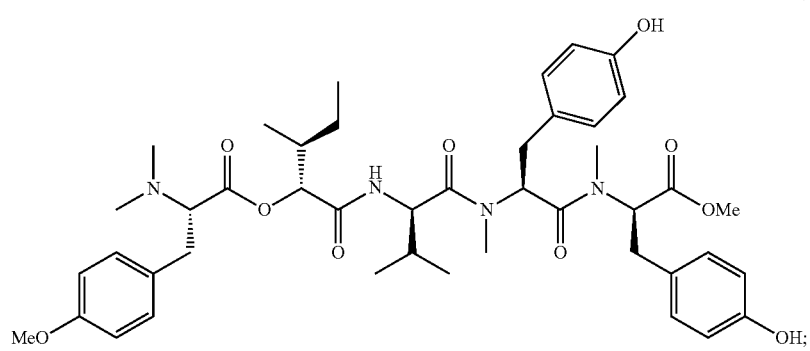
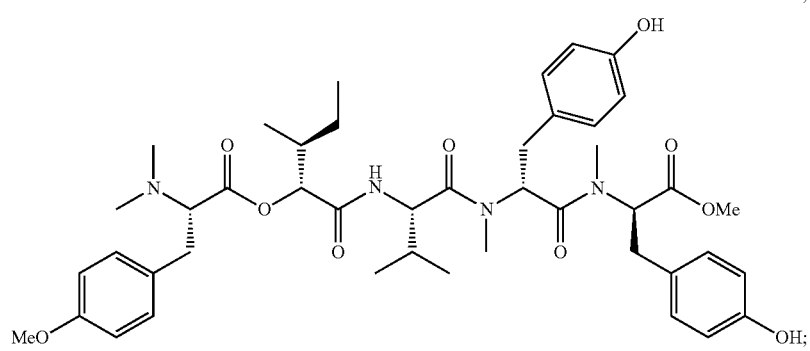
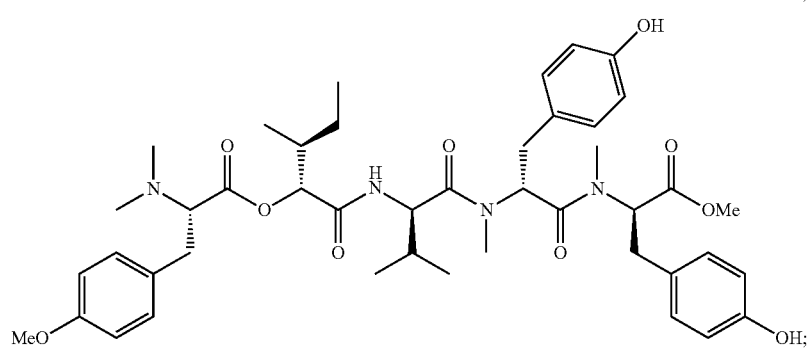

-continued
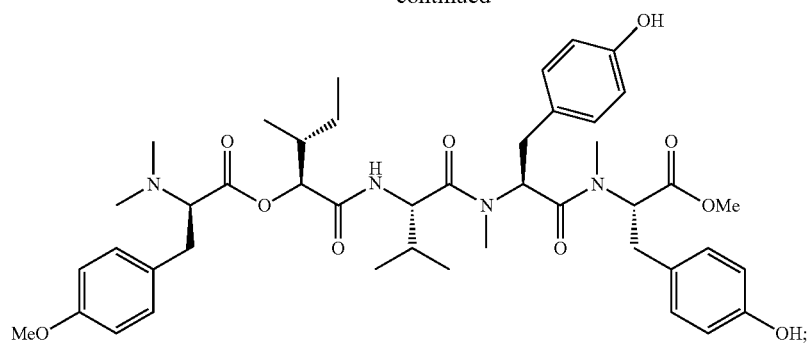
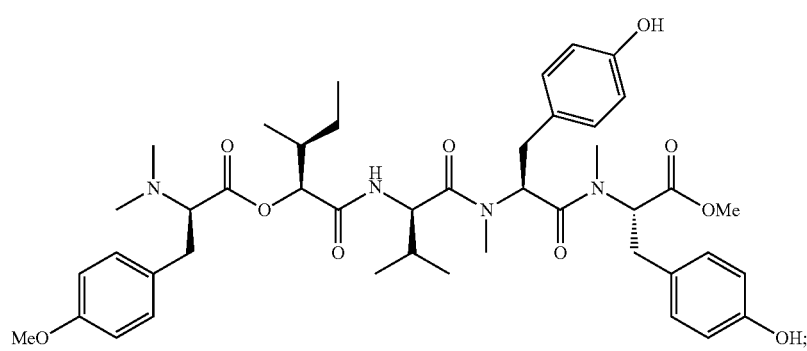
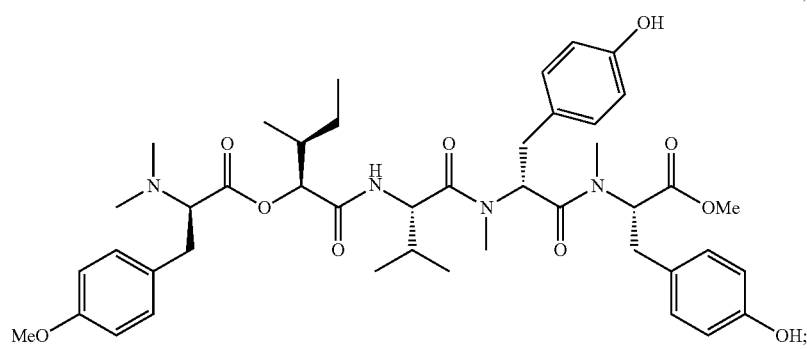
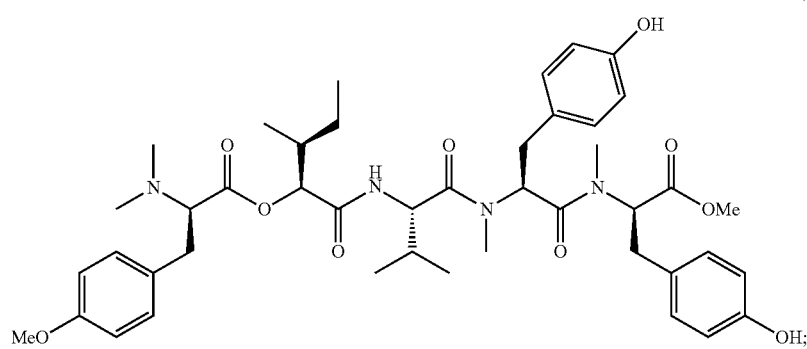
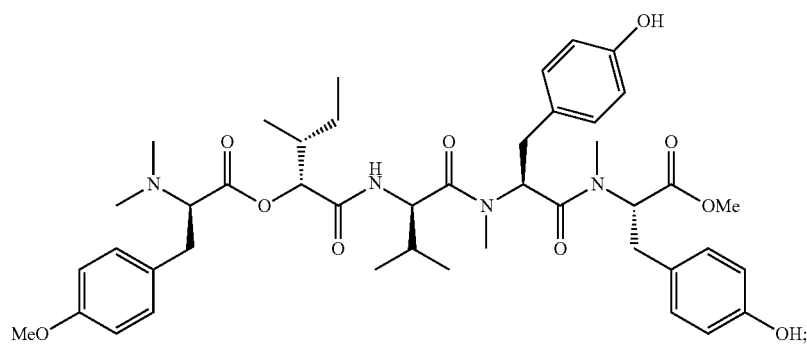

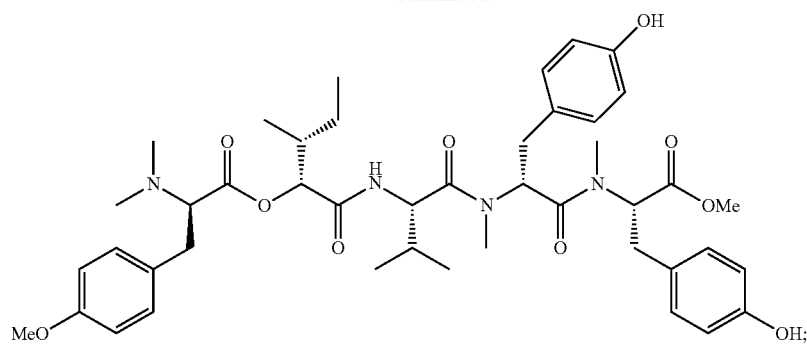
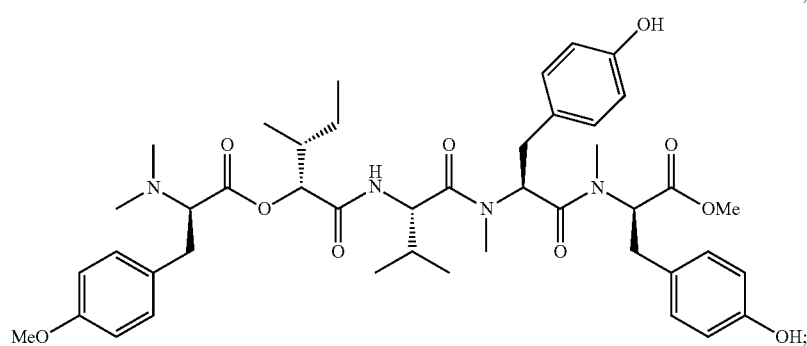
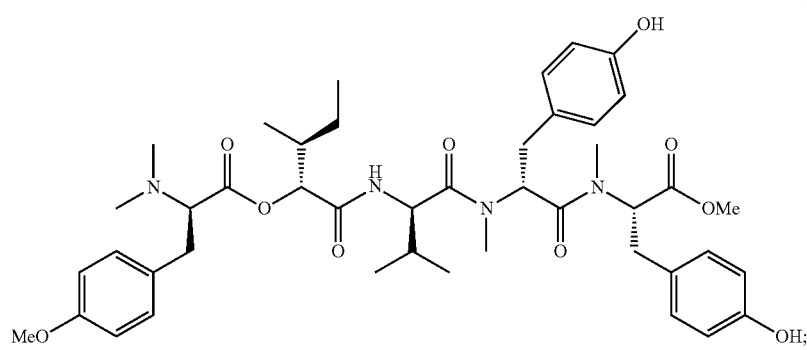
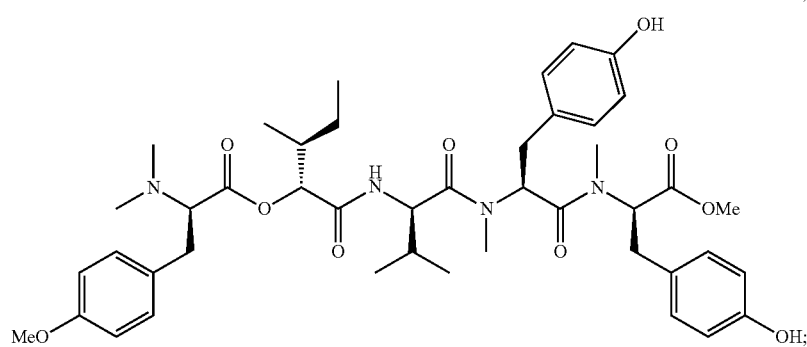
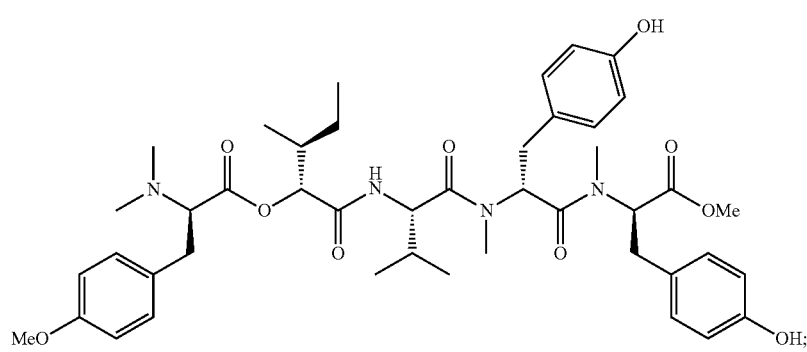

-continued
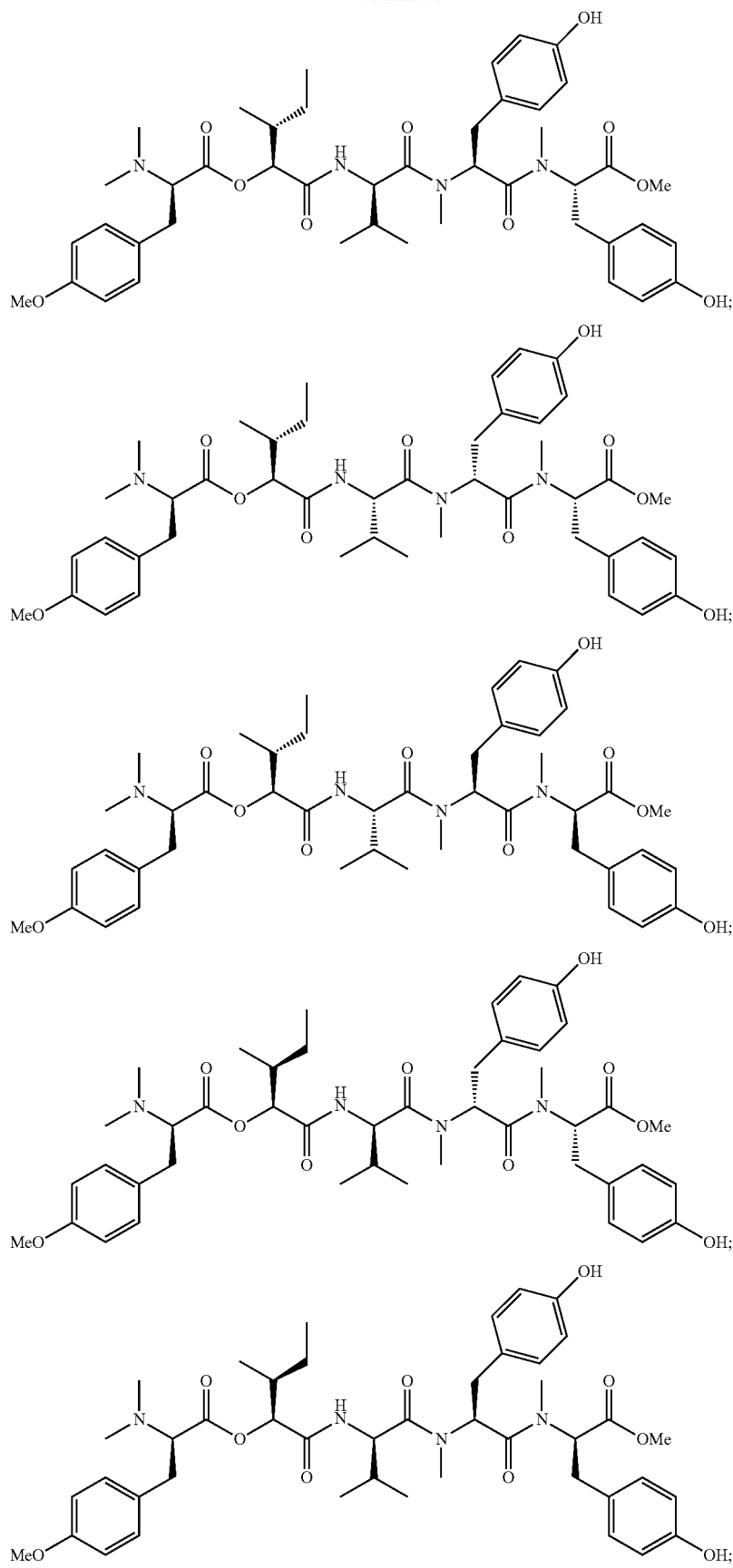

-continued
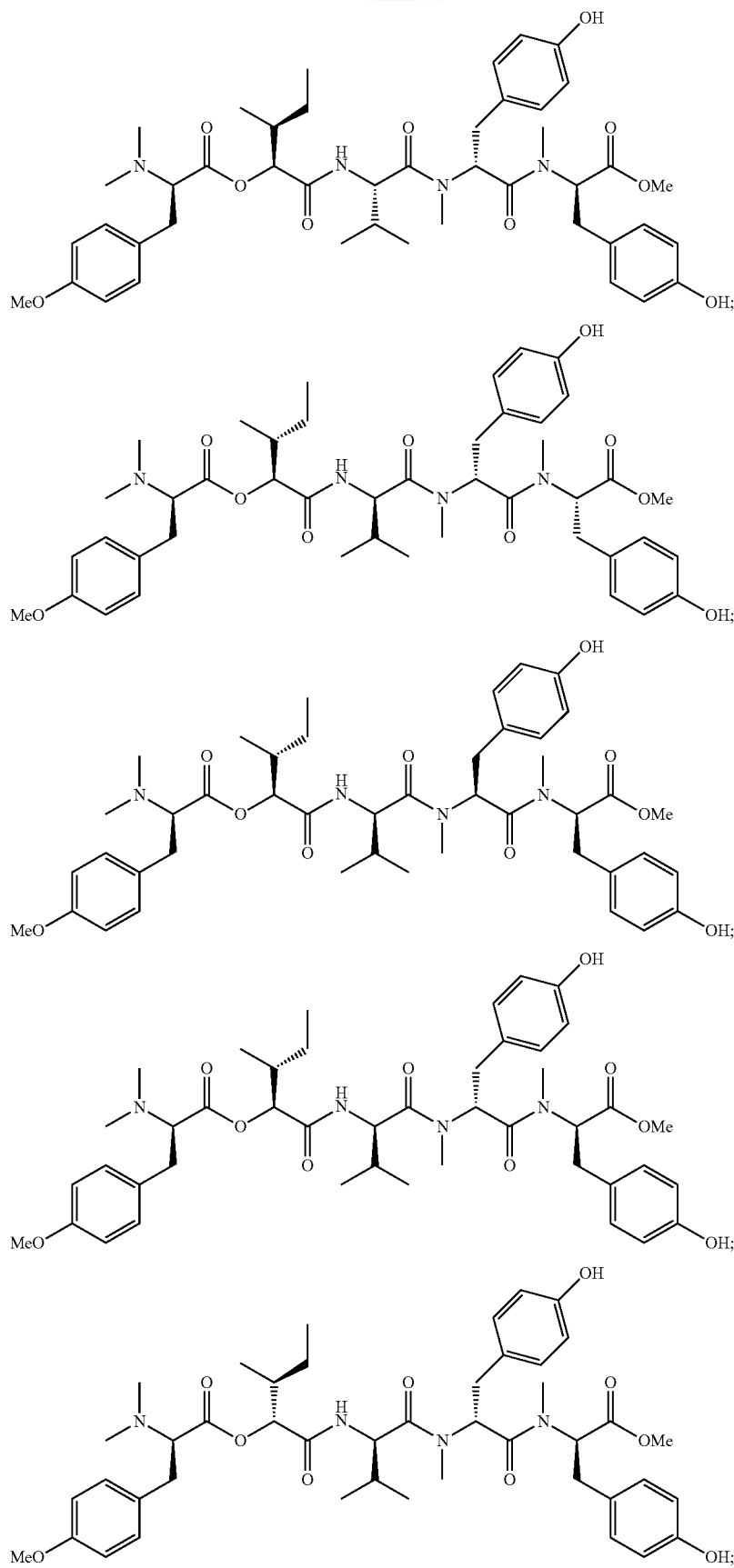

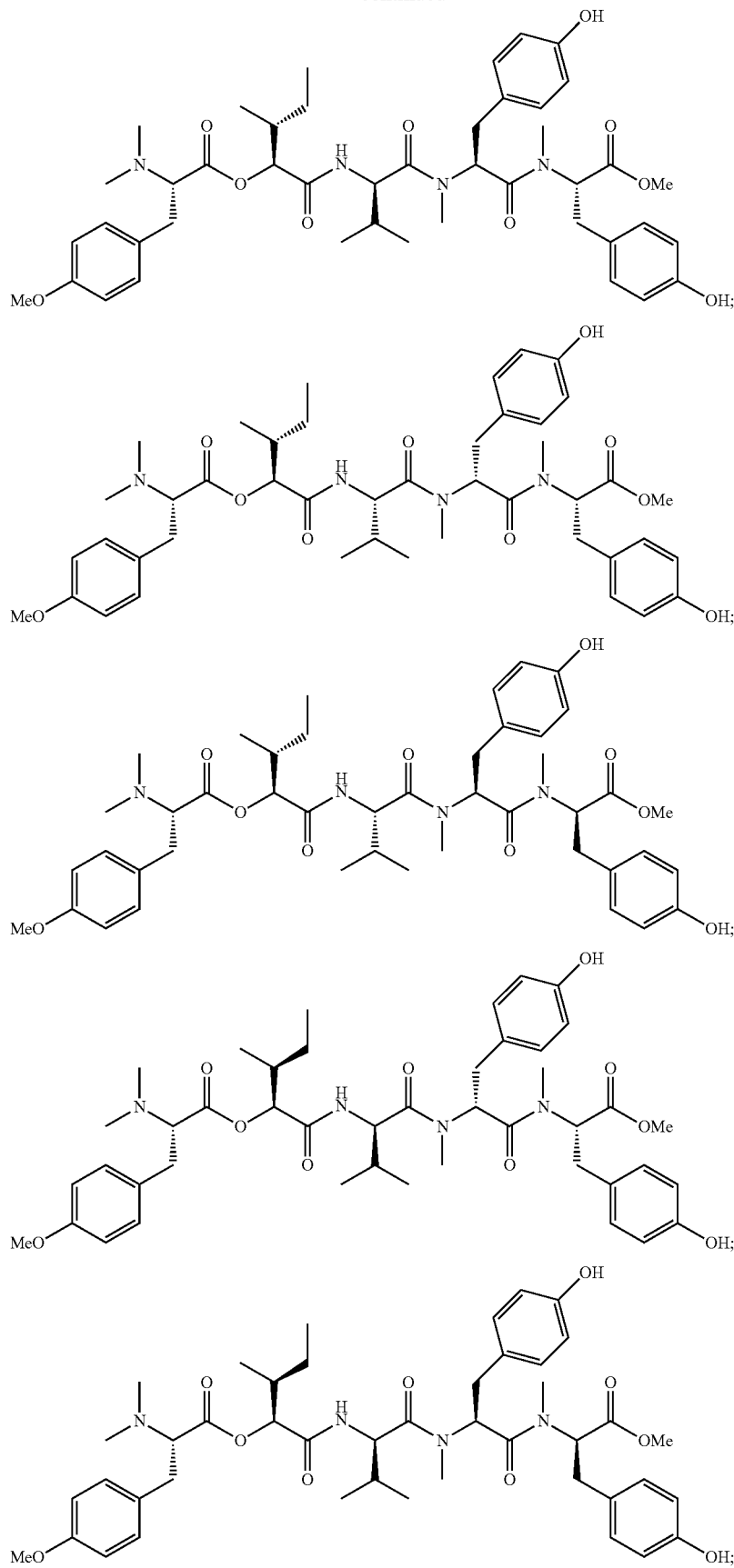

-continued
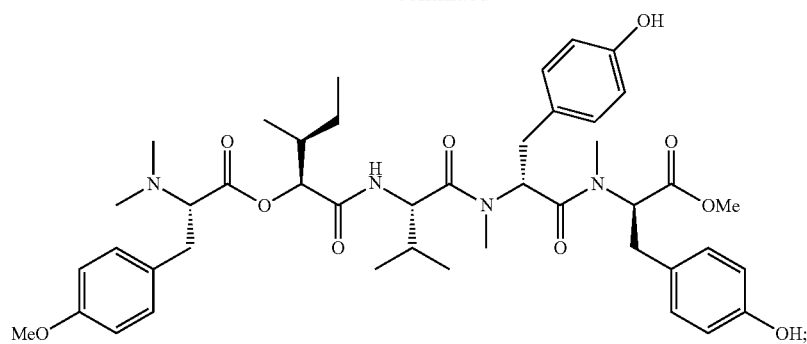
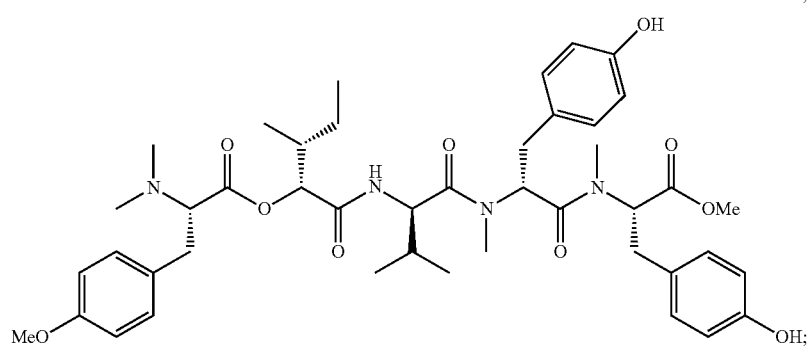
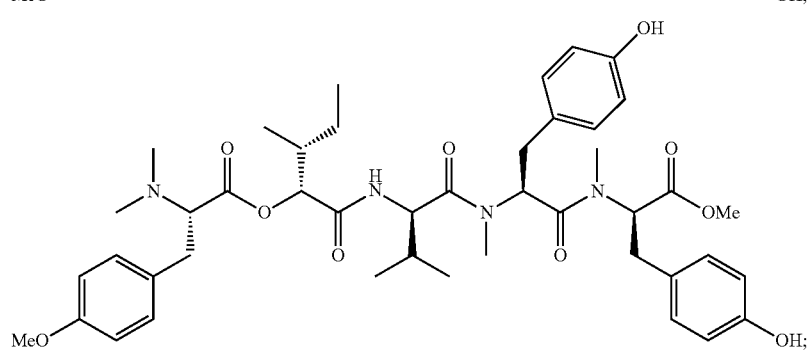
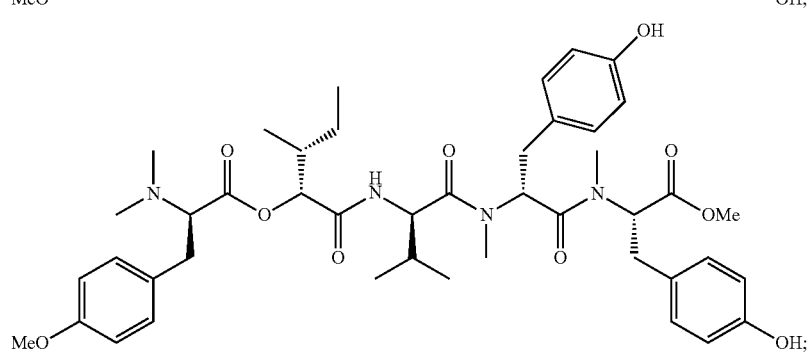
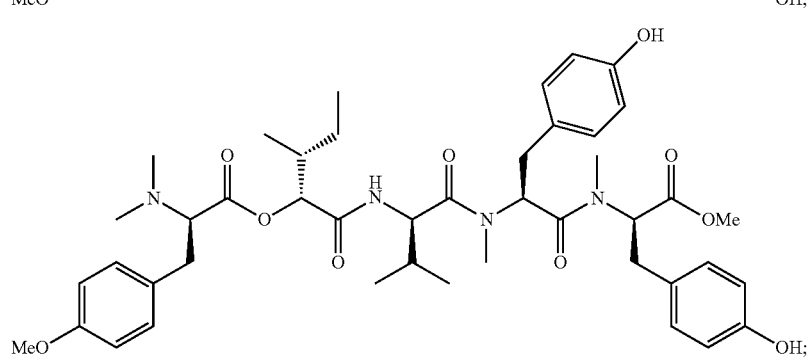

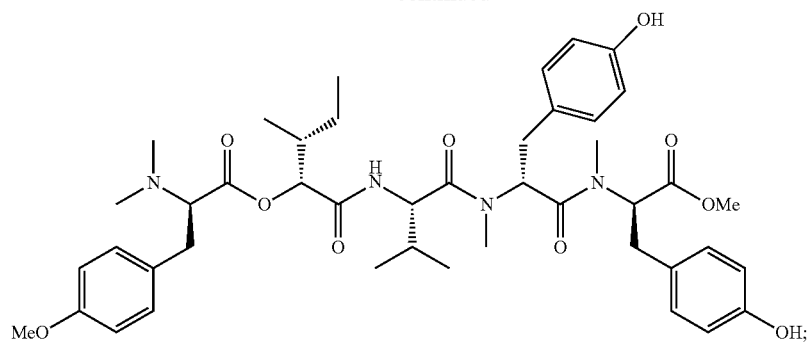
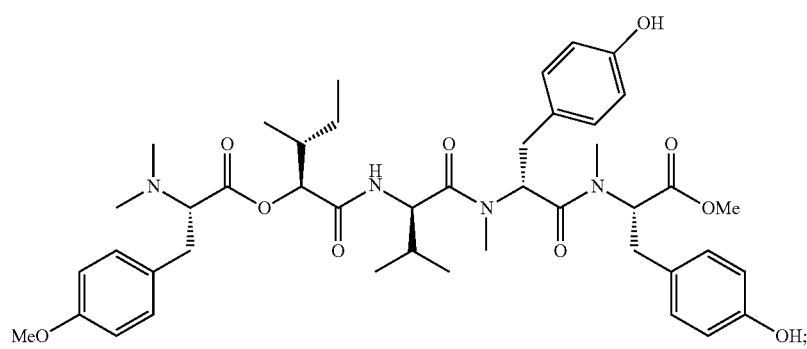
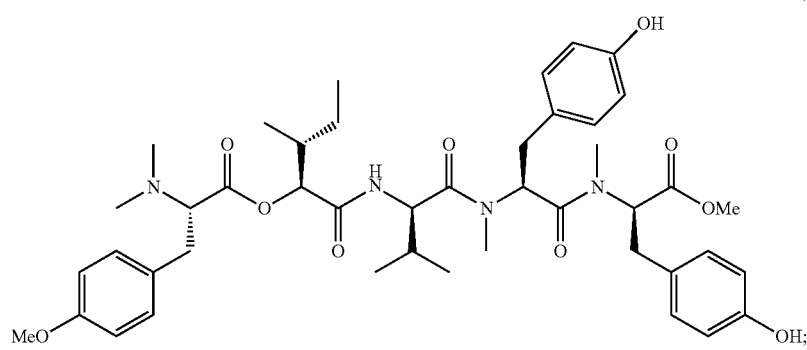
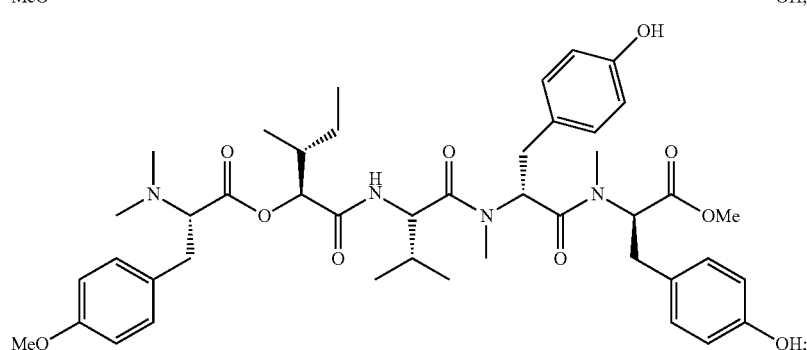
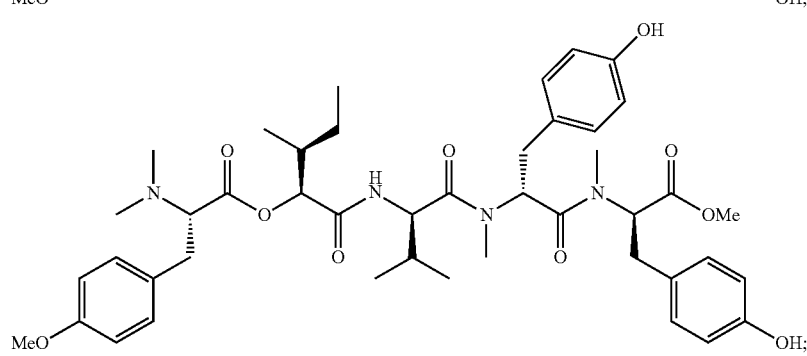

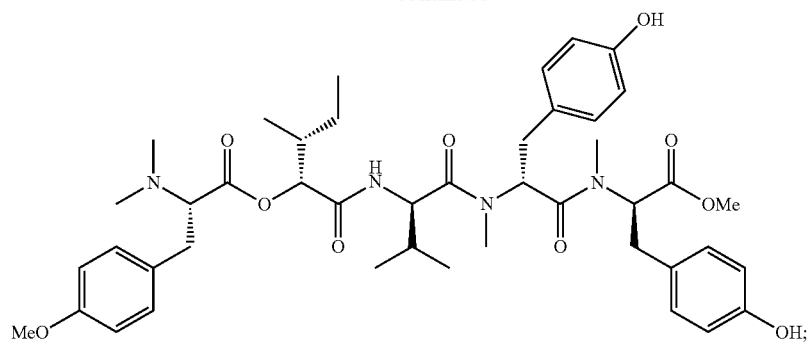
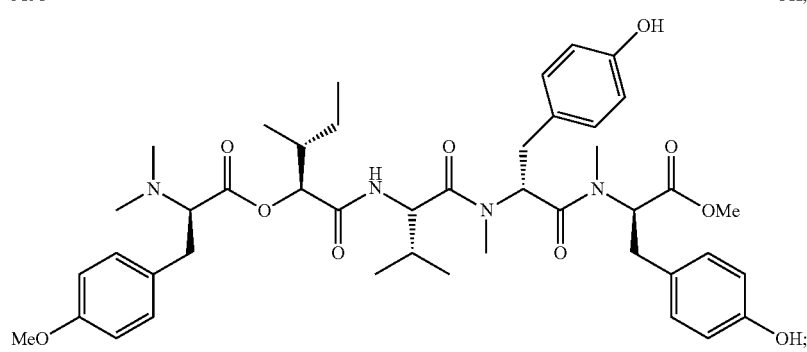
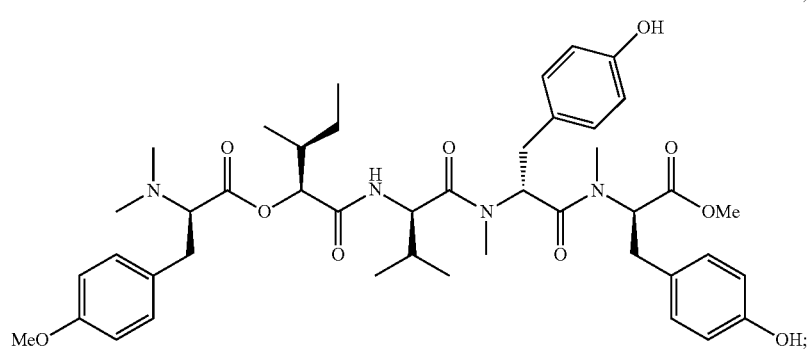
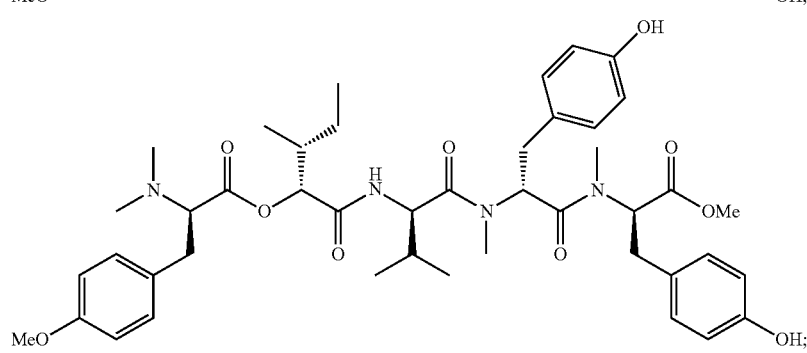
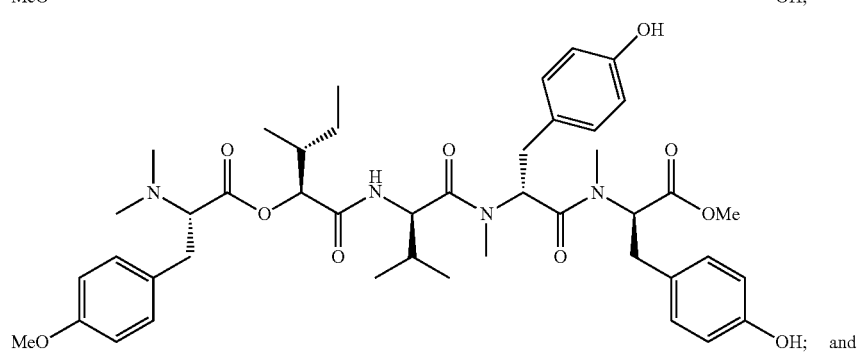

-continued

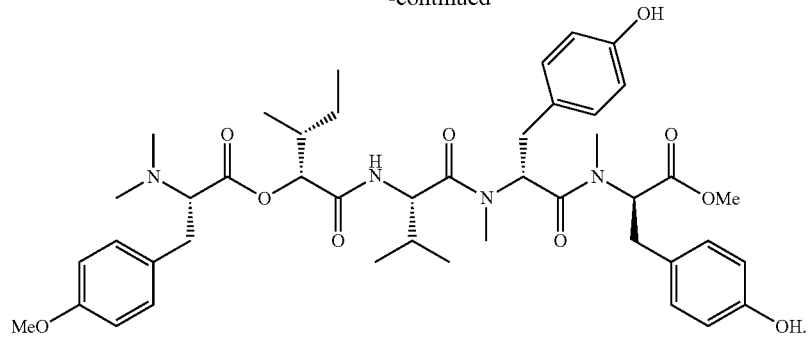

Example 4: Determination of Absolute Configuration

A sample of compound 1 (100 μg) was hydrolyzed with 6 N HCl (0.35 ml) at 110° C. for 20 h. The hydrolyzate was concentrated to dryness, reconstituted in 100 μL of $H_2O$, and then analyzed by chiral HPLC [Chirobiotic TAG (250×4.6 mm), Supelco; solvent: MeOH:10 mM $NH_4OAc$ (40:60, pH 5.48); flow rate 0.5 mL/min; detection by ESIMS in positive ion mode (MRM scan)]. N-Me-L-Tyr, N,N-diMe-L-Tyr (OMe) and Val eluted at $t_R$ 18.5, 190 and 8.2 min, respectively. The retention times ($t_R$, min; MRM ion pair, parent→product) of the authentic amino acids were as follows: N-Me-L-Tyr (19.1; 196.3→77), N-Me-D-Tyr (37.6), N,N-diMe-L-Tyr(OMe) (190.0; 224.3→179.3), N,N-diMe-L-Tyr (OMe) (130.0), L-Val (8.2; 118.3→72), D-Val (15.1). The compound-dependent MS parameters were as follows: N-Me-Tyr: DP 40, EP 5, CE 65, CXP 3, CEP 10; N,N-diMe-Tyr(OMe): DP 38, EP 8, CE 19, CXP 3, CEP 17; Val: DP 135, EP 9, CE 15, CXP 2, CEP 106. The source and gas-dependent MS parameters were as follows: CUR 30, CAD high, IS 4500, TEM 450, GS140, GS2 40.

Hmpa in the hydrolyzate of 1 was detected in negative ion mode [column, Chirobiotic TAG (4.6×250 mm), Supelco; solvent, MeOH-10 mM NH4OAc (40:60, pH 5.33); flow rate, 0.5 mL/min; detection by ESIMS in negative ion mode (MRM scan)]. The MS parameters used were as follows: DP −30, EP −5.0, CE −18, CXP −8, CEP −130, CUR 30, CAD high, IS −4500, TEM 450, GS1 40, and GS2 40. (2R,3S)-Hmpa from the hydrolyzate eluted at $t_R$ 6.4 min. The retention times ($t_R$, min; MRM ion pair, parent→product) of the authentic standards were as follows: (2S,3R)-Hmpa (6.73; 131→85), (2S,3S)-Hmpa (6.9; 131→85), (2R,3S)-Hmpa (7.2; 131→85), and (2R,3R)-Hmpa (7.7; 131→85). The hydrolyzate was examined under different HPLC conditions in order to confirm this assignment [column, Chiralpak MA (+) (4.6×50 mm), Daicel Chemical Industries, Ltd.; solvent, 2 mM $CuSO_4$—$CH_3CN$ (90:10); flow rate, 1.0 mL/min; detection by UV absorption at 254 nm]. (2R,3S)-Hmpa from the hydrolysate eluted at $t_R$ 15.4 min. The retention times ($t_R$, min) of the authentic standards were as follows: (2R,3S)-Hmpa (11.0), (2R,3R)-Hmpa (14.5), (2S, 3R)-Hmpa (18.0), and (2S,3S)-Hmpa (22.0).

Example 5: Cell Culture

Human keratinocyte HaCaT cells and human colon cancer HCT116 cells were cultured in Dulbecco's modified Eagle's medium (DMEM) supplemented with 10% fetal bovine serum at 37° C. humidified air and 5% $CO_2$. Human normal colon (CCD-18Co) cells (ATCC) were cultured in Eagle's minimal essential medium (EMEM) supplemented with 10% fetal bovine serum at 37° C. humidified air and 5% CO2. Human Umbilical Vein Endothelial Cells (HUVEC, cat #CC-2519, Lonza) were cultured in EGM (Lonza cat #CC-3124) under the same condition.

Example 6: Cell Viability Assay (MTT)

Cells were seeded in a 96-well clear bottom plate, and 24 h later cells were treated with various concentrations of the apratyramide or solvent control (DMSO). After 48 h of incubation, cell viability was detected using MTT according to the manufacturer's instructions (Promega, Madison, Wis.). Nonlinear regression analysis was carried out using GraphPad Prism software for $IC_{50}$ value calculations.

Example 7: Measurement of Human VEGF-A Secretion

HaCaT cells were seeded in a 96-well clear bottom plate. Cells were treated with various concentrations of apratyramide or solvent control (DMSO). After 24 h incubation, culture supernatants were collected for detection of VEGF-A using AlphaLISA kits (PerkinElmer, Waltham, Mass.) following the manufacturer's instruction. Briefly, acceptor bead and anti-VEGF-A antibody were incubated with the supernatants for 60 min, donor beads were added later and incubated for another 30 min. Signal was detected using Envision (PerkinElmer). Levels of VEGF-A (pg/mL) were calculated using a standard curve and then normalized based on cell numbers.

Example 8: Immunoblot Analysis

HaCaT cells were seeded in 6-well clear bottom plate the day before treatment. The next day, cells were treated with 1 or solvent control (DMSO). 24 h later, whole cell lysates were collected using PhosphoSafe buffer (EMD Chemicals, Inc, Gibbstown, N.J.). Protein concentrations were measured with the BCA Protein Assay kit (Thermo Fisher Scientific, Rockford, Ill.). Lysates containing equal amounts of protein were separated by SDS polyacrylamide gel electrophoresis (4-12%), transferred to polyvinylidene difluoride membranes, probed with primary and secondary antibodies, and detected with the SuperSignal West Femto Maximum Sensitivity Substrate (Thermo Fisher Scientific). BIP, IRE1, β-actin and secondary anti-mouse and rabbit antibodies were from Cell Signaling Technology, Inc (Danvers, Mass.). ATF4 and ORP150 antibodies were obtained from Santa Cruz (Calif.).

Example 9: In Vitro Angiogenesis Assay

HaCaT cells were seeded in 12-well plates in complete growth medium the day before treatment. The next day, the medium was replaced with fresh medium followed by the treatment of 1 or solvent control. After 24 h or incubation, the conditioned medium was collected for the in vitro angiogenesis assay.

HUVECs (Lonza) were used at passage 4 for this assay. In vitro Angiogenesis Assay Kit (Chemicon) was used according to the manufacturer's recommendation. Briefly, an ice-cold mixture of ECMatrix was transferred into a precooled 96-well plate. After the matrix solution had solidified (>1 h incubation at 37° C., 10,000 cells were mixed with the CM or EGM with or without the presence of VEGF-A protein, 100 ng/mL and plated into each well. After incubation at 37° C. for 14 h, images were captured for each well using a Nikon inverted microscope equipped with NIS-Elements software. Branch point counting was used as quantification method. Three random microscope view-fields were counted and the number of branch points was averaged for each well. Branch point for each group was calculated by averaging eight replicates from two independent experiments.

Example 10: RNA Isolation and Reverse Transcription

HaCaT cells were seeded in 6-well plates at a density of $2 \times 10^5$ per well and incubated further for 24 h in supplement-free medium prior to treatment. RNA was isolated at 3, 12 or 16 h post treatment using the RNeasy mini kit (QIAGEN, Valencia, Calif.). Total RNA was quantified using NanoDrop 2000. From 2 µg of total RNA, cDNA synthesis was done using SuperScript II Reverse Transcriptase (Invitrogen, Carlsbad, Calif.) and oligo (dT) (Invitrogen).

Example 11: Real-Time Quantitative Polymerase Chain Reaction (qPCR) for Transcript Level Determination in HaCaT Cells qPCR after reverse transcription (RT-qPCR) was performed on a 25 µL reaction solution containing a 0.3 µL aliquot of cDNA, 12.5 µL of TaqMan gene expression assay mix, 1.25 µL of probes, and 11 µL RNase-free water. qPCR was carried out on an ABI 7300 sequence detection system using the thermocycler program: 2 min at 50° C., 10 min at 95° C., and 15 s at 95° C. (40 cycles) and 1 min at 60° C. Each experiment was performed in triplicate. VEGF-A (Hs00900055_m1), PDGFB (Hs00266645_m1) and bFGF (Hs00966522_m1) were used as target genes, while GAPDH (Hs02758991_g1) was used as endogenous control. Graphs and data analysis were performed using the Prism software and analyzed using unpaired t test.

Example 12: Transcriptome Profiling

RNA was analyzed using a NanoDrop spectrophotometer and Agilent 2100 Bioanalyzer to determine the RNA concentration and quality, respectively. RNA samples were processed using the GeneChip WT PLUS Reagent Kit (Affymetrix, Santa Clara, Calif.) according to the manufacturer's instruction. In brief, 250 ng of RNA were used for cDNA synthesis by reverse transcription, and the cDNA was utilized as a template for the biotin-labeled RNA prepared by in vitro transcription reaction. The labeled RNA was further purified, fragmented, and hybridized with rotation at 45° C. for 16 h to the GeneChip™ Human Transcriptome Array 2.0. The arrays were washed and stained using the GeneChip Hybridization Wash and Stain kit on an Affymetrix Fluidics Station 450. The chips were scanned using a GeneChip 7G Scanner. Analysis of the microarray data was done according to the reported method (Salvador, L. A., Taori, K., Biggs, J. S., Jakoncic, J., Ostrov, D. A., Paul, V. J., and Luesch, H. (2013) Potent elastase inhibitors from cyanobacteria: Structural basis and mechanisms mediating cytoprotective and anti-inflammatory effects in bronchial epithelial cells. *J. Med. Chem.* 56, 1276-1290). Statistical tests were performed with Bioconductor statistical software (http://www.bioconductor.org/) and R program. Raw data were normalized by the Robust Multichip Analysis approach. Then the probe set's detection call was estimated by using the Wilcoxon signed rank-based algorithm. Probe sets that are absent in all of the study samples were removed from further analyses. A linear modeling approach and the empirical Bayes statistics as implemented in the limma package in the R software were used for differential expression analysis. The P values obtained were controlled for multiple testing (false discovery rate) using the Benjamini-Hochberg method. Differentially expressed genes were then ranked by the P values, and genes with $P<0.05$ (with FDR correction) and fold change $>1.5$ or $<0.67$ were considered as differentially expressed genes at a statistically significant level. Hierarchical clustering of the data was computed on log-transformed and normalized data by using complete linkage and Pearson correlation distances. The transcriptome data are deposited in NCBI's Gene Expression Omnibus with accession number GSE102100.

Example 13: Ex Vivo Organ Culture of Rabbit Corneas

The central 6 mm diameter area of corneas of twelve fresh rabbit globes (Pelfreeze) was ablated to a total depth of 155 microns using a Nidek excimer laser in phototherapeutic keratectomy mode. Ablated corneas were then surgically dissected from the rabbit globes using sterile scalpel and forceps, grasping only the scleral rims and not the clear cornea. The corneas were cultured in DMEM/F-12 1:1 (Thermo Fisher) containing 40 mM HEPES, 10% FBS, 0.01% dextran 40 (Tokyo Chemical Industry, Co., Ltd.) and 0.025% chondroitin sulfate (Chem-Impex International, Inc.) in 6-well plates. Twelve corneas were randomly distributed into four groups (three corneas in each group): DMSO, 25 µM, 50 µM or 100 µM apratyramide. Compounds or solvent (1% DMSO) were added to the media immediately to fully immerse the corneas in the 6-well plates. The corneas were incubated for 18 h at 37° C. in humidified atmosphere containing 5% $CO_2$ before total RNA was extracted.

Example 14: Evaluation of mRNA Level of VEGF-A in Ablated Rabbit Corneas after Treatment with Apratyramide (1)

Figure 7:
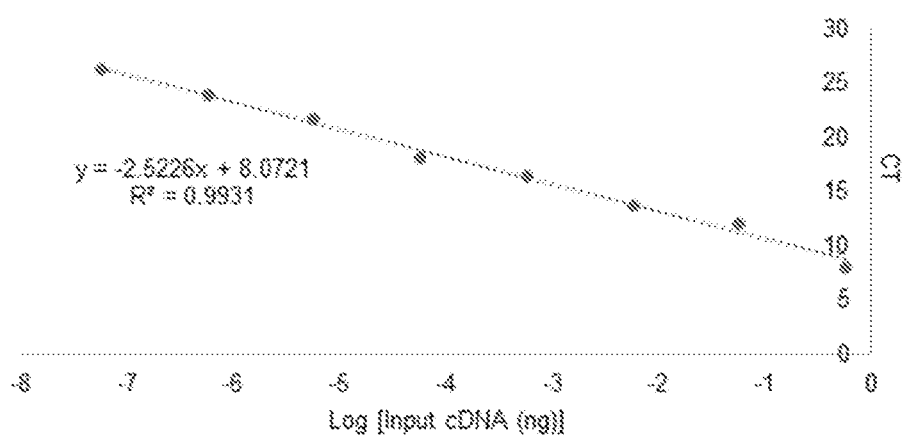
FIG. 7. depicts the standard curve of rabbit VEGF-A probe for quantification.
Figure 8:
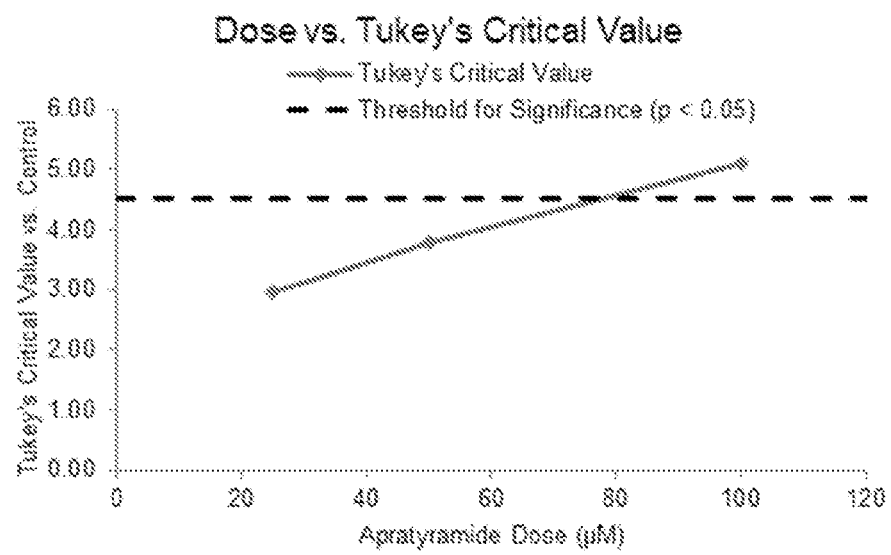
FIG. 8. depicts increasing certainty of effect for ex vivo data analysis.

The central scar-like tissue from each cornea was collected using an 8 mm punch biopsy. RNA was collected from the scar-like tissue using TRIzol Reagent (Life Technologies) according to manufacturer's procedure. To generate and validate the VEGF-A primer set (IDT DNA), cDNA was generated from whole rabbit eye RNA using the iScript™ Select cDNA Synthesis Kit (Bio-Rad) according to manufacturer's procedure. The amplicon obtained from the primer set was gel purified to ensure a single product and then sequenced to confirm the predicted sequence. The purified cDNA was then quantified using nanodrop and used to generate a standard curve. Serial 10-fold dilutions of the quantified cDNA amplicon were subjected to RT-qPCR using SYBR Select Master Mix (Applied Biosystems). A standard curve of Log [cDNA input]) vs observed CT values was made to demonstrate the proportional response to input cDNA for the mRNA target (FIG. 7). GAPDH levels were found to vary more than that of the target gene. Among the biological replicates, the average standard deviation for GAPDH was 1.54 $C_t$ & 1.98 $C_t$ for control and 100 µM treatment, respectively; while it was only 0.09 $C_t$/0.08 $C_t$ for VEGF-A. This degree of variation in GAPDH per unit total RNA demonstrates that GAPDH is a poor internal control for these purposes. The high degree of consistency among biological replicates for mass-normalized VEGF-A supports the choice to normalize to input total RNA. The mass-normalized $C_t$ values for the apratyramide treatment groups and DMSO control group (n=3 biological replicates per group) were analyzed by a one-way ANOVA ($\alpha$=0.05, Microsoft Excel 2010, Analysis Tool Pack) followed by Tukey's HSD post hoc test manually calculated in Excel 2010 (FIG. 8).

Example 15: Results

Figure 9A:
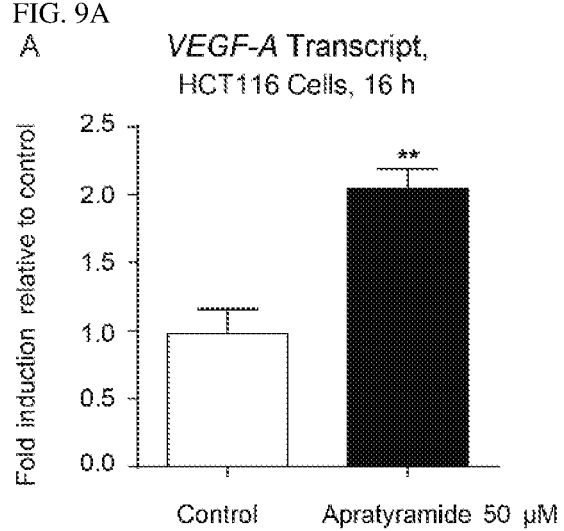
FIG. 9A depicts the transcript level of VEGF-A in HCT116 (human colon cancer) cells, 16 h.
Figure 9B:
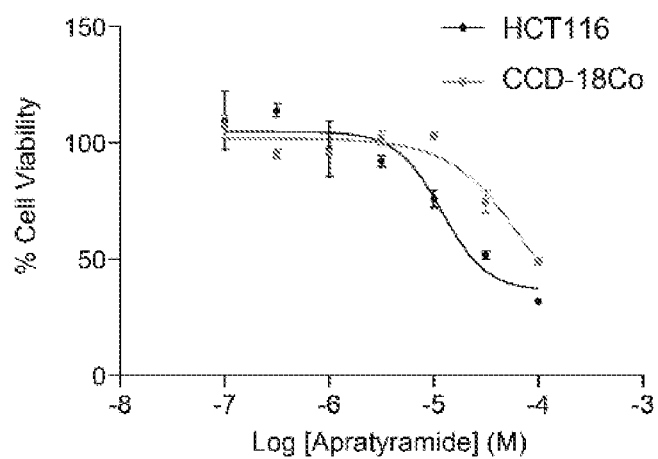
FIG. 9B depicts the antiproliferative effect of 1 on HCT116 and CCD-18Co cells, 48 h.
Figure 10:
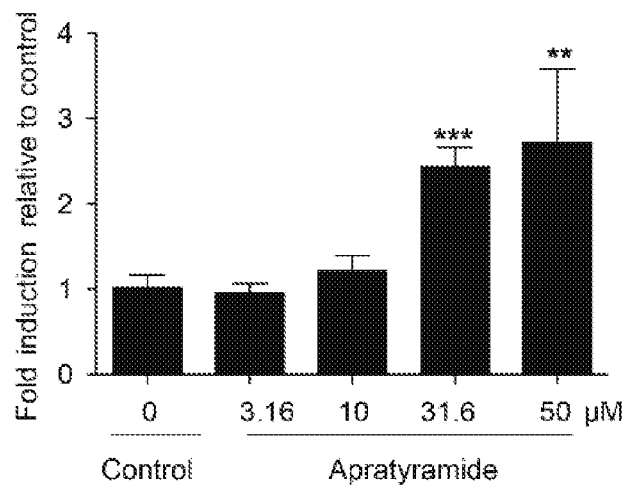
FIG. 10. depicts the transcript level of VEGF-A in CCD-18Co (human normal colon) cells, 16 h.

Apratyramide Induces Transcription of VEGF-A in HCT116 Cells Previously identified apratoxins from the same cyanobacterium were characterized as potent inhibitors by preventing cotranslational translocation of VEGF-A and other secreted proteins (Chen, Q. Y., Liu, Y., Cai, W., and Luesch, H. (2014) Improved total synthesis and biological evaluation of potent apratoxin S4 based anticancer agents with differential stability and further enhanced activity. *J. Med. Chem.* 57, 3011-3029; Chen, Q. Y., Liu, Y., and Luesch, H. (2011) Systematic chemical mutagenesis identifies a potent novel apratoxin A/E hybrid with improved in vivo antitumor activity. *ACS Med. Chem. Lett.* 2, 861-86). Apratyramide (1), however, had the opposite effect. Using human colon cancer HCT116 cells, 1 up-regulated VEGF-A, while displaying minimal cytotoxicity (FIGS. 9A and 9B). Fifty micro-molar apratyramide doubled VEGF-A transcript levels in HCT116 cells (FIG. 9A). Apratyramide (1) also exerted a similar effect in the corresponding normal colon cells (CCD-18Co) with negligible effects on cell viability (FIGS. 10 and 9B).

Figure 11:
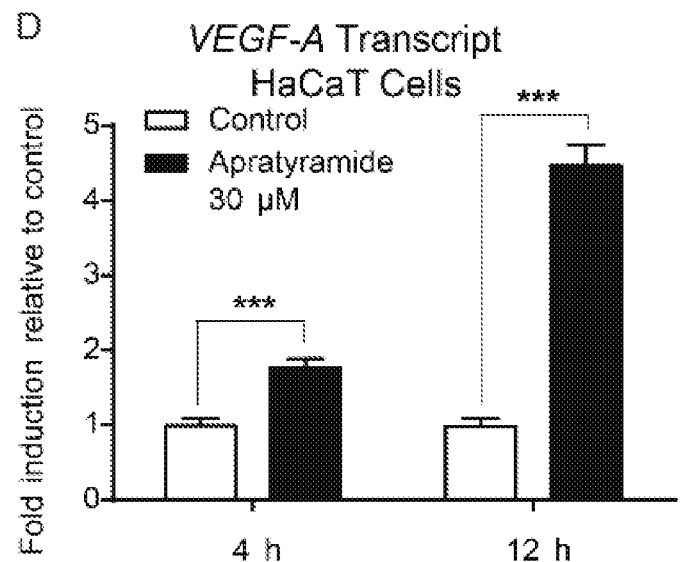
FIG. 11. depicts the transcript level of VEGF-A in HaCaT cells after 4 h and 12 h treatment with 30 μM of 1.
Figure 12:
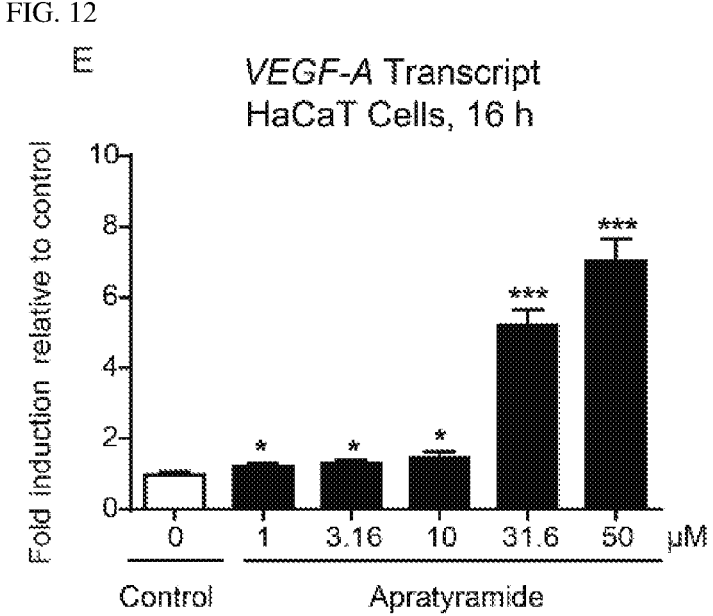
FIG. 12. depicts the transcript level of VEGF-A in HaCaT cells after 16 h.
Figure 13A:
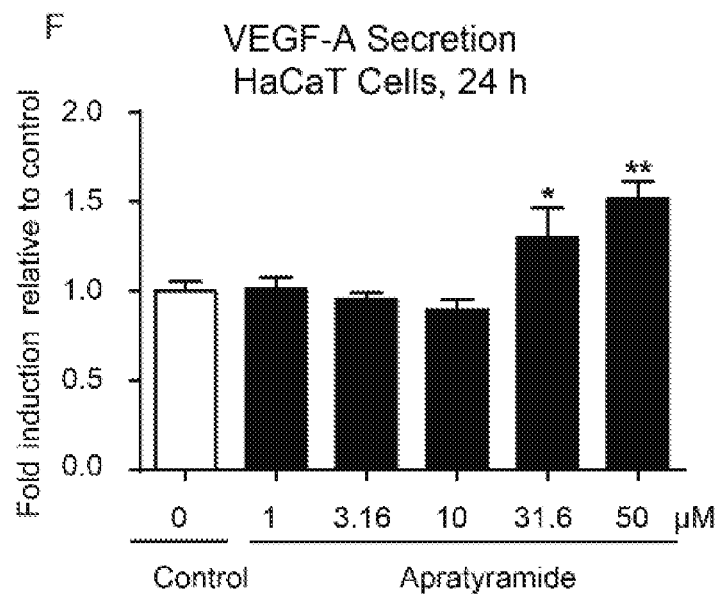
FIG. 13A depicts the level of VEGF-A secretion from HaCaT after 24 h.
Figure 13B:
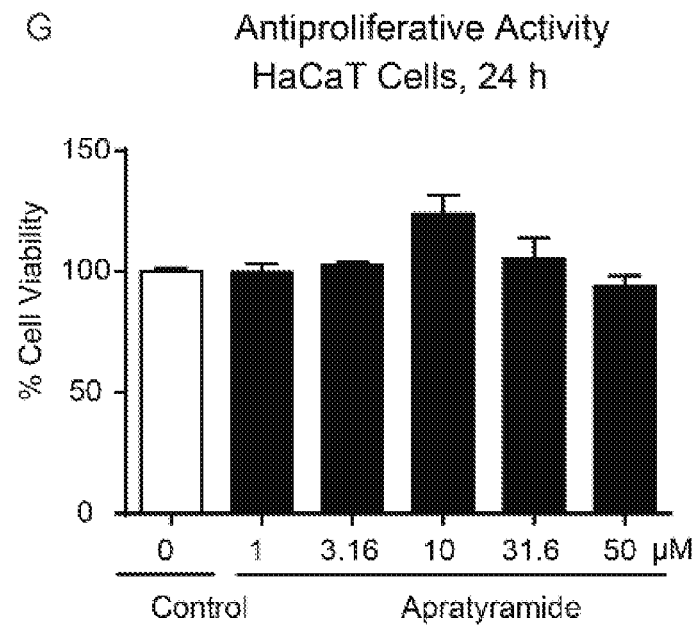
FIG. 13B depicts the antiproliferative activity of 1 on HaCaT cells, 24 h.

Apratyramide Induces Transcription, Secretion of VEGF-A and Transcription of Other Wound-Healing Related Growth Factors in HaCaT Cells As VEGF-A inducers are considered promising therapeutic agents for the treatment of chronic wounds, 1 may also induce VEGF-A in normal cell types that are involved in the wound healing process. Thus, 1 was profiled in an in vitro wound healing model: human keratinocyte cells (HaCaT). As expected, VEGF-A mRNA level was induced 1.7-fold after 4 h treatment with 30 µM of 1 and a greater induction effect was observed after 12 h (FIG. 11). After 16 h, 50 µM of 1 increased VEGF-A transcript levels by 7-fold, while 31.6 µM of 1 led to a 5-fold increase (FIG. 12). Accordingly, 50 µM of 1 induced a 1.5-fold increase of VEGF-A secretion from HaCaT cells after 24 h, and 31.6 µM of 1 induced a 1.3-fold increase without causing cytotoxicity (FIGS. 13A and 13B). Around ninety-percent cell viability was observed at 50 µM of 1 after 24 h (FIG. 13B).

Figure 14A:
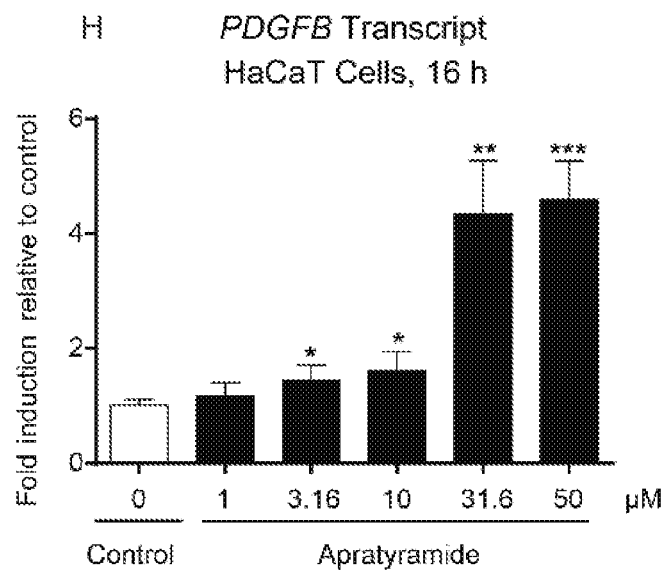
FIG. 14A depicts the transcript level of PDGFB in HaCaT cells, 16 h.
Figure 14B:
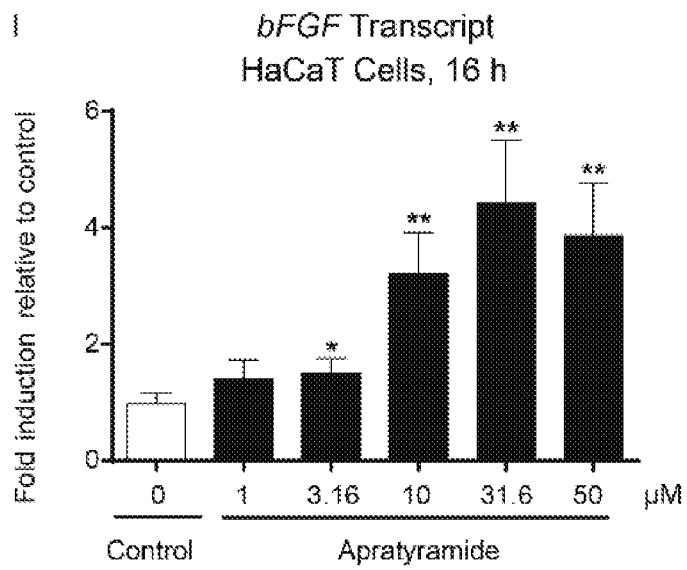
FIG. 14B depicts the transcript level of bFGF in HaCaT cells, 16 h.

Multiple growth factors and cytokines are involved in a complex integration of signals for regulating wound healing processes (Barrientos, S., Brem, H., Stojadinovic, O., and Tomic-Canic, M. (2014) Clinical application of growth factors and cytokines in wound healing. *Wound Repair Regen.* 22, 569-578). Thus, 1 may also induce other growth factors that might work cooperatively with VEGF-A during wound healing. RT-qPCR data indicated that PDGFB and bFGF were all stimulated by 1 (FIGS. 14A and 14B).

Figure 17A:
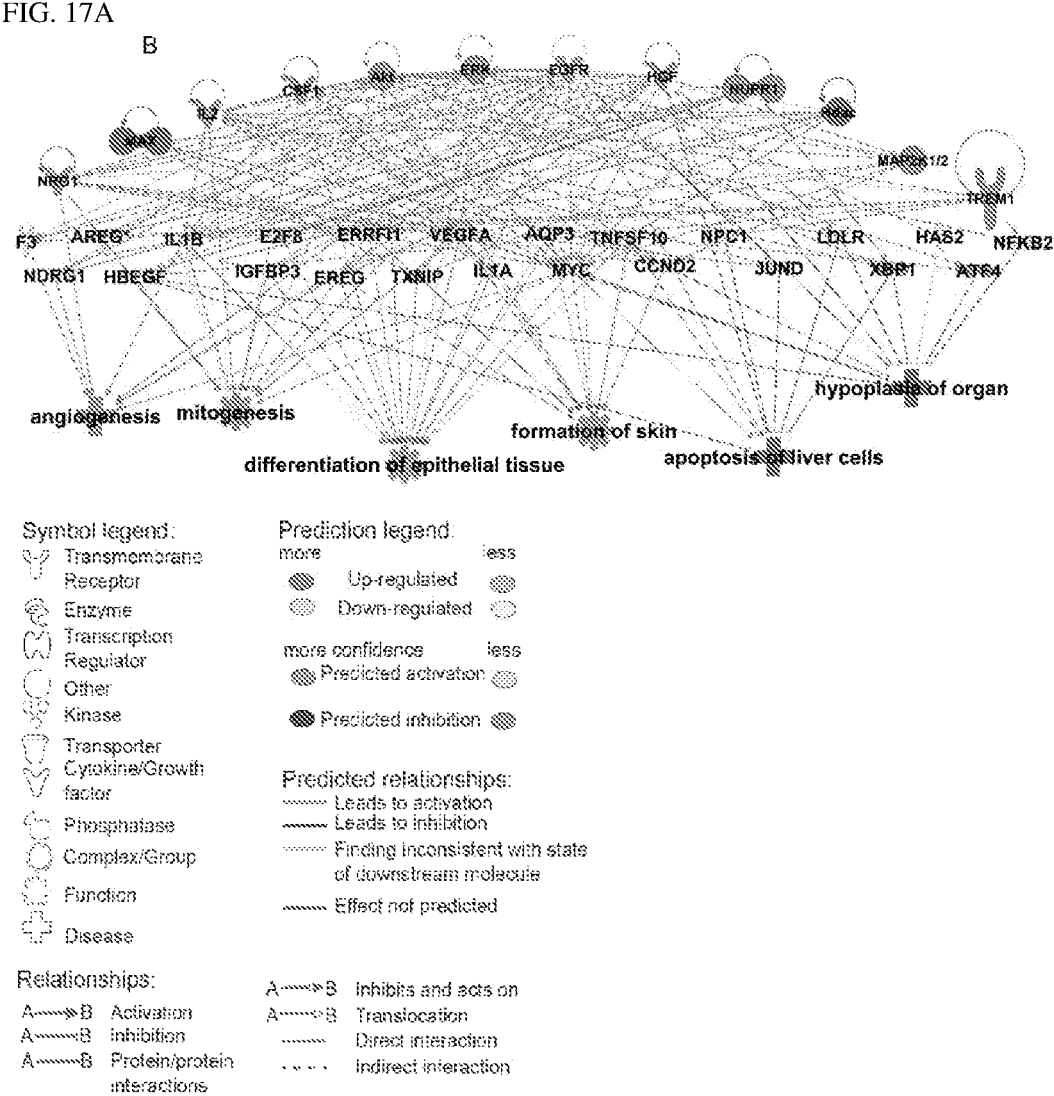
FIG. 17A. depicts the top regulator effect network using Ingenuity Pathway Analysis (IPA) for transcriptome profiling of apratyramide (1)
Figure 17B:
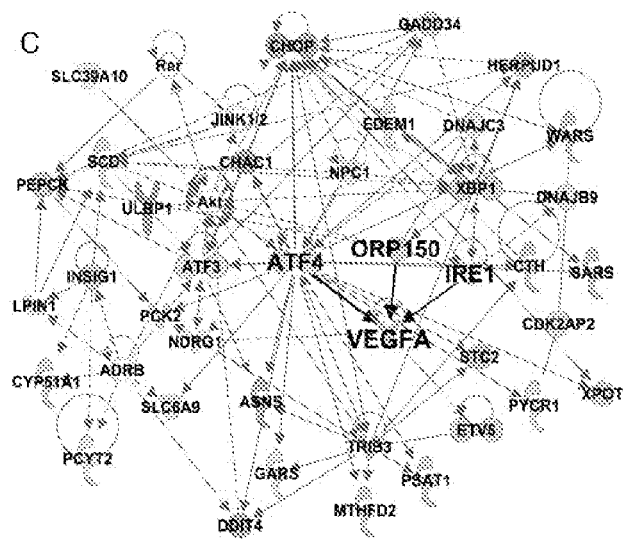
FIG. 17B depicts the top related molecular network associated with the function of cellular compromise and cellular maintenance.
Figure 18:
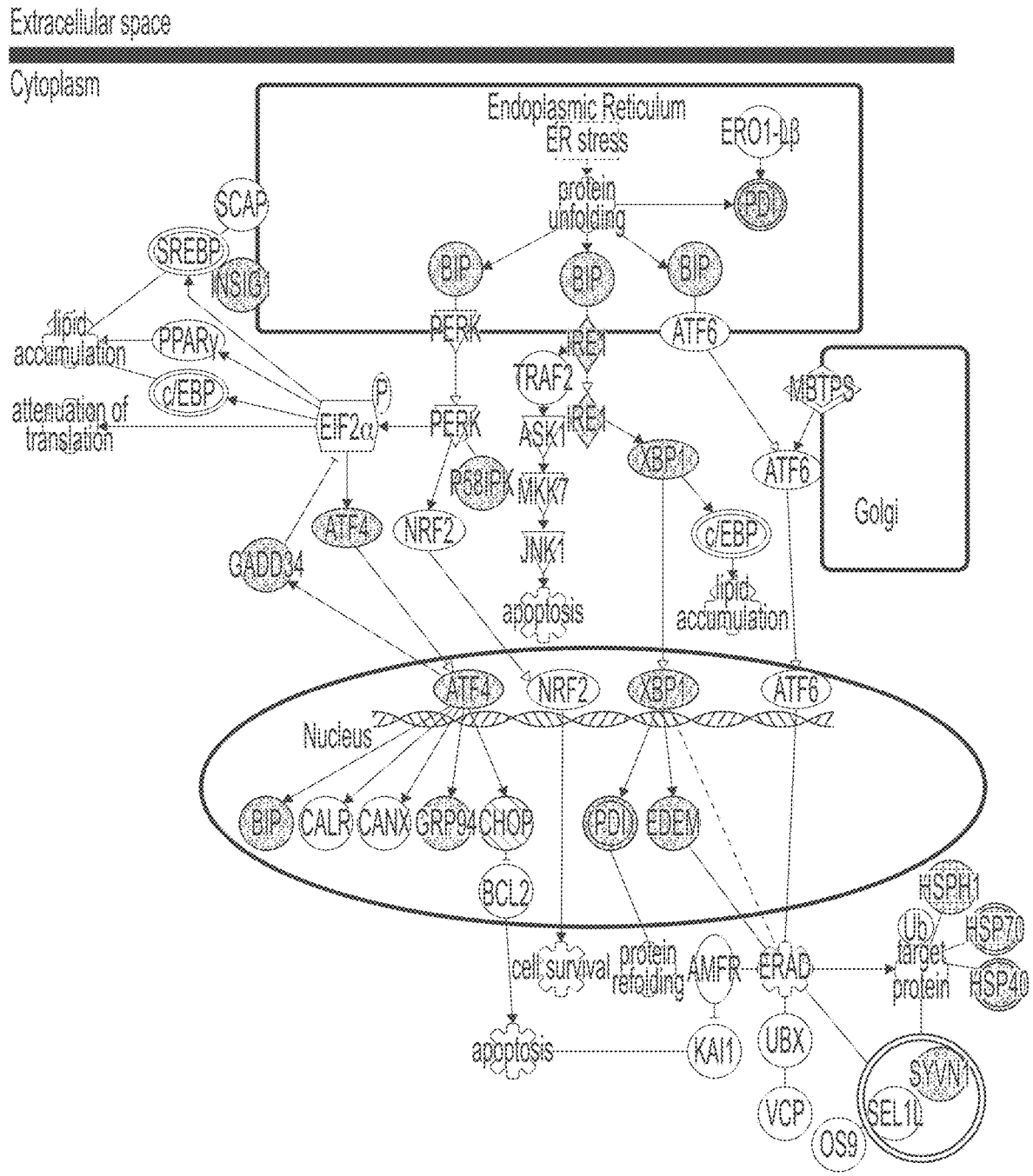
FIG. 18. depicts the identification of the unfolded protein response (UPR) pathway as the top canonical pathway by IPA analysis with a p-value of $1.45 \times 10^{-16}$. Red indicates up-regulated transcripts. Green indicates down-regulated transcripts.

Transcriptome Profiling and Ingenuity Pathway Analysis Indicate that UPR Plays a Role in Mechanisms of Apratyramide-Induced VEGF-A To further elucidate the mode of action of apratyramide through which multiple growth factors are induced, microarray profiling was performed using the Affymetrix GeneChip® Human Transcriptome Array 2.0 and global changes in transcript levels in HaCaT cells treated with apratyramide (1) were determined. Comparative analysis identified 371 differentially expressed genes after 12 h treatment with 30 µM of 1 (P<0.05, FDR corrected, fold change >1.5 or <0.67) (FIG. 15). Consistent with previous data, VEGF-A appeared to be one of the most up-regulated genes (FIG. 16). To examine the molecular functions and genetic networks, the 12 h microarray data was analyzed using Ingenuity Pathways Analysis (IPA) (FIGS. 17A and 17B). The global changes of transcript levels are associated with increased downstream phenotypic effects including angiogenesis, mitogenesis, differentiation of epithelial tissue and formation of skin, and decreased effects such as apoptosis of liver cells and hypoplasia of organs (FIG. 17A). IPA analysis of 371 microarray hits indicated the unfolded protein response (UPR) (FIG. 18) as the top canonical pathway with a p-value of $1.45 \times 10^{-16}$. The IPA also elucidated that the 371 hits were most closely related to a molecular network associated with the function of cellular compromise and cellular maintenance (FIG. 17B). The network contains molecular components from UPR pathway (ATF4, INSIG1, CHOP, DNAJC3, PP1R15A, JINK1/2), NRF2-mediated oxidative stress response signaling (ATF4, DNAJC3, JINK1/2, Akt, HERPUD1, DNAJB9) as well as glucocorticoid receptor signaling (ADRB, Akt, JINK1/2, PEPCK, PCK2).

Cytoprotective Roles of UPR and its Modulatory Effects on Growth Factors

The unfolded protein response (UPR) pathway is a cytoprotective signaling cascade in response to endoplasmic reticulum (ER) stress in cells. UPR coordinates multiple signaling pathways and controls various physiologies in cells and the whole organism including liver development, plasma cell differentiation, bone development, plasma cell differentiation, normal pancreatic homeostasis and placental development and embryonic viability (Reimold, A. M., Etkin, A., Clauss, I., Perkins, A., Friend, D. S., Zhang, J., Horton, H. F., Scott, A., Orkin, S. H., Byrne, M. C., Grusby, M. J., and Glimcher, L. H. (2000) An essential role in liver development for transcription factor XBP-1. *Genes Dev.* 14, 152-157; Zhang, P., McGrath, B., Li, S., Frank, A., Zambito, F., Reinert, J., Gannon, M., Ma, K., McNaughton, K., and Cavener, D. R. (2002) The PERK Eukaryotic Initiation Factor 2α Kinase Is Required for the Development of the Skeletal System, Postnatal Growth, and the Function and Viability of the Pancreas. *Mol. Cell. Biol.* 22, 3864-3874; Yang, X., Matsuda, K., Bialek, P., Jacquot, S., Masuoka, H. C., Schinke, T., Li, L., Brancorsini, S., Sassone-Corsi, P., Townes, T. M., Hanauer, A., and Karsenty, G. (2004) ATF4 is a substrate of RSK2 and an essential regulator of osteoblast biology: Implication for Coffin-Lowry syndrome. *Cell* 117, 387-398; Reimold, a M., Iwakoshi, N. N., Manis, J., Vallabhajosyula, P., Szomolanyi-Tsuda, E., Gravallese, E. M., Friend, D., Grusby, M. J., Alt, F., and Glimcher, L. H.

(2001) Plasma cell differentiation requires the transcription factor XBP-1. *Nature* 412, 300-307; Iwakoshi, N. N., Lee, A. H., Vallabhajosyula, P., Otipoby, K. L., Rajewsky, K., and Glimcher, L. H. (2003) Plasma cell differentiation and the unfolded protein response intersect at the transcription factor XBP-1. *Nat Immunol* 4, 321-329; Scheuner, D., Song, B., McEwen, E., Liu, C., Laybutt, R., Gillespie, P., Saunders, T., Bonner-Weir, S., and Kaufman, R. J. (2001) Translational control is required for the unfolded protein response and in vivo glucose homeostasis. *Mol. Cell* 7, 1165-1176; Iwawaki, T., Akai, R., Yamanaka, S., and Kohno, K. (2009) Function of IRE1 alpha in the placenta is essential for placental development and embryonic viability. *Proc. Natl. Acad. Sci.* 106, 16657-16662). Importantly, UPR is activated after skin injury, suggesting the protective roles of UPR in rescuing wound injuries (Schurmann, C., Goren, I., Linke, A., Pfeilschifter, J., and Frank, S. (2014) Deregulated unfolded protein response in chronic wounds of diabetic ob/ob mice: A potential connection to inflammatory and angiogenic disorders in diabetes-impaired wound healing. *Biochem. Biophys. Res. Commun.* 446, 195-200). Therefore, intervening in ER stress and modulating signaling components of UPR would provide promising therapeutics for the treatment of chronic wounds (Lee, J., and Ozcan, U. (2014) Unfolded protein response signaling and metabolic diseases. *J. Biol. Chem.* 289, 1203-1211).

Figure 19:
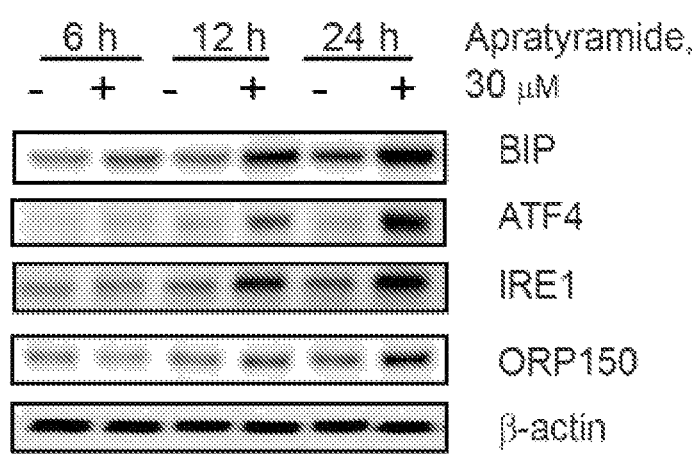
FIG. 19. depicts the validation of selected hits from transcriptome profiling using immunoblot analysis.

Interestingly, studies have unveiled the modulatory effects of the UPR on VEGF-A. The UPR contributes to the transcriptional, protein processing and transportation of VEGF-A in the ER through activation of ATF4, IRE1 and ORP150, which were all up-regulated by apratyramide at transcript and protein levels (FIGS. 17B and 19) (Ghosh, R., Lipson, K. L., Sargent, K. E., Mercurio, A. M., Hunt, J. S., Ron, D., and Urano, F. (2010) Transcriptional regulation of VEGF-A by the unfolded protein response pathway. *PLoS One* 5, e9575; Ozawa, K., Tsukamoto, Y., Hori, O., Kitao, Y., Yanagi, H., Stern, D. M., and Ogawa, S. (2001) Regulation of tumor angiogenesis by oxygen-regulated protein 150, an inducible endoplasmic reticulum chaperone. *Cancer Res.* 61, 4206-4213; Ozawa, K., Kondo, T., Hori, O., Kitao, Y., Stern, D. M., Eisenmenger, W., Ogawa, S., and Ohshima, T. (2001) Expression of the oxygen-regulated protein ORP150 accelerates wound healing by modulating intracellular VEGF transport. *J. Clin. Invest.* 108, 41-50). These findings suggest that apratyramide (1) may induce VEGF-A through the UPR pathway. Besides up-regulating VEGF-A, the UPR has also been reported to enhance angiogenesis by up-regulating a number of other pro-angiogenic factors like FGFs, PDGFs and IL-8 (Pereira, E. R., Liao, N., Neale, G. A., and Hendershot, L. M. (2010) Transcriptional and post-transcriptional regulation of proangiogenic factors by the unfolded protein response. *PLoS One* 5, e12521). These observations are also in accordance with the microarray and RT-qPCR results, indicating that many other pro-angiogenic factors (e.g., bFGF, PDGFB, HB-EGF) were also up-regulated after treatment with apratyramide (1) (FIGS. 10-14, 16, and 20). Collectively, improving ER homeostasis by activating the UPR pathway independent of ER stress may be a promising tool to accelerate wound closure, including diabetes-associated chronic wounds closure and apratyramide (1) has the promising attributes to be one such therapeutic agent (Schurmann, C., Goren, I., Linke, A., Pfeilschifter, J., and Frank, S. (2014) Deregulated unfolded protein response in chronic wounds of diabetic ob/ob mice: A potential connection to inflammatory and angiogenic disorders in diabetes-impaired wound healing. *Biochem. Biophys. Res. Commun.* 446, 195-200).

A closer investigation of these individual molecular components of UPR further enabled the identification of several lines of evidence demonstrating that they also directly attribute to angiogenesis, wound healing and VEGF-A up-regulation dependent or independent of UPR (Iwawaki, T., Akai, R., Yamanaka, S., and Kohno, K. (2009) Function of IRE1 alpha in the placenta is essential for placental development and embryonic viability. *Proc. Natl. Acad. Sci.* 106, 16657-16662; Nathaniel Roybal, C., Hunsaker, L. A., Barbash, O., Vander Jagt, D. L., and Abcouwer, S. F. (2005) The oxidative stressor arsenite activates vascular endothelial growth factor mRNA transcription by an ATF4-dependent mechanism. *J. Biol. Chem.* 280, 20331-20339; Malabanan, K. P., Kanellakis, P., Bobik, A., and Khachigian, L. M. (2008) Activation Transcription Factor-4 Induced by Fibroblast Growth Factor-2 Regulates Regulates VEGF-A transcription in Vascular Smooth Muscle Cells. *Circ. Res.* 103, 378-387; Zhu, K., Jiao, H., Li, S., Cao, H., Galson, D. L., Zhao, Z., Zhao, X., Lai, Y., Fan, J., Im, H. J., Chen, D., and Xiao, G. (2013) ATF4 promotes bone angiogenesis by increasing vegf expression and release in the bone environment. *J. Bone Miner. Res.* 28, 1870-1884).

ATF4 is an important transcription factor in the UPR signaling cascade which activates VEGF-A at both transcript and protein levels (Nathaniel Roybal, C., Hunsaker, L. A., Barbash, O., Vander Jagt, D. L., and Abcouwer, S. F. (2005) The oxidative stressor arsenite activates vascular endothelial growth factor mRNA transcription by an ATF4-dependent mechanism. *J. Biol. Chem.* 280, 20331-20339; Malabanan, K. P., Kanellakis, P., Bobik, A., and Khachigian, L. M. (2008) Activation Transcription Factor-4 Induced by Fibroblast Growth Factor-2 Regulates Regulates VEGF-A transcription in Vascular Smooth Muscle Cells. *Circ. Res.* 103, 378-387; Zhu, K., Jiao, H., Li, S., Cao, H., Galson, D. L., Zhao, Z., Zhao, X., Lai, Y., Fan, J., Im, H. J., Chen, D., and Xiao, G. (2013) ATF4 promotes bone angiogenesis by increasing vegf expression and release in the bone environment. *J. Bone Miner. Res.* 28, 1870-1884). ATF4 promotes bone angiogenesis by increasing VEGF expression and release in the bone environment (Zhu, K., Jiao, H., Li, S., Cao, H., Galson, D. L., Zhao, Z., Zhao, X., Lai, Y., Fan, J., Im, H. J., Chen, D., and Xiao, G. (2013) ATF4 promotes bone angiogenesis by increasing vegf expression and release in the bone environment. *J. Bone Miner. Res.* 28, 1870-1884). It has also been reported that ATF4 expression was induced in smooth muscle cells after artery injuries in rats and its overexpression further enhanced the expression of VEGF-A by an interaction between ATF4 and a recognition element located in the VEGF-A gene. The microarray data as well as immunoblot analysis suggested that ATF4 is activated by apratyramide at both the mRNA and protein level, which subsequently leads to the induction of the transcription of a number of its downstream molecular components: CHOP, SLC6A9, CHAC1, ATF3, SARS, WARS and others (FIGS. 15 and 17-19).

IRE1 is also an ER-located transmembrane protein, which plays an essential role in physiological processes including angiogenesis, placental development and embryonic viability (Iwawaki, T., Akai, R., Yamanaka, S., and Kohno, K. (2009) Function of IRE1 alpha in the placenta is essential for placental development and embryonic viability. *Proc. Natl. Acad. Sci.* 106, 16657-16662; Wang, J. M., Qiu, Y., Yang, Z. Q., Li, L., and Zhang, K. (2017) Inositol-requiring enzyme 1 facilitates Diabetic wound healing through modulating micrornas. *Diabetes* 66, 177-192). It has been shown that VEGF-A expression in the placenta is partially dependent on IRE1. Another recent study identified the deficiency of IRE1 in type 2 diabetic db/db mice and that cell therapies using direct IRE1 gene transfer significantly accelerated cutaneous wound healing in diabetic mice through enhancing angiogenesis. These findings strongly suggested the therapeutic strategy for diabetic wound healing by enhancing IRE1 activity. In addition, IRE1 deletion resulted in elevation of microRNAs, while the supply of IRE1 promoted the angiogenic potential of diabetic (bone marrow-derived progenitor cells) BMPCs through modulating miRNA biogenesis. Accordingly, down-regulation of several microRNAs after 12 h treatment with apratyramide (1) is also observed (FIGS. 16 and 20).

ORP150 is an ER chaperone, the expression of which is regulated by UPR. Overexpression of the ORP150 gene by adenovirus vectors accelerated wound healing by modulating intracellular VEGF transport (Ozawa, K., Kondo, T., Hori, O., Kitao, Y., Stern, D. M., Eisenmenger, W., Ogawa, S., and Ohshima, T. (2001) Expression of the oxygen-regulated protein ORP150 accelerates wound healing by modulating intracellular VEGF transport. *J. Clin. Invest.* 108, 41-50). This observation implied that ORP150 was involved in skin wound healing.

Figure 21A:
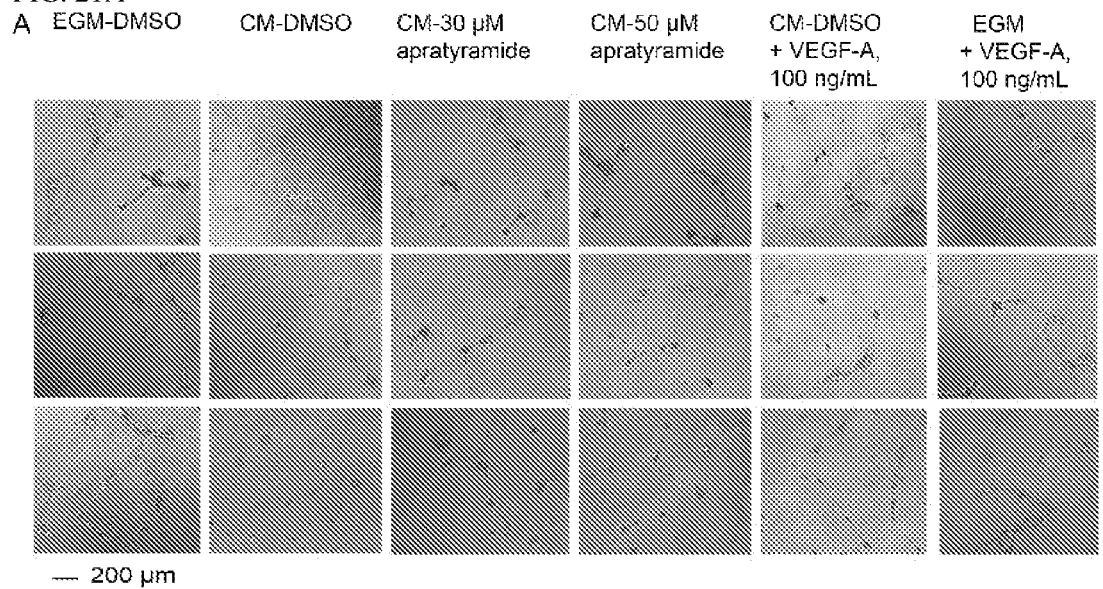
FIG. 21A. depicts conditioned medium (CM) from HaCaT culture with the presence of compound 1 or solvent control DMSO (0.3%), 24 h, induced angiogenesis in vitro, determined by matrigel assay using HUVECs (scale bar 200 μm), 14 h. VEGF-A protein, 100 ng/mL was used as positive control. Complete growth medium (EGM, Lonza) for HUVEC was also used as a positive control.
Figure 21B:
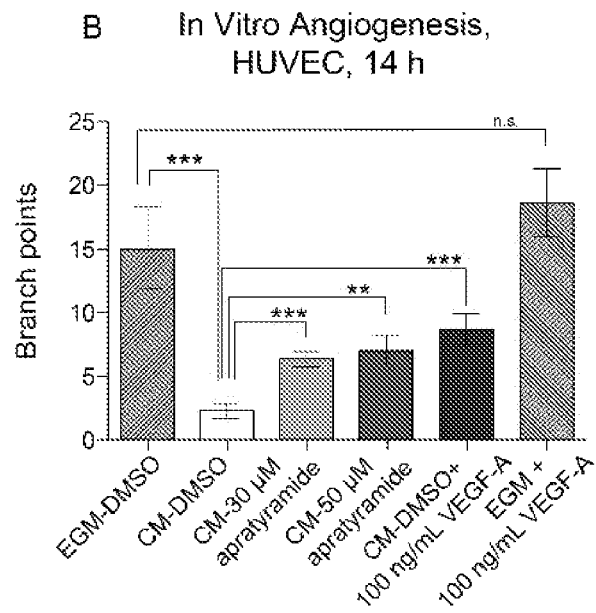
FIG. 21B depicts the branch point counting used as quantification method. Three random microscope view-fields were counted and the number of branch points was averaged for each well. Error bars indicate mean+SEM of eight replicates from two independent experiments. P-values were calculated relative to control (CM-DMSO) using unpaired t test (n=8), P<0.01, *P<0.001.

Conditioned Medium from HaCaT Cell Culture Treated with Apratyramide Induced Angiogenesis In Vitro During wound healing, VEGF-A is secreted to stimulate angiogenesis, which primarily acts on endothelial cells in the wound area (Bao, P., Kodra, A., Tomic-Canic, M., Golinko, M. S., Ehrlich, H. P., and Brem, H. (2009) The Role of Vascular Endothelial Growth Factor in Wound Healing. *J. Surg. Res.* 153, 347-358). Thus, the increased VEGF-A secreted from HaCaT cells induced by 1 may enhance angiogenesis. Conditioned medium (CM) was collected from the HaCaT cell culture with or without the presence of 1 at 24 h, when an increase of VEGF-A secretion is detected. Human endothelial cells (HUVECs) were incubated with the obtained CM and their angiogenic activity were monitored using an in vitro angiogenesis assay (FIGS. 21A and 21B). As a positive control, the complete growth medium (EGM) containing 2% FBS and bovine brain extract (BBE) enabled HUVECs to form tube-like structures from individual cells after 14 h. The CM from HaCaT cell culture (DMEM, 10% FBS) alone, however, had little effect on angiogenesis as most HUVECs remained as individual cells. This is possibly due to a lack of growth supplement required for angiogenesis in endothelial cells in the DMEM. The decreased angiogenesis in the CM-DMSO group was rescued by the treatment with 30 or 50 µM of 1 in HaCaT culture, indicated by an increase of tube-like structure formation. Similar to apratyramide's effect, VEGF-A protein, 100 ng/mL, also induced angiogenesis in vitro. In contrast, the addition of VEGF-A at 100 ng/mL to the complete growth medium did not significantly further induce angiogenesis, probably due to the sufficient amount of angiogenic factors in the BBE. The above results demonstrated that apraytramide (1) indirectly enhanced angiogenesis potentially through an induction of VEGF-A secreted from HaCaT cells.

Apratyramide Induces VEGF-A in a Rabbit Corneal Epithelial Ex Vivo Model.

Figure 22:
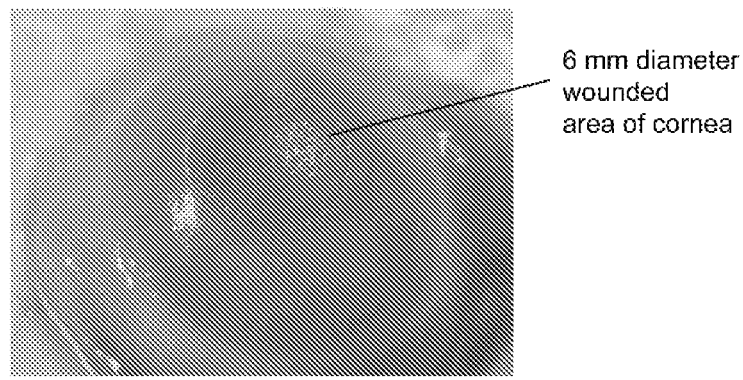
FIG. 22. depicts apratyramide induced VEGF-A in a rabbit corneal epithelial ex vivo model. Data are presented as mean+SEM, *P<0.05.
Figure 23:
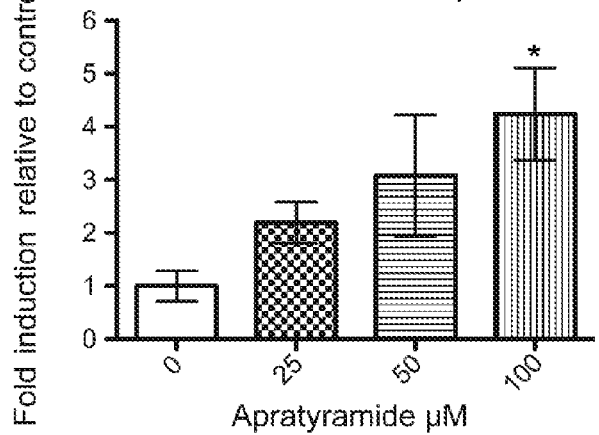
FIG. 23. depicts apratyramide induced VEGF-A in a rabbit corneal epithelial ex vivo model. Data are presented as mean+SEM, *P<0.05.

In order to evaluate apratyramide (1) in a more physiological context, apratyramide (1) was tested in an ex vivo rabbit corneal epithelial model, a validated wound healing model (Gibson, D. J., and Schultz, G. S. (2013) A corneal scarring model. *Methods Mol. Biol.* 1037, 277-298; Sriram, S., Gibson, D. J., Robinson, P., Pi, L., Tuli, S., Lewin, A. S., and Schultz, G. (2014) Assessment of anti-scarring therapies in ex vivo organ cultured rabbit corneas. *Exp. Eye Res.* 125, 173-182). The fresh rabbit eyes were obtained and wounds were induced on the center of the cornea by a laser (FIG. 22). After that, the eyeballs were trimmed to collect cornea tissues which were then cultured in medium with or without the presence of 1. Eighteen hours later, total RNA was collected from cornea tissues and subjected for RT-qPCR analysis. Consistent with the effect in vitro, a dose-dependent increase of VEGF-A mRNA in the cornea was detected after treatment with 1 (FIG. 23).

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed:
1. A compound according to the formula:

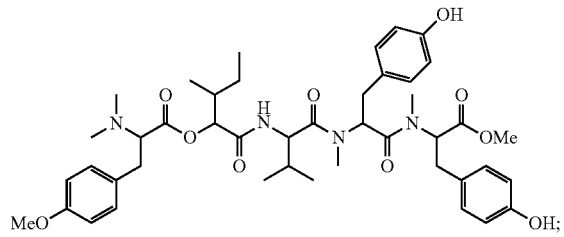 [SMILES: CCC(C)C(OC(=O)C(Cc1ccc(OC)cc1)N(C)C)C(=O)NC(C(=O)N(C)C(Cc1ccc(O)cc1)C(=O)N(C)C(Cc1ccc(O)cc1)C(=O)OC)C(C)C]

or a pharmaceutically acceptable salt, solvate, hydrate, prodrug, or stereoisomer thereof.

2. The compound or pharmaceutically acceptable salt, solvate, hydrate, prodrug, or stereoisomer thereof of claim 1, wherein the compound is:

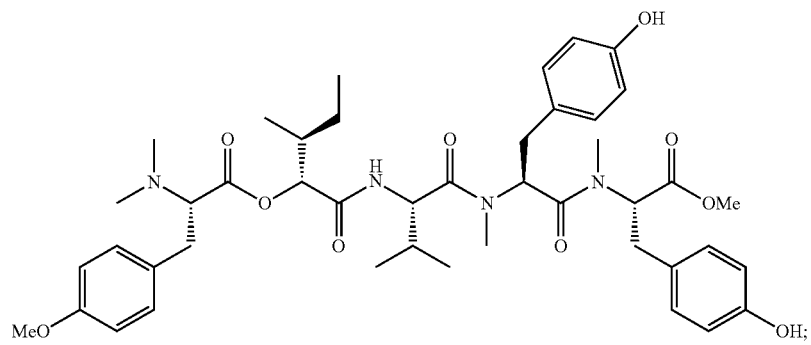

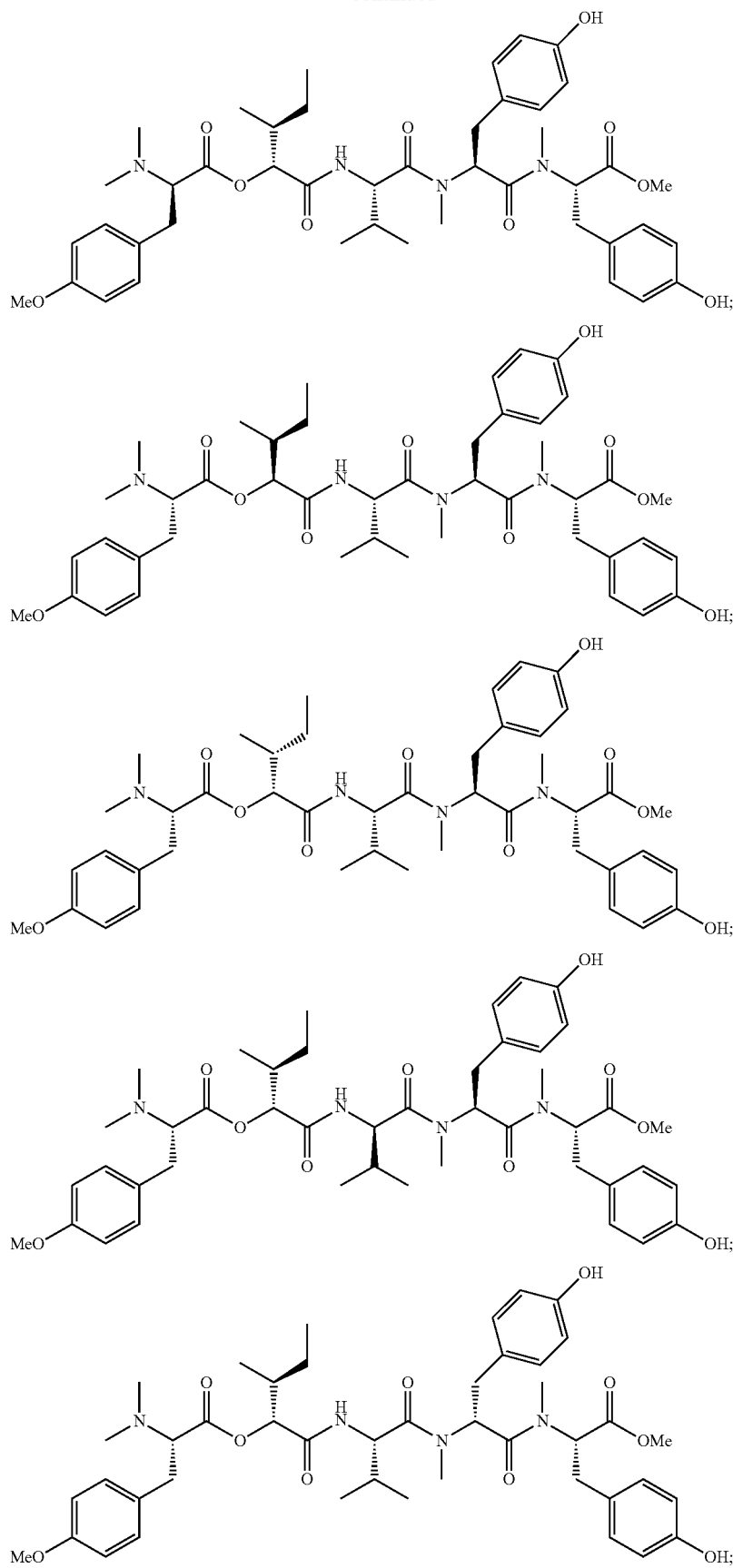

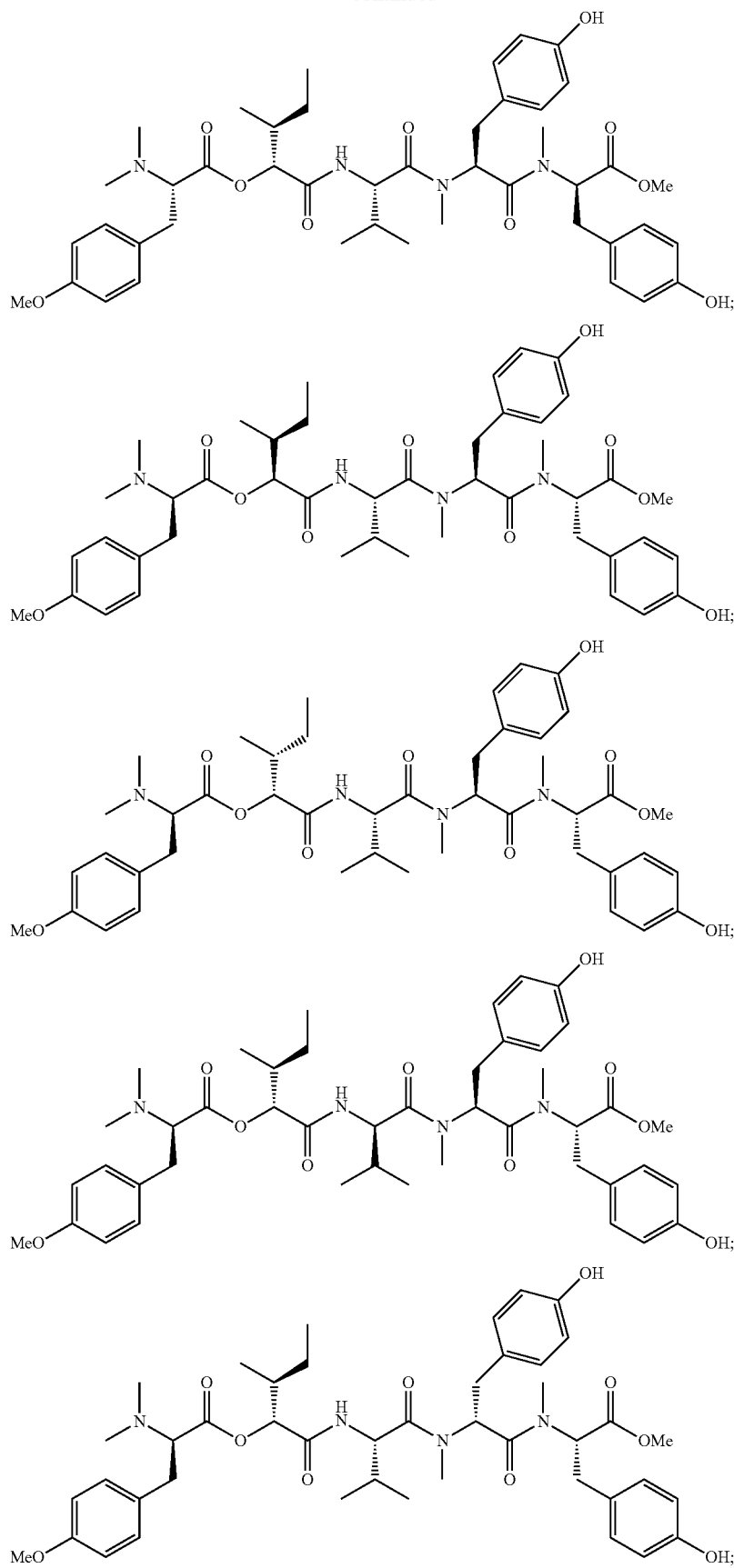

-continued
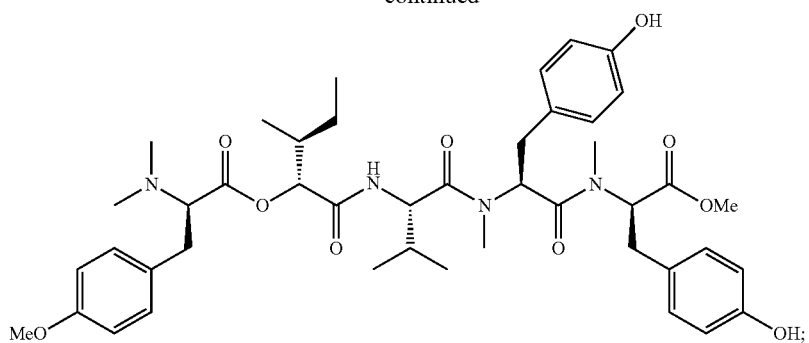
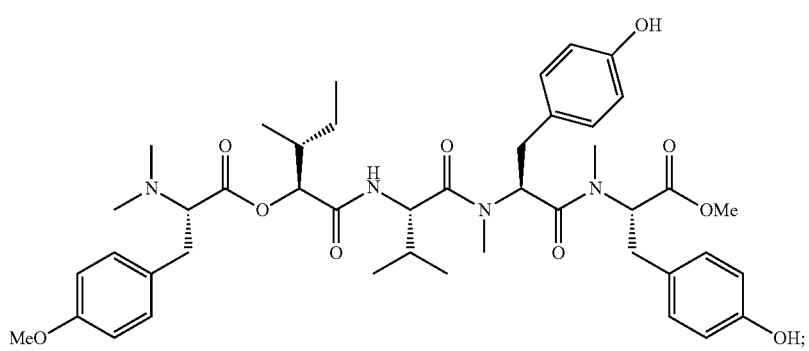
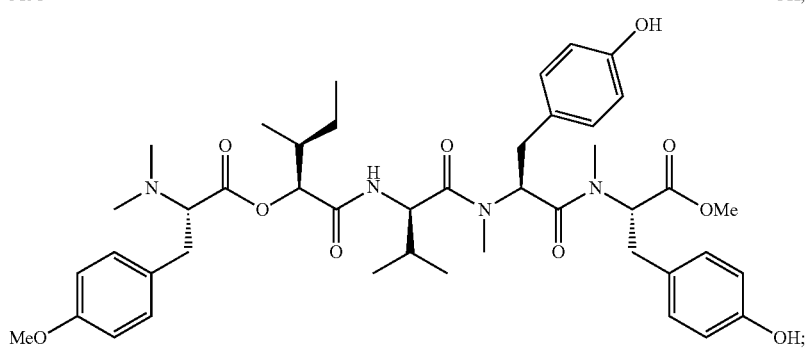
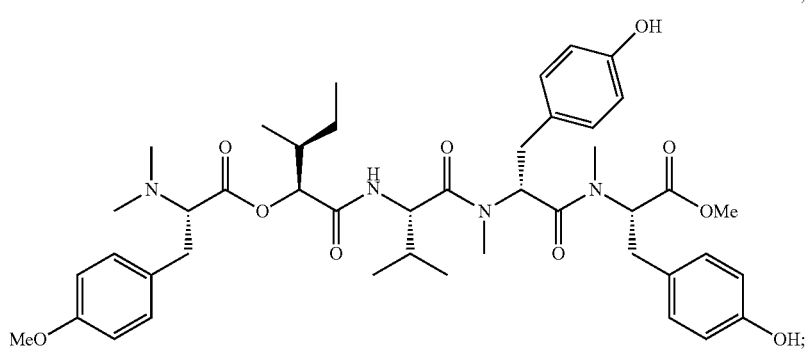
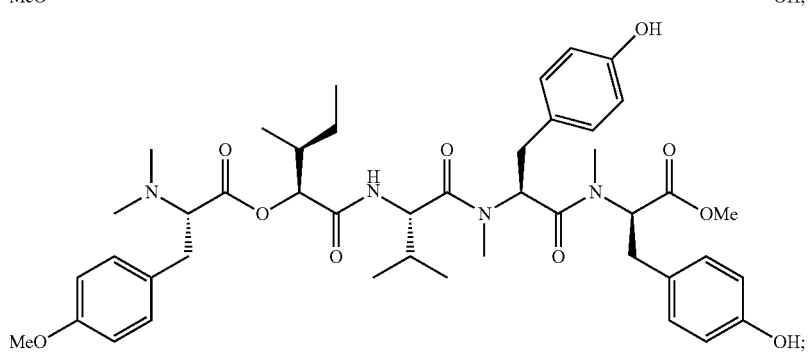

-continued
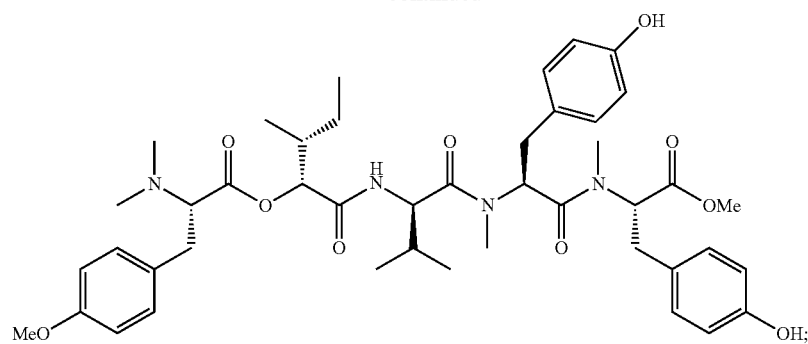
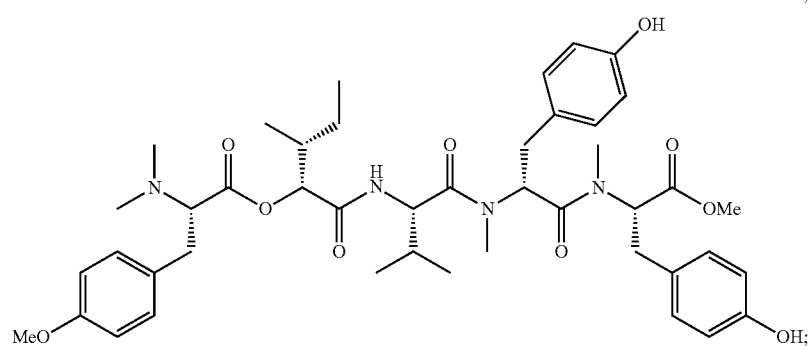
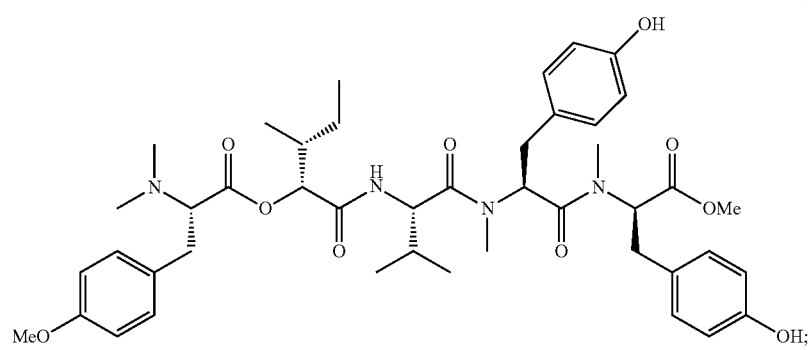
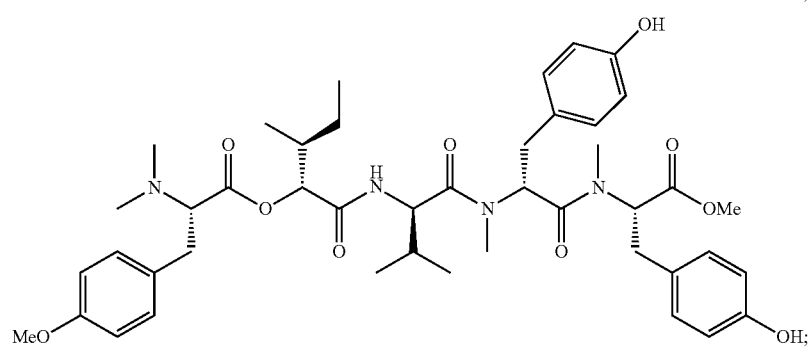
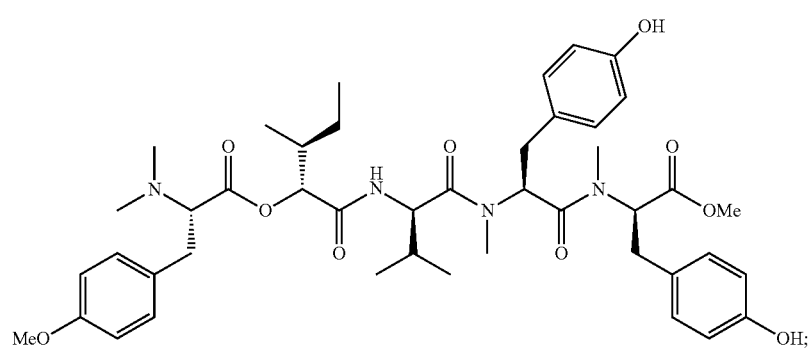

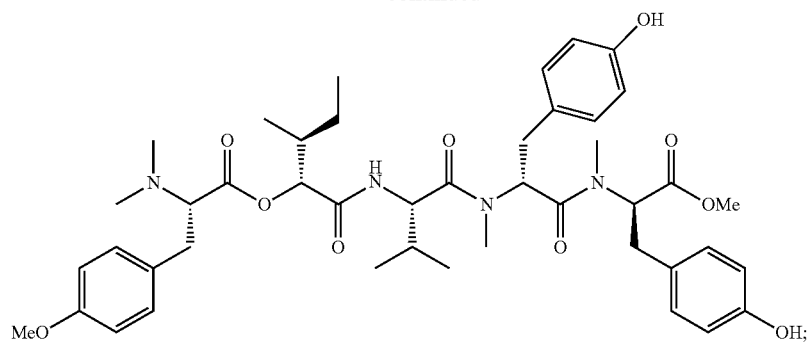
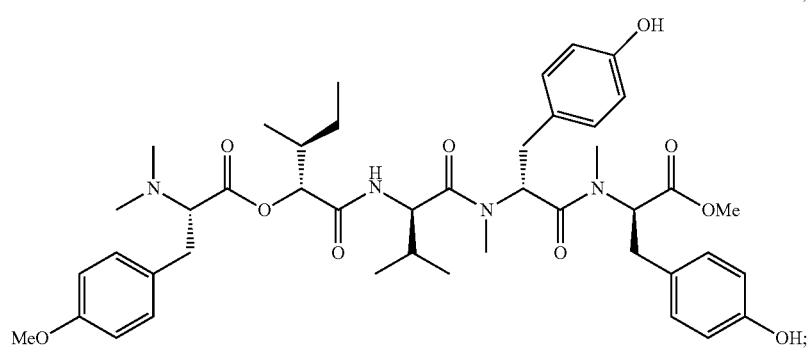
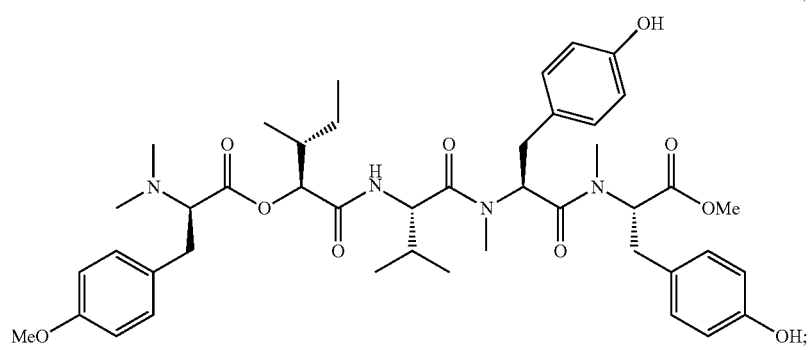
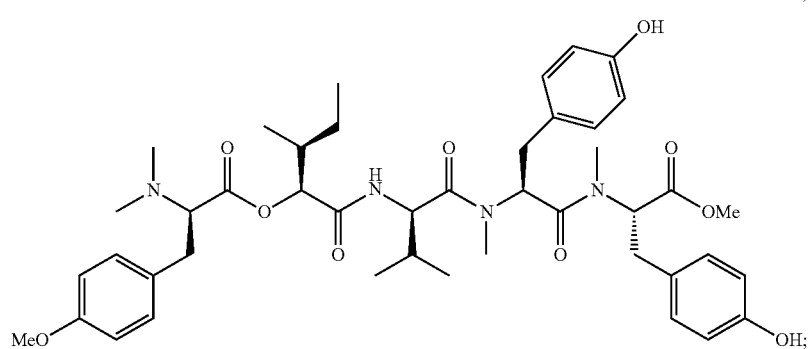
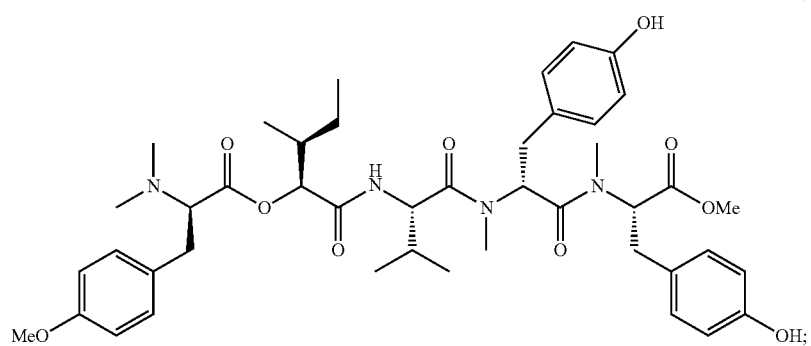

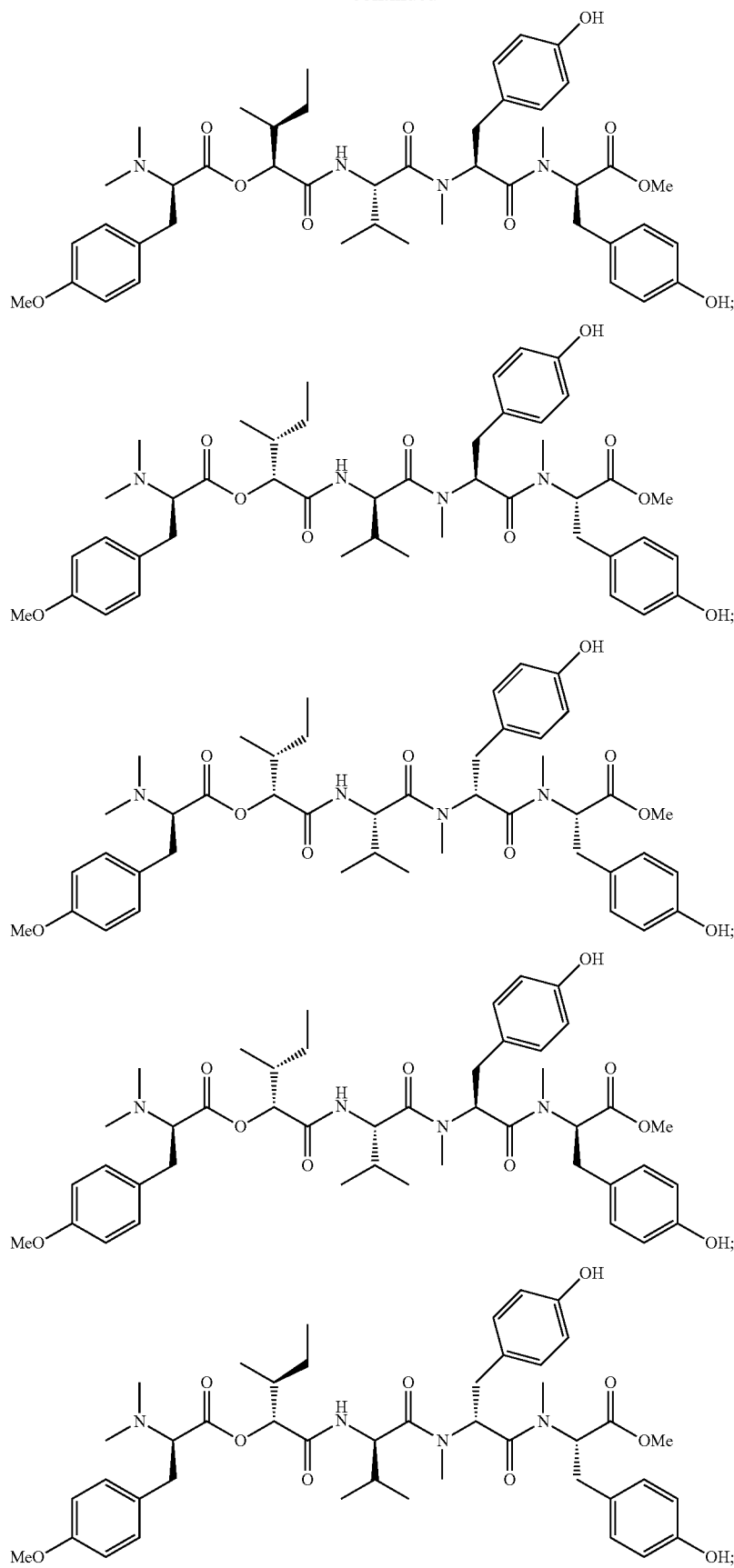

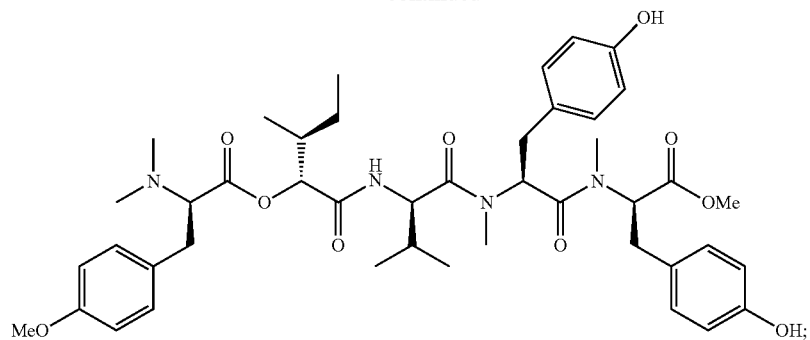
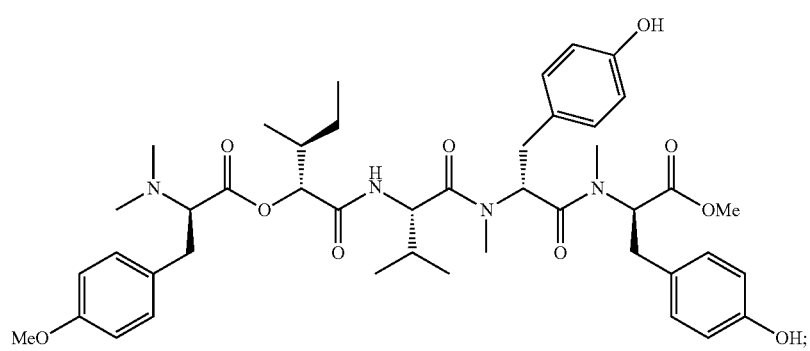
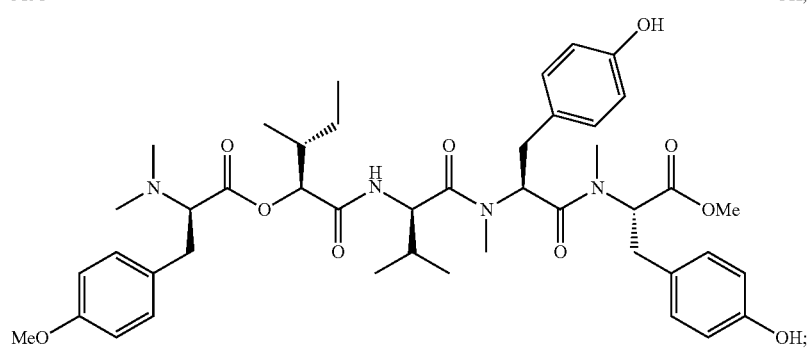
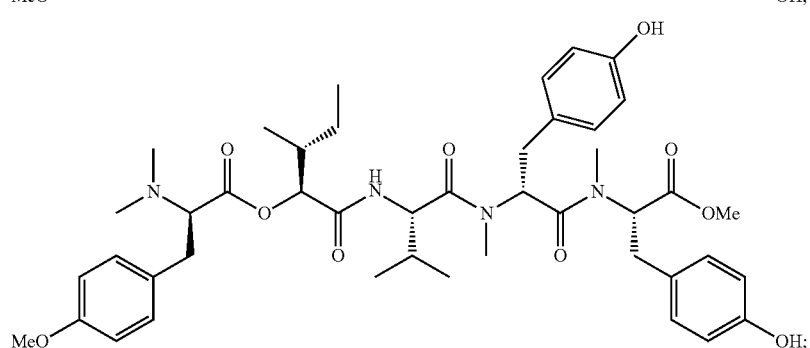
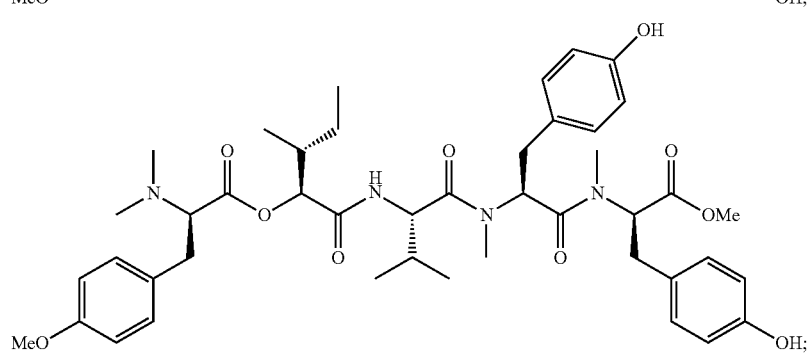

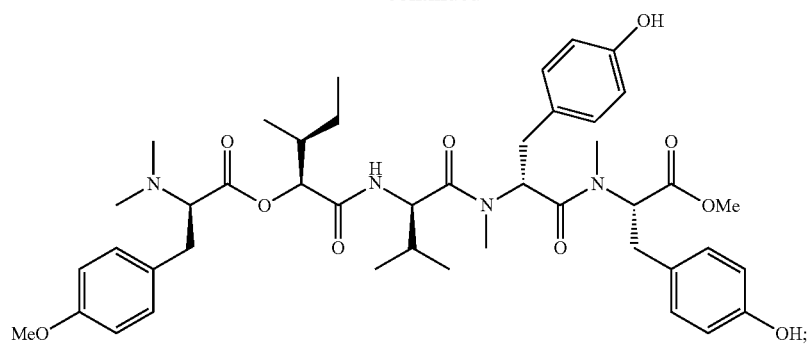
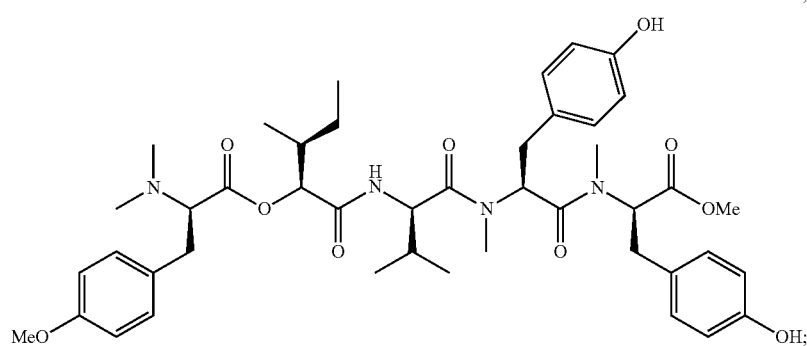
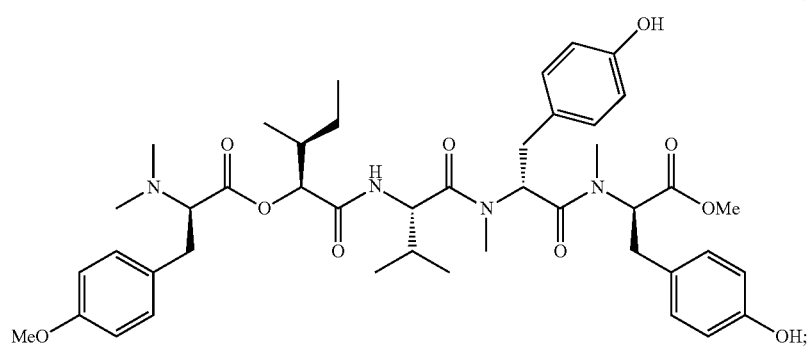
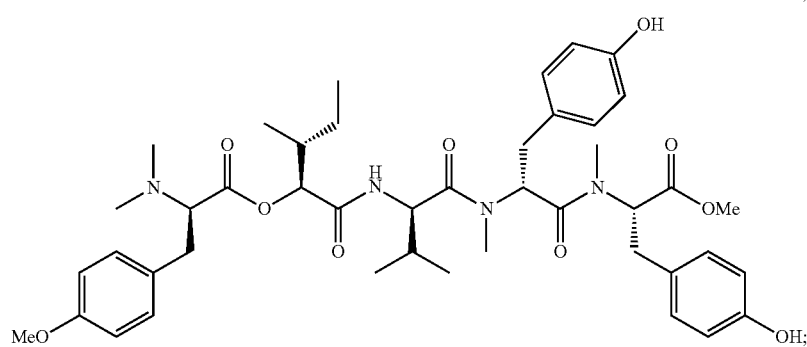
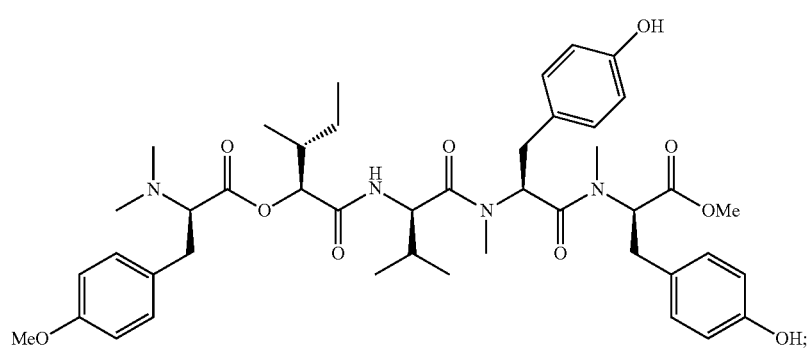

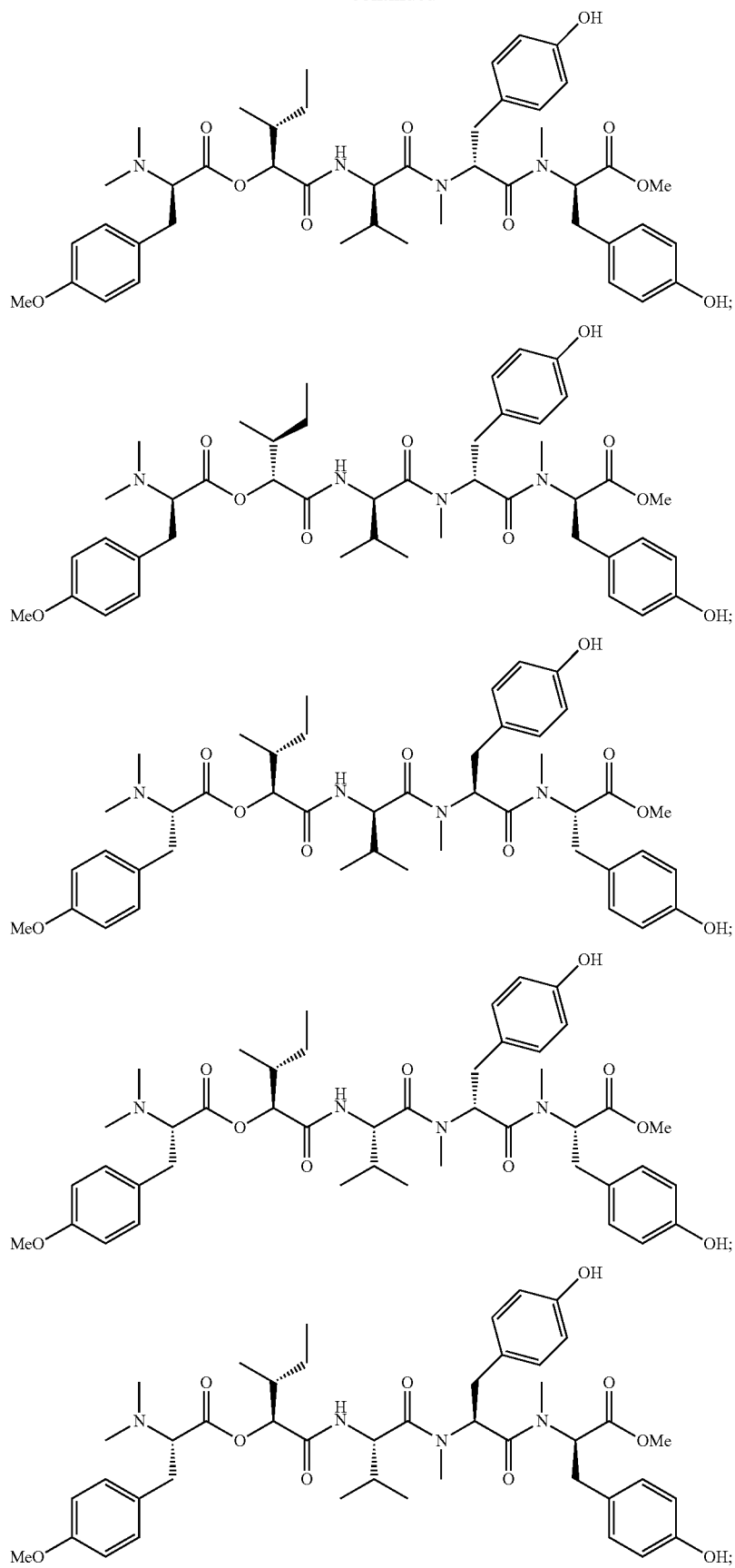

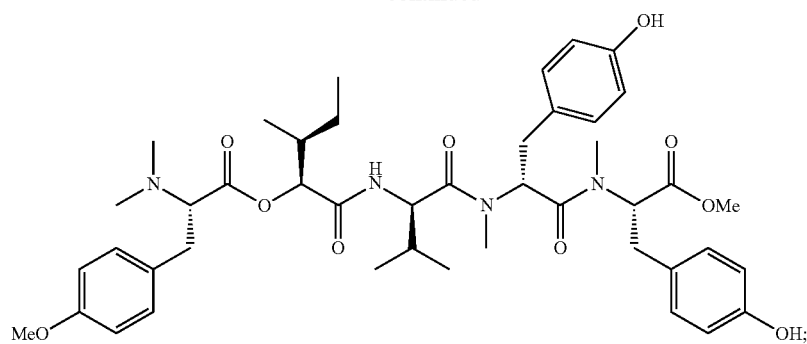
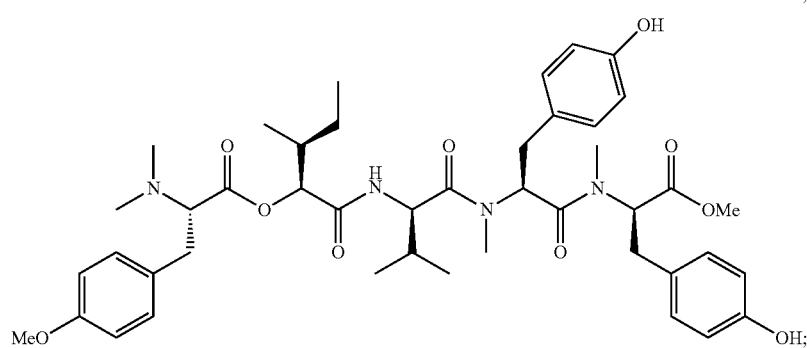
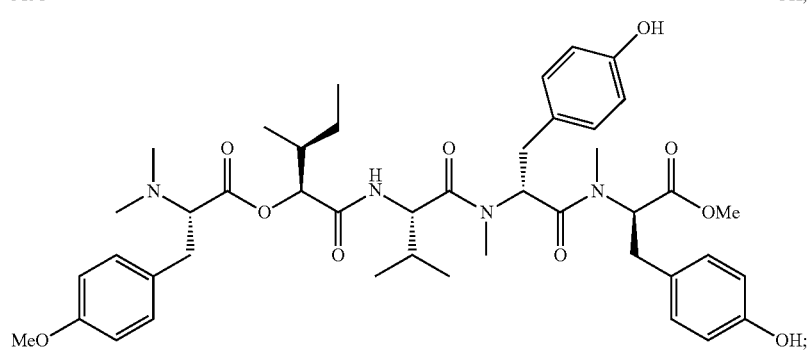
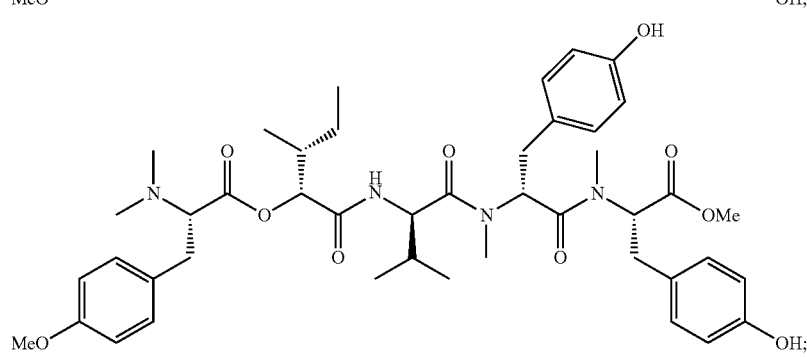
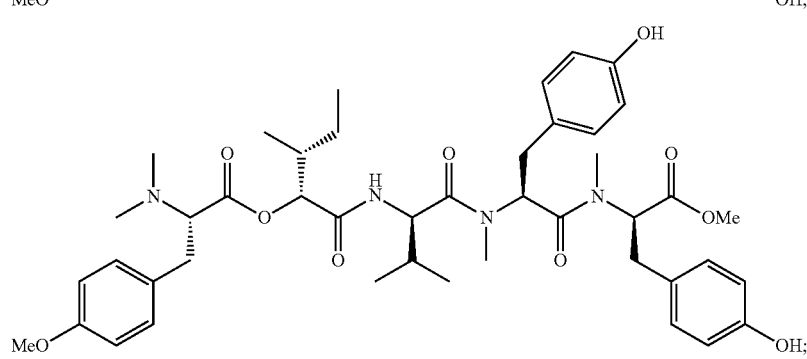

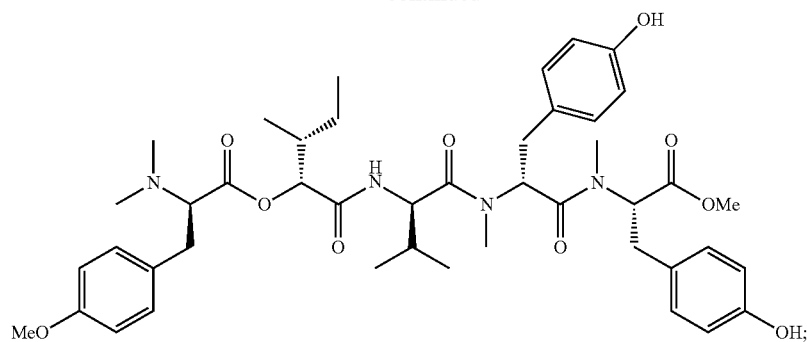
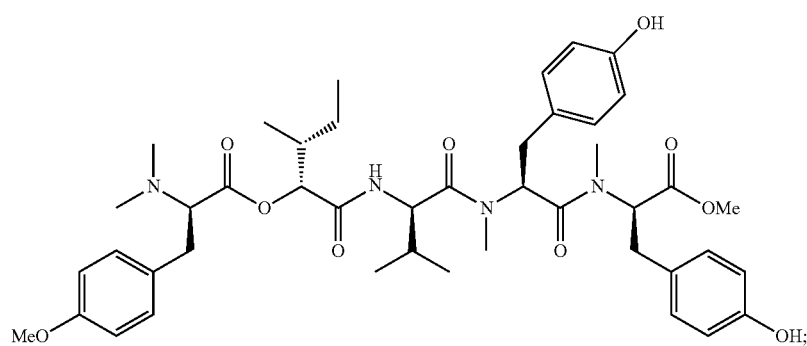
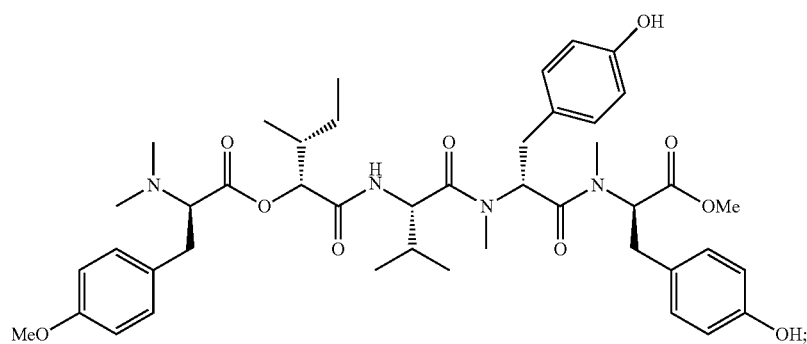
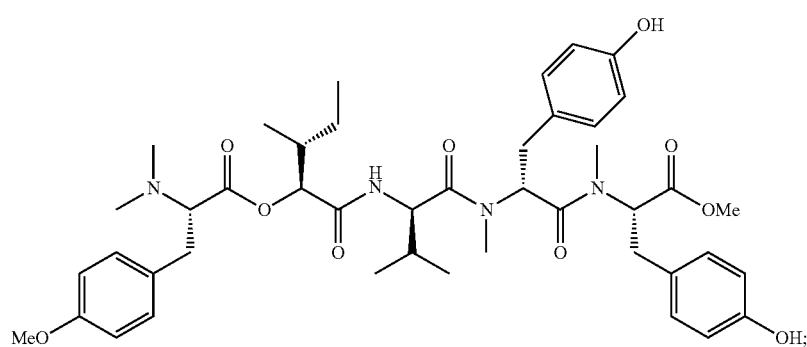
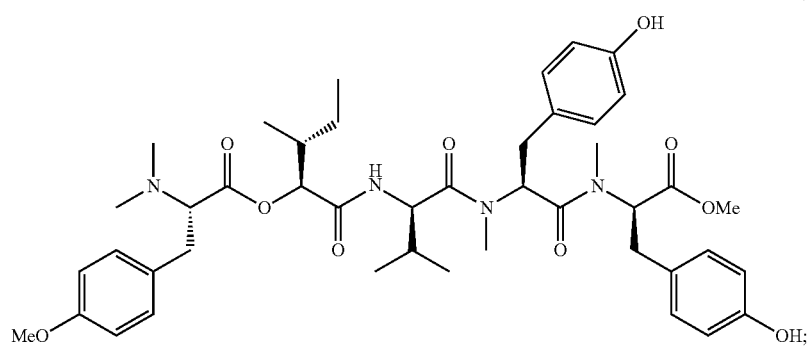

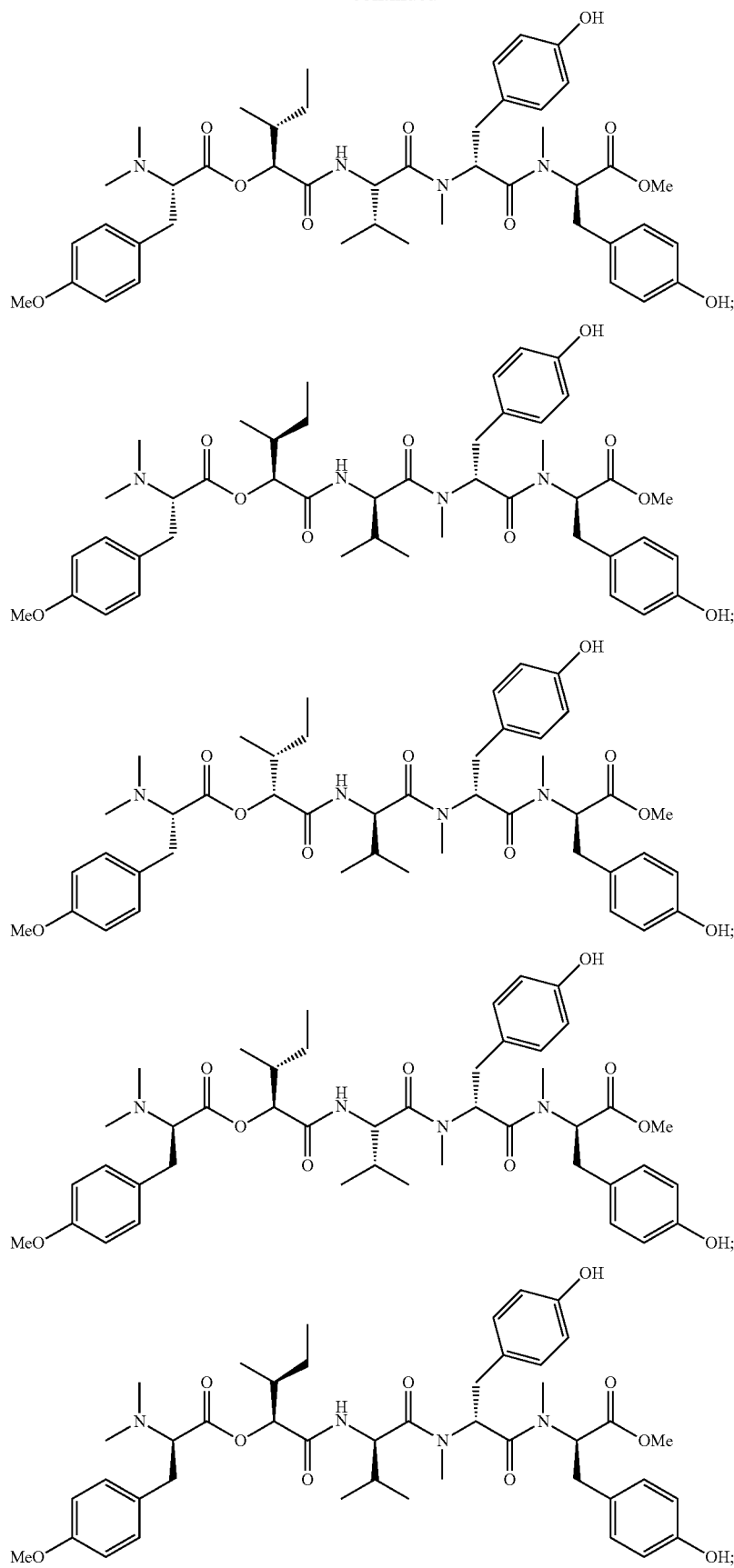

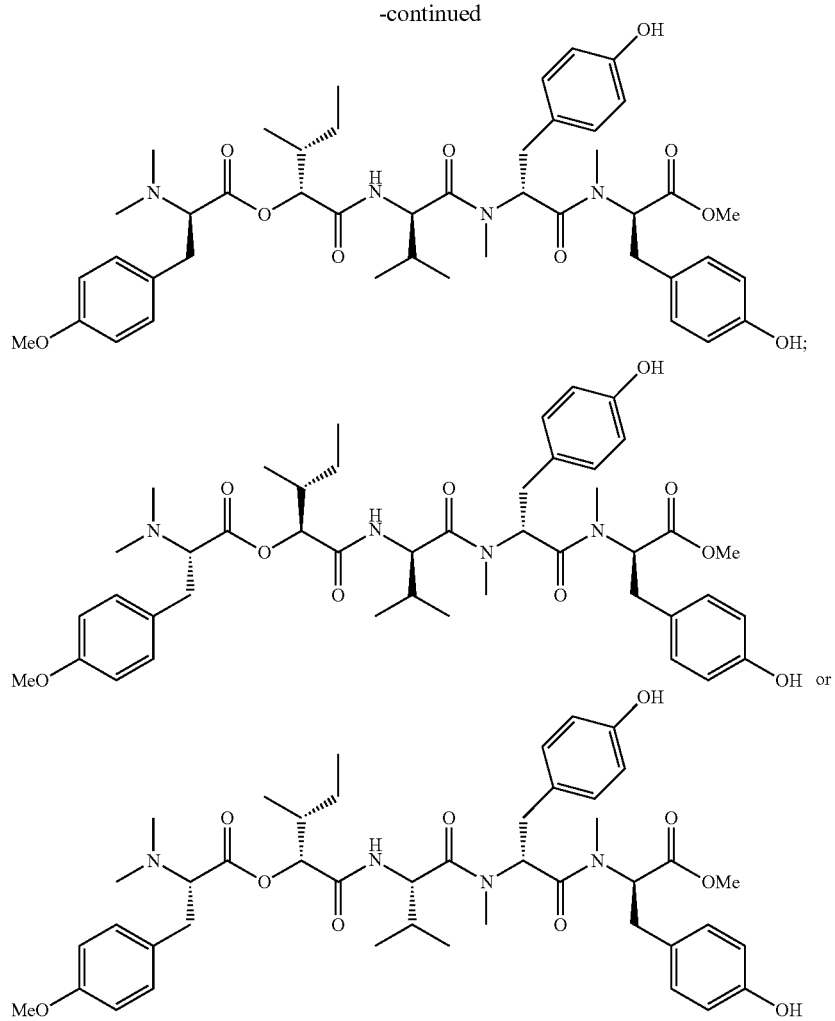

3. A pharmaceutical composition comprising the compound of claim 1, or pharmaceutically acceptable salt, solvate, hydrate, prodrug, or stereoisomer thereof, and a pharmaceutically acceptable carrier.

4. A topical pharmaceutical composition comprising the compound of claim 1, or pharmaceutically acceptable salt, solvate, hydrate, prodrug, or stereoisomer thereof, and a pharmaceutically acceptable topical carrier.

5. A method of treating a subject suffering from or susceptible to a wound, comprising administering to said subject in need thereof, an effective amount of a compound of claim 1, or pharmaceutically acceptable salt, solvate, hydrate, prodrug, or stereoisomer thereof.

6. The method of claim 5, wherein the wound is a chronic wound.

7. The method of claim 5, wherein the wound is a diabetic foot ulcer [DFU], pressure ulcer [PU], or chronic venous leg ulcer [VU].

8. A method of treating a subject suffering from or susceptible to a disorder or disease mediated by VEGF, comprising administering to said subject in need thereof, an effective amount of a compound of claim 1, or pharmaceutically acceptable salt, solvate, hydrate, prodrug, or stereoisomer thereof, wherein the disorder or disease is a wound.

9. The method of claim 8, wherein the disorder or disease is mediated by VEGF-A.

10. The method of claim 8, wherein the wound is a chronic wound.

11. The method of claim 8, wherein the wound is a diabetic foot ulcer [DFU], pressure ulcer [PU], or chronic venous leg ulcer [VU].

12. A method of inducing VEGF expression in a subject, comprising administering to said subject an effective amount of a compound of claim 1, or pharmaceutically acceptable salt, solvate, hydrate, prodrug, or stereoisomer thereof.

* * * * *